US011898152B2

(12) United States Patent
Zhou et al.

(10) Patent No.: US 11,898,152 B2
(45) Date of Patent: Feb. 13, 2024

(54) NUCLEOTIDE SEQUENCES AND CORRESPONDING POLYPEPTIDES CONFERRING MODULATED GROWTH RATE AND BIOMASS IN PLANTS GROWN IN SALINE AND OXIDATIVE CONDITIONS

(71) Applicant: Ceres, Inc., Thousand Oaks, CA (US)

(72) Inventors: Fasong Zhou, Oxnard, CA (US); Kenneth A. Feldmann, Tuscon, AZ (US); Julissa Sosa, Northridge, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 17/813,842

(22) Filed: Jul. 20, 2022

(65) Prior Publication Data

US 2023/0132139 A1    Apr. 27, 2023

Related U.S. Application Data

(60) Division of application No. 17/064,117, filed on Oct. 6, 2020, now Pat. No. 11,459,581, which is a division of application No. 16/694,109, filed on Nov. 25, 2019, now Pat. No. 11,034,972, which is a division of application No. 16/265,525, filed on Feb. 1, 2019, now Pat. No. 10,619,166, which is a division of application No. 15/962,986, filed on Apr. 25, 2018, now Pat. No. 10,233,461, which is a division of application No. 15/679,052, filed on Aug. 16, 2017, now Pat. No. 10,006,043, which is a division of application No. 13/465,841, filed on May 7, 2012, now Pat. No. 9,765,355, which is a division of application No. 11/858,117, filed on Sep. 19, 2007, now abandoned, which is a continuation-in-part of application No. PCT/US2007/006544, filed on Mar. 14, 2007.

(60) Provisional application No. 60/782,735, filed on Mar. 14, 2006.

(51) Int. Cl.
C12N 15/82    (2006.01)
C07K 14/415   (2006.01)

(52) U.S. Cl.
CPC ........ *C12N 15/8273* (2013.01); *C07K 14/415* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 6,281,411 B1 | 8/2001 | Adams et al. | |
| 6,867,351 B2 | 3/2005 | da Costa e Silva et al. | |
| 9,765,355 B2 | 9/2017 | Zhou et al. | |
| 10,006,043 B2 | 6/2018 | Zhou et al. | |
| 10,233,461 B2 | 3/2019 | Zhou et al. | |
| 10,619,166 B2 | 4/2020 | Zhou et al. | |
| 11,028,405 B2 | 6/2021 | Zhou et al. | |
| 11,034,972 B2 | 6/2021 | Zhou et al. | |
| 11,142,772 B2 | 10/2021 | Zhou et al. | |
| 11,447,792 B2 | 9/2022 | Zhou et al. | |
| 11,459,581 B2 | 10/2022 | Zhou et al. | |
| 11,667,926 B2 | 6/2023 | Zhou et al. | |
| 11,674,149 B2 | 6/2023 | Zhou et al. | |
| 2004/0034888 A1 | 2/2004 | Liu et al. | |
| 2006/0107345 A1 | 5/2006 | Alexandrov et al. | |
| 2006/0150283 A1 | 7/2006 | Alexandrov et al. | |
| 2007/0214517 A1 | 9/2007 | Alexandrov et al. | |
| 2013/0042367 A1 | 2/2013 | Nadzan et al. | |
| 2015/0259699 A1 | 9/2015 | Nadzan et al. | |
| 2017/0037426 A1* | 2/2017 | Alexandrov | C12N 15/8271 |
| 2018/0223303 A1 | 8/2018 | Alexandrov et al. | |
| 2020/0165625 A1 | 5/2020 | Zhou et al. | |
| 2020/0181636 A1 | 6/2020 | Zhou et al. | |
| 2021/0095304 A1 | 4/2021 | Zhou et al. | |
| 2021/0317469 A1 | 10/2021 | Zhou et al. | |
| 2021/0348184 A1 | 11/2021 | Zhou et al. | |
| 2023/0116932 A1 | 4/2023 | Zhou et al. | |

FOREIGN PATENT DOCUMENTS

| | | |
|---|---|---|
| EP | 1033405 A2 | 9/2000 |
| WO | WO 1999/061616 A2 | 12/1999 |
| WO | WO 2001/055433 | 8/2001 |
| WO | WO 2004/092326 A2 | 10/2004 |
| WO | WO 20041092326 A3 | 10/2004 |
| WO | WO 2006/026756 A2 | 3/2006 |

OTHER PUBLICATIONS

Smith et al. (Nature Biotechnology, 15:1222-1223, 1997).*
Bork et al. (TIG, 12:425-427, 1996).*
Doerks et al., (TIG, 14:248-250, 1998).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*

(Continued)

*Primary Examiner* — Vinod Kumar
(74) *Attorney, Agent, or Firm* — Dentons US LLP

(57) ABSTRACT

The present invention relates to isolated nucleic acid molecules and their corresponding encoded polypeptides able confer the trait of improved plant size, vegetative growth, growth rate, seedling vigor and/or biomass in plants challenged with saline and/or oxidative stress conditions. The present invention further relates to the use of these nucleic acid molecules and polypeptides in making transgenic plants, plant cells, plant materials or seeds of a plant having plant size, vegetative growth, growth rate, seedling vigor and/or biomass that are improved in saline and/or oxidative stress conditions with respect to wild-type plants grown under similar conditions.

10 Claims, 18 Drawing Sheets

Specification includes a Sequence Listing.

(56) References Cited

OTHER PUBLICATIONS

Thornton et al. (Nature structural Biology, structural genomics supplement, Nov. 2000).*
Keskin et al. (Protein Science, 13:1043-1055, 2004).*
Kang et al. (Cell death and differentiation, 13:84-95, 2006).*
Rhoads et al. (The FASEB Journal, 11:331-340, 1997).*
U.S. Appl. No. 17/063,395, filed Oct. 5, 2020, Zhou et al.
U.S. Appl. No. 17/220,681, filed Apr. 1, 2021, Zhou et al.
U.S. Appl. No. 17/221,604, filed Apr. 2, 2021, Zhou et al.
Aroca et al., "The role of aquaporins and membrane damage in chilling and hydrogen peroxide induced changes in the hydraulic conductance of maize roots", *Plant Physiol.*, 137(1):341-53, 2005, Epub. Dec. 10, 2004.
Aviv et al., "Runaway cell death, but not basal disease resistance, in lsd1 is SA and NIM1/NPR1-dependent", *Plant J.*, 29(3):381-91, 2002.
Borsani et al., "Evidence for the role of salicylic acid in the oxidative damage generated by NaCl and osmotic stress in *Arabidopsis* seedlings," *Plant Physiol.*, 126:1024-1030, 2001.
Brisson et al., "Function of Oxidative CROSS-Linking of Cell Wall Structural Proteins in Plant Disease Resistance," *Plant Cell*, 6(12):1703-1712, 1994.
Cao et al., "Characterization of an *Arabidopsis* mutant that is nonresponsive to inducers of systemic acquired-resistance," *Plant Cell*, 6:1583-1592, 1994.
Dat et al., "Changes in salicylic acid and antioxidants during induced thermotolerance in mustard seedlings," *Plant Physiol.*, 118:1455-1461, 1998.
Delaney et al., "A central role of salicylic acid in plant-disease resistance," *Science*, 266:1247-1250, 1994.
Kim et al.,, "Effects of salicylic acid on paraquat tolerance in *Arabidopsis thaliana* plants," *J. Plant Biol.*, 46:31-37, 2003.
Lamb et al., "The oxidative burst in plant disease resistance," *Annu. Rev. Plant Physiol. Plant Mol. Biol.*, 48:251-275, Jun. 1997.
Larkindale et al., "Protection against heat stress-induced oxidative damage in *Arabidopsis* involves calcium, abscisic acid, ethylene, and salicylic acid," *Plant Physiol.*, 128:682-695, 2002.
Lee et al., "Rapid accumulation of hydrogen peroxide in cucumber roots due to exposure to low temperature appears to mediate decreases in water transport," *J. Exp. Bot.*, 55(403):1733-41, Epub. Jun. 18, 2004.
Levine et al., "H2O2 from the oxidative burst orchestrates the plant hypersensitive disease resistance response," *Cell*, 18,79(4):583-93, 1994.
Luna et al., "Drought controls on H2O2 accumulation, catalase (CAT) activity and CAT gene expression in wheat," *J Exp Bot.*, 56(411):417-23, 2005, Epub. Nov. 29, 2004. 2004.
Martinez et al., "Salicylic acid regulates flowering time and links defence responses and reproductive development," *Plant J*, 37:209-217, 2004.
Noctor et al., "Drought and oxidative load in the leaves of C3 plants: a predominant role for photorespiration?" *Ann Bot (Lond)*, 89:841-50, 2002.
Rusterucci et al., "The disease resistance signaling components EDS1 and PAD4 are essential regulators of the cell death pathway controlled by LSD1 in *Arabidopsis,*" *Plant Cell*, 2001.
Scott et al., "Salicylate accumulation inhibits growth at chilling temperature in *Arabidopsis,*" *Plant Physiol.*, 135:1040-1049, 2004.
Senaratna et al., "Acetyl salicylic acid (Aspirin) and salicylic acid induce multiplestress tolerance in bean and tomato plants," *Plant Growth Regul.*, 30:157-161, 2000.
Surplus et al., "Ultraviolet-B-induced responses in *Arabidopsis thaliana*: role of salicylic acid and reactive oxygen species in the regulation of transcripts encoding photosynthetic and acidic pathogenesis-related proteins," *Plant Cell Environ.*, 21:685-694, 1998.
Zhou et al., "High humidity suppresses ssi4-mediated cell death and disease resistance upstream of MAP kinase activation, H2O2 production and defense gene expression," *Plant J*, 39(6):920-32, 2004.
Zhou et al., "Proton extrusion is an essential signaling component in the HR of epidermal single cells in the barley-powdery mildew interaction," *Plant J.*, 23(2):245-54, 2000.
Ngo et al., *The Protein Folder Problem and Tertiary Structure Prediction*, K. Merz., and S. Le Grand (eds.), 492-495, 1994.
NCBI GenBank Accession No. NP 179785 (Aug. 21, 2001).
NCBI GenBank Accession No. NP 665906 (Jan. 29, 2002).
NCBI GenBank Accession No. NP665305 (Jan. 29, 2002).
NCBI GenBank Accession No. NP567957 (Jan. 30, 2002).
NCBI GenBank Accession No. NP 566785 (Jan. 29, 2002).
NCBI GenBank Accession No. NP_567754 (Jan. 29, 2002).
NCBI GenBank Accession No. NM 129505 (Aug. 21, 2001).
NCBI GenBank Accession No. NM '119581 (Jan. 30, 2002).
NCBI GenBank Accession No. BT018295 (Oct. 27, 2004).
NCBI GenBank Accession No. NM_127763 (Nov. 4, 2005).
NCBI GenBank Accession No. BT003928 (Feb. 14, 2003).
NCBI GenBank Accession No. AY086786 (Jan. 27, 2006).
NCBI GenBank Accession No. AY092961 (Apr. 21, 2002).
NCBI GenBank Accession No. AF410323 (Aug. 27, 2001).
USPTO: Office Action regarding U.S. Appl. No. 16/265,525, dated Sep. 20, 2019.
Response to Office Action regarding U.S. Appl. No. 16/265,525, filed Nov. 19, 2019.
Supplemental Response to Office Action regarding U.S. Appl. No. 16/265,525, filed Nov. 27, 2019.
USPTO: Notice of Allowance regarding U.S. Appl. No. 16/265,525, dated Dec. 4, 2019.
U.S. Appl. No. 17/813,816, filed Jul. 20, 2022, Zhou et al.

* cited by examiner

| | | | | | | |
|---|---|---|---|---|---|---|
| SEQ·ID·NO·85 | KHEAVMKRER | ALAYAFNYQQ | — — — — — — | — — — — — — | — — — V S | 253 |
| SEQ·ID·NO·98 | LHSRRHAGG— | YSPDFNGGDD | — — — — — — | — — — — — — | — — — — — — | 309 |
| SEQ·ID·NO·100 | LQETXXVSG— | TTASGV— — — — | WRLPPLDGHG | WRNDFG | | 310 |
| SEQ·ID·NO·88 | LERQSNYSS— | CCTESLGGE— | — — — — — — | — — — — — — | — — — — — — | 355 |
| SEQ·ID·NO·96 | SEQRSTVSS— | SCAESLGGEP | MSPSSTSD | LRRWLR | | 361 |
| SEQ·ID·NO·93 | SEQRSTVSSL | SCAESVGGEP | ASPSSTTD | LRRWLR | | 373 |
| SEQ·ID·NO·107 | SEQRSNVSS— | SCAESLGGDV | VSPSSTTD | LRRWLR | | 291 |

| | | | |
|---|---|---|---|
| SEQ·ID·NO·42 | FNRFA----- | ----------- | 517 |
| SEQ·ID·NO·47 | FGSEAALHQM | QMEHYTPIR- | 476 |
| SEQ·ID·NO·44 | CSLPNWDRQA | FFK------- | 450 |
| SEQ·ID·NO·54 | ---------- | ----------- | 384 |
| SEQ·ID·NO·43 | ---------- | ----------- | 383 |
| SEQ·ID·NO·41 | YTSFFSSNPL | FFQ------- | 252 |
| SEQ·ID·NO·45 | HSSFLV---- | ----------- | 403 |
| SEQ·ID·NO·60 | Y--------- | ----------- | 477 |
| SEQ·ID·NO·69 | ---------- | ----------- | 464 |
| SEQ·ID·NO·66 | ---------- | ----------- | 457 |
| SEQ·ID·NO·68 | ---------- | ----------- | 455 |

| | | | | | | |
|---|---|---|---|---|---|---|
| SEQ·ID·NO·136 | KSN-- | ---DDDD | SKSTI-SVLSE | RNRRHXI-AGS | SVXDDESLAG | SPALPSYMVP | 394 |
| SEQ·ID·NO·141 | KNGLSQVDDD | ARSVLSVQSE | RPRRHSI-ATS | TVRDDESLTS | SPSLPSYMVP | 144 |
| SEQ·ID·NO·147 | KSGDCDGDDA | RSVVSTVRSE | RPRRHSI-GAS | SVRDDDAG--S | SPSVPSYMAA | 296 |
| SEQ·ID·NO·145 | RDSWLYKEDD | LRSITSI-RSE | RPRRQSTGGA | SVRDDASLTS | TPALPSYMQS | 425 |
| SEQ·ID·NO·140 | RNSWLYKEDD | LRSITSI-RSE | RPRRQSTGGG | SVRDDDTSLTS | TPPLPSYMQS | 422 |
| SEQ·ID·NO·149 | RGSAWGGDED | SRSITFSVQSE | RYRRHSIAGS | SIRDDESLAS | SPSVPSYMAP | 249 |
| SEQ·ID·NO·151 | RGSQWGGYED | SRSI-LSTRSD | RYRRHSIAGS | SMRDDESLTS | SPAVPSYMAP | 405 |

| | | | | | | |
|---|---|---|---|---|---|---|
| SEQ·ID·NO·136 | T--- | KPQSPLG--G | ---- | FTDKASAKKR | LSYPTSPALP | 437 |
| SEQ·ID·NO·141 | T--- | RLQGSAMANG | ---- | -GSTGPAKKKR | LSFQGGTAAA | 188 |
| SEQ·ID·NO·147 | TKSA | RVQSPTL-TDR | AETPEKG | WSSVGSAKKR | LSFPAGTPPP | 346 |
| SEQ·ID·NO·145 | T--- | RYRSI-LLTEK | AAQAETL--- | PLVHSSI-KKKR | LSFPVADKPN | 469 |
| SEQ·ID·NO·140 | T--- | RYRSLLLTEK | FEVPERV-- | PLAHSVVKKR | LSFPVVEKPS | 467 |
| SEQ·ID·NO·149 | TRSQ | RLSSPLG--N | LEVPERA-- | -SVGYVKKR | LSFSASPAGA | 294 |
| SEQ·ID·NO·151 | TQ-- | HI-PSPL--G | NGTPDKA-- | VAGSAKKR | LLFPASPASS | 445 |
| | | | SGTPDRR | | | |

| | | | | | | |
|---|---|---|---|---|---|---|
| SEQ·ID·NO·136 | --K | PRRFSAPPKV | ESGGGVT-- | ---VTNGA | GS------- | 461 |
| SEQ·ID·NO·141 | -SP | MRRHSGPPPKV | E-APPQ-- | -PEALVNGG | SK------- | 217 |
| SEQ·ID·NO·147 | VPAAA | ARRHSGPPPKV | RQAGVEGGTE | ERDSSLA--- | ------- | 378 |
| SEQ·ID·NO·145 | HADKLMER | GRRHSDPPPKV | DPATLK--- | -DVPVS--- | ------- | 500 |
| SEQ·ID·NO·140 | VPTEKPRER | VRRHSGPPPKV | DPASLK--- | -DAPAA--- | ------- | 498 |
| SEQ·ID·NO·149 | ------- | -RRHSGPPPKV | DASAVKDIQM | HREEKMSNGA | SSK------- | 326 |
| SEQ·ID·NO·151 | ------- | -RRHSEPPPKV | DI-SEAR-- | KNQHAPSNGR | QVAW | 474 |

| | | | | | | | | |
|---|---|---|---|---|---|---|---|---|
| SEQ·ID·NO·24 | PSYMAPTASA | KARIRGGQGSP | RIAQEKP-EK | NGTTRRHSLP | PAANGKLSTM | 558 |
| SEQ·ID·NO·33 | PSYMAATQSA | KAKLRGNSSP | KLSSDSA-EK | NGFTRRHSLP | SSNNGKMVSH | 539 |
| SEQ·ID·NO·2 | PSYMATESL | KAKLRAQN--GPP | RVDDSSAEK | NGFTRRHSLP | SGTNS---- | 561 |
| SEQ·ID·NO·19 | PSYMAPTESA | KAKLRI--GPNSP | RLDSDLPVDK | NAFTRRQSLP | SAANN---- | 539 |
| SEQ·ID·NO·13 | PSYMAPTESA | KAKLRGGQNSP | RLDSDSPADM | NGFTRRRQSLP | SSTNNT-- | 564 |
| SEQ·ID·NO·29 | PSYMAATESA | KAKLRGAQGSP | RFIPEAV-EK | NGLNRRYSLP | TSTNSKI- | 513 |
| SEQ·ID·NO·8 | PSYMAATESA | KAKLRAQGSP | RFGQDGS-ER | NNHTRRHSLP | SSTNSKINSP | 547 |
| SEQ·ID·NO·27 | PSYMAATESA | KAKLRMQGSP | RFSEDRV-EK | NNITRRHSLP | SSTNSKISSE | 570 |
| | | | | | | |
| SEQ·ID·NO·24 | SPRAHRLL-A | SAKGSMNSDR | SFSSSKDI-GG | KRFKPITIHK | PFCQFLLHYL | 608 |
| SEQ·ID·NO·33 | SPRTQRPANA | GCKDGAKGDK | AML-SSRDASE | RPLKA----- | ---------- | 574 |
| SEQ·ID·NO·2 | ---------- | ---------- | ---------- | RAIKA----- | ---------- | 566 |
| SEQ·ID·NO·19 | ---------- | ---------- | ---------- | RA-KT----- | ---------- | 544 |
| SEQ·ID·NO·13 | SPHTQRQVRV | AGKGAI-SDK | SQSSSKDAND | KVVRA----- | ---------- | 569 |
| SEQ·ID·NO·29 | SPRTQRPVQS | GGKGGHRSDR | TVSSSRDGNG | KVLQA----- | ---------- | 548 |
| SEQ·ID·NO·8 | SPRTQRAVHG | SGKGGNKSDK | SLLSSRDGNA | KGAQP----- | ---------- | 582 |
| SEQ·ID·NO·27 | ---------- | ---------- | ---------- | ---------- | ---------- | 605 |
| | | | | | | |
| SEQ·ID·NO·24 | HPFNKFSSCL | YQTSRRKLSG | NGESTKAE-- | ---------- | ---------- | 636 |
| SEQ·ID·NO·33 | ---------- | -EWRR----- | ---------- | ---------- | ---------- | 578 |
| SEQ·ID·NO·2 | ---------- | -EWKR----- | ---------- | ---------- | ---------- | 570 |
| SEQ·ID·NO·19 | ---------- | -EWRRW---- | ---------- | ---------- | ---------- | 548 |
| SEQ·ID·NO·13 | ---------- | -EWRR----- | ---------- | ---------- | ---------- | 574 |
| SEQ·ID·NO·29 | ---------- | -EWRR----- | ---------- | ---------- | ---------- | 552 |
| SEQ·ID·NO·8 | ---------- | -EWRR----- | ---------- | ---------- | ---------- | 586 |
| SEQ·ID·NO·27 | ---------- | -EWKRSWCS | SETWSIAGRE | YVD------- | ---------- | 626 |

FIG. 5 (continued)

| SEQ·ID·NO·35 | MRGFPVPVTS | WSSAALLGRS | ISSARDAAEA | SSPITAAEMV | RVAKEVANAA | 50 |
| SEQ·ID·NO·36 | ---------- | -MESRL | ARLARAAATS | TGRAVTAE-- | HLAEVVASAA | 43 |
| SEQ·ID·NO·35 | DACGVSGKKL | LEAAEALSRS | DTDAEPRRRA | AERIFDAASM | VAKEADASGA | 100 |
| SEQ·ID·NO·36 | GDRGFPSGAL | RQAALALARS | -SAPEARPRA | TAEVVRAAAM | VFRAAQEAGS | 92 |
| SEQ·ID·NO·35 | SGLSDAAQNL | TCATYAFSVA | ASGWGSLPES | STSGRDAGDL | LTEPLLGSCQ | 150 |
| SEQ·ID·NO·36 | PGVAEVAGDL | AHAAHDCVRA | ----LVES | GPAAERPRCL | LR--LWRRKN | 134 |
| SEQ·ID·NO·35 | DKNEKMTGEG | KDFSEM--- | RNSAADSSPL | QQSEIKESSL | FGKCKELLNY | 196 |
| SEQ·ID·NO·36 | RHNKNAAGEA | DLEAPLLHPH | ERPSSSSSPI | GASLSEIIEL | SESERDFINY | 184 |
| SEQ·ID·NO·35 | GFLGGPALLP | YL--GSGLRK | TVSPCSPSVF | HYIFSSWWIC | I-------- | 235 |
| SEQ·ID·NO·36 | GMFGALAIFP | YLTRTGGLKS | AYSPLSPSTF | HIIFCTWWIC | VGLDVLCGNR | 234 |
| SEQ·ID·NO·35 | ---------- | ---------- | ---------- | ---------- | ---------- | 235 |
| SEQ·ID·NO·36 | GRAMMKNILA | FILAFYARAS | ARLAILGVSL | LVILYSHLEL | APNEIYTLYI | 284 |
| SEQ·ID·NO·35 | VVGSHEQGDL | KILHIDRITS | HPND--K | 260 | | |
| SEQ·ID·NO·36 | LLGAATCMHL | LVWAMDYMSR | APGDAAD | 311 | | |

FIG. 6

NUCLEOTIDE SEQUENCES AND CORRESPONDING POLYPEPTIDES CONFERRING MODULATED GROWTH RATE AND BIOMASS IN PLANTS GROWN IN SALINE AND OXIDATIVE CONDITIONS

This application is a Divisional of co-pending application Ser. No. 17/064,117 filed on Oct. 6, 2020, which is a Divisional of application Ser. No. 16/694,109 filed on Nov. 25, 2019, which is a Divisional of application Ser. No. 16/265,525, filed on Feb. 1, 2019, now U.S. Pat. No. 10,619,166 which is a Divisional of application Ser. No. 15/962,986, filed on Apr. 25, 2018 now U.S. patent Ser. No. 10/233,461, which is a Divisional of application Ser. No. 15/679,052, filed on Aug. 16, 2017 now U.S. Pat. No. 10,006,043 which is a Divisional of application Ser. No. 13/465,841, filed on May 7, 2012, now issued as U.S. Pat. No. 9,765,355 which is a Divisional of application Ser. No. 11/858,117, filed on Sep. 19, 2007 (abandoned), which is a Continuation in Part of Application No. PCT/US2007/006544, filed on Mar. 14, 2007, which claims priority under 35 U.S.C. § 119 of U.S. Provisional No. 60/782,735, filed on Mar. 14, 2006, the contents of each of which are hereby incorporated by reference in their entirety.

INCORPORATION OF SEQUENCE LISTING

The sequence listing that is contained in the file named "CRES038USD13-revised2", which is 511 KB (as measured in Microsoft Windows®) and was created on Nov. 16, 2022, is filed herewith by electronic submission and is incorporated by reference herein.

TECHNICAL FIELD

The present invention relates to isolated nucleic acid molecules and their corresponding encoded polypeptides able to enhance plant growth under saline and/or oxidative stress conditions. The present invention further relates to using the nucleic acid molecules and polypeptides to make transgenic plants, plant cells, plant materials or seeds of a plant having improved growth rate, vegetative growth, seedling vigor and/or biomass under saline and/or oxidative stress conditions as compared to wild-type plants grown under similar conditions.

BACKGROUND

Plants specifically improved for agriculture, horticulture, biomass conversion, and other industries (e.g. paper industry, plants as production factories for proteins or other compounds) can be obtained using molecular technologies. As an example, great agronomic value can result from enhancing plant growth in saline and/or oxidative stress conditions.

Salinity

A wide variety agriculturally important plant species demonstrate significant sensitivity to saline and/or oxidative stress conditions. Upon salt concentration exceeding a relatively low threshold, many plants suffer from stunted growth, necrosis, and death that results in an overall stunted appearance and reduced yields of plant material, seeds, fruit and other valuable products. Physiologically, plants challenged with salinity experience disruption in ion and water homeostasis, inhibition of metabolism, and damage to cellular membranes that result in developmental arrest and cell death (Huh et al. (2002) *Plant J,* 29(5):649-59).

In many of the world's most productive agricultural regions, agricultural activities themselves lead to increased water and soil salinity, which threatens their sustained productivity. One example is crop irrigation in arid regions that have abundant sunlight. After irrigation water is applied to cropland, it is removed by the processes of evaporation and transpiration. While these processes remove water from the soil, they leave behind dissolved salts carried in irrigation water. Consequently, soil and groundwater salt concentrations build over time, rendering the land and shallow groundwater saline and thus damaging to crops.

In addition to human activities, natural geological processes have created vast tracts of saline land that would be highly productive if not saline. In total, approximately 20% of the irrigated lands are negatively affected by salinity. (Yamaguchi and Blumwald, 2005, *Trends in Plant Science,* 10: 615-620). For these and other reasons, it is of great interest and importance to identify genes that confer improved salt tolerance characteristics to thereby enable one to create transgenic plants (such as crop plants) with enhanced growth and/or productivity characteristics in saline conditions.

Despite this progress, today there continues to be a great need for generally applicable processes that improve forest or agricultural plant growth to suit particular needs depending on specific environmental conditions. To this end, the present invention is directed to advantageously manipulating plant tolerance to salinity in order to maximize the benefits of various crops depending on the benefit sought, and is characterized by expression of recombinant DNA molecules in plants. These molecules may be from the plant itself, and simply expressed at a higher or lower level, or the molecules may be from different plant species.

Oxidative Stress

Plants lead a sessile lifestyle and so are generally destined to reside where their seed germinates. Consequently, they can be exposed to unfavorable environmental conditions arising from weather, pollution and location. Stress conditions, such as extremes in temperature, drought and desiccation, salinity, soil nutrient content, heavy metals, UV radiation, pollutants such as ozone and $SO_2$, mechanical stress, high light and pathogen attack, have a large impact on plant growth and development. These types of stress exposure induce formation of toxic oxygen species, which are generated in all aerobic cells and are associated with oxidative damage at the cellular level. Several recently published reports have characterized toxic oxygen species generation and the subsequent oxidative damage caused by abiotic stresses (see Larkindale and Knight (2002); Borsani et al. (2001); Lee et al (2004); Aroca et al (2005); Luna et al (2005); and Noctor et al (2002)).

The toxic oxygen species are referred to as reactive oxygen species (ROS), reactive oxygen intermediates (ROI) or activated oxygen species (AOS) and are partially reduced or activated derivatives of oxygen. ROS/ROI/AOS include the oxygen-centered superoxide ($O_2$) and hydroxyl (·OH) free radicals as well as hydrogen peroxide ($H_2O_2$), nitric oxide (NO) and $O_2^1$. These oxygen species are generated as byproducts from reactions that occur during photosynthesis, respiration and photorespiration, and are predominantly formed in the chloroplasts, mitochondria, endoplasmic reticulum, microbodies (e.g. peroxisomes and glyoxysomes), plasma membranes and cell walls. While the toxicity of $O_2^-$ and $H_2O_2$ themselves is relatively low, their metal-dependent conversion to highly toxic OH is thought to be responsible for the majority of the biological damage associated with these molecules.

Oxidative stress damages cell structure and affects cell metabolism and catabolism. Membrane lipids are subject to oxidation by ROS/ROI/AOS, resulting in accumulation of high molecular weight, cross-linked fatty acids and phospholipids. Oxidative attack on proteins results in site-specific amino acid modifications, fragmentation of the peptide chain, aggregation of cross-linked reaction products, altered electrical charge and increased susceptibility to proteolysis, all of which frequently leads to elimination of enzyme activity. ROS/ROI/AOS that generate oxygen free radicals, such as ionizing radiation, also induce numerous lesions in DNA at both the sugar and base moieties which cause deletions, mutation and other lethal genetic effects such as base degradation, single strand breakage and cross-linking to proteins. Morphologically, the adverse effects of high levels of ROS accumulation are manifested as stunted growth and necrotic lesions.

Although capable of producing damage, ROS/ROI/AOS are also key regulators of metabolic and defense pathways, playing roles as signaling or secondary messenger molecules. For example, pathogen-induced ROS/ROI/AOS production is critical in disease resistance where these molecules are involved at three different levels: penetration resistance, hypersensitive response (HR) and systemic acquired resistance (Levine et al. (1994); Lamb and Dixon (1997); Zhou et al. (2000); Aviv et al. (2002)). In penetration resistance, ROS/ROI/AOS function by reinforcing cell walls through polyphenolic cross-linking. With respect to hypersensitive response, $H_2O_2$ is an active signaling molecule whose effect is dose dependent. At high dosages, $H_2O_2$ triggers hypersensitive cell death and thus restricts the pathogen to local infection sites (Lamb and Dixon (1997)) while low dosages block cell cycle progression (Reichheld et al. (1999)) and signal secondary wall differentiation (Potikha et al. (1999)). Lastly, ROS/ROI/AOS molecules play a role in broad-spectrum systemic acquired disease resistance by triggering micro-HR systematically after the first pathogen inoculation.

In the signal cascades leading to oxidative stress, salicylic acid (SA) has been identified as an important signaling molecule to mediate ROS/ROI/AOS accumulation in various stress conditions, such as salt and osmotic stress (Borsani et al. (2001)), drought (Senaratna et al. (2000)), heat (Dat et al. (1998)), cold (Scott et al. (2004)), UV-light (Surplus et al. (1998)), paraquat (Kim et al. (2003)) and disease resistance against different pathogens (Zhou et al. (2004)). High levels of SA induce $H_2O_2$ production as well as cell death.

Several signaling components required for SA-mediated ROS/ROI/AOS accumulation and gene expression have been characterized. For example, NPR1 is required for SA-induced PR gene expression and disease resistance (Cao et al. (1994)). The mutations in eds1 and eds5 block SA-mediated signaling and enhance disease susceptibility (Rusterucci et al. (2001)). Over-expression of NahG in various plant species also suppresses SA-induced responses to both abiotic and biotic stresses (Delaney et al. (1994)). Recently, Scott and colleagues (2004) reported that chilling treatment induced accumulation of SA in *Arabidopsis* and the degradation of SA by overexpression of NahG enhanced cold tolerance in a transgenic plant.

SA, as a phytohormone, also promotes early flowering (Martinez et al. (2004)). SA at various levels may play different roles in plant growth and stress responses. However, most of the time, the increased tolerance to high levels of SA appears to be beneficial, since it reduces the side effects of SA accumulation while stimulating SA-mediated stress responses.

Similarly, NO is capable of generating ROS/ROI/AOS and is a plant signaling molecule involved in the regulation of seed germination, stomatal closure (Mata and Lamattina (2001); Desikan et al (2002)), flowering time (He et al. (2004)), antioxidant reactions to suppress cell death (Beligni et al. (2002)) and tolerance to biotic and abiotic stress conditions (Mata and Lamattina (2001)). While the effects of NO can be mimicked through the application of sodium nitroprusside (SNP), endogenous NO production in plants results from the activity of a nitric oxide synthase that uses L-arginine (Guo et al. (2003)) as well as nitrate reductase-mediated reactions (Desikan et al (2002)). NO can react with redox centers in proteins and membranes, thereby causing cell damage and inducing cell death.

In order to control the two-fold nature of ROS/ROI/AOS molecules, plants have developed a sophisticated regulatory system which involves both production and scavenging of ROS/ROI/AOS in cells. During normal growth and development, this pathway monitors the level of ROS/ROI/AOS produced by metabolism and controls the expression and activity of ROS/ROI/AOS scavenging pathways. The major ROS/ROI/AOS scavenging mechanisms include the action of the superoxide dismutase (SOD), ascorbate peroxidase (APX) and catalase (CAT) enzymes as well as nonenzymatic components such as ascorbic acid, α-tocopherol and glutathione.

The antioxidant enzymes are believed to be critical components in preventing oxidative stress, in part because pretreatment of plants with one form of stress, and which induces expression of these enzymes, can increase tolerance for a different stress (cross-tolerance) Allen (1995)). In addition, plant lines selected for resistance to herbicides that function by inducing ROS/ROI/AOS generally have increased levels of one or more of these antioxidant enzymes and also exhibit cross-tolerance (Gressel and Galun (1994)).

Plant development and yield depend on the ability of the plant to manage oxidative stress, whether it is via the signaling or the scavenging pathways. Consequently, improvements in a plant's ability to withstand oxidative stress, or to obtain a higher degree of cross-tolerance once oxidative stress has been experienced, has significant value in agriculture. The sequences and methods of the invention provide the means by which tolerance to oxidative stress can be improved, either via the signaling or the scavenging pathways.

The availability and sustainability of a stream of food and feed for people and domesticated animals has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy.

Manipulation of crop performance has been accomplished conventionally for centuries through selection and plant breeding. The breeding process is, however, both time-consuming and labor-intensive. Furthermore, appropriate breeding programs must be specially designed for each relevant plant species.

On the other hand, great progress has been made in using molecular genetic approaches to manipulate plants to provide better crops. Through the introduction and expression of recombinant nucleic acid molecules in plants, researchers are now poised to provide the community with plant species tailored to grow more efficiently and yield more product despite suboptimal geographic and/or climatic environments. These new approaches have the additional advantage of not being limited to one plant species, but instead being applicable to multiple different plant species (Zhang et al. (2004) *Plant Physiol.* 135:615; Zhang et al. (2001) *Proc. Natl. Acad. Sci.* USA 98:12832).

SUMMARY

This document provides methods and materials related to plants having modulated levels of tolerance to salinity and/or oxidative stress. For example, this document provides transgenic plants and plant cells having increased levels of tolerance to salinity and/or oxidative stress, nucleic acids used to generate transgenic plants and plant cells having increased levels of tolerance to salinity and/or oxidative stress, and methods for making plants and plant cells having increased levels of tolerance to salinity and/or oxidative stress. Such plants and plant cells provide the opportunity to produce crops or plants under saline and/or oxidative stress conditions without stunted growth and diminished yields. Increased levels of tolerance to salinity and/or oxidative stress may be useful to produce biomass which may be converted to a liquid fuel or other chemicals and/or to produce food and feed on land that is currently marginally productive, resulting in an overall expansion of arable land.

Methods of producing a plant and/or plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 30 using an HMM generated from the amino acid sequences depicted in one of FIGS. 1-6. The plant and/or plant tissue has a difference in the level of tolerance to salinity and/or oxidative stress as compared to the corresponding level in tolerance to salinity and/or oxidative stress of a control plant that does not comprise the exogenous nucleic acid. In some embodiments the amino acid sequence of the polypeptide has an HMM bit score greater than about 400 using an HMM generated from the amino acid sequences depicted in FIG. 1. In some embodiments the amino acid sequence of the polypeptide has an HMM bit score greater than about 30 using an HMM generated from the amino acid sequences depicted in FIG. 2. In some embodiments the amino acid sequence of the polypeptide has an HMM bit score greater than about 120 using an HMM generated from the amino acid sequences depicted in FIG. 3. In some embodiments the amino acid sequence of the polypeptide has an HMM bit score greater than about 150 using an HMM generated from the amino acid sequences depicted in FIG. 4. In some embodiments the amino acid sequence of the polypeptide has an HMM bit score greater than about 425 using an HMM generated from the amino acid sequences depicted in FIG. 5. In some embodiments the amino acid sequence of the polypeptide has an HMM bit score greater than about 550 using an HMM generated from the amino acid sequences depicted in FIG. 6.

In another aspect, a method comprises growing a plant cell comprising an exogenous nucleic acid. The exogenous nucleic acid comprises a regulatory region operably linked to a nucleotide sequence encoding a polypeptide having 85 percent or greater sequence identity to an amino acid sequence set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. A plant produced from the plant cell has a difference in the level of tolerance to salinity and/or oxidative stress as compared to the corresponding level in a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 85 percent or greater sequence identity to at least a fragment of a nucleotide sequence set forth in SEQ ID NOs. 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164 and to a nucleotide sequence encoding any of the amino acid sequences set forth in the sequence listing. A plant and/or plant tissue produced from the plant cell has a difference in the level of salinity and/or oxidative stress tolerance as compared to the corresponding level in a control plant that does not comprise the exogenous nucleic acid.

Methods of modulating the level of salt tolerance and/or oxidative stress tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than 30, using an HMM generated from the amino acid sequences depicted in one of FIGS. 1-6. A plant and/or plant tissue produced from the plant cell has a difference in the level of tolerance to salinity and/or oxidative stress as compared to the corresponding level in a control plant that does not comprise the exogenous nucleic acid.

In another aspect, a method comprises introducing into a plant cell an exogenous nucleic acid that comprises a regulatory region operably linked to a nucleotide sequence encoding a polypeptide having 85% percent or greater sequence identity to an amino acid sequence set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140.A plant and/or plant tissue produced from the plant cell has a difference in the level of tolerance to salinity or oxidative stress as compared to the corresponding level in a control plant that does not comprise the exogenous nucleic acid.

In some embodiments, the methods comprise introducing into the plant cell an exogenous nucleic acid encoding polypeptides selected from the group consisting of SEQ ID NOs: 43, 44, 45, 86, 140, 141, 142, 143, 144, and amino acid coordinates 1 to 135 of SEQ ID NO: 140. A plant and/or plant tissue produced from the plant cell has a difference in the level of tolerance to salinity as compared to the corresponding level in a control plant that does not comprise the exogenous nucleic acid. In some embodiments, the methods comprise introducing into the plant cell an exogenous nucleic acid encoding polypeptides selected from the group consisting of SEQ ID NO: 136, and 141, and a plant and/or plant tissue produced from the plant cell has a difference in the level of tolerance to oxidative stress as compared to the corresponding level in a control plant that does not comprise the exogenous nucleic acid.

In another aspect, a method comprises introducing into a plant cell an exogenous nucleic acid, that comprises a regulatory region operably linked to a nucleotide sequence having 85 percent or greater sequence identity to a nucleotide sequence set forth in SEQ ID NOs: 1, 3, 5, 7, 10, 12, 16, 18, 21, 26, 28, 32, 34, 40, 46, 48, 51, 53, 55, 57, 59, 61, 65, 67, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164 and to a nucleotide sequence encoding any of the amino acid sequences set forth in the sequence listing. A plant and/or plant tissue produced from the plant cell has a difference in the level of tolerance to salinity or oxidative stress as compared to the corresponding level in a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than 30, using an HMM based on the amino acid sequences depicted in one of FIGS. 1-6. The plant and/or plant tissue has a difference in the level of tolerance to salinity or oxidative stress as compared to the corresponding level in a control plant that does not comprise the exogenous nucleic acid. In another aspect, the exogenous nucleic acid comprises a regulatory region operably linked to a nucleotide sequence encoding a polypeptide having 85 percent or greater sequence identity to an amino acid sequence selected from the group consisting of SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 A plant and/or plant tissue produced from the plant cell has a difference in the level of tolerance to salinity or oxidative stress as compared to the corresponding level in a control plant that does not comprise the exogenous nucleic acid. In another aspect, the exogenous nucleic acid comprises a regulatory region operably linked to a nucleotide sequence having 85 percent or greater sequence identity to at least a fragment of a nucleotide sequence selected from the group consisting of SEQ ID Nos. 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164, and to a nucleotide sequence encoding any of the amino acid sequences set forth in the sequence listing. A plant and/or plant tissue produced from the plant cell has a difference in the level of tolerance to salinity or oxidative stress as compared to the corresponding level in a control plant that does not comprise the exogenous nucleic acid. A transgenic plant comprising such a plant cell is also provided. In some embodiments, the transgenic plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet). Some embodiments are related to products comprising seed or vegetative tissue from transgenic plants as described above. Some embodiments relate to food or feed products from transgenic plants as described above.

In another aspect, an isolated nucleic acid comprises a nucleotide sequence encoding a polypeptide having 80% or greater sequence identity to the amino acid sequence set forth in SEQ ID Nos. 2, 4, 6, 22, 27, 29, 49, 52, 54, 56, 60, 62, 68, 76, 83, 88, 90, 96, 98, 104, 106, 112, 114, 132, 134, 149, 151, or 160.

In another aspect, methods of identifying a genetic polymorphism associated with variation in the level of salinity and/or oxidative stress tolerance are provided. The methods include providing a population of plants, and determining whether one or more genetic polymorphisms in the population are genetically linked to the locus for a polypeptide selected from the group consisting of the polypeptides depicted in FIGS. 1-6 and functional homologs thereof. The correlation between variation in the level of salinity tolerance and/or oxidative stress tolerance in plants and/or plant tissues of the population and the presence of the one or more polymorphisms in plants of the population is measured, thereby permitting identification of whether or not the one or more polymorphisms are associated with such variation.

In another aspect, methods of making a plant line is provided. The methods include determining whether one or more genetic polymorphisms in a population of plants is associated with the locus for a polypeptide selected from the group consisting of the polypeptides depicted in FIGS. 1-6 and functional homologs thereof, identifying one or more plants in the population in which the presence of at least one allele at the one or more polymorphisms is associated with variation in salt tolerance or oxidative stress tolerance, crossing each of the one or more identified plants with itself or a different plant to produce seed, crossing at least one progeny plant grown from said seed with itself or a different plant, and repeating the crossing steps for an additional 0-5 generations to make the plant line. The at least one allele will be present in the plant line. The method of making a plant line may be applied, for example, to a population of switchgrass plants.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

Figure 1:
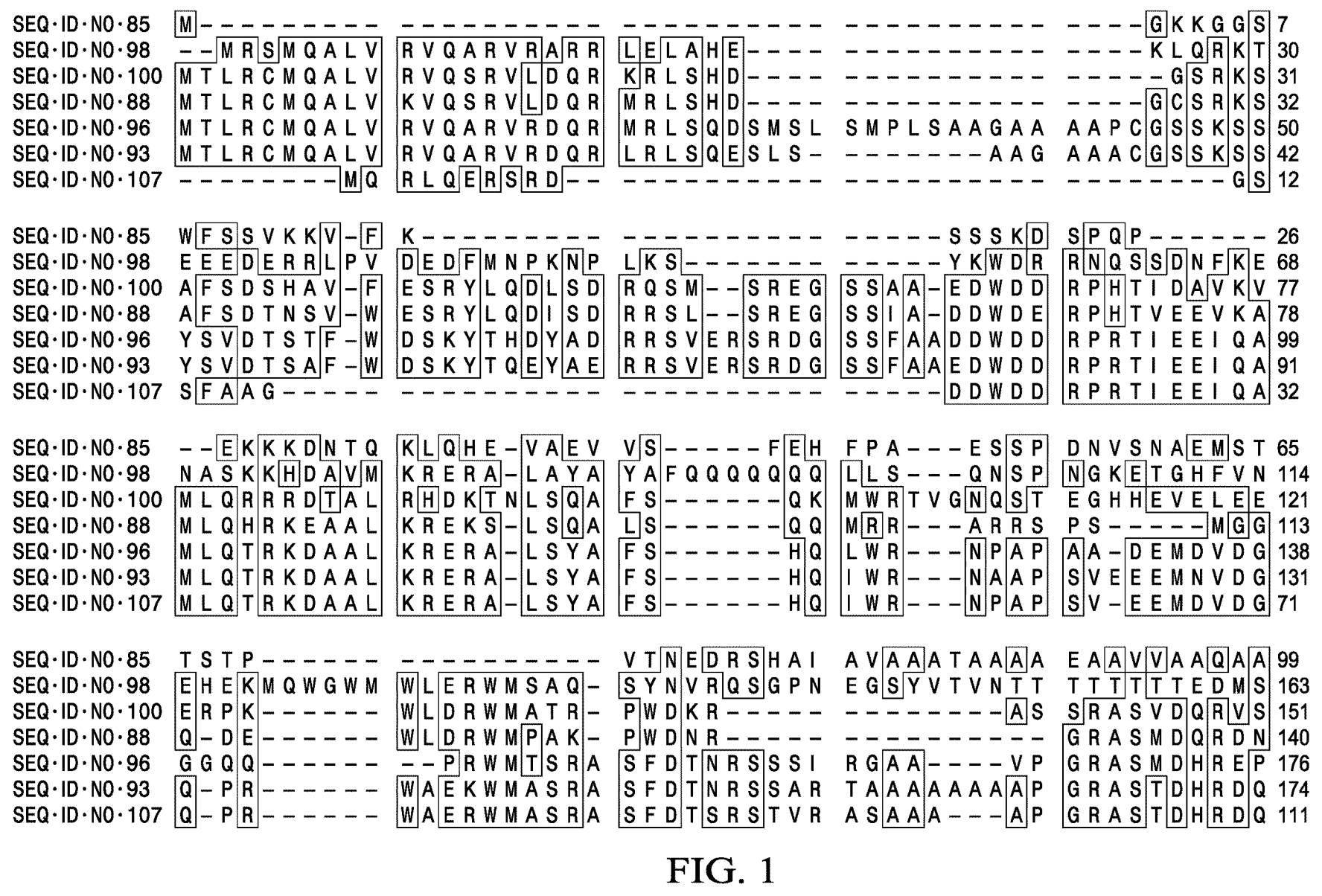
Figure 1:
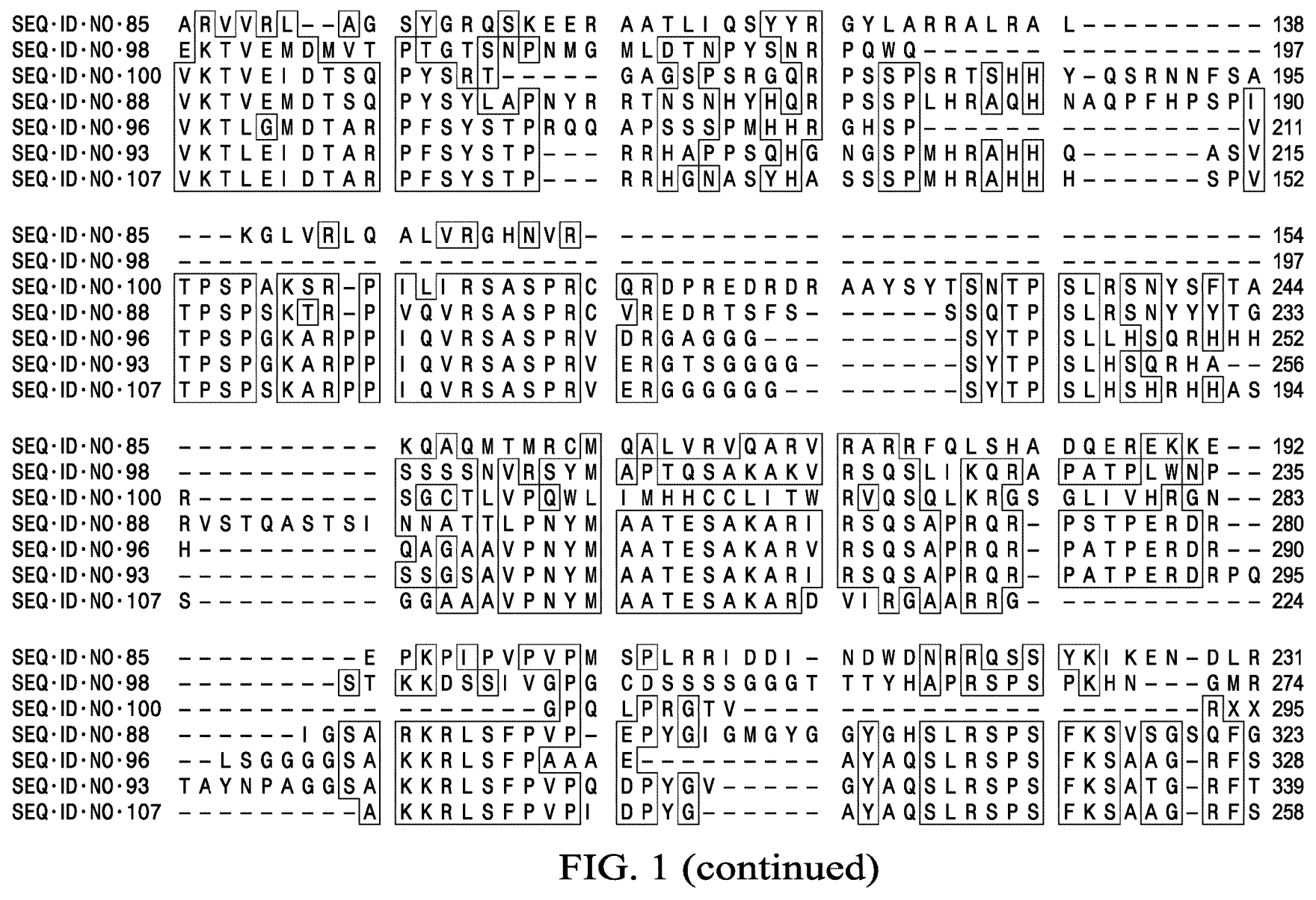

FIG. 1 is an alignment of amino acid sequences of homologues of (ME08768; SEQ ID NO: 86). In all the alignment Figures shown herein, a dash in an aligned sequence represents a gap, i.e., a lack of an amino acid at that position. Identical amino acids or conserved amino acid substitutions among aligned sequences are identified by boxes. FIG. 1 and the other alignment Figures provided herein were generated using the program MUSCLE version 3.52

FIG. 2 is an alignment of amino acid sequences of homologues of ME06748 (SEQ ID NO: 41).

FIG. 3 is an alignment of amino acid sequences of homologues of ME19173 (SEQ ID NO: 109).

FIG. 4 is an alignment of amino acid sequences of homologues of ME02064C (SEQ ID NO: 140).

FIG. 5 is an alignment of amino acid sequences of homologues of Ceres Clone ID No. 1792354 (SEQ ID NO:2).

FIG. 6 is an alignment of amino acid sequences of homologues of Ceres Clone ID No. 56784328 (SEQ ID NO: 35).

DETAILED DESCRIPTION

The invention features methods and materials related to modulating salinity tolerance and/or oxidative stress tolerance levels in plants and/or plant tissues. In some embodiments, the plants may also have increased biomass and/or yield. The methods can include transforming a plant cell with a nucleic acid encoding a salinity and/or oxidative stress tolerance-modulating polypeptide, wherein expression of the polypeptide results in a modulated level of salinity tolerance and/or oxidative stress tolerance. Plant cells produced using such methods can be grown to produce plants having an increased salinity tolerance, oxidative stress tolerance, and/or biomass, in comparison to wild type plants grown under the same conditions. Such plants, and the seeds of such plants, may be used to produce, for example, yield and/or biomass utilized for biofuel production, such as, but not limited to, ethanol and butanol.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

Oxidative stress: Plant species vary in their capacity to tolerate ROS/ROI/AOS. "Oxidative stress" can be defined as the set of environmental conditions under which a plant will begin to suffer the effects of elevated ROS/ROI/AOS concentration, such as decreases in enzymatic activity, DNA breakage, DNA-protein crosslinking, necrosis and stunted growth. For these reasons, plants experiencing oxidative stress typically exhibit a significant reduction in biomass and/or yield.

Elevated oxidative stress may be caused by natural, geological processes and by human activities, such as pollution. Since plant species vary in their capacity to tolerate oxidative stress, the precise environmental conditions that cause stress cannot be generalized. However, under oxidative stress conditions, oxidative stress tolerant plants produce higher biomass, yield and survivorship than plants that are not oxidative stress tolerant. Differences in physical appearance, recovery and yield can be quantified Photosynthetic efficiency: photosynthetic efficiency, or electron transport via photosystem II, is estimated by the relationship between Fm, the maximum fluorescence signal and the variable fluorescence, Fv. A reduction in the optimum quantum yield (Fv/Fm) indicates stress and can be used to monitor the performance of transgenic plants compared to non-transgenic plants under salt or oxidative stress conditions.

Salicylic Acid Growth Index (SAGI): Photosynthetic efficiency×seedling area.

Salt growth index (SGI): Photosynthetic efficiency×seedling area (under salinity stress condition).

Salinity: Plant species vary in their capacity to tolerate salinity. "Salinity" can be defined as the set of environmental conditions under which a plant will begin to suffer the effects of elevated salt concentration, such as ion imbalance, decreased stomatal conductance, decreased photosynthesis, decreased growth rate, increased cell death, loss of turgor (wilting), or ovule abortion. For these reasons, plants experiencing salinity stress typically exhibit a significant reduction in biomass and/or yield.

Elevated salinity may be caused by natural, geological processes and by human activities, such as pollution. Since plant species vary in their capacity to tolerate salinity, the precise environmental conditions that cause stress cannot be generalized. However, under saline conditions, salinity tolerant plants produce higher biomass, yield and survivorship than plants that are not saline tolerant. Differences in physical appearance, recovery and yield can be quantified.

Elevated salinity may be caused by natural, geological processes and by human activities, such as irrigation. Since plant species vary in their capacity to tolerate water deficit, the precise environmental salt conditions that cause stress cannot be generalized. However, under saline conditions, salt tolerant plants produce higher biomass, yield and survivorship than plants that are not salt tolerant. Differences in physical appearance, recovery and yield can be quantified and statistically analyzed using well known measurement and analysis methods.

II. Polypeptides

Polypeptides described herein include salinity tolerance and/or oxidative stress tolerance-modulating polypeptides. Salinity tolerance and/or oxidative stress tolerance—modulating polypeptides can be effective to modulate salinity tolerance and/or oxidative stress tolerance levels when expressed in a plant or plant cell. Such polypeptides typically contain at least one domain indicative of salinity tolerance and/or oxidative stress tolerance-modulating polypeptides, as described in more detail herein. Salinity tolerance and/or oxidative stress tolerance-modulating polypeptides typically have an HMM bit score that is greater than 30, as described in more detail herein. In some embodiments, salinity tolerance and/or oxidative stress tolerance-modulating polypeptides have greater than 85% identity to SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 as described in more detail herein.

A. Domains Indicative of Salinity Tolerance and/or Oxidative Stress Tolerance-Modulating Polypeptides A salinity tolerance and/or oxidative stress tolerance-modulating polypeptide can contain an IQ calmodulin-binding motif domain, which is predicted to be characteristic of an salinity tolerance and/or oxidative stress tolerance-modulating polypeptide. Calmodulin (CaM) is recognized as a major calcium sensor and orchestrator of regulatory events through its interaction with a diverse group of cellular proteins. Three classes of recognition motifs exist for many of the known CaM binding proteins; the IQ motif as a consensus for $Ca_{2+}^-$ independent binding and two related motifs for $Ca^{2+}$-dependent binding, termed 18-14 and 1-5-10 based on the position of conserved hydrophobic residues PUBMED:9141499.

For example, the regulatory domain of scallop myosin is a three-chain protein complex that switches on this motor in response to $Ca^{2+}$ binding. Side-chain interactions link the two light chains in tandem to adjacent segments of the heavy chain bearing the IQ-sequence motif. The $Ca^{2+}$-binding site is a novel EF-hand motif on the essential light chain and is stabilized by linkages involving the heavy chain and both light chains, accounting for the requirement of all three chains for $C^{a2+}$ binding and regulation in the intact myosin molecule PUBMED:8127365.

For example, SEQ ID NO:86 sets forth the amino acid sequence of an *Arabidopsis* clone, identified herein as Ceres SEEDLINE ID no.ME08768, that is predicted to encode a polypeptide containing a IQ calmodulin-binding motif domain from residues 116-136.

In some embodiments, a salinity tolerance and/or oxidative stress tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the salinity tolerance and/or oxidative stress tolerance-modulating activity of a truncated polypeptide. In some embodiments, a truncated polypeptide is a dominant negative polypeptide. SEQ ID NO: 138 sets forth the amino sequence of a salinity tolerance and/or oxidative stress tolerance-modulating polypeptide that is truncated at the 5' end relative to the naturally occurring polypeptide. Expression in a plant of such a truncated polypeptide confers a difference in the level of salinity tolerance and/or oxidative stress tolerance in a plant and/or plant tissue as compared to the corresponding level a control plant and/or tissue thereof that does not comprise the truncation.

B. Functional Homologs Identified by Reciprocal BLAST

In some embodiments, one or more functional homologs of a reference salinity tolerance and/or oxidative stress tolerance-modulating polypeptide defined by one or more of the pfam descriptions indicated above are suitable for use as salinity tolerance and/or oxidative stress tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a salinity tolerance and/or oxidative stress tolerance-modulating polypeptide, or by combining domains from the coding sequences for different naturally-occurring salinity tolerance and/or oxidative stress tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of salinity tolerance and/or oxidative stress tolerance-modulating polypeptides. Sequence analysis can involve BLAST, Reciprocal BLAST, or PSI-BLAST analysis of nonredundant databases using a salinity tolerance and/or oxidative stress tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a salinity tolerance and/or oxidative stress tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in salinity tolerance and/or oxidative stress tolerance-modulating polypeptides, e.g., conserved functional domains.

Conserved regions can be identified by locating a region within the primary amino acid sequence of a salinity tolerance and/or oxidative stress tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Amino acid sequences of functional homologs of the polypeptide set forth in SEQ ID NO: 86 are provided in FIG. 1 and in the Sequence Listing. Such functional homologs include (SEQ ID NO: 88, 90, 91, 93, 94, 96, 98, 100, 101, 102, 104, 106, and 107). In some cases, a functional homolog of SEQ ID NO: 86 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 86.

Figure 2:
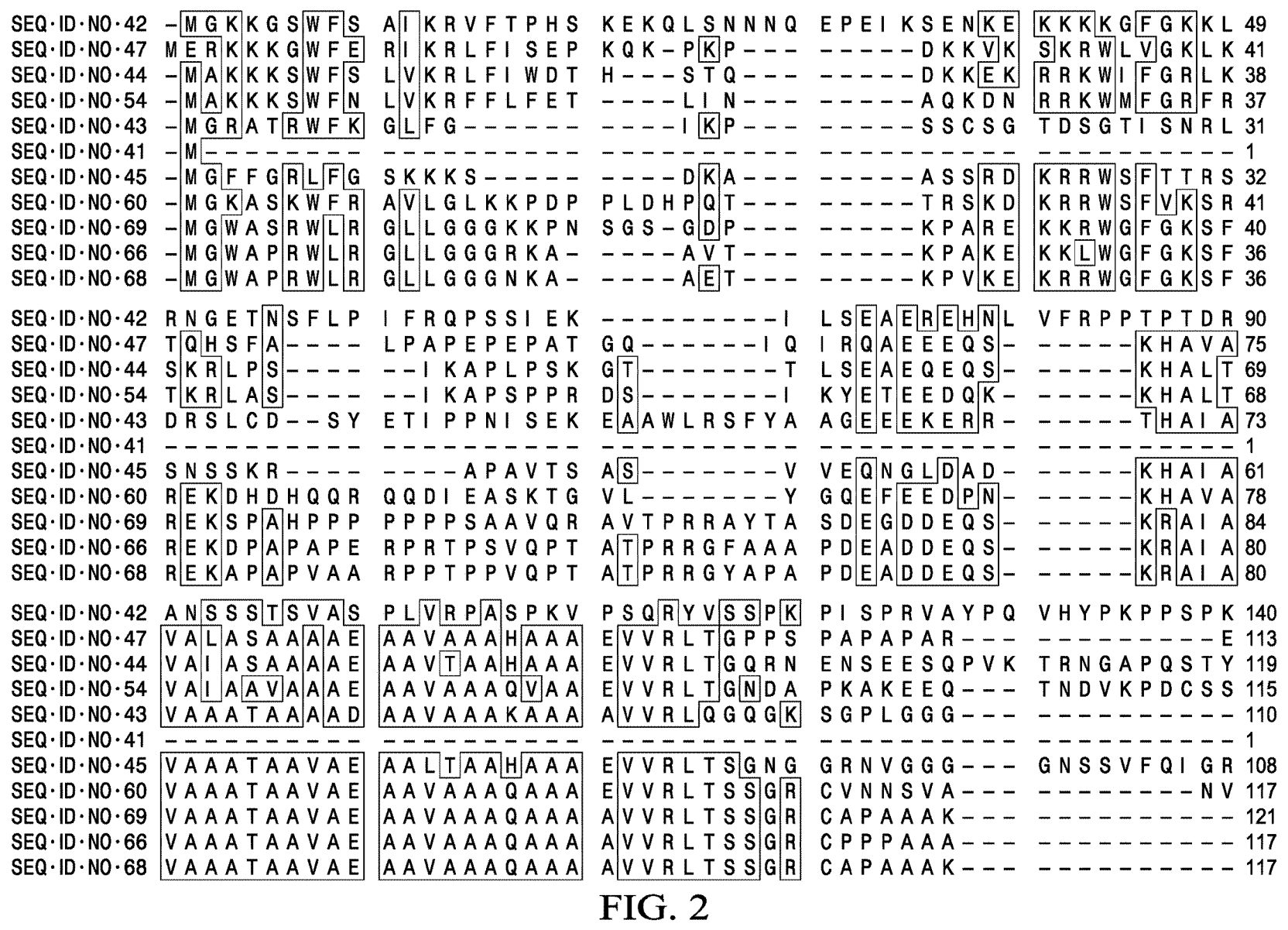
Figure 2:
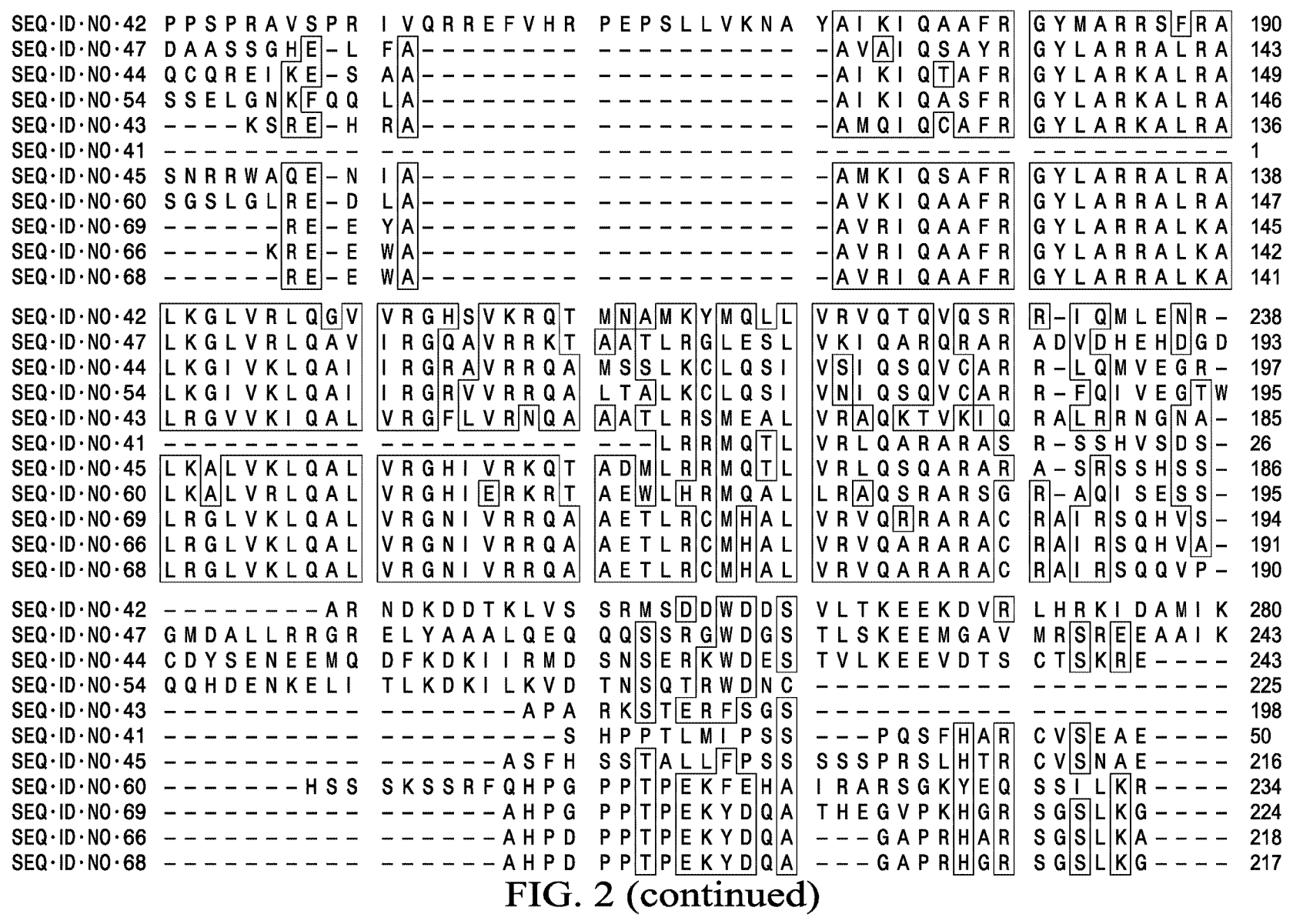
Figure 2:
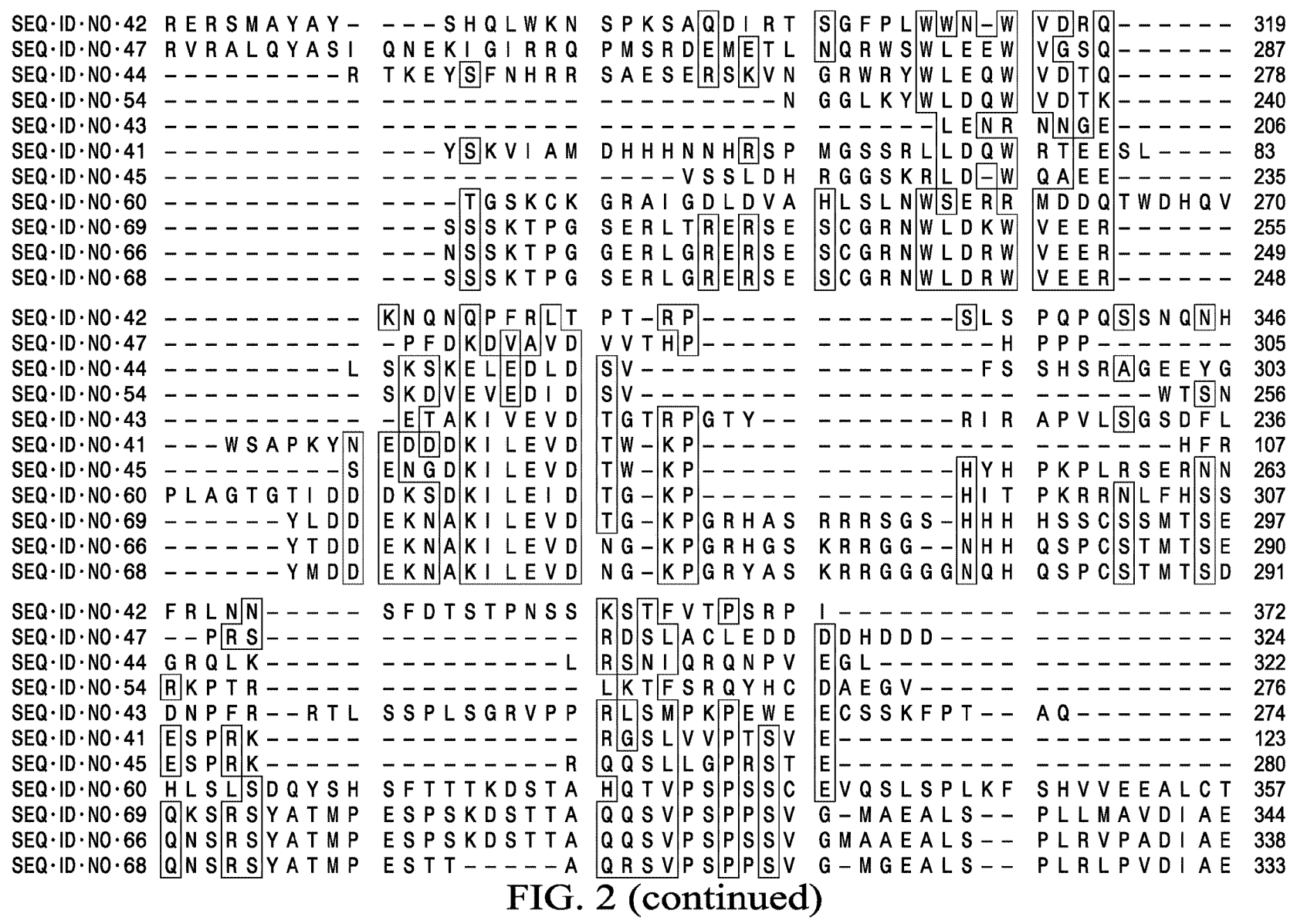
Figure 2:
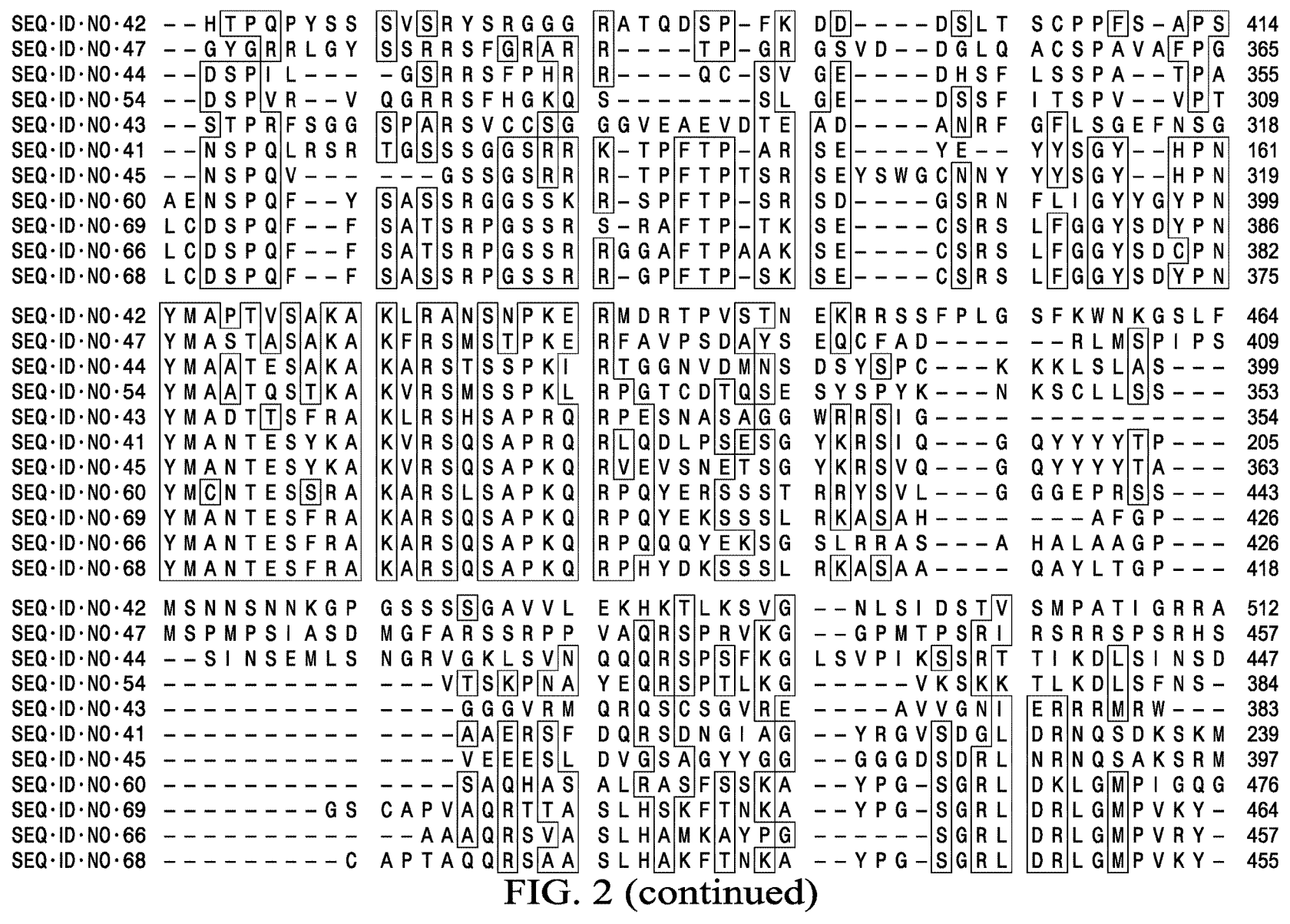

Amino acid sequences of functional homologs of the polypeptide set forth in SEQ ID NO: 41 are provided in FIG. 2. Such functional homologs include (SEQ ID NO: 42, 43, 44, 47, 49, 50, 52, 54, 56, 58, 60, 62, 63, 64, 66, 68, 69, 71, 73, 74, 76, 78, 80, 81, 83, and 84). In some cases, a functional homolog of SEQ ID NO: 41 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 41.

Figure 3:
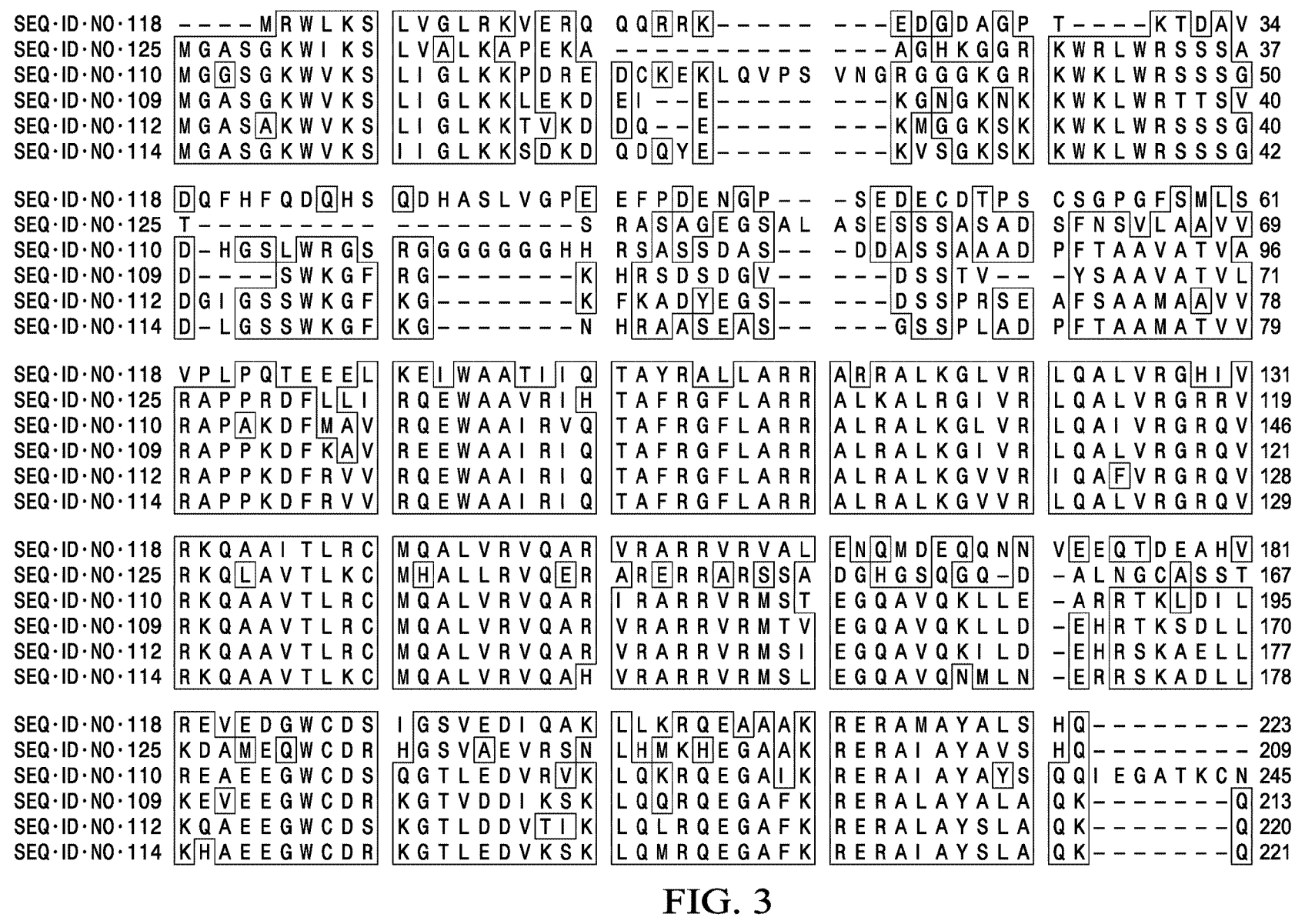
Figure 3:
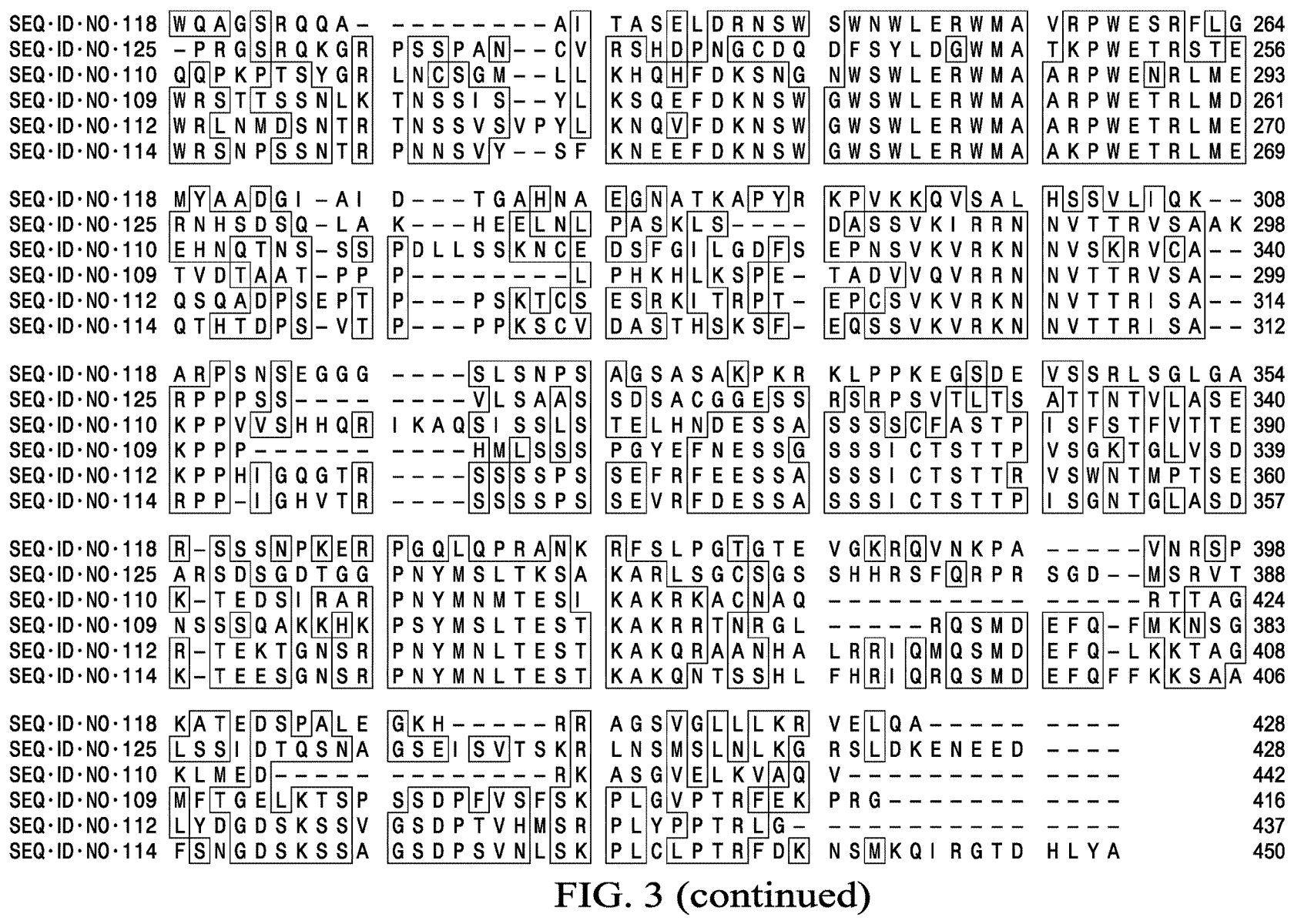

Amino acid sequences of functional homologs of the polypeptide set forth in SEQ ID NO: 109 are provided in FIG. 3. Such functional homologs include (SEQ ID NO: 110, 112, 114, 116, 118, 119, 121, 122, 123, 125, 126, 127, 128, 129, 130, 132, and 134). In some cases, a functional homolog of SEQ ID NO: 109 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 109.

Figure 4:
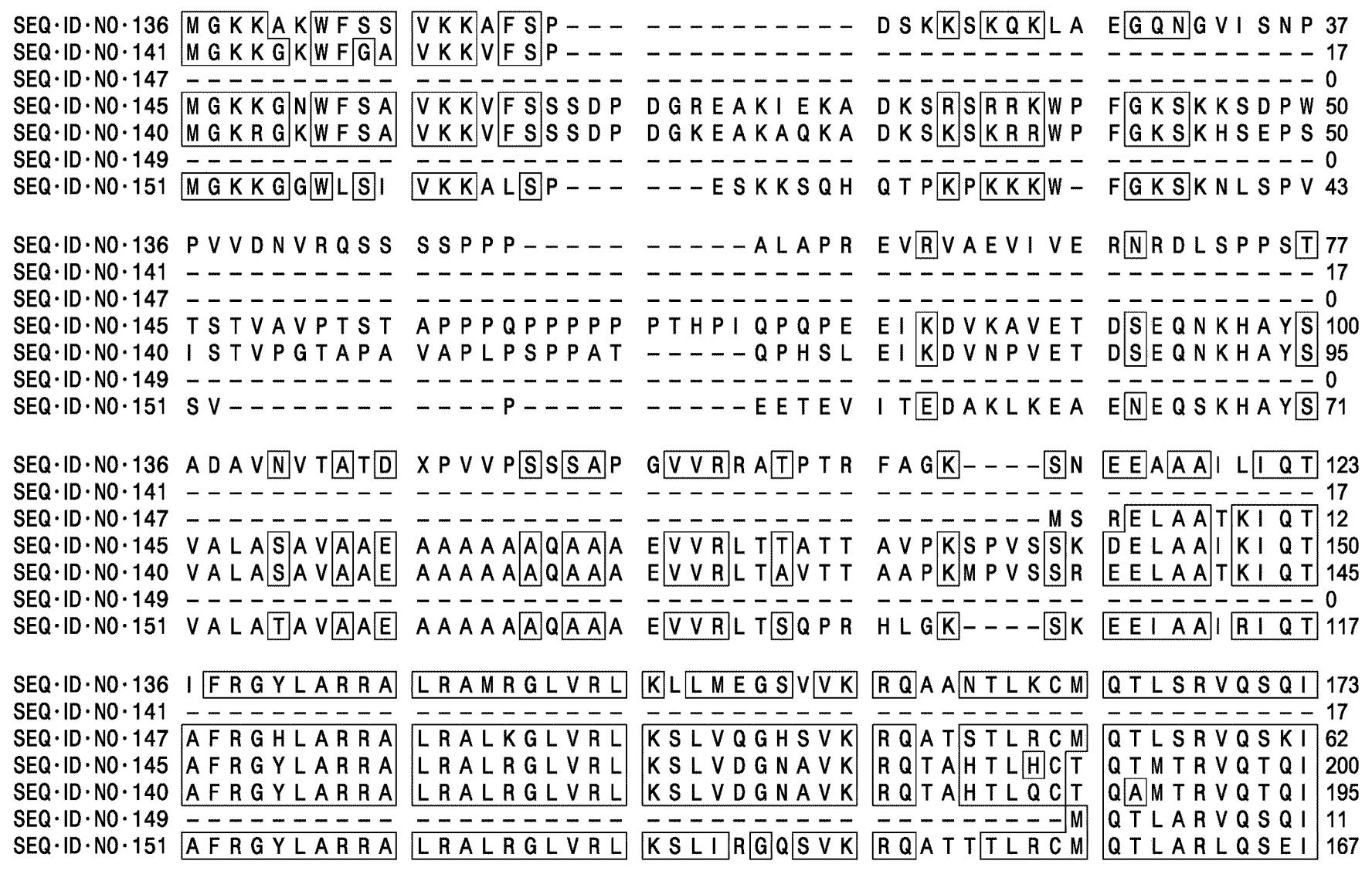
Figure 4:
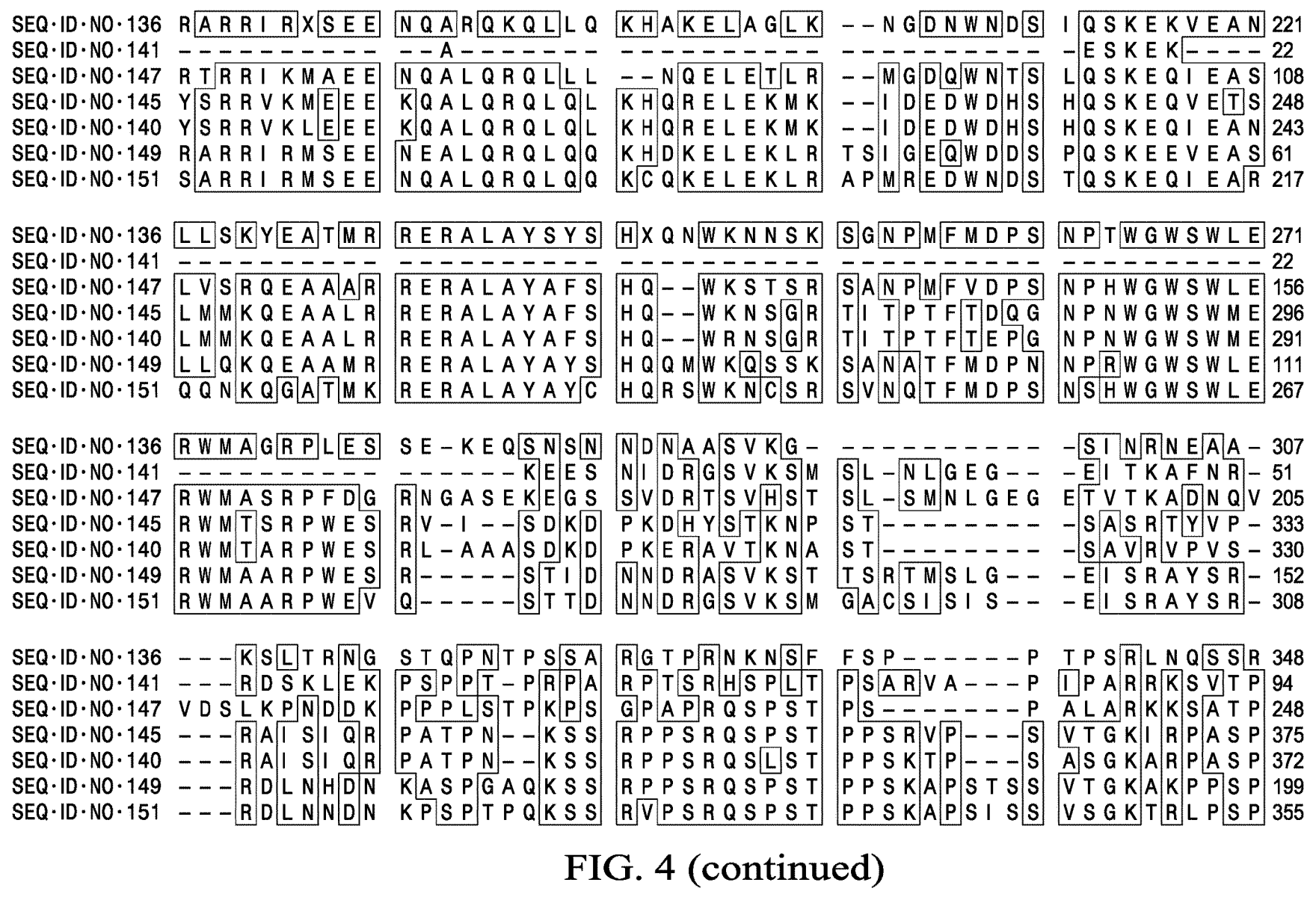

Amino acid sequences of functional homologs of the polypeptide set forth in SEQ ID NO:140 are provided in FIG. 4. Such functional homologs include (SEQ ID NO: 136, 138, 140, 141, 142, 143, 144, 145, 147, 149, 151, 153, 154, 156, 158, 160, 162, 163, 165, 166, 167, and 168). In some cases, a functional homolog of SEQ ID NO: 140 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 140.

Figure 5:
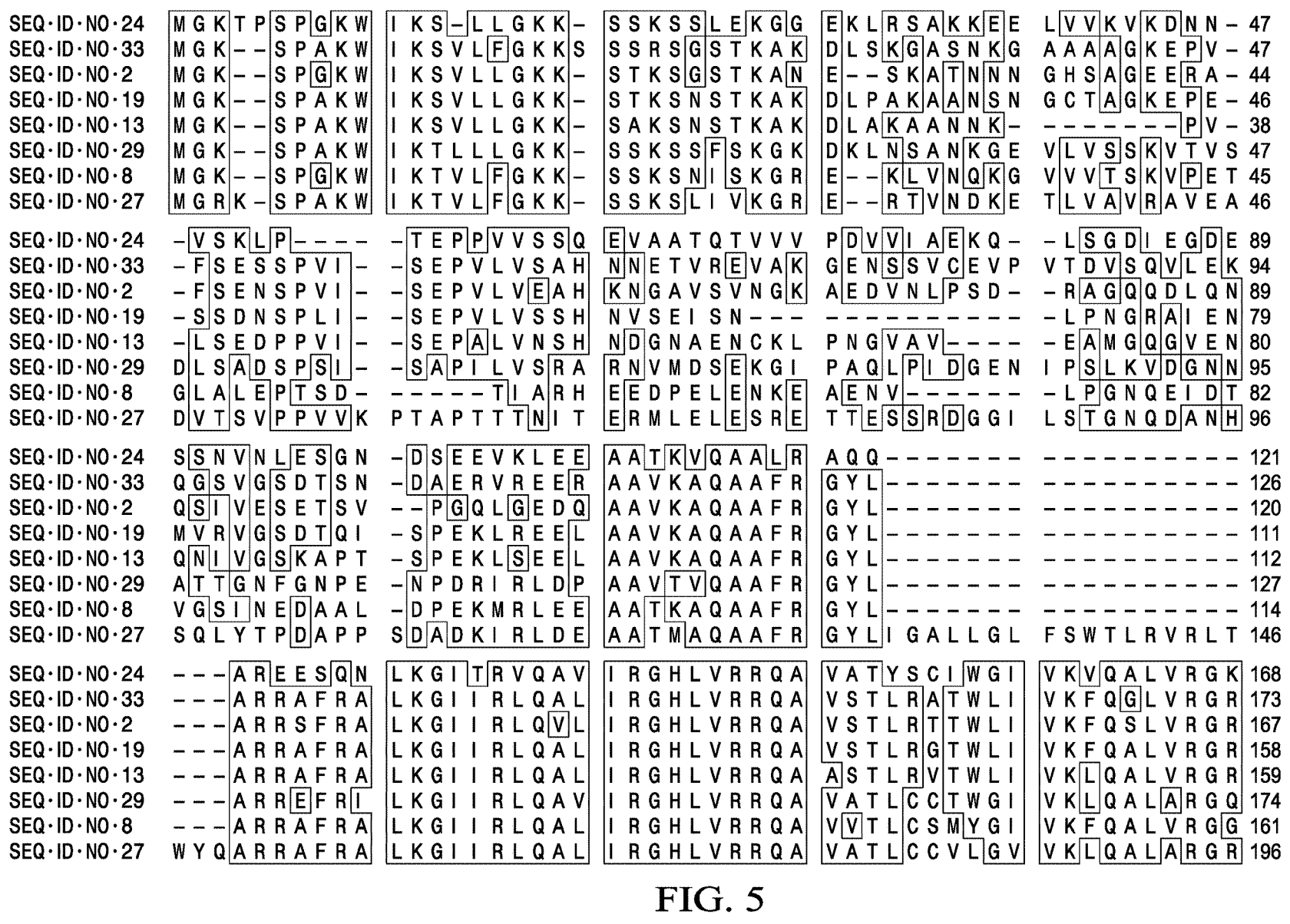
Figure 5:
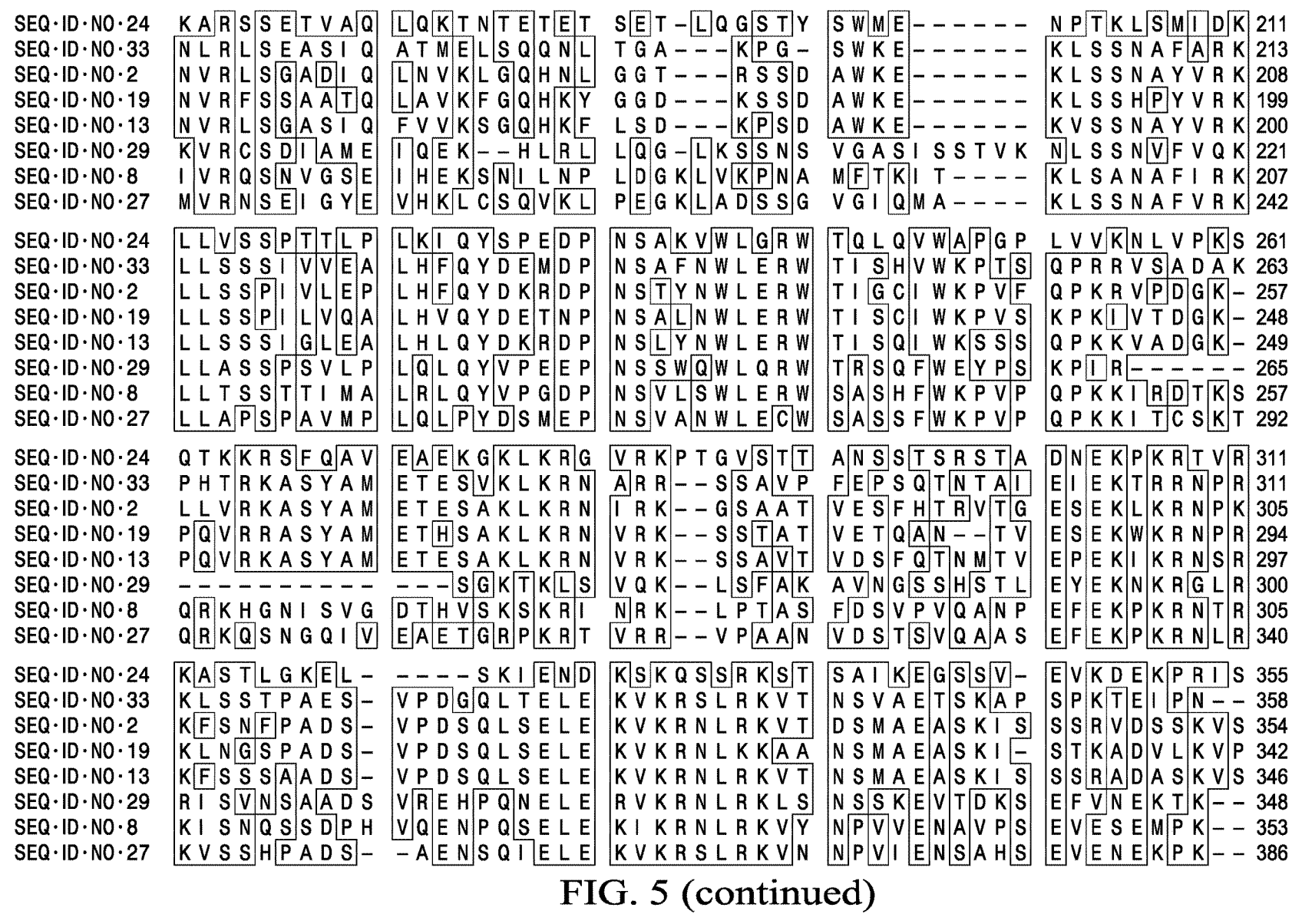
Figure 5:
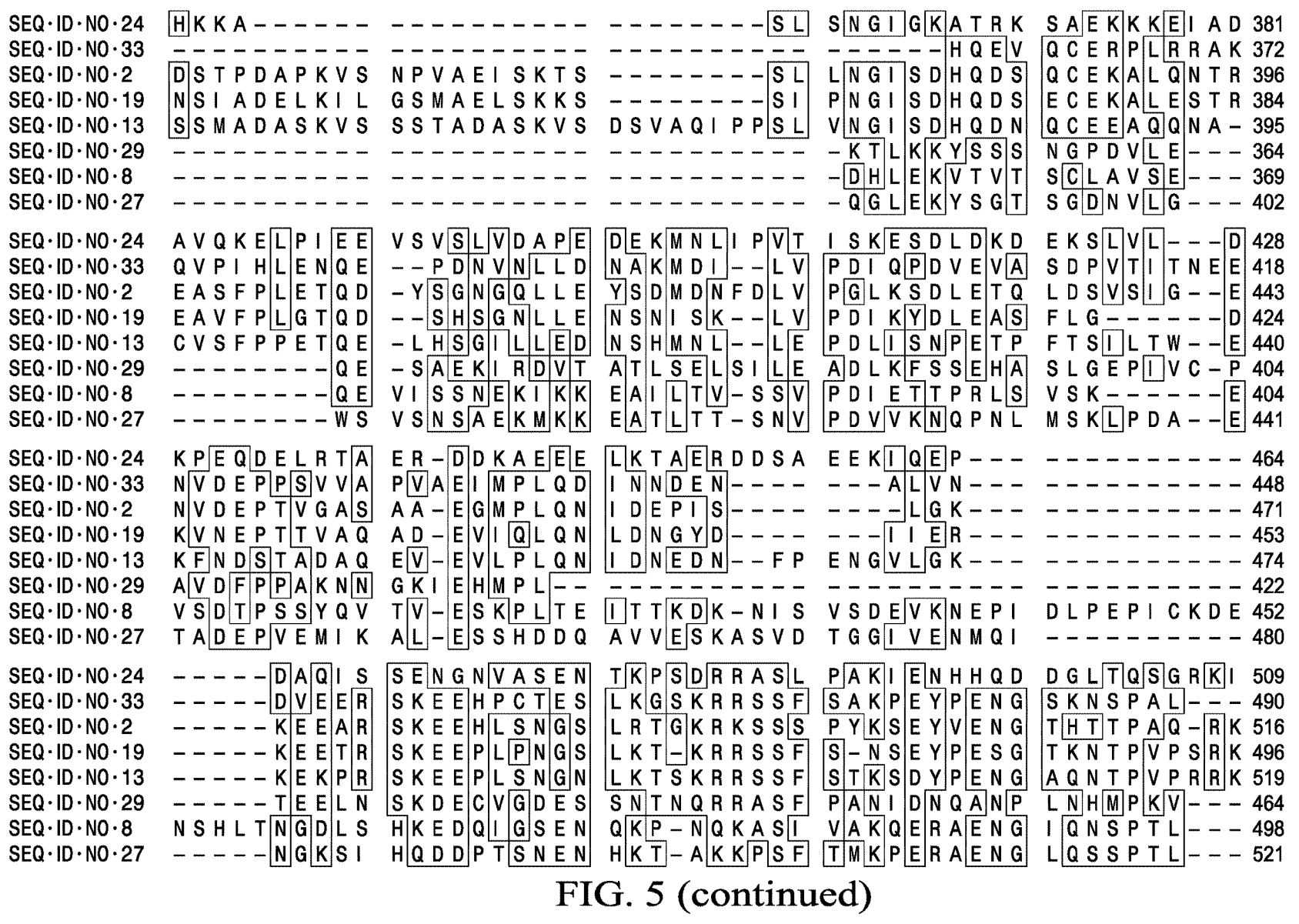

Amino acid sequences of functional homologs of the polypeptide set forth in SEQ ID NO: 2 are provided in FIG. 5. Such functional homologs include (SEQ ID NO: 2, 4, 6, 8, 9, 11, 13, 14, 15, 17, 19, 20, 22, 23, 24, 25, 27, 29, 30, 31, and 33). In some cases, a functional homolog of SEQ ID NO: 2 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2.

Amino acid sequences of functional homologs of the polypeptide set forth in SEQ ID NO: 35 are provided in FIG. 6. Such functional homologs include (SEQ ID NO: 35, 36, 37, 38, and 39). In some cases, a functional homolog of SEQ ID NO: 35 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 35.

The identification of conserved regions in a salinity tolerance and/or oxidative stress tolerance-modulating polypeptide facilitates production of variants of salinity tolerance and/or oxidative stress tolerance-modulating polypeptides. Variants of salinity tolerance and/or oxidative stress tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIGS. 1 thru 6. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologues Identified by HMM

In some embodiments, useful salinity and/or oxidative stress tolerance-modulating polypeptides include those that fit a Hidden Markov Model based on the polypeptides set forth in any one of FIGS. 1-6. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, —consistency REPS of 2; -ir, —iterative-refinement REPS of 100; -pre, —pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web. Hmmbuild outputs the model as a text file.

The HMM for a group of functional homologs can be used to determine the likelihood that a candidate salinity tolerance and/or oxidative stress tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

As those of skill in the art would appreciate, the HMM scores provided in the sequence listing are merely exemplary. Since multiple sequence alignment algorithms, such as ProbCons, can only generate near-optimal results, slight variations of the model can arise due to factors such as the order in which sequences are processed for alignment. Nevertheless, HMM score variability is minor, and so the HMM scores in the sequence listing are representative of models made with the respective sequences.

The salinity and/or oxidative stress-modulating polypeptides discussed below fit the indicated HMM with an HMM bit score greater than 20 (e.g., greater than 20, 30, 40, 50, 60, 80, 90, 100, 200, 300, 400, or 500). In some embodiments, the HMM bit score of a salinity and/or oxidative stress-modulating polypeptide discussed below is about 50%, 60%, 70%, 80%, 90%, or 95% of the HMM bit score of a functional homolog provided in the Sequence Listing. In some embodiments, a salinity and/or oxidative stress-modulating polypeptide discussed below fits the indicated HMM with an HMM bit score greater than 20, and has a domain indicative of an salinity and/or oxidative stress-modulating polypeptide. In some embodiments, a salinity and/or oxidative stress-modulating polypeptide discussed below fits the indicated HMM with an HMM bit score greater than 20, and has 85% or greater sequence identity (e.g., 75%, 80%, 85%, 90%, 95%, or 100% sequence identity) to an amino acid sequence shown in any one of FIGS. 1 thru 6 or to an amino acid sequence correlated in the Sequence Listing to a any one of FIGS. 1 thru 6.

In the Sequence Listing polypeptides are provided that have HMM bit scores greater than 400, 450, 500, 550, 600, 650, 700, 750, 800, 850, 900, 950, 1000, 1050, or 1100, when fitted to an HMM generated from the amino acid sequences set forth in FIG. 1. Such polypeptides include Ceres SEEDLINE ID no.ME08768, Ceres CLONE ID no.1943807, Ceres ANNOT ID no.1471392, Public GI ID no.6715635, Ceres CLONE ID no.910109, Public GI ID no.115474509, Ceres CLONE ID no.1780908, Ceres ANNOT ID no.1520883, Ceres CLONE ID no.148018, Public GI ID no.18378797, Public GI ID no.21553500, Ceres ANNOT ID no.1444522, Ceres ANNOT ID no.146751, and Public GI ID no.125559938 (SEQ ID NO: 86, 88, 90, 91, 93, 94, 96, 98, 100, 101, 102, 104, 106, and 107)

In the Sequence Listing polypeptides are provided that have HMM bit scores greater than 30, 50, 100, 150, 200, 250, 300, 350, 400, 450, 500, 550, 600, 650, 700, 750, 800, 850, 900, 950, or 1000 when fitted to an HMM generated from the amino acid sequences set forth in FIG. 2. Such polypeptides include Ceres SEEDLINE ID no.ME06748, Ceres SEEDLINE ID no.ME20711, Ceres SEEDLINE ID no.ME18973, Ceres SEEDLINE ID no.ME08732, Ceres SEEDLINE ID no.ME19657, Ceres CLONE ID no.835818, Ceres CLONE ID no.1796745, Public GI ID no.125543896, Ceres ANNOT ID no.1483984, Ceres CLONE ID no.1924654, Ceres ANNOT ID no.1468861, Ceres CLONE ID no.1641776, Ceres ANNOT ID no.1438750, Ceres ANNOT ID no.1447395, Public GI ID no.79482785, Public GI ID no.3292832, Ceres CLONE ID no.1559074, Ceres CLONE ID no.1726548, Public GI ID no.115459996, Ceres CLONE ID no.697034, Ceres CLONE ID no.353438, Public GI ID no.125593074, Ceres CLONE ID no.1920115, Ceres CLONE ID no.21821, Ceres CLONE ID no.560066, Public GI ID no.115453071, Ceres CLONE ID no.1968211, and Public GI ID no.116310011_(SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84).

In the Sequence Listing polypeptides are provided that have HMM bit scores greater than 120, 150, 200, 250, 300, 350, 400, 450, 500, 550, 600, 650, 700, 750, 800, 850, 900, 950, 1000, 1050, 1100, 1150, or 1200 when fitted to an HMM generated from the amino acid sequences set forth in FIG. 3. Such polypeptides include Ceres SEEDLINE ID no.ME19173, Public GI ID no.115435054, Ceres CLONE ID no.1847857, Ceres ANNOT ID no.1455219, Ceres CLONE ID no.352452, Ceres CLONE ID no.787908, Ceres LOCUS ID no.Os01m00929_AP002743, Ceres CLONE ID no.246398, Public GI ID no.125527441, Public GI ID no.125595056, Ceres CLONE ID no.236071, Public GI ID no.125524760, Public GI ID no.125569365, Public GI ID no.115439499, Public GI ID no.15225258, Public GI ID no.115465173, Ceres ANNOT ID no.1477059, and Ceres ANNOT ID no.1530547 (SEQ ID NO: 110, 112, 114, 116, 118, 119, 121, 122, 123, 125, 126, 127, 128, 129, 130, 132, and 134).

In the Sequence Listing polypeptides are provided that have HMM bit scores greater than 150, 200, 250, 300, 350, 400, 450, 500, 550, 600, 650, 700, 750, 800, 850, 900, 950, 1000, 1050, 1100, 1150, 1200, 1250, 1300, or 1350 when fitted to an HMM generated from the amino acid sequences set forth in FIG. 4. Such polypeptides include Ceres SEEDLINE ID no.ME24091, Ceres CLONE ID no.375578, Ceres CLONE ID no.375578, Ceres SEEDLINE ID no.ME10681, Ceres SEEDLINE ID no.ME03140, Ceres SEEDLINE ID no.ME24076, Ceres SEEDLINE ID no.ME24217, Public GI ID no.115440873, Ceres CLONE ID no.826796, Ceres ANNOT ID no.1465047, Ceres CLONE ID no.1919901, Ceres CLONE ID no.520008, Public GI ID no.7413581, Ceres CLONE ID no.228069, Ceres CLONE ID no.467508, Ceres CLONE ID no.1829581, Ceres CLONE ID no.229668, Public GI ID no.125550655, Ceres CLONE ID no.106263, Public GI ID no.15231175, Public GI ID no.145357576, and Public GI ID no.125528277 (SEQ ID NO: 136, 138, 140, 141, 142, 143, 144, 145, 147, 149, 151, 153, 154, 156, 158, 160, 162, 163, 165, 166, 167, and 168).

In the Sequence Listing polypeptides are provided that have HMM bit scores greater than 425, 450, 500, 550, 600, 650, 700, 750, 800, 850, 900, 950, 1000, 1050, 1100, 1150, 1200, 1250, 1300, 1350, 1400, 1450, 1500, or 1550, when fitted to an HMM generated from the amino acid sequences set forth in FIG. 5. Such polypeptides include Ceres CLONE ID no.1792354, Ceres CLONE ID no.1925477, Ceres ANNOT ID no.1521592, Ceres CLONE ID no.463594, Public GI ID no.22330633, Ceres CLONE ID no.345954, Ceres LOCUS ID no. Os01m05025_AP003288, GI ID no. 56784330, Public GI ID no.125527495, Public GI ID no.125553119, Ceres CLONE ID no.236431, Ceres CLONE ID no.908518, Public GI ID no.115465121, Ceres CLONE ID no.1791910, Public GI ID no.125595019, Public GI ID no.42568886, Public GI ID no.2947062, Ceres ANNOT ID no.1468228, Ceres CLONE ID no.1942388, Public GI ID no.12324824, Public GI ID no.5882749, and Ceres CLONE ID no.325403 (SEQ ID NO: 2, 4, 6, 8, 9, 11, 13, 14, 15, 17, 19, 20, 22, 23, 24, 25, 27, 29, 30, 31, and 33).

In the Sequence Listing polypeptides are provided that have HMM bit scores greater than 550, 600, 650, or 700 when fitted to an HMM generated from the amino acid sequences set forth in FIG. 6. Such polypeptides include Ceres GI ID no.56784328, Public GI ID no.56784330, Public GI ID no.125528718, Public GI ID no.125572975, and Public GI ID no.125528716 (SEQ ID NO: 35, 36, 37, 38, and 39).

D. Percent Identity

In some embodiments, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 4, 6, 8, 9, 11, 13, 14, 17, 19, 20, 22, 23, 24, 25, 27, 29, 30, 31, 33, 35, 36, 37, 38, 39, 41, 42, 43, 44, 45, 47, 49, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. Polypeptides having such a percent sequence identity often have a domain indicative of a salinity and/or oxidative stress-modulating polypeptide and/or have an HMM bit score that is greater than 20, as discussed above. Examples of amino acid sequences of salinity and/or oxidative stress tolerance-modulating polypeptides having at least 85% sequence identity to one of the amino acid sequences set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 are provided in FIGS. 1-6.

"Percent sequence identity" refers to the degree of sequence identity between any given reference sequence, e.g., SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140, and a candidate salinity and/or oxidative stress-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to one or more of the amino acid sequence set forth in SEQ ID NO: 86 Amino acid sequences of polypeptides having high sequence identity to the polypeptide set forth in SEQ ID NO: 86 are provided in the Sequence Listing. Such polypeptides include SEQ ID NO: 88, 90, 91, 93, 94, 96, 98, 100, 101, 102, 104, 106, and 107.

In some cases, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 41. Amino acid sequences of polypeptides having high sequence identity to the polypeptide set forth in SEQ ID NO: 41 are provided in the Sequence Listing. Such polypeptides include SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 109. Amino acid sequences of polypeptides having high sequence identity to the polypeptide set forth in SEQ ID NO: 109 are provided in the Sequence Listing. Such polypeptides include SEQ ID NO: 110, 112, 114, 116, 118, 119, 121, 122, 123, 125, 126, 127, 128, 129, 130, 132, and 134.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 140. Amino acid sequences of polypeptides having high sequence identity to the polypeptide set forth in SEQ ID NO: 140 are provided in the Sequence Listing. Such polypeptides include SEQ ID NO: 136, 138, 141, 142, 143, 144, 145, 147, 149, 151, 153, 154, 156, 158, 160, 162, 163, 165, 166, 167, and 168.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. Amino acid sequences of polypeptides having high sequence identity to the polypeptide set forth in SEQ ID NO: 2 are provided in the Sequence Listing. Such polypeptides include SEQ ID NO: 4, 6, 8, 9, 11, 13, 14, 15, 17, 19, 20, 22, 23, 24, 25, 27, 29, 30, 31, and 33.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 35. Amino acid sequences of polypeptides having high sequence identity to the polypeptide set forth in SEQ ID NO: 35 are provided in the Sequence Listing. Such polypeptides include SEQ ID NO: 36, 37, 38, and 39.

E. Other Sequences

It should be appreciated that a salinity and/or oxidative stress tolerance-modulating polypeptide can include additional amino acids that are not involved in salinity and/or oxidative stress tolerance modulation, and thus such a polypeptide can be longer than would otherwise be the case. For example, a salinity and/or oxidative stress-tolerance modulating polypeptide can include a purification tag, a chloroplast transit peptide, an amyloplast transit peptide, a mitochondrial transit peptide, or a leader sequence added to the amino or carboxy terminus. In some embodiments, a salinity and/or oxidative stress-tolerance modulating polypeptide includes an amino acid sequence that functions as a reporter, e.g., a green fluorescent protein or yellow fluorescent protein.

III. Nucleic Acids

Nucleic acids described herein include nucleic acids that are effective to modulate salinity and/or oxidative stress tolerance levels when transcribed in a plant or plant cell. Such nucleic acids include, without limitation, those that encode a salinity and/or oxidative stress tolerance-modulating polypeptide and those that can be used to inhibit expression of a salinity tolerance and/or oxidative stress tolerance-modulating polypeptide via a nucleic acid based method.

A. Nucleic Acids Encoding Salinity Tolerance and/or Oxidative Stress Tolerance-Modulating Polypeptides Nucleic acids encoding salinity tolerance and/or oxidative stress tolerance-modulating polypeptides are described herein. Such nucleic acids include SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164, as described in more detail below.

A salinity tolerance and/or oxidative stress tolerance-modulating nucleic acid can comprise the nucleotide sequence set forth in SEQ ID NO: 85. Alternatively, a salinity tolerance and/or oxidative stress tolerance-modulating nucleic acid can be a variant of the nucleic acid having the nucleotide sequence set forth in SEQ ID NO: 85. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 85, 87, 89, 92, 95, 97, 99, 103, and 105.

A salinity tolerance and/or oxidative stress tolerance-modulating nucleic acid can comprise the nucleotide sequence set forth in SEQ ID NO: 40. Alternatively, a salinity tolerance and/or oxidative stress tolerance-modulating nucleic acid can be a variant of the nucleic acid having the nucleotide sequence set forth in SEQ ID NO: 40. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 40, 46, 48, 51, 53, 55, 57, 59, 61, 65, 67, 70, 72, 75, 77, 79, and 82.

A salinity tolerance and/or oxidative stress tolerance-modulating nucleic acid can comprise the nucleotide sequence set forth in SEQ ID NO: 108. Alternatively, a salinity tolerance and/or oxidative stress tolerance-modulating nucleic acid can be a variant of the nucleic acid having the nucleotide sequence set forth in SEQ ID NO: 108. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 108, 111, 113, 115, 117, 120, 124, 131, and 133.

A salinity tolerance and/or oxidative stress tolerance-modulating nucleic acid can comprise the nucleotide sequence set forth in SEQ ID NO: 139. Alternatively, a salinity tolerance and/or oxidative stress tolerance-modulating nucleic acid can be a variant of the nucleic acid having the nucleotide sequence set forth in SEQ ID NO: 139. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 135, 137, 139, 146, 148, 150, 152, 155, 157, 159, 161, and 164.

A salinity tolerance and/or oxidative stress tolerance-modulating nucleic acid can comprise the nucleotide sequence set forth in SEQ ID NO: 1. Alternatively, a salinity tolerance and/or oxidative stress tolerance-modulating nucleic acid can be a variant of the nucleic acid having the nucleotide sequence set forth in SEQ ID NO: 1. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1, 3, 5, 7, 12, 16, 18, 21, 26, 28, and 32.

A salinity tolerance and/or oxidative stress tolerance-modulating nucleic acid can comprise the nucleotide sequence set forth in SEQ ID NO: 34. Alternatively, a salinity tolerance and/or oxidative stress tolerance-modulating nucleic acid can be a variant of the nucleic acid having the nucleotide sequence set forth in SEQ ID NO: 34. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:34.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Salinity Tolerance and/or Oxidative Stress Tolerance-Modulating Polypeptide A nucleic acid encoding one of the salinity tolerance and/or oxidative stress tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular salinity tolerance and/or oxidative stress tolerance-modulating polypeptide; i.e., for many amino acids, there is more than one nucleotide triplet that serves as the codon for the amino acid. Thus, codons in the coding sequence for a given salinity tolerance and/or oxidative stress tolerance-modulating polypeptide can be modified such that optimal expression in a particular plant species is obtained, using appropriate codon bias tables for that species.

In some cases, expression of a salinity tolerance and/or oxidative stress tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Salinity Tolerance and/or Oxidative Stress Tolerance-Modulating Polypeptide Polynucleotides and recombinant constructs described herein can be used to inhibit expression of a salinity tolerance and/or oxidative stress tolerance-modulating polypeptide in a plant species of interest. See, e.g., Matzke and Birchler, Nature Reviews Genetics 6:24-35 (2005); Akashi et al., Nature Reviews Mol. Cell Biology 6:413-422 (2005); Mittal, Nature Reviews Genetics 5:355-365 (2004); Dorsett and Tuschl, Nature Reviews Drug Discovery 3: 318-329 (2004); and Nature Reviews RNA interference collection, Oct. 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., Proc. Natl. Acad. Sci. USA, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, NJ. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a salinity tolerance and/or oxidative stress tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the salinity tolerance and/or oxidative stress tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a salinity tolerance and/or oxidative stress tolerance-modulating polypeptide, and the other strand of the stem portion of the double stranded RNA comprises a sequence that is similar or identical to the sequence that is complementary to the 3' or 5' untranslated region, respectively, of the mRNA encoding the salinity tolerance and/or oxidative stress tolerance-modulating polypeptide. In other embodiments, one strand of the stem portion of a double stranded RNA comprises a sequence that is similar or identical to the sequence of an intron in the pre-mRNA encoding a salinity tolerance and/or oxidative stress tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a salinity tolerance and/or oxidative stress tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a salinity tolerance and/or oxidative stress tolerance-modulating polypeptide. In some embodiments, the sense or antisense sequence is identical or complementary to a sequence of the regulatory region that drives transcription of the gene encoding a salinity tolerance and/or oxidative stress tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a salinity tolerance and/or oxidative stress tolerance-modulating polypeptide described herein. The sense sequence complementary to the antisense sequence can be a sequence present within the mRNA of the salinity tolerance and/or oxidative stress tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotries ter backbone.

C. Constructs/Vectors

Recombinant constructs provided herein can be used to transform plants or plant cells in order to modulate salinity tolerance and/or oxidative stress tolerance levels. A recombinant nucleic acid construct can comprise a nucleic acid encoding a salinity tolerance and/or oxidative stress tolerance-modulating polypeptide as described herein, operably linked to a regulatory region suitable for expressing the salinity tolerance and/or oxidative stress tolerance-modulating polypeptide in the plant or cell. Thus, a nucleic acid can comprise a coding sequence that encodes any of the salinity tolerance and/or oxidative stress tolerance-modulating polypeptides as set forth in SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164. Examples of nucleic acids encoding salinity tolerance and/or oxidative stress tolerance-modulating polypeptides are set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. The salinity tolerance and/or oxidative stress tolerance-modulating polypeptide encoded by a recombinant nucleic acid can be a native salinity tolerance and/or oxidative stress tolerance-modulating polypeptide, or can be heterologous to the cell. In some cases, the recombinant construct contains a nucleic acid that inhibits expression of a salinity tolerance and/or oxidative stress tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner Some suitable promoters initiate transcription only, or predominantly, in certain cell types. The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner Some suitable regulatory regions initiate transcription only, or predominantly, in certain cell types. Methods for identifying and characterizing regulatory regions in plant genomic DNA are known, including, for example, those described in the following references: Jordano et al., *Plant Cell,* 1:855-866 (1989); Bustos et al., *Plant Cell,* 1:839-854 (1989); Green et al., *EMBO J.,* 7:4035-4044 (1988); Meier et al., *Plant Cell,* 3:309-316 (1991); and Zhang et al., *Plant Physiology,* 110:1069-1079 (1996).

Examples of various classes of regulatory regions are described below. Some of the regulatory regions indicated below as well as additional regulatory regions are described in more detail in U.S. Patent Application Ser. Nos. 60/505, 689; 60/518,075; 60/544,771; 60/558,869; 60/583,691; 60/619,181; 60/637,140; 60/757,544; 60/776,307; 10/957, 569; 11/058,689; 11/172,703; 11/208,308; 11/274,890; 60/583,609; 60/612,891; 11/097,589; 11/233,726; 11/408, 791; 11/414,142; 10/950,321; 11/360,017; PCT/US05/ 011105; PCT/US05/23639; PCT/US05/034308; PCT/US05/ 034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/ US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/ 62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens,* the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP des aturase promoter (Slocombe et al., *Plant Physiol.,* 104(4): 167-176 (1994)), the soybean α' subunit of β-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOs-FIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (Plant Cell Rep (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb 1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)), and the rice tungro bacilliform virus (RTBV) promoter (Dai et al., Proc. Natl. Acad. Sci. USA, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a salt and/or oxidative stress tolerance modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant having the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous salinity tolerance and/or oxidative stress tolerance-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a salinity tolerance and/or oxidative stress tolerance-modulating polypeptide or nucleic acid. Physical and biochemical methods can be used to identify expression levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of salinity tolerance and/or oxidative stress tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a salinity tolerance and/or oxidative stress tolerance level relative to a control plant that lacks the transgene. Selected or screened transgenic plants have an altered phenotype as compared to a corresponding control plant, as described in the "Transgenic Plant Phenotypes" section herein.

A population of transgenic plants can be screened and/or selected for those members of the population that have a trait or phenotype conferred by expression of the transgene. For example, a population of progeny of a single transformation event can be screened for those plants having a desired level of expression of a saline and/or oxidative stress tolerance-modulating polypeptide and/or nucleic acid. Physical and biochemical methods can be used to identify expression levels. These include Southern analysis or PCR amplification for detection of a polynucleotide; Northern blots, RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of saline and/or oxidative stress tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a saline and/or oxidative stress tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis, and Zea.

Suitable species include Panicum spp., Sorghum spp., Miscanthus spp., Saccharum spp., Erianthus spp., Populus spp., Andropogon gerardii (big bluestem), Pennisetum purpureum (elephant grass), Phalaris arundinacea (reed canarygrass), Cynodon dactylon (bermudagrass), Festuca arundinacea (tall fescue), Spartina pectinata (prairie cordgrass), Medicago sativa (alfalfa), Arundo donax (giant reed), Secale cereale (rye), Salix spp. (willow), Eucalyptus spp. (eucalyptus), Triticosecale (triticum—wheat X rye) and bamboo.

Suitable species also include Helianthus annuus (sunflower), Carthamus tinctorius (safflower), Jatropha curcas (jatropha), Ricinus communis (castor), Elaeis guineensis (palm), Linum usitatissimum (flax), and Brassica juncea.

Suitable species also include Beta vulgaris (sugarbeet), and Manihot esculenta (cassava).

Suitable species also include Lycopersicon esculentum (tomato), Lactuca sativa (lettuce), Musa paradisiaca (banana), Solanum tuberosum (potato), Brassica oleracea (broccoli, cauliflower, brusselsprouts), Camellia sinensis (tea), Fragaria ananassa (strawberry), Theobroma cacao (cocoa), Coffea arabica (coffee), Vitis vinifera (grape), Ananas comosus (pineapple), Capsicum annum (hot & sweet pepper), Allium cepa (onion), Cucumis melo (melon), Cucumis sativus (cucumber), Cucurbita maxima (squash), Cucurbita moschata (squash), Spinacea oleracea (spinach), Citrullus lanatus (watermelon), Abelmoschus esculentus (okra), and Solanum melongena (eggplant).

Suitable species also include Papaver somniferum (opium poppy), Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica., Digitalis lanata, Digitalis purpurea, Dioscorea spp., Andrographis paniculata, Atropa belladonna, Datura stomonium, Berberis spp., Cephalotaxus spp., Ephedra sinica, Ephedra spp., Erythroxylum coca, Galanthus wornorii, Scopolia spp., Lycopodium serratum (=Huperzia serrata), Lycopodium spp., Rauwolfia serpentina, Rauwolfia spp., Sanguinaria canadensis, Hyoscyamus spp., Calendula officinalis, Chrysanthemum parthenium, Coleus forskohlii, and Tanacetum parthenium.

Suitable species also include Parthenium argentatum (guayule), Hevea spp. (rubber), Mentha spicata (mint), Mentha piperita (mint), Bixa orellana, and Alstroemeria spp.

Suitable species also include Rosa spp. (rose), Dianthus caryophyllus (carnation), Petunia spp. (petunia) and Poinsettia pulcherrima (poinsettia).

Suitable species also include Nicotiana tabacum (tobacco), Lupinus albus (lupin), Uniola paniculata (oats), bentgrass (Agrostis spp.), Populus tremuloides (aspen), Pinus spp. (pine), Abies spp. (fir), Acer spp. (maple, Hordeum vulgare (barley), Poa pratensis (bluegrass), Lolium spp. (ryegrass) and Phleum pratense (timothy).

Thus, the methods and compositions can be used over a broad range of plant species, including species from the dicot genera Brassica, Carthamus, Glycine, Gossypium, Helianthus, Jatropha, Parthenium, Populus, and Ricinus; and the monocot genera Elaeis, Festuca, Hordeum, Lolium, Oryza, Panicum, Pennisetum, Phleum, Poa, Saccharum, Secale, Sorghum, Triticosecale, Triticum, and Zea. In some embodiments, a plant is a member of the species Panicum virgatum (switchgrass), Sorghum bicolor (sorghum, sudangrass), Miscanthus giganteus (miscanthus), Saccharum sp. (energycane), Populus balsamifera (poplar), Zea mays (corn), Glycine max (soybean), Brassica napus (canola), Triticum aestivum (wheat), Gossypium hirsutum (cotton), Oryza sativa (rice), Helianthus annuus (sunflower), Medicago sativa (alfalfa), Beta vulgaris (sugarbeet), or Pennisetum glaucum (pearl millet).

In certain embodiments, the polynucleotides and vectors described herein can be used to transform a number of monocotyledonous and dicotyledonous plants and plant cell systems, wherein such plants are hybrids of different species or varieties of a species (e.g., Saccharum sp. X Miscanthus sp.)

D. Transgenic Plant Phenotypes

In some embodiments, a plant in which expression of a salinity and/or oxidative stress modulating polypeptide is modulated can have increased levels of tolerance to salinity and/or oxidative stress. For example, a salinity and/or oxidative stress-modulating polypeptide described herein can be expressed in a transgenic plant, resulting in increased levels of tolerance to salinity and/or oxidative stress. The salinity and/or oxidative stress tolerance levels can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to those levels in a corresponding control plant that does not express the transgene.

The nucleic acid molecules and polypeptides of the present invention are of interest because when the nucleic acid molecules are mis-expressed (i.e., when expressed at a non-natural location or in an increased or decreased amount relative to wild-type) they produce plants that exhibit improved salt tolerance and/or oxidation tolerance as compared to wild-type plants, as evidenced in part by the results of various experiments disclosed below. In particular, plants transformed with the nucleic acid molecules and polypeptides of the present invention can have any of a number of modified characteristics as compared to wild-type plants. Examples of modified characteristics include photosynthetic efficiency, seedling area, and biomass as it may be measured by plant height, leaf or rosette area, or dry mass. The modified characteristics may be observed and measured at different plant developmental stages, e.g. seed, seedling, bolting, senescense, etc. Often, salt or oxidative tolerance can be expressed as ratios or combinations of measurements, such as salt growth index values, or salicylic acid growth index values. For example, plants transformed with the sequences of the present invention can exhibit increases in SGI, seedling area and/or SAGI values of at least 5%, at least 10%, at least 25%, at least 50%, at least 75%, at least 100%, at least 200%, at least 300%, at least 400%, or even at least 500%. These traits can be used to exploit or maximize plant products. For example, the nucleic acid molecules and polypeptides of the present invention are used to increase the expression of genes that cause the plant to have improved biomass, growth rate and/or seedling vigor in saline and/or oxidative conditions, in comparison to wild type plants under the same conditions.

Because the disclosed sequences and methods increase vegetative growth and growth rate in saline and/or oxidative conditions, the disclosed methods can be used to enhance plant growth in plants grown in saline and/or oxidative conditions. For example, plants of the present invention show, under saline and/or oxidative conditions, increased photosynthetic efficiency and increased seedling area as compared to a plant of the same species that is not genetically modified for substantial vegetative growth. Examples of increases in biomass production include increases of at least 5%, at least 20%, or even at least 50%, when compared to an amount of biomass production by a wild-type plant of the same species under identical conditions.

Typically, a difference in the amount of tolerance to salinity and/or oxidative stress in a transgenic plant or cell relative to a control plant or cell is considered statistically significant at $p<0.05$ with an appropriate parametric or non-parametric statistic, e.g., Chi-square test, Student's t-test, Mann-Whitney test, or F-test. In some embodiments, a difference in the amount of tolerance to salinity and/or oxidative stress is statistically significant at $p<p<0.005$, or $p<0.001$.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. Plant Breeding

Genetic polymorphisms are discrete allelic sequence differences in a population. Typically, an allele that is present at 1% or greater is considered to be a genetic polymorphism. The discovery that polypeptides disclosed herein can modulate salinity tolerance and/or oxidative stress tolerance content is useful in plant breeding, because genetic polymorphisms exhibiting a degree of linkage with loci for such polypeptides are more likely to be correlated with variation in a salinity tolerance and/or oxidative stress tolerance trait. For example, genetic polymorphisms linked to the loci for such polypeptides are more likely to be useful in marker-assisted breeding programs to create lines having a desired modulation in the salinity tolerance and/or oxidative stress tolerance traits.

Thus, one aspect of the invention includes methods of identifying whether one or more genetic polymorphisms are associated with variation in a salinity tolerance and/or oxidative stress tolerance trait. Such methods involve determining whether genetic polymorphisms in a given population exhibit linkage with the locus for one of the polypeptides depicted in FIGS. 1 thru 6 and/or a functional homolog thereof, such as, but not limited to, those in the Sequence Listing. The correlation is measured between variation in the salinity tolerance and/or oxidative stress tolerance traits in plants of the population and the presence of the genetic polymorphism(s) in plants of the population, thereby identifying whether or not the genetic polymorphism(s) are associated with variation for the traits. If the presence of a particular allele is statistically significantly correlated with a desired modulation in the salinity tolerance and/or oxidative stress tolerance traits, the allele is associated with variation for one or both of the traits and is useful as a marker for one or more of the traits. If, on the other hand, the presence of a particular allele is not significantly correlated with the desired modulation, the allele is not associated with variation for one or more of the traits and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Patent Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol. 82, "*Arabidopsis* Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), The Maize Handbook, c. 1994 by Springer-Verlag New York, NY, USA; Berlin Germany; Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the salinity tolerance and/or oxidative stress tolerance trait(s). Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, other biofuel molecules, and/or sugar-derived co-products per kilogram of plant material, relative to control plants. By providing higher yields at an equivalent or even decreased cost of production relative to controls, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

Enhanced salt and/or oxidative stress tolerance gives the opportunity to grow crops in saline or oxidative stress conditions without stunted growth and diminished yields due to salt-induced ion imbalance, disruption of water homeostasis, inhibition of metabolism, damage to membranes, and/or cell death. The ability to grow plants in saline or oxidative stress conditions would result in an overall expansion of arable land and increased output of land currently marginally productive due to elevated salinity or oxidative stress conditions.

Seed or seedling vigor is an important characteristic that can greatly influence successful growth of a plant, such as crop plants. Adverse environmental conditions, such as saline and/or oxidative conditions, can affect a plant growth cycle, germination of seeds and seedling vigor (i.e. vitality and strength under such conditions can differentiate between successful and failed plant growth). Seedling vigor has often been defined to comprise the seed properties that determine "the potential for rapid, uniform emergence and development of normal seedlings under a wide range of field conditions". Hence, it would be advantageous to develop plant seeds with increased vigor, particularly in elevated salinity and/or in oxidative stress conditions.

For example, increased seedling vigor would be advantageous for cereal plants such as rice, maize, wheat, etc. production. For these crops, germination and growth can often be slowed or stopped by salination and/or oxidation. Genes associated with increased seed vigor under saline and/or oxidative stress conditions have therefore been sought for producing improved plant varieties. (Walia et al. (2005) *Plant Physiology* 139:822-835).

The invention will be further described in the following examples, which do not limit the scope of the invention described in the claims.

VII. EXAMPLES

Example 1: *Agrobacterium*-Mediated Transformation of *Arabidopsis*

Host Plants and Transgenes: Wild-type *Arabidopsis thaliana* Wassilewskija (WS) plants were independently transformed with Ti plasmids containing clones encoding polypeptides at SEQ ID NOs: 43, 44, 45, 86, 136, 138, 140, 141, 142, 143, 144, and amino acid coordinates 1 to 135 of SEQ ID NO: 140. Examples include Ceres CLONE ID no.1792354, Ceres SEEDLINE ID no.ME06748, Ceres SEEDLINE ID no.ME08768, Ceres SEEDLINE ID no.ME19173, and Ceres CLONE ID no.375578. Unless otherwise indicated, each Ceres Clone and/or Seedline derived from a Clone is in the sense orientation relative to either the 35S promoter in a Ti plasmid. A Ti plasmid vector useful for these constructs, CRS 338, contains the Ceres-constructed, plant selectable marker gene phosphinothricin acetyltransferase (PAT), which confers herbicide resistance to transformed plants.

Preparation of Soil Mixture: 24 L Sunshine Mix #5 soil (Sun Gro Horticulture, Ltd., Bellevue, WA) is mixed with 16 L Therm-O-Rock vermiculite (Therm-O-Rock West, Inc., Chandler, AZ) in a cement mixer to make a 60:40 soil mixture. To the soil mixture is added 2 Tbsp Marathon 1% granules (Hummert, Earth City, MO), 3 Tbsp OSMO-COTE® 14-14-14 (Hummert, Earth City, MO) and 1 Tbsp Peters fertilizer 20-20-20 (J. R. Peters, Inc., Allentown, PA), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an OD 600 of approximately 1.0) and inoculated one culture vessel per construct by transferring 1 mL from appropriate well in the starter block. Cultures are then incubated with shaking at 27° C. Cultures are spun down after attaining an OD 600 of approximately 1.0 (about 24 hours). 200 mL infiltration media is added to resuspend *Agrobacterium* pellets. Infiltration media is prepared by adding 2.2 g MS salts, 50 g sucrose, and 5 pL 2 mg/ml benzylaminopurine to 900 ml water.

Dipping Infiltration: The pots are inverted and submerged for 5 minutes so that the aerial portion of the plant is in the *Agrobacterium* suspension. Plants are allowed to grow normally and seed is collected.

Example 2: Saline Condition Screening

Saline condition screening: Screening is routinely performed by high-salt agar plate assay and also by high-salt soil assay. Traits assessed in high-salt conditions include: seedling area, photosynthesis efficiency, salt growth index and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under salt stress conditions.

Salt growth index=seedling area×photosynthesis efficiency (Fv/Fm).

Regeneration ability: the ability of a plant to regenerate shoots in saline soil after stems are cut off and the soil is irrigated with 200 mM NaCl solution.

Transformant identification: PCR was used to amplify the cDNA insert in one randomly chosen $T_2$ plant. This PCR product was then sequenced to confirm the sequence in the plants.

Identification of Tolerant Plant to Salt Stress: A superpool of seeds was screened for transgenic plants that show enhanced tolerance to SA, as detailed below, and high salt. Three independent candidate plants were sequenced and the transgene sequence matched ME02064.

Assessing Tolerance to Salt Stress: Generally, between four and ten independently transformed plant lines are selected and qualitatively evaluated for their tolerance to salt stress in the $T_1$ generation. Two or three of the transformed lines that qualitatively show the strongest tolerance to salt stress in the $T_1$ generation are selected for further evaluation in the $T_2$ and $T_3$ generations. This evaluation involves sowing seeds from the selected transformed plant lines on MS agar plates containing either 100 mM or 150 mM NaCl and incubating the seeds for 5 to 14 days to allow for germination and growth. For example, for ME02064 five $T_2$ events were compared to wild-type Ws for salt stress tolerance on salt plates. Three events, ME02064-01, -03 and -04 were selected based on the measurement of seedling area on 36 plants of each event as compared to the control, Ws. Further evaluation of salt tolerance in ME02064-01, -03 and -04 was performed with $T_2$ and $T_3$ generations.

Calculating SGI: After germination and growth, seedling area and photosynthesis efficiency of transformed lines and a wild-type control are determined. From these measurements, the Salt Growth Index (SGI) is calculated and compared between wild-type and transformed seedlings. The SGI calculation is made by multiplying seedling area with photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 15:1 generally indicates two copies of the transgene, and such a segregation ratio of 3:1 generally indicates one copy of the transgene.

Example 3: Oxidative Stress Conditions Screening

Under normal growth conditions, *Arabidopsis* rosette contains about 0.5 µg/g fresh weight of free SA. In response to stress conditions or pathogen attacks, the free SA levels can reach as high as 10 µg/g fresh weight, which is approximately equivalent to 60 µM. The exogenous application of 100-500 µM SA to *Arabidopsis* leaves by spraying is able to induce strong defense responses without triggering obvious necrotic lesion formation. Once the SA concentration increases to 5 mM or above, the cell death in form of necrotic lesions will appear on the sprayed leaves. If SA is applied through growth media, *Arabidopsis* is more sensitive to SA-induced oxidative stress, probably because of continuous absorption. The addition of 100-150 µM SA to growth media significant reduces plant growth but does not kills the plants in wild type *Arabidopsis* Ws. Therefore we use this range of SA to screen for enhanced oxidative stress tolerance.

Salicylic Acid Screening: Screening is routinely performed by agar plate assay using 100 µM or 150 µM exogenous sodium salicylate. Media contains 1/2X MS (Sigma), 150 µM sodium salicylate (Sigma), 0.5 g MES hydrate (Sigma) and 0.7% phytagar (EM Science), adjusted to pH 5.7 using 10N KOH.

To screen superpools, seeds are surface sterilized in 30% bleach solution for 5 minutes and then rinsed repeatedly with sterile water. Approximately 2500 seeds are sown on media plates in a monolayer at a density of 850 seeds per plate. Wild-type and positive controls are grown on comparable plates. Plates are wrapped with vent tape and placed at 4° C. in the dark for three days to stratify. At the end of this time, plates are transferred to a Conviron growth chamber set at 22° C., 16:8 hour light:dark cycle, 70% humidity with a combination of incandescent and fluorescent lamps emitting a light intensity of ~100 ρEinsteins.

Seedlings are screened daily starting at 6 days. Seedlings that grow larger and stay greener compared to WS control plants are selected as positive candidates and transferred to soil for recovery and seed set.

Candidate plants are re-screened by placing 36 seeds from each candidate together with a WS control on the same sodium salicylate plate. Plates are treated as described above and seedling screening begun after at 4 days after germination. Leaf tissue is harvested from confirmed tolerant candidates for DNA extraction and amplification of the transgene by PCR.

Alternatively, superpool seeds are sown directly on soil and sprayed with 10 mM SA. Leaf tissue is harvested from tolerant candidate plants to isolate DNA for PCR amplification of the transgene and subsequent sequencing of the PCR product.

Traits assessed under sodium salicylate conditions include: seedling area, photosynthesis efficiency, salicylic acid growth index (SAG) and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under oxidative stress conditions.

Salicylic Acid Growth (SAG) Index=seedling area $(cm^2)\times$ photosynthesis efficiency (Fv/Fm).

PCR was used to amplify the cDNA insert in one randomly chosen $T_2$ plant. This PCR product was then sequenced to confirm the sequence in the plants.

Assessing Tolerance to Oxidative Stress: Initially, All available independently transformed $T_2$ plant lines are qualitatively evaluated for their tolerance to oxidative stress as compared to wild-type controls. The positive transgenic lines that qualitatively show the strongest tolerance to oxidative stress are selected for further evaluation in the $T_2$ and $T_3$ generations using internal non-transgenic segregants as controls. This evaluation involves sowing seeds from the selected transformed plant lines on MS agar plates containing 100 µM or 150 µM sodium salicylate and incubating the seeds for at least 4 days to allow for germination and growth and transgene status analysis.

Calculating SAG: After germination and growth, seedling area and photosynthesis efficiency of transformed lines and a wild-type control are determined. From these measurements, the Salicylic Acid Growth Index (SAG) is calculated and compared between wild-type and transformed seedlings. The SAG calculation is made by multiplying seedling area with photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 15:1 generally indicates two copies of the transgene, and such a segregation ratio of 3:1 generally indicates one copy of the transgene.

In some cases, validation is performed using media that is further supplemented with 100 uM SNP.

Example 4: ME02064 (Ceres Clone 375578; SEQ ID No.138)

Wild-type *Arabidopsis thaliana* Wassilewskija was transformed with a Ti plasmid carrying the 35S promoter and Ceres Clone 375578. Three transformed lines, ME02064-01 and ME02064-03, ME02064-04, showed the strongest qualitative tolerance to salt stress in a prevalidation assay (Table 4-1). Their tolerance to 150 mM NaCl was further evaluated in a validation assay for two generations. Segregation ratios (BASTA™ resistant: BASTA™ sensitive) indicated ME02064-01 and ME02064-03, ME02064-04 transformed lines each carry one copy of the transgene.

TABLE 4-1

Prevalidation assay of ME02064 salt tolerance as compared to wild-type Ws

|  | Ws Wild-type | ME02064-01 | ME02064-02 | ME02064-03 | ME02064-04 | ME02064-05 |
|---|---|---|---|---|---|---|
| Mean* | 0.0359 | 0.0435 | 0.0346 | 0.0441 | 0.0438 | 0.0305 |
| Standard Error | 0.0016 | 0.0048 | 0.004 | 0.0041 | 0.0035 | 0.0019 |

*Average seedling area of 36 plants grown on MS agar plates containing 150 mM NaCl for 14 days When grown on MS agar plates containing 150 mM NaCl, ME02064-01 and ME02064-03, ME02064-04 transgenic plants showed significantly greater seedling area and SGI relative to non-transgenic plants. As shown in Table 4-2, the $T_2$-generation SGI value for ME02064-01 seedlings increased by 110% while ME02064-03 seedlings increased by 131% and ME02064-04 seedlings increased by 72% compared to non-transgenic control seedlings. In the $T_3$ generation, the SGI increase was 43% for ME02064-01, 47% for ME02064-03, and 64% for ME02064-04. The differences between transgenic and non-transgenic seedlings are statistically significant, and clearly demonstrate that the enhanced tolerance to salt stress was a result of the ectopic expression of Ceres Clone 375578 in the ME02064 transformant lines.

TABLE 4-2

Validation assay of ME02064 on salt tolerance in two generations

| ME Events | SGI* of transgenics Avg | SE | N | SGI of pooled non-transgenics Avg | SE | N | t-Test t-value | $t_{0.05}$ | % of SGI increase |
|---|---|---|---|---|---|---|---|---|---|
| ME02064-01-$T_2$ | 2.057 | 0.249 | 12 | 0.977 | 0.205 | 17 | 3.35 | 1.70 | 110.5 |
| ME02064-03-$T_2$ | 2.237 | 0.371 | 5 | 0.968 | 0.140 | 24 | 3.20 | 1.70 | 131.1 |
| ME02064-04-$T_2$ | 1.810 | 0.146 | 14 | 1.055 | 0.135 | 13 | 3.81 | 1.70 | 71.6 |
| ME02064-01-$T_3$ | 2.438 | 0.170 | 21 | 1.708 | 0.289 | 9 | 2.18 | 1.70 | 42.7 |
| ME02064-03-$T_3$ | 2.837 | 0.257 | 20 | 1.927 | 0.271 | 14 | 2.43 | 1.70 | 47.2 |
| ME02064-04-$T_3$ | 2.770 | 0.318 | 16 | 1.688 | 0.188 | 19 | 2.93 | 1.70 | 64.1 |

*SGI (Salt Growth Index) = seedling area × Fv/Fm (photosynthesis efficiency)

Summary of Results:

Ectopic expression of Ceres Clone 375578 under the control of the 35S promoter enhances tolerance to salt stress that causes necrotic lesions and stunted growth in wild-type Ws seedlings.

Example 5: ME03140; Clone 375578; SEQ ID No.142

Wild-type *Arabidopsis thaliana* Wassilewskija was transformed with a Ti plasmid carrying the 35S promoter operatively linked to Ceres Clone 375578 (SEQ ID NO: 142), and five transgenic lines, ME03140-01, ME03140-02, ME03140-03, ME03140-04 and ME03140-05 were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME03140-01, ME03140-02, ME03140-03, ME03140-04 and ME03140-05 transgenic plants showed significantly greater seedling area and SGI relative to non-transgenic plants. As shown in Table 5, the $T_2$-generation SGI value for ME03140-01 seedlings increased 102.18%, ME03140-02 seedlings increased 60.78%, ME03140-03 seedlings increased 120.32%, ME03140-04 seedlings increased 45.07% and ME03140-05 seedlings increased 90.53% as compared to non-transgenic control seedlings. The differences in SGI values between transgenic and non-transgenic seedlings have statistically significant P values for all transgenic lines, and these quantitative experiments clearly demonstrate that ectopic expression of Ceres Clone 375578 confers enhanced tolerance to salt stress in transgenic seedlings.

TABLE 5

Validation assay of ME03140 salt stress tolerance in one generation

| ME Events | SGI* of transgenics Avg | SE | N | SGI of pooled non-transgenics Avg | SE | N | P value | % of SGI increase |
|---|---|---|---|---|---|---|---|---|
| ME03140-01-$T_2$ | 4.34 | 0.590403017 | 17 | 2.15 | 0.478695 | 26 | 3.10E−03 | 102.18% |
| ME03140-02-$T_2$ | 4.09 | 0.395692005 | 18 | 2.54 | 0.367281 | 28 | 3.22E−03 | 60.78% |
| ME03140-03-$T_2$ | 4.03 | 0.646365854 | 12 | 1.83 | 0.397508 | 36 | 2.86E−03 | 120.32% |

TABLE 5-continued

Validation assay of ME03140 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME03140-04-$T_2$ | 4.86 | 0.534320049 | 17 | 3.35 | 0.446161 | 36 | 1.74E−02 | 45.07% |
| ME03140-05-$T_2$ | 4.31 | 0.5237326 | 25 | 2.26 | 0.665646 | 20 | 9.91E−03 | 90.53% |

*SGI (Salt Growth Index) = seedling area × Fv/Fm (photosynthesis efficiency)

Summary of Results:

Ectopic expression of Ceres Clone 375578 under the control of the 35S promoter enhances tolerance to salt stress that causes necrotic lesions and stunted growth in wild-type Ws seedlings.

Example 6: ME08732; clone 560066; SEQ ID No. 44

Wild-type *Arabidopsis thaliana* Wassilewskija was transformed with a Ti plasmid carrying the 35S promoter operatively linked to Ceres Clone 560066 (SEQ ID NO: 44), and three transgenic lines, ME08732-01, ME08732-02 and ME08732-03, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME08732-01, ME08732-02 and ME08732-03 transgenic plants showed significantly greater seedling area and SGI relative to non-transgenic plants. As shown in Table 6, the $T_2$-generation SGI value for ME08732-01 seedlings increased 88.35%, ME08732-02 seedlings increased 41.72% and ME08732-03 seedlings increased 26.23%, as compared to non-transgenic control seedlings. The differences in SGI values between transgenic and non-transgenic seedlings have statistically significant P values for ME08732-01 and ME08732-02 transgenic lines, and these quantitative experiments clearly demonstrate that ectopic expression of Ceres Clone 560066 confers enhanced tolerance to salt stress in transgenic seedlings.

Summary of Results:

Ectopic expression of Ceres Clone 560066 under the control of the 35S promoter enhances tolerance to salt stress that causes necrotic lesions and stunted growth in wild-type Ws seedlings.

Example 7: ME08768; Clone 539458; SEQ ID No.86

Wild-type *Arabidopsis thaliana* Wassilewskija was transformed with a Ti plasmid carrying the 35S promoter operatively linked to Ceres Clone 539458 (SEQ ID NO: 86), and five transgenic lines, ME08768-01, ME08768-02, ME08768-03, ME08768-04 and ME08768-05, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME08768-01, ME08768-02, ME08768-03, ME08768-04 and ME08768-05 transgenic plants showed significantly greater seedling area and SGI relative to non-transgenic plants. As shown in Table 7, the $T_2$-generation SGI value for ME08768-01 seedlings increased 80.04%, ME08768-02 seedlings increased 111.63%, ME008768-03 seedlings increased 22.62%, ME008768-04 seedlings increased 115.40% and ME008768-05 seedlings increased 74.41% as compared to non-transgenic control seedlings. The differences in SGI values between transgenic and non-transgenic seedlings have statistically significant P values for ME08768-01, ME08768-02, ME08768-04 and ME08768-05 transgenic lines, and these quantitative experiments clearly demonstrate that ectopic expression of Ceres Clone 539458 confers enhanced tolerance to salt stress in transgenic seedlings.

TABLE 6

Validation assay of ME08732 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME08732-01-$T_2$ | 4.07 | 0.164301729 | 24 | 2.16 | 0.472565 | 14 | 2.57E−04 | 88.35% |
| ME08732-02-$T_2$ | 3.42 | 0.391450599 | 21 | 2.41 | 0.336042 | 26 | 2.86E−02 | 41.72% |
| ME08732-03-$T_2$ | 4.71 | 0.566761111 | 10 | 3.73 | 0.285925 | 52 | 6.44E−02 | 26.23% |

*SGI (Salt Growth Index) = seedling area × Fv/Fm (photosynthesis efficiency)

TABLE 7

Validation assay of ME08768 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME08768-01-$T_2$ | 14.48 | 1.254125111 | 20 | 8.04 | 1.321838 | 26 | 4.91E−04 | 80.04% |
| ME08768-02-$T_2$ | 11.09 | 0.822117225 | 20 | 5.24 | 0.751908 | 32 | 1.55E−06 | 111.63% |
| ME08768-03-$T_2$ | 13.72 | 1.676864172 | 21 | 11.19 | 1.57188 | 30 | 0.1380406 | 22.62% |
| ME08768-04-$T_2$ | 14.82 | 1.3958585 | 16 | 6.88 | 0.777162 | 40 | 3.58E−06 | 115.40% |
| ME08768-05-$T_2$ | 10.02 | 1.365308 | 13 | 5.75 | 0.751134 | 38 | 4.23E−03 | 74.41% |

*SGI (Salt Growth Index) = seedling area × Fv/Fm (photosynthesis efficiency)

Summary of Results:
Ectopic expression of Ceres Clone 539458 under the control of the 35S promoter enhances tolerance to salt stress that causes necrotic lesions and stunted growth in wild-type Ws seedlings.

Example 8: ME10681; Clone 335348 SEQ ID No.141

Wild-type *Arabidopsis thaliana* Wassilewskija was transformed with a Ti plasmid carrying the 35S promoter operatively linked to Ceres Clone 335348 (SEQ ID NO: 141), and six transgenic lines, ME10681-01-$T_2$, ME10681-01-$T_3$, ME10681-02-$T_2$, ME10681-02-$T_3$, ME10681-04-T 2 and ME10681-05-$T_2$, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME10681-01-$T_2$, ME10681-01-T 3, ME10681-02-$T_2$, ME10681-02-T 3, ME10681-04-T 2 and ME10681-05-T 2 transgenic plants showed significantly greater seedling area and SGI relative to non-transgenic plants. As shown in Table 8, the $T_2$-generation SGI value for ME010681-01-T 2 seedlings increased 39.17%, ME010681-01-T 3 seedlings increased 19.77%%, ME10681-02-$T_2$ seedlings increased 119.17%, ME10681-02-T 3 seedlings increased 6.21%, ME010681-04-$T_2$ seedlings increased 113.51% and ME010681-05-T 2 seedlings increased 103.98%, as compared to non-transgenic control seedlings. The differences in SGI values between transgenic and non-transgenic seedlings have statistically significant P values for ME10681-01-T 3, ME10681-02-$T_2$, ME10681-04-T 2 and ME10681-05-T 2 transgenic lines, and these quantitative experiments clearly demonstrate that ectopic expression of Ceres Clone 335348 confers enhanced tolerance to salt stress in transgenic seedlings.

TABLE 8

Validation assay of ME10681 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME10681-01-$T_2$ | 3.87 | 0.683711333 | 9 | 2.78 | 0.302501 | 48 | 7.54E−02 | 39.17% |
| ME10681-01-$T_3$ | 4.7 | 0.31544415 | 23 | 3.93 | 0.3015141 | 43 | 3.99E−02 | 19.77% |
| ME10681-02-$T_2$ | 4.13 | 0.3353564 | 25 | 1.89 | 0.3969 | 22 | 4.16E−05 | 119.17% |
| ME10681-02-$T_3$ | 3.65 | 0.258400663 | 31 | 3.44 | 0.3060094 | 34 | 0.2980488 | 6.21% |
| ME10681-04-$T_2$ | 6.22 | 0.478672159 | 12 | 2.91 | 0.39405 | 30 | 2.04E−06 | 113.51% |
| ME10681-05-$T_2$ | 5.25 | 0.391550037 | 20 | 2.57 | 0.4265902 | 30 | 1.44E−05 | 103.98% |

*SGI (Salt Growth Index) = seedling area × Fv/Fm (photosynthesis efficiency)

Summary of Results:
Ectopic expression of Ceres Clone 335348 under the control of the 35S promoter enhances tolerance to salt stress that causes necrotic lesions and stunted growth in wild-type Ws seedlings.

Example 9: ME18973; Ceres cDNA ID 23457556; SEQ ID No.43

Wild-type *Arabidopsis thaliana* Wassilewskija was transformed with a Ti plasmid carrying the 35S promoter operatively linked to Ceres cDNA ID 23457556 (SEQ ID NO: 43), and six transgenic lines, ME18973-01-$T_2$, ME18973-02-$T_2$, ME18973-02-01-T 3, ME18973-03-$T_2$, ME18973-05-T 2 and ME18973-05-03-T 3 were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME18973-01, ME18973-02-$T_2$, ME18973-02-01-T 3, ME18973-03-$T_2$, ME18973-05-T 2 and ME18973-05-03-T 3 transgenic plants showed significantly greater seedling area and SGI relative to non-transgenic plants. As shown in Table 9, the $T_2$ & $T_3$-generation SGI value for ME018973-01-T 2 seedlings increased 230.01%, ME18973-02-T 2 seedlings increased 22.44%, ME18973-02-01-T 3 seedlings increased 14.96%, ME18973-05-T 2 seedlings increased 16.12% and ME18973-05-03-T 3 seedlings increased 13.97%, as compared to non-transgenic control seedlings. The differences in SGI values between transgenic and non-transgenic seedlings have statistically significant P values for the ME18973 transgenic lines, and these quantitative experiments clearly demonstrate that ectopic expression of Ceres cDNA ID 23457556 results in enhanced tolerance to salt stress in transgenic seedlings.

tively linked to Ceres cDNA ID 23621377 (SEQ ID NO: 45), and two transgenic lines, ME19657-01-$T_2$, ME19657-01-05-T 3, ME19657-01-08-T 3, ME19657-02-$T_2$, ME19657-03-$T_2$, ME19657-04-T 2 and ME19657-04-01-T 3, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, ME19657-01-$T_2$, ME19657-01-05-T 3, ME19657-01-08-T 3, ME19657-02-$T_2$, ME19657-03-$T_2$, ME19657-04-$T_2$ and ME19657-04-01-T 3 transgenic plants showed significantly greater seedling area and SGI relative to non-transgenic plants. As shown in Table 10, the $T_2$ & $T_3$-generation SGI value for ME19657-01-T 2 seedlings increased 82.29%, ME19657-01-05-T 3 seedlings increased 82.29%, ME19657-01-08-T 3 seedlings increased 21.90%, ME19657-02-T 2 seedlings increased 39.50%, ME19657-03-T 2 seedlings increased 98.28%, and ME19657-04-$T_2$ seedlings increased 4.38% and ME19657-04-01-T 2 seed-

TABLE 9

Validation assay of ME18973 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME18973-01-$T_2$ | 4.41 | 0.253654648 | 26 | 1.34 | 0.367022 | 18 | 1.03E−08 | 230.01% |
| ME18973-02-$T_2$ | 4.47 | 0.373604899 | 27 | 3.65 | 0.526316 | 18 | 0.1058348 | 22.44% |
| ME18973-02-01-$T_3$ | 4.82 | 0.205971746 | 44 | 4.19 | 0.3832982 | 25 | 7.71E−02 | 14.96% |
| ME18973-05-$T_2$ | 4.74 | 0 | 1 | 4.09 | 0.503725 | 26 | 0.160517 | 16.12% |
| ME18973-05-03-$T_3$ | 4.38 | 0.233610226 | 32 | 3.84 | 0.503725 | 37 | 6.89E−02 | 13.97% |

*SGI (Salt Growth Index) = seedling area × Fv/Fm (photosynthesis efficiency)

Summary of Results:

Ectopic expression of Ceres cDNA ID 23457556 under the control of the 35S promoter enhances tolerance to salt stress that causes necrotic lesions and stunted growth in wild-type Ws seedlings.

Example 10: ME19657; cDNA ID 23621377; SEQ ID No.45

Wild-type *Arabidopsis thaliana* Wassilewskija was transformed with a Ti plasmid carrying the 35S promoter operalings increased 7.44%, as compared to non-transgenic control seedlings. The differences in SGI values between transgenic and non-transgenic seedlings have statistically significant P values for ME19657-01-$T_2$, ME19657-01-05-T 3, ME19657-01-08-T 3, ME19657-02-T 2 and ME19657-03-T 2 transgenic lines, and these quantitative experiments clearly demonstrate that ectopic expression of Ceres cDNA ID 23621377 results in enhanced tolerance to salt stress in transgenic seedlings.

TABLE 10

Validation assay of ME19657 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME19657-01-$T_2$ | 4.54 | 0.311964078 | 21 | 2.49 | 0.539972 | 15 | 5.62E−05 | 82.29% |
| ME19657-01-05-$T_3$ | 0.7 | 0.311964078 | 21 | 0.7 | 0.5399721 | 15 | 1.18E−03 | 82.29% |
| ME19657-01-08-$T_3$ | 5.4 | 0.278520121 | 27 | 4.43 | 0.3061552 | 36 | 1.18E−03 | 21.90% |
| ME19657-02-$T_2$ | 3.97 | 0.32089576 | 23 | 2.84 | 0.527849 | 18 | 0.0111868 | 39.50% |
| ME19657-03-$T_2$ | 4.79 | 0.313786256 | 22 | 2.41 | 0.299954 | 22 | 3.83E−02 | 98.28% |

TABLE 10-continued

Validation assay of ME19657 salt stress tolerance in two generations

| ME | SGI* of transgenics | | | SGI of pooled non-transgenics | | | P | % of SGI |
|---|---|---|---|---|---|---|---|---|
| Events | Avg | SE | N | Avg | SE | N | value | increase |
| ME19657-04-$T_2$ | 3.67 | 0.341681304 | 15 | 3.52 | 0.324049 | 40 | 1.15E−06 | 4.38% |
| ME19657-04-01-$T_3$ | 4.56 | 0.495154 | 9 | 4.25 | 0.3487774 | 37 | 0.3723989 | 7.44% |

*SGI (Salt Growth Index) = seedling area × Fv/Fm (photosynthesis efficiency)

Summary of Results:

Ectopic expression of Ceres cDNA ID 23621377 under the control of the 35S promoter enhances tolerance to salt stress that causes necrotic lesions and stunted growth in wild-type Ws seedlings.

Example 11: ME24076; Clone 229668; SEQ ID No. 143

Wild-type *Arabidopsis thaliana* Wassilewskija was transformed with a Ti plasmid carrying the 35S promoter operatively linked to Ceres Clone: 229668 (SEQ ID NO: 143), and two transgenic lines, ME24076-01 and ME24076-02, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, only ME024076-01-T 2 and transgenic plants showed significantly greater seedling area and SGI relative to non-transgenic plants. As shown in Table 11, the $T_2$-generation SGI value for ME24076-01-T 2 seedlings increased 65.57% and ME24076-02-T 2 seedlings decreased by 1.12%, as compared to non-transgenic control seedlings. The differences in SGI values between transgenic and non-transgenic seedlings have statistically significant P values for transgenic line ME24076-01, and these quantitative experiments clearly demonstrate that ectopic expression of Ceres Clone 229668 results in enhanced tolerance to salt stress in transgenic seedlings.

Summary of Results:

Ectopic expression of Ceres Clone 229668 under the control of the 35S promoter enhances tolerance to salt stress that causes necrotic lesions and stunted growth in wild-type Ws seedlings.

Example 12: ME24217; Clone 375578; SEQ ID No. 144

Wild-type *Arabidopsis thaliana* Wassilewskija was transformed with a Ti plasmid carrying the 35S promoter operatively linked to Ceres Clone 375578 (SEQ ID NO: 144), and two transgenic lines, ME24217-07-T 2 and ME24217-09-$T_2$, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, ME24217-07-T 2 and ME24217-09-T 2 transgenic plants showed significantly greater seedling area and SGI relative to non-transgenic plants. As shown in Table 12, the $T_2$-generation SGI value for ME24217-07 seedlings increased 30.41% and ME24217-09 seedlings increased 134.46%, as compared to non-transgenic control seedlings. The differences in SGI values between transgenic and non-transgenic seedlings have statistically significant P values for ME24217-07-T 2 and ME24217-09-T 2 transgenic lines, and these quantitative experiments clearly demonstrate that ectopic expression of Ceres Clone 375578 results in enhanced tolerance to salt stress in transgenic seedlings.

TABLE 11

Validation assay of ME24076 salt stress tolerance in one generation

| ME | SGI* of transgenics | | | SGI of pooled non-transgenics | | | P | % of SGI |
|---|---|---|---|---|---|---|---|---|
| Events | Avg | SE | N | Avg | SE | N | value | increase |
| ME24076-01-$T_2$ | 11.18 | 0.924279499 | 17 | 6.75 | 0.9761984 | 32 | 9.45E−04 | 65.57% |
| ME24076-02-$T_2$ | 0.7 | 0.082529059 | 10 | 0.7 | 0.0506174 | 48 | 0.4675565 | −1.12% |

*SGI (Salt Growth Index) = seedling area × Fv/Fm (photosynthesis efficiency)

TABLE 12

Validation assay of ME24217 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME24217-07-$T_2$ | 4.69 | 0.413823734 | 20 | 3.6 | 0.4284669 | 30 | 3.62E−02 | 30.41% |
| ME24217-09-$T_2$ | 4.92 | 0.446345081 | 22 | 2.1 | 0.506974 | 22 | 7.20E−05 | 134.46% |

*SGI (Salt Growth Index) = seedling area × Fv/Fm (photosynthesis efficiency)

Summary of Results:
Ectopic expression of Ceres Clone 375578 under the control of the 35S promoter enhances tolerance to salt stress that causes necrotic lesions and stunted growth in wild-type Ws seedlings.

Example 13: ME02064C; Clone 375578C; SEQ ID No. 140

Wild-type *Arabidopsis thaliana* Wassilewskija was transformed with a Ti plasmid carrying the 35S promoter operatively linked to Ceres Clone 375578 (SEQ ID NO: 140), and six transgenic lines, ME02064C-01-$T_2$, ME02064C-02-$T_2$, ME02064C-03-$T_2$, ME02064C-04-$T_2$, ME02064C-05-T 2 and ME02064C-06-T 2 were investigated for tolerance to salt stress. When grown on MS agar plates containing 150 mM NaCl, most of these transgenic lines did not show tolerance to salt stress in quantitative assays as compared to non-transgenic control seedlings.

Table 13 shows that, when grown on MS agar plates containing 100 mM NaCl, the $T_2$-generation SGI value for: ME02064C-01-T 2 seedlings as compared to non-transgenic control seedlings was 0.55%; ME02064C-02-T 2 seedlings as compared to non-transgenic control seedlings was 1.31%; ME02064C-03-T 2 seedlings as compared to non-transgenic control seedlings was 9.67%; ME02064C-04-T 2 seedlings as compared to non-transgenic control seedlings was −7.78%; ME02064C-05-T 2 seedlings as compared to non-transgenic control seedlings was −15.77%; and ME02064C-06-T 2 seedlings as compared to non-transgenic control seedlings 17.78%.

Summary of Results:
Ectopic expression of Ceres Clone 375578 under the control of the 35S might not promote enhances tolerance to salt stress that causes necrotic lesions and stunted growth in wild-type Ws seedlings.

Example 14: ME02064P1; Clone 375578P1-Amino Acids 1 to 135 of SEQ ID No. 140

Wild-type *Arabidopsis thaliana* Wassilewskija was transformed with a Ti plasmid carrying the 35S promoter operatively linked to a nucleic acid encoding Ceres Clone 375578P1 (amino acids 1 to 135 of SEQ ID NO: 140), a 3' truncation variant of Ceres Clone 375578 described above in Example 1. Five transgenic lines, ME02064P1-03-$T_2$, ME02064P1-07-$T_2$, ME02064P1-09-$T_2$, ME02064P1-10-$T_2$ and ME02064P1-15-$T_2$ were investigated for tolerance to salt stress. All five of these transgenic lines showed tolerance to salt stress in quantitative assays as compared to non-transgenic control seedlings. As shown in Table 10, the $T_2$-generation SGI value for ME02064P1 seedlings increased by 32.57%, 89.52%, 66.84%, 25.43%, 36.95%. compared to non-transgenic control seedlings.

When grown on MS agar plates containing 150 mM NaCl, ME02064P1-03, ME02064P1-07, ME02064P1-09, ME02064P1-10 and ME02064P1-15 transgenic plants showed significantly greater seedling area and SGI relative to non-transgenic plants. As shown in Table 14, the $T_2$-generation SGI value for ME02064P1-03 seedlings increased 32.57%, ME02064P1-07 seedlings increased 89.52%, ME02064P1-09 seedlings increased 66.84%, ME02064P1-

TABLE 13

Validation assay of ME02064C salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064C-01-$T_2$ | 10.89 | 0.735174679 | 33 | 10.83 | 0.707901 | 34 | 0.4769106 | 0.55% |
| ME02064C-02-$T_2$ | 10.7 | 0.595225094 | 50 | 10.56 | 0.971548 | 21 | 0.4517289 | 1.31% |
| ME02064C-03-$T_2$ | 9.39 | 0.582009053 | 48 | 8.56 | 0.958475 | 23 | 0.2314441 | 9.67% |
| ME02064C-04-$T_2$ | 10.66 | 0.555387069 | 51 | 11.56 | 1.046386 | 21 | 0.2252269 | −7.78% |
| ME02064C-05-$T_2$ | 10.84 | 0.60377588 | 48 | 12.87 | 0.839921 | 24 | 2.68E−02 | −15.77% |
| ME02064C-06-$T_2$ | 12.55 | 0.608556025 | 44 | 10.65 | 0.764179 | 28 | 2.83E−02 | 17.78% |

*SGI (Salt Growth Index) = seedling area × Fv/Fm (photosynthesis efficiency)

10 seedlings increased 25.43% and ME02064P1-15 seedlings increased 36.95% as compared to non-transgenic control seedlings. The differences in SGI values between transgenic and non-transgenic seedlings have statistically significant under P values for trans genic lines ME02064P1-03-$T_2$, ME02064P1-07-$T_2$, ME02064P1-09-$T_2$, ME02064P1-10-T 2 and ME02064P1-15-$T_2$, and these quantitative experiments clearly demonstrate that ectopic expression of Ceres Clone 37558P1 results in enhanced tolerance to salt stress in transgenic seedlings.

Table 15 shows that, when grown on MS agar plates containing 100 mM NaCl, the $T_2$-generation SGI value for: ME02064P2-01-T 2 seedlings as compared to non-transgenic control seedlings was 1.62%, ME02064P2-04-T 2 seedlings as compared to non-transgenic control seedlings was 20.31%, ME02064P2-05-T 2 seedlings as compared to non-transgenic control seedlings was 31.24%, ME02064P2-06-T 2 seedlings as compared to non-transgenic control seedlings was 41.14%, ME02064P2-07-T 2 seedlings as compared to non-transgenic control seedlings was 15.91%,

TABLE 14

Validation assay of ME02064P1 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064P1-03-$T_2$ | 10.76 | 0.507929031 | 47 | 8.12 | 0.925474 | 25 | 7.29E−03 | 32.57% |
| ME02064P1-07-$T_2$ | 13.26 | 0.561088966 | 54 | 7 | 1.165372 | 16 | 3.87E−06 | 89.52% |
| ME02064P1-09-$T_2$ | 12.23 | 0.654850534 | 54 | 7.33 | 1.141553 | 17 | 1.99E−04 | 66.84% |
| ME02064P1-10-$T_2$ | 15.63 | 0.570291003 | 40 | 12.46 | 0.845552 | 32 | 1.36E−03 | 25.43% |
| ME02064P1-15-$T_2$ | 11.84 | 0.607966 | 42 | 8.64 | 0.959856 | 30 | 3.20E−03 | 36.95% |

*SGI (Salt Growth Index) = seedling area × Fv/Fm (photosynthesis efficiency)

Summary of Results:

Ectopic expression of Clone 375587P1 under the control of the 35S promoter enhances tolerance to salt stress.

Example 15: ME02064P2; Clone 375578P2-Amino Acids 188 to 498 of SEQ ID No.140

Wild-type *Arabidopsis thaliana* Wassilewskija was transformed with a Ti plasmid carrying the 35S promoter and a nucleic acid encoding Ceres Clone 375578P2 (amino acids 188 to 498 of SEQ ID NO: 140), a 5' truncation variant of Ceres Clone 375578 described above in Example 1. Eight ME02064P2 transgenic lines were investigated for tolerance to salt. Four transgenic lines, ME02064P2-01-$T_2$, ME02064CP2-04-$T_2$, ME02064P2-05-$T_2$, ME02064P2-06-T 2 ME02064P2-07-$T_2$, ME02064P2-T 2-08 and ME02064P2-09-T 2 did show statistically significant salt tolerance in quantitative assays as compared to non-transgenic control seedlings; and one transgenic lines, ME02064P2-10-$T_2$, showed statistically significant reduction in salt tolerance as compared to non-transgenic control seedlings.

ME02064P2-08-T 2 seedlings as compared to non-transgenic control seedlings was 40.82%, ME02064P2-09-T 2 seedlings as compared to non-transgenic control seedlings was 135.79%, and ME02064P2-10-T 2 was −12.36% as compared to non-transgenic control seedlings.

When grown on MS agar plates containing 100 mM NaCl, ME02064P2-01-$T_2$, ME02064P2-04-$T_2$, ME02064P2-05-$T_2$, ME02064P2-06-$T_2$, ME02064P2-07-$T_2$, ME02064P2-08-T 2 and ME02064P2-09-T 2 transgenic plants showed significantly greater seedling area and SGI relative to non-transgenic plants. However as shown in Table 3, the $T_2$-generation SGI value for ME02064P2-10-T 2 seedlings showed a decrease in SGI compared to non-transgenic control seedlings.

TABLE 15

Validation assay of ME02064P2 on salt tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064P2-01-$T_2$ | 9.84 | 0.687493743 | 53 | 9.68 | 1.261045 | 19 | 0.4567634 | 1.62% |
| ME02064P2-04-$T_2$ | 5.2 | 0.558723451 | 47 | 4.32 | 0.560634 | 25 | 0.1357713 | 20.31% |
| ME02064P2-05-$T_2$ | 8.42 | 0.714218299 | 45 | 6.41 | 0.623421 | 27 | 0.0190578 | 31.24% |
| ME02064P2-06-$T_2$ | 8.56 | 0.515029349 | 48 | 6.07 | 0.654098 | 24 | 1.88E−03 | 41.14% |
| ME02064P2-07-$T_2$ | 12.3 | 0.647077232 | 47 | 10.61 | 0.8768 | 25 | 6.29E−02 | 15.91% |
| ME02064P2-08-$T_2$ | 9.16 | 0.724681422 | 37 | 6.51 | 0.73405 | 35 | 6.08E−03 | 40.82% |
| ME02064P2-09-$T_2$ | 5.72 | 0.489863069 | 47 | 2.43 | 0.182583 | 24 | 1.19E−08 | 135.79% |
| ME02064P2-10-$T_2$ | 9.32 | 0.908174851 | 21 | 10.63 | 0.70877 | 51 | 0.1289273 | 12.36% |

*SGI (Salt Growth Index) = seedling area × Fv/Fm (photosynthesis efficiency)

Summary of Results:

Ectopic expression of Clone 375587P2 under the control of the 35S promoter enhances tolerance to salt stress.

Ceres Clone 375578P2 retains the α-β domains of Ceres Clone 375578 located within amino acid residues 137-157 of SEQ ID NO: 140) but does not retain the 6-r domains of Ceres Clone 375578 of SEQ ID NO: 140.

Example 16: ME10681; Clone 335348 SEQ ID No. 141

Wild-type *Arabidopsis thaliana* Wassilewskija was transformed with a Ti plasmid carrying the 35S promoter operatively linked to Ceres cDNA 335348 (SEQ ID NO: 141). Wildtype Ws seedlings showed necrotic lesions and stunted growth on plates containing 100 or 150 µM SA, whereas the transgenic plants showed significantly better growth.

Three transformed lines, ME10681-01, ME10681-02 and ME10681-05, were quantitatively studied by growth on MS agar plates containing 100 µM SA. After 14 days, plates were scanned using an EPSON color scanner or fluorescence scanner and SAGI calculated for each plant. The data is summarized in Table 16.

When grown on MS agar plates containing 100 µM SA, ME10681-02-T 2 and ME10681-05-T 2 transgenic plants showed significantly increased seedling area and SAGI relative to non-transgenic plants. However ME10681-01-T 2 showed a slight decrease in SAGI relative to non-transgenic plants. As shown in Table 12, the $T_2$ generation SAGI value for ME10681-01-$T_2$, ME10681-02-T 2 and ME10681-05-T 2 seedlings was −3.29%, 17.65% and 51.84%, respectively. The differences between transgenic and non-transgenic seedlings have statistically significant P values for lines ME10681-02-T 2 and ME10681-05-$T_2$, and clearly demonstrate enhanced tolerance to oxidative stress is a result of the ectopic expression of Ceres cDNA 36505846 in the ME10681 transformant lines.

tively linked to Ceres cDNA 016263 (SEQ ID NO: 135). Wildtype Ws seedlings showed necrotic lesions and stunted growth on plates containing 100 or 150 µM SA, whereas the transgenic plants showed significantly better growth.

Ten transformed lines, ME24091-01-$T_2$, ME24091-02-$T_2$, ME24091-03-$T_2$, ME24091-04-T 2 ME24091-05-$T_2$, ME24091-06-$T_2$ME24091-07 ME24091-08-$T_2$, ME24091-09-T 2 and ME24091-10-$T_2$, were quantitatively studied by growth on MS agar plates containing 100 µM SA. After 14 days, plates were scanned using an EPSON color scanner or fluorescence scanner and SAGI calculated for each plant.

When grown on MS agar plates containing 100 µM SA, ME24091-01-$T_2$, ME24091-02-$T_2$, ME24091-03-$T_2$, ME24091-04-01-$T_3$, ME24091-04-$T_2$, ME24091-05-01-$T_3$, ME24091-05 ME24091-06-01, ME24091-06, ME24091-07-01, ME24091-07, ME24091-08-01, ME24091-08, ME24091-09-01, ME24091-09, ME24091-10-01 and ME24091-10 transgenic plants showed significantly increased seedling area and SAGI relative to non-transgenic plants. As shown in Table 17, the $T_2$ generation SAGI value for ME24091-01, ME24091-02, ME24091-03, ME24091-04 ME24091-05, ME24091-06 ME24091-07, ME24091-08, ME24091-09 and ME24091-10 seedlings increased by 119.47%, 198.00% and 133.67%, 241.50%, 143.70% and 248.12%, 186.59%, 188.86%, 285.42% and 180.46%

TABLE 16

Salicylic acid validation assay of ME10681 in one generation

| ME Events | Seedling area of transgenics | | | Seedling area of pooled non-transgenics | | | P value | % Seedling area increase |
|---|---|---|---|---|---|---|---|---|
| | Avg | SE | N | Avg | SE | N | | |
| ME10681-01-$T_2$ | 0.56 | 0.096445 | 18 | 0.58 | 0.061856 | 53 | 0.434159 | −3.29% |
| ME10681-02-$T_2$ | 0.67 | 0.06042 | 38 | 0.38 | 0.079644 | 32 | 0.002198 | 17.65% |
| ME10681-05-$T_2$ | 0.68 | 0.072271 | 43 | 0.45 | 0.108539 | 25 | 0.039761 | 51.84% |

Summary of Results:

In sum, ectopic expression of Ceres Clone 335348 under the control of the 35S promoter enhances oxidative stress tolerance that causes necrotic lesions and stunted growth in wild-type WS seedlings.

Example 17: ME24091; Clone 106263; SEQ ID No. 136

Wild-type *Arabidopsis thaliana* Wassilewskija was transformed with a Ti plasmid carrying the 35S promoter operarespectively. The differences between transgenic and non-transgenic seedlings have statistically significant P values for transgenic lines ME24091-01, ME24091-02, ME24091-03, ME24091-04-01, ME24091-04 ME24091-05-01, ME24091-05, ME24091-06-01, ME24091-06, ME24091-07-01, ME24091-07, ME24091-08, ME24091-09-01, ME24091-09, and ME24091-10, and clearly demonstrate that the enhanced tolerance to oxidative stress is a result of the ectopic expression of Ceres Clone 106263 in the ME24091 transformant lines.

TABLE 17

Salicylic acid validation assay of ME24091 in two generations

| ME Events | Seedling area of transgenics | | | Seedling area of pooled non-transgenics | | | P value | % Seedling area increase |
|---|---|---|---|---|---|---|---|---|
| | Avg | SE | N | Avg | SE | N | | |
| ME24091-01-$T_2$ | 0.69 | 0.055882059 | 29 | 0.58 | 0.070002209 | 38 | 0.105475324 | 19.47% |
| ME24091-02-$T_2$ | 0.44 | 0.050576014 | 41 | 0.22 | 0.054717602 | 27 | 0.002577564 | 98.00% |
| ME24091-03-$T_2$ | 0.58 | 0.054269056 | 43 | 0.44 | 0.085715224 | 26 | 0.076183067 | 33.67% |
| ME24091-04-$T_2$ | 0.54 | 0.050859903 | 45 | 0.22 | 0.077668008 | 19 | 0.000634704 | 141.50% |

TABLE 17-continued

Salicylic acid validation assay of ME24091 in two generations

| ME Events | Seedling area of transgenics | | | Seedling area of pooled non-transgenics | | | P value | % Seedling area increase |
|---|---|---|---|---|---|---|---|---|
| | Avg | SE | N | Avg | SE | N | | |
| ME24091-04-01-$T_3$ | 0.39 | 0.07715765 | 20 | 0.24 | 0.07271465 | 20 | 0.081950663 | 61.93% |
| ME24091-05-$T_2$ | 0.55 | 0.048581793 | 42 | 0.38 | 0.072915009 | 27 | 0.029849118 | 43.70% |
| ME24091-05-01-$T_3$ | 0.38 | 0.068463201 | 21 | 0.15 | 0.05109963 | 30 | 0.005958129 | 144.90% |
| ME24091-06-$T_2$ | 0.71 | 0.049360913 | 39 | 0.29 | 0.063969074 | 23 | 1.13831E−06 | 148.12% |
| ME24091-06-01-$T_2$ | 0.49 | 0.073404661 | 19 | 0.22 | 0.063271768 | 22 | 0.004691952 | 118.19% |
| ME24091-07-$T_2$ | 0.69 | 0.054095931 | 37 | 0.37 | 0.07390372 | 25 | 0.000414138 | 86.59% |
| ME24091-07-01-$T_3$ | 0.49 | 0.052850446 | 33 | 0.19 | 0.049649799 | 22 | 5.3153E−05 | 162.61% |
| ME24091-08-$T_2$ | 0.64 | 0.059981819 | 24 | 0.34 | 0.071776729 | 23 | 0.00111815 | 88.86% |
| ME24091-08-01-$T_3$ | 0.44 | 0.050181996 | 27 | 0.40 | 0.074557785 | 26 | 0.306877156 | 11.48% |
| ME24091-09-$T_2$ | 0.81 | 0.056031311 | 38 | 0.29 | 0.067403065 | 22 | 5.88685E−08 | 185.42% |
| ME24091-09-01-$T_3$ | 0.45 | 0.055439617 | 36 | 0.28 | 0.05131548 | 31 | 0.0116714 | 62.95% |
| ME24091-10-$T_2$ | 0.56 | 0.048643058 | 39 | 0.31 | 0.062146975 | 29 | 0.001240527 | 80.46% |
| ME24091-10-01-$T_3$ | 0.36 | 0.051198395 | 31 | 0.26 | 0.066281225 | 22 | 0.114418402 | 39.44% |

Summary of Results:

In sum, ectopic expression of Ceres cDNA Clone 106263 under the control of the 35S promoter enhances oxidative stress tolerance that causes necrotic lesions and stunted growth in wild-type Ws seedlings.

Example 18: Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., Proc. Natl. Acad. Sci. USA, (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID Nos. 2, 35, 41, 43, 44, 86, 109, 135, 136, 138, 140, 141, 142, 143 and to amino acids X-Y of SEQ ID NO: 140 and to amino acids X-Y of SEQ ID NO: 140 are shown in FIGS. 1-6 and the Sequence Listing.

Example 19: Determination of Functional Homologs by Hidden Markov Models

Hidden Markov Models (HMMs) were generated by the program HMMER 2.3.2. To generate each HMM, the default HMMER 2.3.2 program parameters, conFigured for glocal alignments, were used.

An HMM was generated using the sequences shown in FIG. 1 as input. These sequences were input into the model and the HMM bit score for each sequence is shown in the Sequence Listing. Additional sequences were input into the model, and the HMM bit scores for the additional sequences are shown in the Sequence Listing. The results indicate that these additional sequences are functional homologs of SEQ ID NO: 86.

HMMs were also generated using the sequences shown in FIGS. 2-6 as input. These sequences were input into the respective models and the corresponding HMM bit score for each sequence is shown in the Sequence Listing. Additional sequences were input into the models, and the HMM bit scores for the additional sequences are shown in the Sequence Listing. The results indicate that these additional sequences are functional homologs of the groups in FIGS. 2-6.

In an alternative embodiment, the HMM is generated with the proviso that none of the amino acids specifically described in PCT/US2007/06544 are used. In particular the following amino acids appearing in the Sequence Listing of PCT/US2007/06544 are excluded: SEQ ID NO:99, SEQ ID NO:100, SEQ ID NO:102, SEQ ID NO:103, SEQ ID NO:104, SEQ ID NO:180, SEQ ID NO:252, SEQ ID NO:298, SEQ ID NO:300, SEQ ID NO:301, SEQ ID NO:306 and SEQ ID NO:312.

REFERENCES

The following references are cited in the Specification. Each of the references from the patent and periodical literature cited herein is hereby expressly incorporated in its entirety by such citation.

Zhang et al. (2004) *Plant Physiol.* 135:615.
Salomon et al. (1984) *EMBO J.* 3:141.
Herrera-Estrella et al. (1983) *EMBO J.* 2:987.
Escudero et al. (1996) *Plant J.* 10:355.
Ishida et al. (1996) *Nature Biotechnology* 14:745.
May et al. (1995) Bio/Technology 13:486)
Armaleo et al. (1990) *Current Genetics* 17:97.
Smith. T. F. and Waterman, M. S. (1981) *Adv. App. Math.* 2:482.
Needleman and Wunsch (1970) *J. Mol. Biol.* 48:443.
Pearson and Lipman (1988) *Proc. Natl. Acad. Sci.* (USA) 85: 2444.
Yamauchi et al. (1996) *Plant Mol Biol.* 30:321-9.
Xu et al. (1995) Plant Mol. Biol. 27:237.
Yamamoto et al. (1991) Plant Cell 3:371.
P. Tijessen, "Hybridization with Nucleic Acid Probes" In Laboratory Techniques in Biochemistry and Molecular Biology, P. C. vand der Vliet, ed., c. 1993 by Elsevier, Amsterdam.
Bonner et al., (1973) *J. Mol. Biol.* 81:123.
Sambrook et al., Molecular Cloning: A Laboratory Manual, Second Edition, Cold Spring Harbor Laboratory Press, 1989, New York.
Shizuya et al. (1992) *Proc. Natl. Acad. Sci. USA,* 89: 8794-8797.
Hamilton et al. (1996) *Proc. Natl. Acad. Sci. USA,* 93: 9975-9979.
Burke et al. (1987) *Science,* 236:806-812.
Sternberg N. et al. (1990) *Proc Natl Acad Sci USA.,* 87:103-7.
Bradshaw et al. (1995) *Nucl Acids Res,* 23: 4850-4856.
Frischauf et al. (1983) *J. Mol Biol,* 170: 827-842.
Huynh et al., Glover N M (ed) DNA Cloning: A practical Approach, Vol. 1 Oxford: IRL Press (1985).
Walden et al. (1990) *Mol Cell Biol* 1: 175-194.
Vissenberg et al. (2005) *Plant Cell Physiol* 46:192.
Husebye et al. (2002) *Plant Physiol* 128:1180.
Plesch et al. (2001) *Plant J* 28:455.
Weising et al. (1988) *Ann. Rev. Genet.,* 22:421.
Christou (1995) *Euphytica,* v. 85, n.1-3:13-27.
Newell (2000) Griesbach (1987) *Plant Sci.* 50:69-77.
Fromm et al. (1985) *Proc. Natl. Acad. Sci. USA* 82:5824.
Paszkowski et al. (1984) *EMBO J.* 3:2717.
Klein et al. (1987) *Nature* 327:773.
Willmitzer, L. (1993) Transgenic Plants. In: iotechnology, A Multi-Volume Comprehensive treatise (H. J. Rehm, G. Reed, A. Piller, P. Stadler, eds., Vol. 2, 627-659, VCH Weinheim-New York-Basel-Cambridge).
*Crit. Rev. Plant. Sci.* 4:1-46.
Fromm et al. (1990) *Biotechnology* 8:833-844.
Cho et al. (2000) *Planta* 210:195-204.
Brootghaerts et al. (2005) *Nature* 433:629-633.
Lincoln et al. (1998) *Plant Mol. Biol. Rep.* 16:1-4.
Lacomme et al. (2001), "Genetically Engineered Viruses" (C. J. A. Ring and E. D. Blair, Eds). Pp. 59-99, BIOS Scientific Publishers, Ltd. Oxford, U K.
Huh G H, Damsz B, Matsumoto T K, Reddy M P, Rus A M, Ibeas J I, Narasimhan M L, Bressan R A, Hasegawa P M, 2002, Salt causes ion disequilibrium-induced programmed cell death in yeast and plants. *Plant J* 29(5): 649-59.
Kang D K, Li X M, Ochi K, Horinouchi S, 1999, Possible involvement of cAMP in aerial mycelium formation and secondary metabolism in *Streptomyces griseus.* Microbiology, 145 (Pt 5):1161-72.
Kerk D, Bulgrien J, Smith D W, Gribskov M, 2003, *Arabidopsis* proteins containing similarity to the universal stress protein domain of bacteria. *Plant Physiol.*131(3): 1209-19.
Zhu J K, 2001, Cell signaling under salt, water and cold stresses. *Curr Opin Plant Biol.* 4(5):401-6.
Susstrunk U, Pidoux J, Taubert S, Ullmann A, Thompson C J, 1998, Pleiotropic effects of cAMP on germination, antibiotic biosynthesis and morphological development in *Streptomyces coelicolor. Mol Microbiol* 30(1):33-46.
Davletova S, Schlauch K, Coutu J, Mittler R., 2005, The zinc-finger protein Zat12 plays a central role in reactive oxygen and abiotic stress signaling in *Arabidopsis. Plant Physiol* 139(2):847-56.
Fowler S G, Cook D, Thomashow M F., 2005, Low temperature induction of *Arabidopsis* CBF1, 2, and 3 is gated by the circadian clock. *Plant Physiol* 137(3):961-8.
Nachin L, Nannmark U, Nystom T (2005) Differential roles of the universal stress proteins of *Escherichia coli* in oxidative stress resistance, adhesion and motility *J Bacteriol* 187(18):6265-72.
Rizhsky L, Davletova S, Liang H, Mittler R, 2004, The zinc finger protein Zat12 is required for cytosolic ascorbate peroxidase 1 expression during oxidative stress in *Arabidopsis. J Biol Chem.* 19;279(12): 11736-43.
Vogel J T, Zarka D G, Van Buskirk H A, Fowler S G, Thomashow M F, 2005, Roles of the CBF2 and ZAT12 transcription factors in configuring the low temperature transcriptome of *Arabidopsis. Plant J.* 41(2):195-211.
Sanchez-Barrena M J, Martinez-Ripoll M, Zhu J K, Albert A.,2005, The structure of the *Arabidopsis thaliana* SOS3: molecular mechanism of sensing calcium for salt stress response *J Mol Biol.* 345(5):1253-64.
Griffen, H. G, and Gasson, M. J. (1995) The Gene (aroK) Encoding Shikimate Kinase I from *E. Coli.* DNA Seq., 5(3):195-197.
Susstrunk et al. (1998) *Mol Microbiol,* 30(1):33-46 Kang et al. (1999) *Microbiology,* 145:1161-72.
Sauter M, Rzewuski G, Marwedel T, Lorbiecke R (2002) The novel ethylene-regulated gene OsUspl from rice encodes a member of a plant protein family related to prokaryotic universal stress proteins. *J Exp Bot* 53 (379): 2325-31.
Kasuga et al. (1999) *Nature Biotech* 17: 287-291.
Rus et al. (2001) *PNAS* 98:14150-14155.
Shi et al. (2000) *PNAS* 97:6896-6901.
Apse et al. (1999) *Science* 285:1256-1258.
Zhang et al. (2001) *PNAS* 98:12832-12836.
Berthomieu et al. (2003) *EMBO J* 22:2004-2014.
Ren et al. (2005) *Nat Genet.* 37:1029-30 Davletova et al (2005) *Plant Physiol.* 139:847-56

The invention claimed is:

1. A plant cell transformed with an exogenous nucleic acid said exogenous nucleic acid comprising a heterologous promoter operably linked to a nucleotide sequence encoding a polypeptide wherein said polypeptide has 95 percent or greater sequence identity to the amino acid sequence of SEQ ID NO: 44, and wherein overexpression of said polypeptide in a transformed plant grown from said transformed plant cell results in an increased level of tolerance to salinity or oxidative stress as compared to the corresponding level in tolerance to salinity or oxidative stress of a control plant of the same species cultivated under the same conditions that does not comprise said exogenous nucleic acid.

2. The plant cell of claim 1, wherein the nucleotide sequence encodes a polypeptide having 97 percent or greater sequence identity to the amino acid sequence of SEQ ID NO: 44.

3. The plant cell of claim 1, wherein the nucleotide sequence encoding said polypeptide exhibits 98 percent or greater sequence identity to the amino acid sequence of SEQ ID NO: 44.

4. A transgenic plant comprising the plant cell of claim 1.

5. The transgenic plant of claim 4, wherein said plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

6. A seed tissue or vegetative tissue comprising the plant cell of claim 1, wherein said seed tissue or vegetative tissue comprises the exogenous nucleic acid.

7. A food or feed product comprising the seed or vegetative tissue of claim 6, wherein the food or feed product comprises the exogenous nucleic acid.

8. The transformed plant cell of claim 1, wherein the polynucleotide sequence encodes a polypeptide comprising the amino acid sequence of SEQ ID NO: 44.

9. The transgenic plant of claim 4, wherein the polynucleotide sequence encodes a polypeptide comprising the amino acid sequence of SEQ ID NO: 44.

10. A seed produced by the transgenic plant of claim 4, wherein the seed comprises the exogenous nucleic acid.

* * * * *

SEQUENCE LISTING

```
Sequence total quantity: 168
SEQ ID NO: 1            moltype = DNA   length = 2343
FEATURE                 Location/Qualifiers
source                  1..2343
                        mol_type = other DNA
                        organism = Panicum virgatum
misc_feature            1..2343
                        note = Ceres CLONE ID no.1792354
misc_feature            1..2343
                        note = Encodes the peptide sequence at SEQ ID NO. 2
SEQUENCE: 1
agtgactagt gagctcactc cctcctcctt cccacttgac tctgcccgcc agctactgaa   60
ccaaccaaca aatacctccg ggctccctcc ggctttgcca ctcccatgga ttggaggttg  120
gaggcctgaa gggggaggtg ggtcgccgga cagggacggg gagacggcga gagggcgttc  180
cgcaggagcc gttcccgtgc ttcctccacc gaccgggccg acgcgccgcg ccgctgtttc  240
aggttccaga atttcaagta ttggccgctt taggatacta tgggaaagtc cccgggggaag  300
tggatcaagt ctgtgctctt ggggaagaaa tcgactaaat ccggttctac caaggcaaat  360
gagtcgaagg ctacaaataa caatggacac tcagctgggg aggagcgtgc attttctgaa  420
aattctccag tgatctctga gccggtgctt gttgaagccc acaaaaatgg agctgtttca  480
gttaatggga aggctgaaga tgtcaatttg ccaagtgaca gggctggcca acaagatctg  540
cagaaccaaa gtattgttga gtccgaaaca tcagttcctg ggcaattggg agaagaccaa  600
gctgcagtga aggcacaggc agcatttcgc ggttacctag cacgaaggtc attccgtgca  660
ttgaaaggta tcataagact ccaggtactg attcgagggc atcttgtaag gagacaggct  720
gtttcaaccc ttcgaactac ttggttgatt gtgaagtttc aatctctagt tcgtgggaaga  780
aatgtcagac tctctggtgc tgacattcaa ctcaatgtga agcttggcca acataacctt  840
ggtggcacta gatcatctga tgcatggaaa gagaagttat cttcaaatgc ctatgttcgg  900
aagcttctgt cttcaccaat agtgctagaa cctcttcact tccagtatga caagagggat  960
cccaattcaa cctataactg gctagagaga tggaccatag gctgcatctg gaagcctgtt 1020
tttcaaccaa aaagagttcc tgatgggaaa ctgctggtaa ggaaggctag ttatgcaatg 1080
gaaactgaat cagccaagtt aaagcgcaac attaggaagg gctctgctgc tacagttgag 1140
agtttccata caagagtgac tggtgaatct gagaaactta aacgtaatcc aaagaaattc 1200
tcaaacttcc ctgctgactc agtaccagat agccagttat ctgaacttga gaaggttaaa 1260
aggaacctga ggaaggtaac tgattccatg gctgaagcct caaagatctc tagttccagg 1320
gttgattcct caaggtatc tgattctaca cctgatgctc caaaagtatc taatcctgtg 1380
gccgaaatct caaagacatc tagtctcctg aacgggatct ctgaccatca agacagccaa 1440
tgtgaaaaag cactacagaa tacacgtgag gcttcatttc ctcttgaaac tcaagattac 1500
tctggcaatg gtcagctatt ggaatattca gatatggata acttcgactt ggtacctggt 1560
ttgaaaagtg atctggaaac tcagcttgat tcagtttcta taggagaaaa tgttgatgag 1620
cccactgttg gtgcttcagc agctgaaggt atgccactgc agaacattga tgagcccatt 1680
agtttaggga agaagagga gcaaggtcc aaggaagagc atctgtctaa tggaagccttt 1740
agaactggca agaaaagtc ttcatcccca tacaaatcag aatatgtgga aaacgggact 1800
cacactactc ctgctcagcc aaggaagcca agctatatgg ctgcaacgga gtctgcgaag 1860
gcgaaattac gagcacagaa ttcacccagg gtggattctg attcatcagc agaaaagaat 1920
ggcttcactc gacgccactc tcttccttcc ggtacaaaca gtaggggcgat caaagctgaa 1980
tggaagcgct gaggaggcat tgacttgaat tgaatagtgc gattgtctga atctctgctg 2040
ggtgaactct gccgctgctt gctccttttt atttatcctg cgatgtaaag agaagacatt 2100
gtccctgtat tgaacaatct ttgtgatgag tgcgtctggt tcagtctgtg gtaggttcac 2160
gtgccaggcc tagtgcccg ttcattgtat agtcacagtt ctctcgggat tgaaatgcat 2220
tcctcgtgta agctgatgtt aggactgcag tctgatcgaa taacatcatc cgcttgcaca 2280
ctgccttaag cccttaattg atatgatacc gggcaatttc gtgaaaaaaa aaaaaaaaaa 2340
aaa                                                               2343

SEQ ID NO: 2            moltype = AA   length = 570
FEATURE                 Location/Qualifiers
source                  1..570
                        mol_type = protein
                        organism = Panicum virgatum
REGION                  1..570
                        note = Ceres CLONE ID no.1792354
REGION                  1..570
                        note = Score of 822.8 for HMM of FIGURE 5.
REGION                  106..126
                        note = Pfam Name: IQ Pfam Description: IQ
                        calmodulin-binding motif
SEQUENCE: 2
MGKSPGKWIK SVLLGKKSTK SGSTKANESK ATNNNGHSAG EERAFSENSP VISEPVLVEA   60
HKNGAVSVNG KAEDVNLPSD RAGGQDLQNQ SIVESETSVP GQLGEDQAAV KAQAAFRGYL  120
ARRSFRALKG IIRLQVLIRG HLVRRQAVST LRTTWLIVKF QSLVRGRNVR LSGADIQLNV  180
KLGQHNLGGT RSSDAWKEKL SSNAYVRKLL SSPIVLEPLH FQYDKRDPNS TYNWLERWTI  240
GCIWKPVFQP KRVPDGKLLV RKASYAMETE SAKLKRNIRK GSAATVESFH TRVTGESEKL  300
KRNPKKFSNF PADSVPDSQL SELEKVKRNL RKVTDSMAEA SKISSSRVDS SKVSDSTPDA  360
PKVSNPVAEI SKTSSLLNGI SDHQDSQCEK ALQNTREASF PLETQDYSGN GQLLEYSDMD  420
NFDLVPGLKS DLETQLDSVS IGENVDEPTV GASAAEGMPL QNIDEPISLG KKEEARSKEE  480
HLSNGSLRTG KRKSSSPYKS EYVENGTHTT PAQPRKPSYM AATESAKAKL RAQNSPRVDS  540
DSSAEKNGFT RRHSLPSGTN SRAIKAEWKR                                   570

SEQ ID NO: 3            moltype = DNA   length = 2278
FEATURE                 Location/Qualifiers
```

| source | 1..2278 |
| --- | --- |
| | mol_type = other DNA |
| | organism = Gossypium hirsutum |
| misc_feature | 1..2278 |
| | note = Ceres CLONE ID no.1925477 |
| misc_feature | 1..2278 |
| | note = Encodes the peptide sequence at SEQ ID NO 4 |

SEQUENCE: 3

```
cccgctccat tgatgtcact aaccctaatt atacttacac acctacttct cttgtgattc    60
attttacaca tttaatttct gaaggccgtt ttcatctctt tcttagcttt tatttagttt   120
taaattcact ccaaaaaaaa aaaaaaaaac actgcacggg aatctcttgt tcgaggaatc   180
cttcacggta cgaaattcgt tcttcagatc tctgaatgct cactgtttaa ctgttccttg   240
gtttttcttc ctggtaatgg cagcttagta gcgaacaagc acttcaaatt tgctgcattt   300
ttcagatttc cagatttaga aacttggaat tttaattatt tttgggtcta acggagatgg   360
gaaaatctcc agcaaaatgg atcaagacct tacttcttgg gaagaaatct tcaaagtcca   420
gtttctcaaa aggaaagag aagctgaaat ctgcaaataa aggtgaggtt ttggtttctt   480
ccaaggtgac tgtgtctgac ctatcagtgg atcctccatc aatttcagca cctattctag   540
tgaatagcgc taggaatgtg gtggactctg agaagggtat acctgcccaa ttgccaaatg   600
atggggcaaa tattccatct ccaaaagtgg atggaaatga tgccacaact ggtaattttg   660
gtaacccaga aaatcctgat aggattgggc ttgacccagc tgctgtgacg gtacaggctg   720
ctttcagagg ttatctggct cgcagggcat ttcgaaccct caagggcatt ataaggctgc   780
aagcagttat tcgtggtcac ttggttagaa gacaagctgt tgctacttta tgctgtacat   840
ggggaattgt taagttgcaa gcactagctc gtggtcaaaa ggtcagatgt tcagatattg   900
ccatggaaat acaagaaaaa catctcaagac tgcttcaggg ttctaaaagc tcggattcta   960
ttggagtgag cacatcttct aaggtgaaga atttatcaaa taatgtgttt gttcagaagc  1020
ttttggcctc atcaccttct gtattacctc taaacttca atatgttcca gaggagccta  1080
actcatcctg gcagtggctt ctacgatgga caatgtcaca ttttttggga tcccctttaa  1140
aaccagttag gagtggaaag acaaaacgaa gtattcagaa actgtccaat gcaaagttg   1200
ttaatggatc tagtcattct accttggagc atgaaaaaaa caaacgaggt gtgaggagag  1260
tttctggcaa ctcagcagca gattcagttc ggaagcatcc acaaaatgag cttgagaggg  1320
ttaagcgcag tttacgaaag ctttctgact cttcaaagga ggtttctgat aagtctgaag  1380
ttttttaatga gaaaacaaag aagactccga aaaaaacttc taattctaat gaccctgatt  1440
tttcagaaca ggaatccgct gagaagataa gagatgtgac tgcaacacta tcagaactgt  1500
caattcttga ggcagatctg aaaatttccc tagaagatcc ttctcttggt gagcctaatc  1560
tctgtcctgc agttgatttg tcacctgctg aaaacaatcg taaacttgag gtaatagagg  1620
agttaatctc taaagacaag caggttggtg atgagagctc aaacacaagc caaagaagag  1680
cttctttccc tgcaaaaatt gataatcagg cgaatgggtt aaatctcatg ccaaagtgc   1740
ccagttatat ggcagcaact gaatcctgcaa aagctagact taggggtcaa ggctccccaa  1800
tgtttacccc ggaggctgtt gagaaaaatg ggttaaacag gcgatattct ctgccatctt  1860
caacctatag taatcaagt tcacagtccc cacatggtca aagacgggtt cgagtagctg  1920
gcaaaggtgc taacatcagt gacaaatctc aatcatcctc taaagatgct aatgataagg  1980
ttgtcagagc tgagtggagg aggtaattct tgcatgggga attgtttcga tgaagtttcc  2040
atggagtttg tgcacggatg ctacttaaca aaacttccct tatgtgttgt aaacttctga  2100
tgtttggttg tagaagcagg agagtgaatc atctaatctt ttgttgcttg gtgtatcttt  2160
ttaagtttcc ttggcacttt caggtttgta gatgggtaaa tatttgtaga tgttacagtt  2220
ggttatttgg tttatttggt tcgtttgtgt ttgtacgcaa aaaaaaaaaa aaaaaaa     2278
```

| SEQ ID NO: 4 | moltype = AA  length = 549 |
| --- | --- |
| FEATURE | Location/Qualifiers |
| source | 1..549 |
| | mol_type = protein |
| | organism = Gossypium hirsutum |
| REGION | 1..549 |
| | note = Ceres CLONE ID no.1925477 |
| REGION | 1..549 |
| | note = Score of 1112.9 for HMM of FIGURE 5. |
| REGION | 1..549 |
| | note = Functional Homolog Of Ceres CLONE ID no. 1792354 at SEQ ID NO. 2 |
| REGION | 113..133 |
| | note = Pfam Name: IQ Pfam Description: IQ calmodulin-binding motif |

SEQUENCE: 4

```
MGKSPAKWIK TLLLGKKSSK SSFSKGKEKL KSANKGEVLV SSKVTVSDLS VDPPSISAPI    60
LVNSARNVVD SEKGIPAQLP NDGANIPSPK VDGNDATTGN FGNPENPDRI GLDPAAVTVQ   120
AAFRGYLARR AFRTLKGIIR LQAVIRGHLV RRQAVATLCC TWGIVKLQAL ARGQKVRCSD   180
IAMEIQEKHL RLLQGSKSSD SIGVSTSSKV KNLSNNVFVQ KLLASSPSVL PLQLQYVPEE   240
PNSSWQWLLR WTMSHFWVSP LKPVRSGKTK RSIQKLSNAK VVNGSSHSTL EHEKNKRGVR   300
RVSGNSAADS VRKHPQNELE RVKRSLRKLS DSSKEVSDKS EVFNEKTKKT PKKTSNSNDP   360
DFSEQESAEK IRDVTATLSE LSILEADLKI SLEDPSLGEP NLCPAVDLSP AENNRKLEVI   420
EELISKDKQV GDESSNTSQR RASFPAKIDN QANGLNLMPK VPSYMAATES AKARLRGQGS   480
PMFTPEAVEK NGLNRRYSLP SSTYSNTSSQ SPHGQRRVRV AGKGANISDK SQSSSKDAND   540
KVVRAEWRR                                                            549
```

| SEQ ID NO: 5 | moltype = DNA  length = 1908 |
| --- | --- |
| FEATURE | Location/Qualifiers |
| source | 1..1908 |
| | mol_type = other DNA |
| | organism = Populus balsamifera |

-continued

|  |  |  |
|---|---|---|
|  | sub_species = trichocarpa |  |
| misc_feature | 1..1908 |  |
|  | note = Ceres ANNOT ID no.1521592 |  |
| misc_feature | 1..1908 |  |
|  | note = Encodes the peptide sequence at SEQ ID NO 6 |  |

SEQUENCE: 5

```
atggggagaa aatcacctgc gaaatggata agactgttt tgtttggaaa gaagtcttcc   60
aaatctctta ttgtcaaagg aagggagaga actgtgaatg acaaagagac attggttgct  120
gtcagagccg tggaagctga tgtgacctca gttcctccgg tggtcaagcc gacagccccc  180
actaccacta atatcgtaca aaggatgtta gagctagaga gcaaggaaac tacagaatca  240
tcacgtgatg gaggtatatt gtcaactgga aatcaagatg caaatcattc tcaattatac  300
actcctgatg ctcctccatc tgatgctgac aaaataaggc ttgatgaagc tgcgacaatg  360
gcacaagccg catttagggg ttacttggct cgccgagctt tcgagctct taaaggcata  420
ataaggcttc aggctcttat ccgtggacac ttggttagaa ggcaagctgt tgctactctc  480
tgctgtgtgc tcggagttgt caagttacag gctcttgctc gaggaagaat ggttaggaat  540
tcagagattg ctatgaggt tcataaatta tgcagccaag taaaactgcc ggagggcaag  600
cttgcagatt ctagtggagt tggtatacaa atggccaagc tgtcatcaaa tgcttttgtt  660
cgcaagcttc ttgctccatc acctgctgta atgcctttgc aactccccta tgattccatg  720
gaaccaaact cagttgcaaa ctggttagag tgctggtcag cgtcctcttt ctggaaacca  780
gttcccaac caaaaaaaat tacttgctca aaaactcaga aaagcagag taatggtcaa  840
atagtggaag ctgaaactgg taggccaaag cgcactgttc ggagggtccc tgctgcaaat  900
gttgacagta cctcagtaca agcagcctct gaatttgaaa acccaagcg caatttgagg  960
aaagttcaa gccatccagc tgattcagca gaaattcac agattgagct tgaaaaggta 1020
aagcgcagct taagaaaggt taataacccc gttatagaaa actctgctca ttcagaggtt 1080
gaaaatgaaa agcaaagca aggtctagaa aaggtatctg gcacttcagg tgataatgtt 1140
tgggatggga gcgtaagtaa ttcagctgag aagtgaaaa agaagctac cttgacaaca 1200
tccaatgtac ctgatgtggt gaagaatgat ccaaacttga tgtccaagtt gcctgatgca 1260
gagacagctg atgaacctgt agaaatgatc aaggcattgg aatcatcaca tgacgatcaa 1320
gctgtggtag aatctaaagc ttcagtagat actggtggta tagttgagaa tatgcaaata 1380
aatgggaagt ccatacacca ggatgatcca acaagcaatg aaaatccaa aactgccaaa 1440
aaaccttcat tcacaatgaa accagaacgt gccgagaatg gctacagag cagtcccacc 1500
ctccctagct acatggcagc aactgaatct gcaaaggcaa agctgagaat gcaaggctcc 1560
ccaagattta gtgaagatcg agttgagaaa ataacatca cccgtcgtca ttctctgccc 1620
tcttcaacta atagcaaaat cagctccgag tccccgagga caaagagc agttcatggt 1680
agtggcaaag gggggaataa gagtgacaag tctttattgt cttcaagaga tggaaatgct 1740
aagggagccc aaccagagtg gaagagatca tggtgtagca gtgaaacatg gtctatagcc 1800
ggaagggggg gaataaagag aaaagaagga aaaaaaaata aaagtccacc aatgacaaac 1860
caaccaccta acattgacac gcgtcgcccc aaaataaaga ggacatga            1908
```

| SEQ ID NO: 6 | moltype = AA length = 589 |
|---|---|
| FEATURE | Location/Qualifiers |
| source | 1..589 |
|  | mol_type = protein |
|  | note = subspecies = trichocarpa |
|  | organism = Populus balsamifera |
| REGION | 1..589 |
|  | note = Ceres ANNOT ID no.1521592 |
| REGION | 1..589 |
|  | note = Score of 1414.1 for HMM of FIGURE 5. |
| REGION | 1..589 |
|  | note = Functional Homolog Of Ceres CLONE ID no. 1792354 at SEQ ID NO. 2 |
| REGION | 115..135 |
|  | note = Pfam Name: IQ Pfam Description: IQ calmodulin-binding motif |

SEQUENCE: 6

```
MGRKSPAKWI KTVLFGKKSS KSLIVKGRER TVNDKETLVA VRAVEADVTS VPPVVKPTAP   60
TTTNITERML ELESRETTES SRDGGILSTG NQDANHSQLY TPDAPPSDAD KIRLDEAATM  120
AQAAFRGYLA RRAFRALKGI IRLQALIRGH LVRRQAVATL CCVLGVVKLQ ALARGRMVRN  180
SEIGYEVHKL CSQVKLPEGK LADSSGVGIQ MAKLSSNAFV RKLLAPSPAV MPLQLPYDSM  240
EPNSVANWLE CWSASSFWKP VPQPKKITCS KTQRKQSNGQ IVEAETGRPK RTVRRVPAAN  300
VDSTSVQAAS EFEKPKRNLR KVSSHPADSA ENSQIELEKV KRSLRKVNNP VIENSAHSEV  360
ENEKPKQGLE KVSGTSGDNV LGWSVSNSAE KMKKEATLTT SNVPDVVKND PNLMSKLPDA  420
ETADEPVEMI KALESSHDDQ AVVESKASVD TGGIVENMQI NGKSIHQDDP TSNENHKTAK  480
KPSFTMKPER AENGLQSSPT LPSYMAATES AKAKLRMQGS PRFSEDRVEK NNITRRHSLP  540
SSTNSKISSE SPRTQRAVHG SGKGGNKSDK SLLSSRDGNA KGAQPEWKR             589
```

| SEQ ID NO: 7 | moltype = DNA length = 2059 |
|---|---|
| FEATURE | Location/Qualifiers |
| source | 1..2059 |
|  | mol_type = other DNA |
|  | organism = Glycine max |
| misc_feature | 1..2059 |
|  | note = Ceres CLONE ID no.463594 |
| misc_feature | 1..2059 |
|  | note = Encodes the peptide sequence at SEQ ID NO 8 |

SEQUENCE: 7

```
attgtttggt tctggttctc aggaatggta gatttgaggt gaagacgttc acattggtc    60
aggtcccgat ctcacgatgg ggaagtcacc aggaaaatgg atcaaaactg tactgttcgg  120
```

-continued

```
gaaaaagtca tctaaatcaa atatttcaaa aggcagagag aagcttgtta atcaaaaagg    180
agtagtagtt acctccaagg tgccagaaac tggtttggct ttagaaccaa cctccgatac    240
tattgccaga catgaggaag atccagagct ggaaaataaa gaagcagaaa atgtttacc     300
cgggaatcaa gaaatagaca cagtgggatc aattaatgaa gatgctgcac tagatccaga    360
gaaaatgagg ctggaggaag cagctacaaa ggcacaagct gctttcaggg gttatttggc    420
tcggagagca tttagggctc taaaaggaat aataaggttg caagcactca tccgtgggca    480
cttggttagg agacaagctg ttgttacatt atgctcaatg tatggtattg tcaagtttca    540
agcacttgtt cgtggaggaa tagttagaca gtctaatgtt ggatctgaaa tccatgagaa    600
gtccaatata ttgaaccctc tggatggcaa gcttgtcaag ccaaatgcta tgttcacgaa    660
aattaccaag ctgtctgcaa atgctttcat tcggaagctt cttacttcgt caactacaat    720
aatggcgctg cggttgcaat atgttccggg cgatccaaat tcagtcctaa gttggttgga    780
gcgctggtca gcatctcact tttggaaacc agttccccaa cccaagaaaa ttcgagatac    840
taagtctcag agaaagcatg gcaatatttc agttggagat actcatgtga gcaagtcaaa    900
acgaatcaac aggaagcttc ctactgcaag ttttgactcg gtcccagtgc aagcaaatcc    960
tgaatttgaa aaaccaaaac gaaacacaag gaaaatttca aaccaatcct cagatcctca   1020
tgtgcaggaa aacccacaaa gtgagcttga aaagattaaa cgtaacttga aaaggtta    1080
taacccagtt gttgagaatg ctgttccgtc agaagttgaa tccgaaatgc caaggatca    1140
tttggaaaag gtaacagtta cctcatgcct tgctgttcaa gcaagaggc tcattagttc   1200
taatgagaag atcaagaagg aagcaatatt aactgttttcc agtgtgccag atatagaaac   1260
tactccaaga ctttcagtta gtaaggaggt gtctgacaca ccaagcagtt atcaagtgac   1320
tgtggaatca aaaccattga ctgagattac aactaaagat aaaaacattt ctgtttctga   1380
cgaagtaaaa aatgagccca tagatttacc agagcctatt tgtaaagatg aaaattctca   1440
cttaacaaat ggagatttga gtcacaagga gatcaaata ggcagtgaaa accagaaacc   1500
aaaccaaaaa gcctcaattg tagcaaagca ggaacgtgca gagaatggta tacagaatag   1560
tccaacatta ccgagttaca tggcagcaac tgaatctgca aaggcaaagt tgagggcaca   1620
aggatcccca agatttggac aggatggaag tgaaagaaac aaccatactc ggcgacattc   1680
tctgccatcc tcaactaaca gcaaaattaa ttccaccttca cctaggacac agagaccagt   1740
tcaatcaggt ggcaaaggtg gccacagaag tgacagaact gtatcatctt ctagagatgg   1800
gaatggaaag gtaattcaag cagagtggag gcggtaattt gaggaaggcc gatgttctgg   1860
aggaacatga ggagggcgaa accgtgtgtg gtttatatgt atctttgatg agaattgttg   1920
aatgagtagg actataggtg tgcttgaatt caggttattt cttcatttgc tgcatttggg   1980
gctttgaggg tgatttgtac attataggtt tctagttttg catgatgcaa ctataactaa   2040
atttaattat gttttaagc                                                2059
```

```
SEQ ID NO: 8          moltype = AA   length = 586
FEATURE               Location/Qualifiers
source                1..586
                      mol_type = protein
                      organism = Glycine max
REGION                1..586
                      note = Ceres CLONE ID no.463594
REGION                1..586
                      note = Score of 730.7 for HMM of FIGURE 5.
REGION                1..586
                      note = Functional Homolog Of Ceres CLONE ID no. 1792354 at
                        SEQ ID NO. 2
REGION                100..120
                      note = Pfam Name: IQ Pfam Description: IQ
                        calmodulin-binding motif
SEQUENCE: 8
MGKSPGKWIK TVLFGKKSSK SNISKGREKL VNQKGVVVTS KVPETGLALE PTSDTIARHE    60
EDPELENKEA ENVLPGNQEI DTVGSINEDA ALDPEKMRLE EAATKAQAAF RGYLARRAFR   120
ALKGIIRLQA LIRGHLVRRQ AVVTLCSMYG IVKFQALVRG GIVRQSNVGS EIHEKSNILN   180
PLDGKLVKPN AMFTKITKLS ANAFIRKLLT SSTTIMALRL QYVPGDPNSV LSWLERWSAS   240
HFWKPVPQPK KIRDTKSQRK HGNISVGDTH VSKSKRINRK LPTASFDSVP VQANPEFEKP   300
KRNTRKISNQ SSDPHVQENP QSELEKIKRN LRKVYNPVVE NAVPSEVESE MPKDHLEKVT   360
VTSCLAVSEQ EVISSNEKIK KEAILTVSSV PDIETTPRLS VSKEVSDTPS SYQVTVESKP   420
LTEITTKDKN ISVSDEVKNE PIDLPEPICK DENSHLTNGD LSHKEDQIGS ENQKPNQKAS   480
IVAKQERAEN GIQNSPTLPS YMAATESAKA KLRAQGSPRF GQDGSERNNH TRRHSLPSST   540
NSKINSPSPR TQRPVQSGGK GGHRSDRTVS SRDGNGKVI QAEWRR                   586
```

```
SEQ ID NO: 9          moltype = AA   length = 587
FEATURE               Location/Qualifiers
source                1..587
                      mol_type = protein
                      organism = Arabidopsis thaliana
REGION                1..587
                      note = Public GI ID no.22330633
REGION                1..587
                      note = Score of 545.5 for HMM of FIGURE 5.
REGION                1..587
                      note = Functional Homolog Of Ceres CLONE ID no. 1792354 at
                        SEQ ID NO. 2
REGION                113..132
                      note = Pfam Name: IQ Pfam Description: IQ
                        calmodulin-binding motif
SEQUENCE: 9
MGKSTKWLKN VLLGKKTSKS SGSKDKERVV SGKEVLVTSK VEESDVVSDL PSFEVAETNT    60
VDRSGGMLET QNVGPEEISD DEIELPEGKS TDSQNVAPVQ DHSLSDAERI QREIAATSVQ   120
```

```
AAFRGYLARR AFWALKGIIR LQALIRGHLV RRQAVATLFS VMGIVRLQAF ARGREIRKSD  180
IGVQVYRKCR LQLLQGNKLA NPTDAYLGIK KLTANAFAQK LLASSPKVLP VHAYDTSNPN  240
SNLIWLENWS ASCFWKPVPQ PKKTISRKPQ NRLLVEAESA KPKKSVRKVP ASNFESSSVQ  300
TSFEFEKPKR SFRKVSSQSI EPPAVEDPQI ELEKVKRSLR KVHNPVVESS IQPQRSPRKE  360
VEKPKLGVEK TRESSYPLVH ETAEEPVNVC DEKKKQEISE QPEEEVHALE MEVHTPGPLE  420
TNEALDSSLV NQIDSNEKAM VEEKPSMEKD TKEEKTPKPN NKENSAGKEN QKSRKKGSAT  480
SKTEREESNG HHETSPSIPS YMQATKSAKA KLRLQGSPKS AEQDGTEKAT VPRRHSLPSP  540
GNGRITSHSP RTTRLANSGD KTGNKKEKPL LSSREGNAKT TPAERKR                587

SEQ ID NO: 10          moltype = DNA  length = 2049
FEATURE                Location/Qualifiers
source                 1..2049
                       mol_type = other DNA
                       organism = Zea mays
misc_feature           1..2049
                       note = Ceres CLONE ID no.345954
misc_feature           1..2049
                       note = Encodes the peptide sequence at SEQ ID NO 11
SEQUENCE: 10
gtttttcgcc gagcagttcg cgtgctcccc tccacaggcc gacgcggcga cgccgctgtt   60
tcaggttctg gaatttccag tgcgggtgca ttaggctgct atgggcaagt cgccgggaa   120
gtggatcaaa tcggtgcttt tggggaagaa atctaccaag tcctca ccaagtcgaa     180
tgaatctaag gctgacaaca acagatactc gaccggggag gaccgcacat tgtctgagag   240
ttctcctgtg atttctgagc cggtactagt taacatccac aagaacgtag ctatcaatgg   300
gaaggctgca gatgccagtg ataggcacg gcaacaagat ccgcagagcc aaagcgttgt   360
tgagtccaga tcatcggctc cagctgtcca gctgggagaa gatcaagctg cagcgaaggc   420
acaggcagcc tttcgtggtt acctggcacg aaggtcattc cgtgcattaa aaggtatcgt   480
aagactccag gcgctgattc gagggtatct tgtaaggagg caggctgtat caaccccttcg   540
cgcaacatgt tgattgtga gtttcaggc tctagttcgt ggaagaaatg ttagactctc   600
tggcagtcgc atgcagctca atgtgaagtt tggtcagagt aactttgggg tgttagatc   660
gtctgatgca tggaaagaga agctatcttc aaatgcttat gttcggaagc ttctgtcttc   720
accaattgtt ttagaacctc ttcacttcca gtatgacaag agggatccca attcaaccta   780
taactggttt gagagatgga ccataggttg catctggaag cctgctttc aacccaaaag   840
agttgctgat gggaaaccac tggtaaagaa ggctagttat gcaatggaaa ctcaatgca   900
caagttaaaa cgcaacattc ggaagggttc tgctgctatc gctgggagtt tccatacatc   960
tggtgaatct gataaagtaa aaaggaatcc aaagaatttc tctagcttcc ctgctgattc  1020
agtaccagat agccagttat ctgaacttga aaaggttaaa aggaacctca ggaaggtaac  1080
tgattcgatg gctgaagcct caaagatatc tagttccagg gttgattcct cgaaggtatg  1140
taattctaca gctgaggttc caaaggaatc taatcctgtg aaaaatct caaagatacg  1200
tagtctcctg aatgggatct ctgaccatca ggatattcaa tgtgagaata cacgtgaatc  1260
ttcatttcct cttggaactc aagaagactc tgacaatgat catctattgc gatattcaaa  1320
tatggatagc ttggacttgg tacctggttt gaaaagtgat caggaaattc agctggattc  1380
ggtttctata ggagaaaatt ttgatgatcc cactgttgtt gctccagcag ttgaagaaat  1440
gtcaccgcaa acattgata cggaagacaa tgttttatgc aagaaagagg aagcaaggtc  1500
caaggaagag cacttgtcta atggaagcct tagaactagc aagaggaagt cttcattccc  1560
caacaaatca gaatatgtag aaaatgggac tcacgctact cctgttcagc aacgcagcc  1620
aagctatatg gctgcaacgg agtccgcaaa ggcgaaattg cgagcccaga attcacccag  1680
tctggattct gattcagcgg cagaaaagaa tggtttcacc cgacgccact ctcttccttc  1740
cagtacaaag agtagagcac ttaaagctga atggaagcgc tgaagaggca acccatcgtc  1800
cacttgaatt gaattgtgca ctgctctgaa acttcgctgg atgaactcga ccggtcttgt  1860
cccatgttct tgctgtattg aacaaccct tgtgaagttg cgattctggt tcagtttgtt  1920
gtaggttcat gtgcaaccac tagtgccttg tgtcgtatat tgcatggttc ttgtcgaagg  1980
aacaatgcct gcgaaagctg atgttaggac tgcattaact gaataacatc acccagttgc  2040
ccaggtctt                                                         2049

SEQ ID NO: 11          moltype = AA  length = 560
FEATURE                Location/Qualifiers
source                 1..560
                       mol_type = protein
                       organism = Zea mays
REGION                 1..560
                       note = Ceres CLONE ID no.345954
REGION                 1..560
                       note = Score of 757.6 for HMM of FIGURE 5.
REGION                 1..560
                       note = Functional Homolog Of Ceres CLONE ID no. 1792354 at
                         SEQ ID NO. 2
REGION                 101..121
                       note = Pfam Name: IQ Pfam Description: IQ
                         calmodulin-binding motif
SEQUENCE: 11
MGKSPGKWIK SVLLGKKSTK SGPTKSNESK ADNNRYSTGE DRTLSESSPV ISEPVLVNIH   60
KNVAINGKAA DASDRARQQD PQSQVVESR SSAPAAQLGE DQAAAKAQAA FRGYLARRSF   120
RALKGIVRLQ ALIRGYLVRR QAVSTLRATW LIVKFQALVR GRNVRLSGSR MQLNVKFGQS   180
NFGGVRSSDA WKEKLSSNAY VRKLSSPIV LEPLHFQYDK RDPNSTYNWF ERWTIGCIWK   240
PAFQPKRVAD GKPLVKKASY AMETQSAKLK RNIRKGSAAI AGSFHTSGES DKVKRNPKNF   300
SSFPADSVPD SQLSELEKVK RNLRKVTDSM AEASKISSSR VDSSKVCNST AEVPKESNPV   360
AEISKIRSLL NGISDHQDIQ CENTRESSFP LGTQEDSDND HLLRYSNMDS LDLVPGLKSD   420
QEIQLDSVSI GENVDDPTVV APAVEEMSPQ NIDTEDNVLC KKEEARSKEE HLSNGSLRTS   480
```

```
KRKSSFPNKS EYVENGTHAT PVQPTQPSYM AATESAKAKL RAQNSPSLDS DSAAEKNGFT    540
RRHSLPSSTK SRALKAEWKR                                                560

SEQ ID NO: 12           moltype = DNA  length = 2049
FEATURE                 Location/Qualifiers
source                  1..2049
                        mol_type = other DNA
                        organism = Zea mays
misc_feature            1..2049
                        note = Ceres CLONE ID no.345954
misc_feature            1..2049
                        note = Encodes the peptide sequence at SEQ ID NO 11
SEQUENCE: 12
gtttttcgcc gagcagttcg cgtgctcccc tccacaggcc gacgcggcga cgccgctgtt   60
tcaggttctg gaatttccag tgcgggtgca ttaggctgct atgggcaagt cgccggggaa   120
gtggatcaaa tcggtgcttt tggggaagaa atctaccaag tcaggtccta ccaagtcgaa   180
tgaatctaag gctgacaaca acagatactc gaccggggag gaccgcacat tgtctgagag   240
ttctcctgtg atttctgagc cggtactagt taacatcccc aagaacgtag ctatcaatgg   300
gaaggctgca gatgccagtg atagggcacg gcaacaagat ccgcagagcc aaagcgttgt   360
tgagtccaga tcatcggctc cagctgctca gctgggagaa gatcaagctg cagcgaaggc   420
acaggcagcc tttcgtggtt acctggcacg aaggtcattc cgtgcattaa aaggtatcgt   480
aagactccag gcgctgattc gagggtatct tgtaaggagg cagctgtat caaccttcg    540
cgcaacatgg ttgattgtga agtttcaggc tctagttcgt ggaagaaatg ttagactctc   600
tggcagtcgc atgcagctca atgtgaagtt tggtcagagt aactttgggg tgttagatc    660
gtctgatgca tggaaagaga agctatcttc aaatgcttat gttcggaagc ttctgtcttc   720
accaattgtt ttagaacctc ttcacttcca gtatgacaaa agggatccca attcaaccta   780
taactggttt gagagatgga ccataggttg catctggaag cctgcttttc aacccaaaag   840
agttgctgat gggaaaccac tggtaaagaa ggctagttat gcaatggaaa ctcaatcagc   900
caagttaaaa cgcaacattc ggaagggttc tgctgctatc gctgggagtt ccatacatc    960
tggtgaatct gataaagtaa aaaggaatcc aagaaatttc tctagcttcc ctgctgattc   1020
agtaccagat agccagttat ctgaacttga aaaggttaaa aggaacctca ggaaggtaac   1080
tgattcgatg gctgaagcct caaagatatc tagttccagg gttgattcct cgaaggtatg   1140
taattctaca gctgaggttc caaaggaatc taatcctgtg gcagaaatct caaagatacg   1200
tagtctcctg aatgggatct ctgaccatca ggatattcaa tgtgagaata cacgtgaatc   1260
ttcatttcct cttggaactc aagaagactc tgacaatgat catctattgc gatattcaaa   1320
tatggatagc ttggacttgg tacctggttt gaaaagtgat caggaaattc agctggattc   1380
ggtttctata ggagaaaatg ttgatgatcc cactgttgtt gctccagcag ttgaagaaat   1440
gtcaccgcaa acattgata cggaagacaa tgttttatgc aagaaagagg aagcaaggtc   1500
caaggaagag cacttgtcta atggaagcct tagaactagc gaagaggaag t cttcattccc   1560
caacaaatca gaatatgtag aaaatggac tcacgctact cctgttcagc aacgcagcc    1620
aagctatatg gctgcaacgg agtccgcaaa ggcgaaattg cgagcccaga attcaccag    1680
tctgattct gattcagcgg cagaaaagaa tggtttcacc cgacgccact ctcttccttc    1740
cagtacaaag agtagagcac ttaaagctga atggaagcgc tgaagaggca acccatccgt   1800
cacttgaatt gaattgtgca ctgctctgaa acttcgctgg atgaactcga ccggtcttgt   1860
cccatgttct tgctgtattg aacaacccct tgtgaagttg cgattctggt tcagtcttgtc   1920
gtaggttcat gtgcaaccac tagtgccttg tgtcgtatat gcatggttc ttgtcgaagg    1980
aacaaatgcc gcgaaagctg atgttaggac tgcattaact gaataacatc acccagttgc   2040
ccaggtctt                                                           2049

SEQ ID NO: 13           moltype = AA  length = 574
FEATURE                 Location/Qualifiers
source                  1..574
                        mol_type = protein
                        organism = Zea mays
REGION                  1..574
                        note = Ceres LOCUS ID no. Os01m05025_AP003288
REGION                  1..574
                        note = Score of 858.7for HMM of FIGURE 5.
REGION                  1..574
                        note = Functional Homolog Of Ceres CLONE ID no. 1792354 at
                         SEQ ID NO. 2
REGION                  98..118
                        note = Pfam Name: IQ Pfam Description: IQ
                         calmodulin-binding motif
SEQUENCE: 13
MGKSPAKWIK SVLLGKKSAK SNSTKAKDLA KAANNKPVLS EDPPVISEPA LVNSHNDGNA   60
ENCKLPNGVA VEAMGQGVEN QNIVGSKAPT SPEKLSEELA AVKAQAAFRG YLARRAFRAL   120
KGIIRLQALI RGHLVRRQAA STLRVTWLIV KLQALVRGRN VRLSGASIQF VVKSGQHKFL   180
SDKPSDAWKE KVSSNAYVRK LLSSSIGLEA LHLQYDKRDP NSLYNWLERW TISQIWKSSS   240
QPKKVADGKP QVRKASYAME TESAKLKRNV RKSSAVTVDS FQTNMTVEPE KIKRNSRKFS   300
SSAADSVPDS QLSELEKVKR NLRKVTNSMA EASKISSSRA DASKVSSSMA DASKVSSSTA   360
DASKVSDSVA QIPPSLVNGI SDHQDNQCEE AQQNACVSFP PETQELHSGI LLEDNSHMNL   420
LEPDLISNPE TPFTSILTWE KFNDSTADAQ EVEVLPLQNI DNEDNFPENG VLGKKEKPRS   480
KEEPLSNGNL KTSKRRSSFS TKSDYPENGA QNTPVPRRKP SYMAATESAK AKLRGQNSPR   540
LDSDSPADMN GFTRRQSLPS STNNRAIRAE WRRW                                574

SEQ ID NO: 14           moltype = AA  length = 582
FEATURE                 Location/Qualifiers
source                  1..582
```

```
                        mol_type = protein
                        note = subspecies = indica
                        organism = Oryza sativa
REGION                  1..582
                        note = Public GI ID no.125527495
REGION                  1..582
                        note = Score of 851.5 for HMM of FIGURE 5.
REGION                  1..582
                        note = Functional Homolog Of Ceres CLONE ID no. 1792354 at
                          SEQ ID NO. 2
REGION                  98..118
                        note = Pfam Name: IQ Pfam Description: IQ
                          calmodulin-binding motif
SEQUENCE: 14
MGKSPAKWIK SVLLGKKSAK SNSTKAKDLA KAANNKPVLS EDPPVISEPA LVNSHNDGNA    60
ENCKLPNGVA VEAMGQGVEN QNIVGSKAPT SPEKLSEELA AVKAQAAFRG YLARRAFRAL   120
KGIIRLQALI RGHLVRRQAA STLRVTWLIV KLQALVRGRN VRLSGASIQF VVKSGQHKFL   180
SDKPSDAWKE KVSSNAYVRK LLSSSIGLEA LHLQYDKRDP NSLYNWLERW TISQIWKSSS   240
QPKKVADGKP QVRKASYAME TESAKLKRNV RKSSAVTVDS FQTNMTVEPE KIKRNSRKFS   300
SSAADSVPDS QLSELEKVKR NLRKVTNSMA EASKISSSRA DASKVSSSMA DASKVSSSTA   360
DASKVSDSVA QIPPSLVNGI SDHQDNQCEE AQQNACVSFP PETQELHSGI LLEDNSHMNL   420
LEPDLISNPE TPFTSILTWE KFNDSTADAQ EVEVLPLDVN DNEDNFPENG VLGKKEKPRS   480
KEEPLSNGNL KTSKRRSSFS TKSDYPENGA QNTPVPRRKP SYMAATESAK AKLRGQNSPR   540
LDSDSPADMN GFTRRQSLPS STNSKLNPHS PHTQGPIYFK FD                      582

SEQ ID NO: 15           moltype = AA  length = 580
FEATURE                 Location/Qualifiers
source                  1..580
                        mol_type = protein
                        note = subspecies = indica
                        organism = Oryza sativa
REGION                  1..580
                        note = Public GI ID no.125553119
REGION                  1..580
                        note = Score of 656.4 for HMM of FIGURE 5.
REGION                  1..580
                        note = Functional Homolog Of Ceres CLONE ID no. 1792354 at
                          SEQ ID NO. 2
SEQUENCE: 15
MGKSPAKWIK SVLFGKKSSR SGSTKAKDLS KGSNNKGYAA AGKDAGFESS PVISEPVLVT    60
PHNNEAVQEV GRGENSSLQG EVVVRDVSQD LEKQNTVVSD ASNDPERLRE EQAAVKAQAA   120
FRGYLHGIGP GTSGIPCVER NHKTPSPDSW ASRKEASRCN SSCNMVDCEV SSSSPWLTRP   180
HTRNMCPNLL ALKPHKQPIM LYKSYKSGKR DAWKEKLSSN AFARKLLASP ILVEALHFQY   240
DERDPNSAFN WLERWTIGRV WRPISHPKRA AVTDAKPHTR KASYAMETES GKLKRNSRRS   300
SAAPVESSQT NMAMETEKSR RNPRKFTSST ADSVPESQLT ELEKVKRNLR KVTNSMAEAS   360
KVSTPATEIP ERQEVQCEKP QRTAEEVPNY PEIQEPQNGN LLENAKTDIL VPDLQPEPEV   420
PSYQVETEEK VAELTVADPA VETMPLQDIH NEENALVNDN EQRSKEEPLS TESLKSSKRR   480
SSFSTKTEYP ENGSKNPAV PSYMAATQSA KAKLRGQNLP RLSSDSAEKN GFTRRHSLPS   540
SNGKLNSHSP RTQRPTHAGG KEGVKADKSM LSSRDASGKL                         580

SEQ ID NO: 16           moltype = DNA  length = 2368
FEATURE                 Location/Qualifiers
source                  1..2368
                        mol_type = other DNA
                        organism = Zea mays
misc_feature            1..2368
                        note = Ceres CLONE ID no.236431
misc_feature            1..2368
                        note = Encodes the peptide sequence at SEQ ID NO 17
SEQUENCE: 16
agctgattta ttttctctcg ctctcgcctt cgcggcgctg cctgcgcagt actacgagct    60
agcaggctag cagcaccagg accaggagcc tcttcccaca cttccgctct tcctctctct   120
cttttcctct gagaatggtt gtgtaggcgg gcgcaggagg gaggagagag aggggagcta   180
gctagggttt tgcgtcgccg cctttctgtta ccctaggct ctgaacccct ccggtccagt   240
gcggcggcgg attaggctcc gatgggaag tctccggcga agtggatcaa gtccgtgctc   300
ttcggtaaaa agtcgtcgtc gaggtccggc tccaccaagg ccaaggattt atcgaagggt   360
accactaaca aagcggcggc tgctgctgct gccgggaagg agcctgcgtt ctctgagagc   420
tctccggtca tctcggagcc tgtgcttgtt agcgcccaca acaatgagac cgcgcgggag   480
gccgctaagg gtgagaattc cagcgtgcaa gaagtgccag tgactgatgt tagtcaagac   540
ttggagaagc agggcactgt tggggtctgat acgtctaatg atgctgagag gttgagggaa   600
gagcaagcgg ccgtgaaggc acaagctgcc ttccgtggtt atctggcacg ccgagcattc   660
cgtgccctga aagggatcat aagactacag gcactgattc ggggacatct tgtaaggagg   720
caagctgttt caactctccg tgctacatgg ttgattgtga agtttcaagc ccttgtccgt   780
ggaaggaacg ttagacttt taaagttt cc attcaaccag ctagcatccg ttcccaacag   840
aacttcgggg gttctaaacc tggttcctgg aaggagaagt tgtcttcaaa tgcatttgct   900
cggaagcttc tctcttcacc aattgtggtt gaggctcttc atgtccagta tgatgagatg   960
gaccctaatt cggccttcaa ttggttagag aggtggacag taagtcatgt ctggaagcct  1020
atttcccaac caaagagagt tggtgctgat actaagcctc atacaaggaa ggccagttat  1080
gcaatggaaa cagagtcagc gaaattaaag cgtaatgcac ggaagagccc tgcagtgcca  1140
```

```
tttgagcctt ctcaaacaaa caccaccatt gaaaatgaga agacaagacg gaatccaagg    1200
aaattaagta gcactcctgc tgagtcagtt cccgatggcc agttaacaga acttgagaag    1260
gttaaacgta gccttaggaa ggttactagt tccatggttg aaacctcaaa ggtgcctagc    1320
ccaacaactg agattcctga ccgtcaagag gtacaatgtg agagaccact aagaagtgca    1380
aagcaagctc caattcatgt tgagaatcaa gaacctacga atgttaatct atcggacaat    1440
gcaaagatgg atattctggt accagatatc cagcctgacg tggaagttgc ttcagatcta    1500
gtcacaatca caaatgaaga aaaagttgat gagacaccgt ctgttgttgc tccagcgact    1560
gaaattatgc cactgcaaga catcaacagc gaagaaaatg ctttggtgaa tgatgtggaa    1620
gagagatcca aagaagaaca tccatctact gataacctga aaggcagcaa gaggaggtct    1680
tcattctcag ttaagcctga atatccagaa aatggctcca aaaattctcc agctctgcca    1740
agctacatgg ctgctacaca atctgcaaag gcgaaactgc gggggaattg ttccaagaa    1800
cttagctctg attcagcaga gaaaaacggg ttcactcgtc gtcactccct tccgtcccct    1860
aacaatggta agataaattc acattctcca cgtacgcaaa ggccaaccca tgctggtggc    1920
aaggacggag caaaaggcga caaggctatg ctgtcatcaa gagatgcgag cgagagacca    1980
ctgaaagctg agtggagacg ctgaggtggc gaatcaaaac cccaaaccct ccatttggtt    2040
agtgcaacta tttgggttgg tggatggcgt ctgcagtttg ctccgattgt tttgcttgtg    2100
atgtaaaaaa gacgttatca tcatcatccg aggcgatgaa cgggttcagc tttgttgtga    2160
tgaatctgct gggagtcaac ttatttacag ggttttgggt catgccttt gtgatgtata    2220
gctgaagtat tttcccggtt tgttttttgtt tcccagaccc ccagactccc ccctcccct    2280
cctgcttgct gagagggctg ctgatgttag agagaacgag aacctgtatg gattgagttg    2340
aacagaacaa tcttagtccc gtttggtc                                       2368

SEQ ID NO: 17          moltype = AA   length = 580
FEATURE                Location/Qualifiers
source                 1..580
                       mol_type = protein
                       organism = Zea mays
REGION                 1..580
                       note = Ceres CLONE ID no.236431
REGION                 1..580
                       note = Score of 1099.7 for HMM of FIGURE 5.
REGION                 1..580
                       note = Functional Homolog Of Ceres CLONE ID no. 1792354 at
                       SEQ ID NO. 2
REGION                 114..134
                       note = Pfam Name: IQ Pfam Description: IQ
                       calmodulin-binding motif
SEQUENCE: 17
MGKSPAKWIK SVLFGKKSSS RSGSTKAKDL SKGTTNKAAA AAAAGKEPAF SESSPVISEP     60
VLVSAHNNET AREAAKGENS SVQEVPVTDV SQDLEKQGTV GSDTSNDAER LREEQAAVKA    120
QAAFRGYLAR RAFRALKGII RLQALIRGHL VRRQAVSTLR ATWLIVKFQA LVRGRNVRLS    180
KVSIQPTTEL SQQNFGGSKP GSWKEKLSSN AFARKLLSSP IVVEALHVQY DEMDPNSAFN    240
WLERWTVSHV WKPISQPKRV GADTKPHTRK ASYAMETESA KLKRNARKSP AVPFEPSQTN    300
TTIENEKTRR NPRKLSSTPA ESVPDGQLTE LEKVKRSLRK VTSSMVETSK VPSPTTEIPD    360
RQEVQCERPL RSAKQAPIHV ENQEPQNVNL SDNAKMDILV PDIQPDVEVA SDLVTITNEE    420
KVDETPSVVA PATEIMPLQD INSEENALVN DVEERSKEEH PSTDNLKGSK RRSSFSVKPE    480
YPENGSKNSP ALPSYMAATQ SAKAKLRGNC SPRLSSDSAE KNGFTRRHSL PSPNNGKIIS    540
HSPRTQRPTH AGGKDGAKGD KAMLSSRDAS ERPLKAEWRR                          580

SEQ ID NO: 18          moltype = DNA   length = 2129
FEATURE                Location/Qualifiers
source                 1..2129
                       mol_type = other DNA
                       organism = Triticum aestivum
misc_feature           1..2129
                       note = Ceres CLONE ID no.908518
misc_feature           1..2129
                       note = Encodes the peptide sequence at SEQ ID NO 19
SEQUENCE: 18
agaacctctc tctctcctct gctccacgcc acagaagaga acaaacagta ggaggagcgc     60
tctccttcgg ccgcgagcgt ctgcgtcccg caatggaggc gtgatggttg gcgcggatag    120
aggggtagcg ggacagggaa ggtgagcaat ctgccgggag agcgccgacg ccccgcccag    180
tccagcccga gtccagaatt tccggtgttt gagcagtttt agtaggctgc tatggggaag    240
tccccggcca agtggataaa gtccgtgctc ctcgggaaga aatcaacaaa atccaattct    300
accaaggcaa aggatcttcc agcaaaggct gcaaacagca acggatgcac tgctgggaag    360
gagcctgaat cctctgataa ttctccccta atctcggagc cggtacttgt tagctcccac    420
aatgtgtctg aaatttccaa cttgcccaat gggagggcaa tcgaaaacat ggttagagtt    480
gggtccgaca cgcaaaattag tccagagaaa ctgagagaa aactagcaag agtgaaggcg    540
cgccgcgctt ttcgaggtta cctggcagcc agggccttcc gcgcattaaa aggtatcatc    600
agacttcagg cactgattcg agggcatctt gtaaggaggc aggccgtttc aacccttcgt    660
ggaacatggt tgattgtgaa gtttcaagct ctagttcgtg gaagaaatgt tagatttctct   720
agtgctgcca cgcaattagc tgtgaagttt ggtcaacata gtatgggggg tgacaagtcg    780
tcggatgcat ggaaggagaa gctatcttca catccatatg ttcaaagct tctgtcttca    840
ccaattttgg tacaagtctct tcacgttctg tatgatgaga caaacccaa ttcagcctct    900
aactggctgg agagatggac aataagctgc atctgaagc ctgttccaa accaaaata     960
gttactgacg ggaaaccaca gtaaggagg ccagttatg ccatggaaac tcactcagca   1020
aagttaaagc gcaatgttcg gaagtcttct actgccactg ttgagactca ggcaaatacc   1080
gttgaatctg aaaaatggaa aagaaaccca cggaaattga atggctcacc tgctgattca   1140
gtaccagaca gccagttatc tgaacttgag aaggttaaaa ggaaccttaa gaaggcagct   1200
```

-continued

```
aactccatgg ctgaagcctc taagatatct accaaggctg atgtgttgaa ggtacctaat  1260
tccatagctg atgagctgaa gatacttggt tccatggctg aactatcaaa aaaatccagc  1320
ataccaaacg gtatctctga ccatcaagac agcgaatgcg agaaagcact agagagtaca  1380
cgtgaggctg tgtttcctct tggaactcaa gattctcaca gtggcaatct tttggaaaat  1440
tcaaatataa gtaagttggt acctgacata aaatatgatc tagaagcatc attcttaggg  1500
gacaaagtta atgaacccac tactgtcgct caagcagatg aagtcataca actgcagaac  1560
cttgataacg gatatgatat tatagaaagg aagaagaga ctaggtccaa ggaagaacct  1620
ctgcctaatg gaagcttaa aaccaagaga aggtcttcgt tctctaattc agaataccct  1680
gagagtggaa ccaagaacac tccagttcca tcaaggaagc caagctatat ggctccaaca  1740
gaatcgttaa aggcgaaatt gcgaggacca cccagattag actctgatct accagtggac  1800
aagaatgcct tcactcgccg tcagtctctt ccttctgctg caaacaatag agcaatcaaa  1860
acagaatgga ggcggtgaag aggctatcaa gcttccaaca gaagggtgca ttattgtgga  1920
agaaatttca agctgtataa attattgatt agtttatgaa gtttgctgat gtctacctgt  1980
ctctgtcctt gttgttctgt ctacgttata aacatatgtt cttacgccct tttcgaacta  2040
gcttgtggtg atatgtttgg tgctattttt tcctcgagtt atcttatagt tccttggtcc  2100
gtgtattaaa tgtaaaaaaa aaaaaaaaa                                    2129
```

```
SEQ ID NO: 19          moltype = AA  length = 548
FEATURE                Location/Qualifiers
source                 1..548
                       mol_type = protein
                       organism = Triticum aestivum
REGION                 1..548
                       note = Ceres CLONE ID no.908518
REGION                 1..548
                       note = Score of 1274.3 for HMM of FIGURE 5.
REGION                 1..548
                       note = Functional Homolog Of Ceres CLONE ID no. 1792354 at
                         SEQ ID NO. 2
REGION                 97..117
                       note = Pfam Name: IQ Pfam Description: IQ
                         calmodulin-binding motif
SEQUENCE: 19
MGKSPAKWIK SVLLGKKSTK SNSTKAKDLP AKAANSNGCT AGKEPESSDN SPLISEPVLV   60
SSHNVSEISN LPNGRAIENM VRVGSDTQIS PEKLREELAA VKAQAAFRGY LARRAFRALK  120
GIIRLQALIR GHLVRRQAVS TLRGTWLIVK FQALVRGRNV RFSSAATQLA VKFGQHKYGG  180
DKSSDAWKEK LSSHPYVRKL LSSPILVQAL HVQYDETNPN SALNWLERWT ISCIWKPVSK  240
PKIVTDGKPQ VRRASYAMET HSAKLKRNVR KSSTATVETQ ANTVESEKWK RNPRKLNGSP  300
ADSVPDSQLS ELEKVKRNLK KAANSMAEAS KISTKADVLK VPNSIADELK ILGSMAELSK  360
KSSIPNGISD HQDSECEKAL ESTREAVFPL GTQDSHSGNL LENSNISKLV PDIKYDLEAS  420
FLGDKVNEPT TVAQADEVIQ LQNLDNGYDI IERKEETRSK EEPLPNGSLK TKRRSSFSNS  480
EYPESGTKNT PVPSRKPSYM APTESLKAKL RGPPRLDSDL PVDKNAFTRR QSLPSAANNR  540
AIKTEWRR                                                          548

SEQ ID NO: 20          moltype = AA  length = 574
FEATURE                Location/Qualifiers
source                 1..574
                       mol_type = protein
                       note = subspecies = Japonica
                       organism = Oryza sativa
REGION                 1..574
                       note = Public GI ID no.115465121
REGION                 1..574
                       note = Score of 966.7 for HMM of FIGURE 5.
REGION                 1..574
                       note = Functional Homolog Of Ceres CLONE ID no. 1792354 at
                         SEQ ID NO. 2
REGION                 111..131
                       note = Pfam Name: IQ Pfam Description: IQ
                         calmodulin-binding motif
SEQUENCE: 20
MGKSPAKWIK SVLFGKKSSR SGSTKAKDLS KGSNNKGYAA AGKDAGFESS PVISEPVLVT   60
PHNNEAVQEV GRGENSSLQG EVVVRDVSQD LEKQNTVVSD ASNDPERLRE EQAAVKAQAA  120
FRGYLARRAF RALKGIIRLQ ALIRGHLVRR QAVATLRATW LIVKFQALVR GRNVRLSTNT  180
IQVNWKLVQQ QSGSGKRDAW KEKLSSNAFA RKLLASPILV EALHFQYDER DPNSAFNWLE  240
RWTIGRVWRP ISHPKRAAVT DAKPHTRKAS YAMETESGKL KRNSRRSSAA PVESSQTNIA  300
METEKSRRNP RKFTSSTADS VPESQLTELE KVKRNLRKVT NSMAEASKVS TPATEIPERQ  360
EVQCEKPQRT AEEVPNYPEI QEPQNGNLLE NAKTDILVPD LQPEPEVPSY QVETEEKVAE  420
LTVADPTVET MPLQDIHNEE NALVNDMEQR SKEEPLSTES LKSSKRRSSF STKTEYPENG  480
SKNSPAVPSY MAATQSAKAK LRGQNSPRLS SDSAEKNGFT RRHSLPSSNG KLNSHSPRTQ  540
RPTHAGGKEG VKADKSMLSS RDASERPAKA EWKR                             574

SEQ ID NO: 21          moltype = DNA  length = 2529
FEATURE                Location/Qualifiers
source                 1..2529
                       mol_type = other DNA
                       organism = Panicum virgatum
misc_feature           1..2529
                       note = Ceres CLONE ID no.1791910
```

| misc_feature | 1..2529 |
| --- | --- |
| | note = Encodes the peptide sequence at SEQ ID NO 22 |

SEQUENCE: 21

```
ggattggagg ttggaggcct gaaggggggag gtgggtcgcc ggacagggac ggggagacgg   60
cgagagggcg ttccgcagga gccgttcccg tgcttcctcc accgaccggg ccgacgcgtc  120
gcgccgctgt ttcaggttcc cgcccctgca tttttctgct tgtgcttgcg ctagttgcga  180
gggtaggttg cggcgttaga gattggttcg cggcttctgt gcggcgctgt gtttgtttgg  240
ccagatccgc gtgtgtgctg ctgactcttc gtgatttcct cttctgtttg agctttcctt  300
gctcggcttt gtgctgctgc ctgccgctg ctttcttttc tggccactgc atttgggttg  360
tgtgccgcgc tacttatcct gctctgcttg tgtttaagat tacagctcgt gtttctttca  420
acgatatttt cacctttgtt tcatcacttg ggaagctggt gccgtaaaag agtctgctaa  480
accatgctaa ctttagcgaa attactgtta ctccagctgt ccagcatgtt ccttccttca  540
tcttagtgaa aataaagtat gttgtggcat actggtatgg atctgtgcat tgctgagagtc  600
ctctgtttac aggttccaga atttcaagta ttggccgctt taggatacta tgggaaagtc  660
cccggggaag tggatcaagt ctgtgctctt ggggaagaaa tcgactaaat ccggttctac  720
caaggcaaat gagtcggcta caaataacaa tggacactca gctggggagg agctgtgcatt  780
ttctgaaaat tctccagtga tctctgagcc ggtgcttgtt gaagcccaca aaaatggagc  840
tgtttcagtt aatgggaagg ctgaagatgt caatttgcca agtgacaggg ctggccaaca  900
agatctgcag aaccaaagta ttgttgagtc cgaaacatca gttcctgggc aattgggaga  960
agaccaagct gcagtgaagg cacaggcagc atttcgcggt tacctagcac gaaggtcatt 1020
ccgtgcattg aaaggtatca taagactcca ggcactgatt cgaggcatc ttgtaaggag 1080
acaggctgtt tcaacccttc aaactacttg gttgattgtg aagtttcaat ctctagttcg 1140
tggaagaaat gtcagactct ctggtgctga cattcaactc aatgtgaagc ttggccaaca 1200
taaccttggt ggcactagat catctgatgc atggaaagag aagttatctt caaatgccta 1260
tgttcggaag cttctgtctt caccaatagt gctagaacct cttcacttcc agtatgacaa 1320
gagggatccc aattcaacct ataactggct agagagatgc accataggct gcatctggaa 1380
gcctgttttt caaccaaaaa gagttcctga tgggaaactg ctggtaagga aggctagtta 1440
tgcaatggaa actgaatcag ccaagttaaa gcgcaacatt aggaagggct ctgctgctac 1500
agttgagagt ttccatacaa gagtgactgg tgaatctgag aaacttaaac gtaatccaaa 1560
gaaattctca aacttccctg ctgactcagt accagatagc cagttatctg aacttgagaa 1620
ggttaaaagg aacctgagga aggtaactga ttccatggct gaagcctcaa agatctctag 1680
ttccagggtt gattcctcaa aggtatcgaa ttctacacct gatgctccaa aagtatctaa 1740
tcctgtggcc gaaatctcaa agacatctag tctcctgaac gggatctctg accatcaaga 1800
cagccaatgt gaaaaagcac tacagaatac acgtgaggct tcatttcctc ttgaaactca 1860
agattactct ggcaatggtc agctattgga atattcagat atggataact tcgacttggt 1920
acctggtttg aaaagtggatc tggaaactca gcttgattca gtttctatag gagaaaatgt 1980
tgatgagccc actgttggtg cttcagcagc tgaaggtatg ccactgcaga acattgataa 2040
gcccaatagt ttagggaaga aagaggaagc aaggtccaag gaagagcatc tgtctaatgg 2100
aagccttaga actggcaaga gaaagtcttc atccccatac aaatcagaat atgtggaaaa 2160
cgggactcac actactcctg ctcagccaag gaagccaagc tatatggctg caacggagtc 2220
tgcgaaggcg aaattacgag cacagaattc acccagggtg gattctgatt catcagcaga 2280
aaagaatggc ttcactcgac gccactctct tccttccggt acaaacagta gggcgatcaa 2340
agctgaatgg aagcgctgag gaggcattgg cttgaattga gtgtcgat tgtctgaatc 2400
tctgctgggt gaactctgcc gctgcttgct ccttttatt tatcctgcga tgtaaagaga 2460
agacgttgtc cctgtattga acaatctttg tgatgagtgc gtctggttca aaaaaaaaaaa 2520
aaaaaaaaa                                                        2529
```

| SEQ ID NO: 22 | moltype = AA length = 569 |
| --- | --- |
| FEATURE | Location/Qualifiers |
| source | 1..569 |
| | mol_type = protein |
| | organism = Panicum virgatum |
| REGION | 1..569 |
| | note = Ceres CLONE ID no.1791910 |
| REGION | 1..569 |
| | note = Score of 824.9 for HMM of FIGURE 5. |
| REGION | 1..569 |
| | note = Functional Homolog Of Ceres CLONE ID no. 1792354 at SEQ ID NO. 2 |
| REGION | 105..125 |
| | note = Pfam Name: IQ Pfam Description: IQ calmodulin-binding motif |

SEQUENCE: 22

```
MGKSPGKWIK SVLLGKKSTK SGSTKANESA TNNNGHSAGE ERAFSENSPV ISEPVLVEAH   60
KNGAVSVNGK AEDVNLPSDR AGQQDLQNQS IVESETSVPG QLGEDQAAVK AQAAFRGYLA  120
RRSFRALKGI IRLQALIRGH LVRRQAVSTL QTTWLIVKFQ SLVRGRNVRL SGADIQLNVK  180
LGQHNLGGTR SSDAWKEKLS SNAYVRKLLS SPIVLEPLHF QYDKRDPNST YNWLERCTIG  240
CIWKPVFQPK RVPDGKLLVR KASYAMETES AKLKRNIRKG SAATVESPHT RVTGESEKLK  300
RNPKKFSNFP ADSVPDSQLS ELEKVKRNLR KVTDSMAEAS KISSSRVDSS KVSDSTPDAP  360
KVSNPVAEIS KTSSLLNGIS DHQDSQCEKA LQNTREASFP LETQDYSGNG QLLEYSDMDN  420
FDLVPGLKSD LETQLDSVSI GENVDEPTVG ASAAEGMPLQ NIDKPNSLGK KEEARSKEEH  480
LSNGSLRTGK RKSSSPYKSE YVENGTHTTP AQPRKPSYMA ATESAKAKLR AQNSPRVDSD  540
SSAEKNGFTR RHSLPSGTNS RAIKAEWKR                                    569
```

| SEQ ID NO: 23 | moltype = AA length = 567 |
| --- | --- |
| FEATURE | Location/Qualifiers |
| source | 1..567 |
| | mol_type = protein |
| | note = subspecies = Japonica |

```
                          organism = Oryza sativa
REGION                    1..567
                          note = Public GI ID no.125595019
REGION                    1..567
                          note = Score of 928.2 for HMM of FIGURE 5.
REGION                    1..567
                          note = Functional Homolog Of Ceres CLONE ID no. 1792354 at
                            SEQ ID NO. 2
REGION                    111..131
                          note = Pfam Name: IQ Pfam Description: IQ
                            calmodulin-binding motif
SEQUENCE: 23
MGKSPAKWIK SVLFGKKSSR SGSTKAKDLS KGSNNKGYAA AGKDAGFESS PVISEPVLVT   60
PHNNEAVQEV GRGENSSLQG EVVVRDVSQD LEKQNTVVSD ASNDPERLRE EQAAVKAQAA  120
FRGYLARRAF RALKGIIRLQ ALIRGHLVRR QAVATLRATW LIVKFQALVR GRNVRLSTNT  180
IQVNWKLVQQ QSGSGKRDAW KEKLSSNAFA RKLLASPILV EALHFQYDER DPNSAFNWLE  240
RWTIGRVWRP ISHPKRAAVT DAKPHTRKAS YAMETESGKL KRNSRRSSAA PVESSQTNIA  300
METEKSRRNP RKFTSSTADS VPESQLTELE KVKRNLRKVT NSMAEASKVS TPATEIPERQ  360
EVQCEKPQRT AEEVPNYPEI QEPQNGNLLE NAKTDILVPD LQPEPEVPSY QVETEEKVAE  420
LTVADPTVET MPLQDIHNEE NALVNDMEQR SKEEPLSTES LKSSKRRSSF STKTEYPENG  480
SKNSPAVPSY MAATQSAKAK LRGQNSPRLS SDSAEKNGFT RRHSLPSSNG KLNSHSPRTQ  540
RPTHAGGKEG VKADKSMLSS RDASGKL                                     567

SEQ ID NO: 24             moltype = AA  length = 636
FEATURE                   Location/Qualifiers
source                    1..636
                          mol_type = protein
                          organism = Arabidopsis thaliana
REGION                    1..636
                          note = Public GI ID no.42568886
REGION                    1..636
                          note = Score of 1517.7 for HMM of FIGURE 5.
REGION                    1..636
                          note = Functional Homolog Of Ceres CLONE ID no. 1792354 at
                            SEQ ID NO. 2
REGION                    129..149
                          note = Pfam Name: IQ Pfam Description: IQ
                            calmodulin-binding motif
SEQUENCE: 24
MGKTPSPGKW IKSLLGKKSS KSSLEKGGEK LRSAKKEELV VKVKDNNVSK LPTEPPVVSS   60
QEVAATQTVV VPDVVIAEKQ LSGDIEGDES SNVNLESGND SEEVKLEEAA TKVQAALRAQ  120
QAREESQNLK GITRVQAVIR GHLVRRQAVA TYSCIWGIVK VQALVRGKKA RSSETVAQLQ  180
KTNTETETSE TLQGSTYSWM ENPTKLSMID KLLVSSPTTL PLKIQYSPED PNSAKVWLGR  240
WTQLQVWAPG PLVVKNLVPK SQTKKRSFQA VEAEKGKLKR GVRKPTGVST TANSSTSRST  300
ADNEKPKRTV RKASTLGKEL SKIENDKSKQ SSRKSTSAIK EGSSVEVKDE KPRISHKKAS  360
LSNGIGKATR KSAEKKKEIA DAVQKELPIE EVSVSLVDAP EDEKMNLIPV TISKESDLDK  420
DEKSLVLDKP EQDELRTAER DDKAEEELKT AERDDSAEEK IQEPDAQISS ENGNVASENT  480
KPSDRRASLP AKIENHHQDD GLTQSGRKIP SYMAPTASAK ARIRGQSPSR IAQEKPEKNG  540
TTRRHSLPPA ANGKLSTMSP RAHRLLIASA KGSMNSDRSF SSSKDIGGKR FKPITIHKPF  600
CQFLLHYLHP FNKFSSCLYQ TSRRKLSGNG ESTKAE                           636

SEQ ID NO: 25             moltype = AA  length = 650
FEATURE                   Location/Qualifiers
source                    1..650
                          mol_type = protein
                          organism = Arabidopsis thaliana
REGION                    1..650
                          note = Public GI ID no.2947062
REGION                    1..650
                          note = Score of 1502.4 for HMM of FIGURE 5.
REGION                    1..650
                          note = Functional Homolog Of Ceres CLONE ID no. 1792354 at
                            SEQ ID NO. 2
REGION                    143..163
                          note = Pfam Name: IQ Pfam Description: IQ
                            calmodulin-binding motif
SEQUENCE: 25
MGKTPSPGKW IKSLLGKKSS KSSLEKGGEK LVRRVNRSAK KEELVVKVKD NNVSKLPTEP   60
PVVSSQEVAA TQTVVVPDVV IAEKQLSGDI EGDESSNVNL ESGNDSEEVK LEEAATKVQA  120
ALRAQQVNVY IFDILAREES QNLKGITRVQ AVIRGHLVRR QAVATYSCIW GIVKVQALVR  180
GKKARSSETV AQLQKTNTET ETSETLQGST YSWMENPTKL SMIDKLLVSS PTTLPLKIQY  240
SPEDPNSAKV WLGRWTQLQV WAPGPLVVKN LVPKSQTKKR SFQAVEAEKG KLKRGVRKPT  300
GVSTTANSST SRSTADNEKP KRTVRKASTL GKELSKIEND KSKQSSRKST SAIKEGSSVE  360
VKDEKPRISH KKASLSNGIG KATRKSAEKK KEIADAVQKE LPIEEVSVSL VDAPEDEKMN  420
LIPVTISKES DLDKDEKSLV LDKPEQDELR TAERDDKAEE ELKTAERDDS AEEKIQEPDA  480
QISSENGNVA SENTKPSDRR ASLPAKIENH HQDDGLTQSG RKIPSYMAPT ASAKARIRGQ  540
GSPRIAQEKP EKNGTTRRHS LPPAANGKLS TMSPRAHRLL IASAKGSMNS DRSFSSSKDI  600
GGKRFKPITI HKPFCQFLLH YLHPFNKFSS CLYQTSRRKL SGNGESTKAE            650
```

-continued

```
SEQ ID NO: 26           moltype = DNA   length = 1881
FEATURE                 Location/Qualifiers
source                  1..1881
                        mol_type = other DNA
                        organism = Populus balsamifera
                        sub_species = trichocarpa
misc_feature            1..1881
                        note = Ceres ANNOT ID no.1468228
misc_feature            1..1881
                        note = Encodes the peptide sequence at SEQ ID NO 27
SEQUENCE: 26
atggggagaa aatcacctgc gaaatggata aagactgttt tgtttggaaa gaagtcttcc    60
aaatctctta ttgtcaaagg aagggagaga actgtgaatg acaaagagac attggttgct   120
gtcagagccg tggaagctga tgtgacctca gttcctccgg tggtcaagcc gacagcccgt   180
actaccacta atatcactga aaggatgtta gagctagaga gcagggaaac tacagaatca   240
tcacgtgatg gaggtatatt gtcaactgga aatcaagatg caaatcattc tcaattatac   300
actcctgatg ctcctccatc tgatgctgac aaaataaggc ttgatgaagc tgcgacaatg   360
gcacaagccg catttagggg ttacttgata ggtgcactac tggggctgtt tcatggaccc   420
ttgagggttc gactgacttg gtaccaggct cgccgagcat ttcgagctct taaaggcata   480
ataaggcttc aggctcttat ccgtggacac ttggttagaa ggcaagctgt tgctactctc   540
tgctgtgtgc tcggagttgt caagttacag gctcttgctc gaggaagaat ggttaggaat   600
tcagagattg gctatgaggt tcataaaatta tgcagccaag taaaactgcc gagggcaaag   660
cttgcagatt ctagtggagt tggtatacaa atgccaagc tgtcatcaaa tgcttttgtt    720
cgcaagcttc ttgctccatc acctgctgta atgcctttgc aactccccta tgattccatg   780
gaaccaaact cagttgcaaa ctggttagag tgctggtcag cgtcctcttt ctggaaacca   840
gttccccaac caaaaaaaat tacttgctca aaaactcaga gaaagcaag taatggttca   900
atagtggaag ctgaaactgg taggccaaag cgcactgttc ggagggtccc tgctgcaaat   960
gttgacagta cctcagtaca agcagcctct gaatttgaga aacccaagcg caatttgagg  1020
aaagtttcaa gccatccagc tgattcagca gaaaattcac agattgagct tgaaaaggta  1080
aagcgcagct taagaaaggt taataacccc gttataaaa actctgctca ttcagaggtt  1140
gaaaatgaaa agccaaagca aggtctagaa aaggtatctg gcacttcagg tgataatgtt  1200
ttgggatgga gcgtaagtaa ttcagctgag aagatgaaga agaagctac cttgacaaca  1260
tccaatgtac ctgatgtggt gaagaatgat ccaaacttga tgtccaagtt gcctgatgca  1320
gagacagctg atgaacctgt agaaatgatc aaggcattgg aatcatcaca tgacgatcaa  1380
gctgtggtag aatctaaagc ttcagtagat actggtggta gttgagaa tatgcaaata  1440
aatgggaagt ccatacacca ggatgatcca acaagcaatg aaaatcacaa aactgccaag  1500
aaaccttcat tcacaatgaa accagaacgt gccgagaatg gctacgagag cagtcccacc  1560
ctccctagct acatggcagc aactgaatct gcaaaggcaa agctgagaat gcaaggctcc  1620
ccaagattta gtgaagatcg agttgagaaa aataacatca cccgtcgtca ttctctgccc  1680
tcttcaacta atagcaaaat cagctccgag tccccgagga cacaaagagc agttcatggt  1740
agtggcaaag gggggaataa gagtgacaag tctttattgt cttcaagaga tggaaatgct  1800
aagggagccc aaccagagtg gaagagatca tggtgtagca gtgaaacatg gtctatagcc  1860
ggaagggagt atgtggatta a                                            1881

SEQ ID NO: 27           moltype = AA   length = 626
FEATURE                 Location/Qualifiers
source                  1..626
                        mol_type = protein
                        note = subspecies =Trichocarpa
                        organism = Populus balsamifera
REGION                  1..626
                        note = Ceres ANNOT ID no.1468228
REGION                  1..626
                        note = Score of 1490.5 for HMM of FIGURE 5.
REGION                  1..626
                        note = Functional Homolog Of Ceres CLONE ID no. 1792354 at
                         SEQ ID NO. 2
REGION                  157..177
                        note = Pfam Name: IQ Pfam Description: IQ
                         calmodulin-binding motif
SEQUENCE: 27
MGRKSPAKWI KTVLFGKKSS KSLIVKGRER TVNDKETLVA VRAVEADVTS VPPVVKPTAP    60
TTTNITERML ELESRETTES SRDGGILSTG NQDANHSQLY TPDAPPSDAD KIRLDEAATM   120
AQAAFRGYLI GALLGLFSWT LRVRLTWYQA RRAFRALKGI IRLQALIRGH LVRRQAVATL   180
CCVLGVVKLQ ALARGRMVRN SEIGYEVHKL CSQVKLPEGK LADSSGVGIQ MAKLSSNAFV   240
RKLLAPSPAV MPLQLPYDSM EPNSVANWLE CWSASSFWKP VPQPKKITCS KTQRKQSNGQ   300
IVEAETGRPK RTVRRVPAAN VDSTSVQAAS EFEKPKRNLR KVSSHPADSA ENSQIELEKV   360
KRSLRKVNNP VIENSAHSEV ENEKPKQGLE KVSGTSGDNV LGWSVSNSAE KMKKEATLTT   420
SNVPDVVKND PNLMSKLPDA ETADEPVEMI KALESSHDDQ AVVESKASVD TGGIVENMQI   480
NGKSIHQDDP TSNENHKTAK KPSFTMKPER AENGLQSSPT LPSYMAATES AKAKLRMQGS   540
PRFSEDRVEK NNITRRHSLP SSTNSKISSE SPRTQRAVHG SGKGGNKSDK SLLSSRDGNA   600
KGAQPEWKRS WCSSETWSIA GREYVD                                       626

SEQ ID NO: 28           moltype = DNA   length = 2050
FEATURE                 Location/Qualifiers
source                  1..2050
                        mol_type = other DNA
                        organism = Gossypium hirsutum
misc_feature            1..2050
```

```
                       note = Ceres CLONE ID no.1942388
misc_feature           1..2050
                       note = Encodes the peptide sequence at SEQ ID NO 29
SEQUENCE: 28
atttagtttt aaattcacta aaaaaaagcc tgcacgagat tctccttgttc gaggaatcct   60
tcacgatctc tgaatgctca cagttccggt aatggcagct tagtaccgaa caaggacttc  120
atatttgata ctcttttcag atttccagat ttagaaactt gggattttaa ttattttgg   180
gtttaactga gatggggaaa tctccagcga aatggatcaa gaccttgctt cttgggaaga  240
aatcttcaaa gtccagtttc tcaaaaggaa aagataagct gaattctgca aataaaggtg  300
aggttttggt ttcttccaag gtaactgtgt ctgacctatc agcggattct ccatcgattt  360
cagcacctat tctagtgagc cgtgctagga atgtgatgga ctctgagaag gtataccctg  420
cccaattgcc gattgatggg gaaaatattc catctctaaa agtggatgga ataatgccaa  480
caaccggtaa ttttggtaac ccagaaaatc ctgataggat taggcttgac ccagctgctg  540
tgacagtaca ggctgctttc agaggttatc tggctgcccg ggaatttcga atcctcaagg  600
gcattataag gctgcaggca gttattcgtg tcacttggt tagaagacaa gctgttgcta   660
cttatgctg tacatgggga attgttaagt tgcaagcact agctcgtggt caaaaggtca   720
gatgttcaga tattgccatg gaaatacagg aaaaacatct aagactgctt cagggtttga  780
aaagctcaaa ttctctagga gcgagcatat cttctacagt gaagaattta tcaagtaatg  840
tgtttgttca gaagcttttg gcctcgtcac cttctgtatt gcctactaca cttcagtatg  900
ttccagagga gcctaactca tcctggcaat ggcttcaacg atggacaaga tcacaatttt  960
gggaataccc ctcaaaacca attaggagtg aaagacaaa gctaagtgtt cagaaactat   1020
cctttgcaaa agctgttaat ggatctagtc attctacatt ggagtatgaa aaaaataaac  1080
gaggtctgag gagaattct gtcaactcag cagcagattc agttcgggag catccacaaa   1140
atgagctcga gagggttaag cgcaatttaa gaaagctttc caactcttca aaggaggtta  1200
ctgataagtc tgagtttgtt aatgagaaaa caaagaagac tctgaaaaaa tattctagtt  1260
ctaatggccc tgatgtttta gaacaggaat ctgctgagaa gataagagat gtgactgcaa  1320
cactatcaga actgtcaatt cttgaggcag atctgaaatt ttcctcagaa catgcttctc  1380
ttggtgagcc tattgtctgt cctgcagttg attttccacc ggccaaaaac aatggtaaaa  1440
ttgagcacat gccactaaca gaggagttaa actctaagga tgagcaggtc ggtgatgaga  1500
gctcaaacac aaaccaaaga agagcttctt tcccagcaaa tattgataat caggcaaatc  1560
ggttaaatca catgccaaaa gtgcccagtt atatggcacc aactgaatct gcgaaagcta  1620
gacttagggg tcaagggtcc ccaaggttta tccccgaggc tgttgagaaa aatgggttaa  1680
acaggcggta ttctttgcca acttcaacca atagtaatac aggttcacaa tccccacata  1740
ctcaaagaca ggttcgagta gctggcaaga gtgctcatca cagtgacaaa tctcaatcat  1800
cctctaaaga tgctaatgat aaggtggtca gagccgagtg gaggaggtaa ttcttgcaca  1860
aggaattgtt tcgatgaagt ttccatgggg aaatatttgt agatgttaca gttgtttatt  1920
tggttcgttt ttgtttggac gtaaaattct ttggatcccc tgttcactct tttctaccat  1980
ttaatatcat aggaatagag tgtgcccatc tccatatctg gctttcgtag aaaaaaaaaa  2040
aaaaaaaaaa                                                          2050

SEQ ID NO: 29          moltype = AA  length = 552
FEATURE                Location/Qualifiers
source                 1..552
                       mol_type = protein
                       organism = Gossypium hirsutum
REGION                 1..552
                       note = Ceres CLONE ID no.1942388
REGION                 1..552
                       note = Score of 1315.8 for HMM of FIGURE 5.
REGION                 1..552
                       note = Functional Homolog Of Ceres CLONE ID no. 1792354 at
                         SEQ ID NO. 2
REGION                 113..133
                       note = Pfam Name: IQ Pfam Description: IQ
                         calmodulin-binding motif
SEQUENCE: 29
MGKSPAKWIK TLLLGKKSSK SSFSKGKDKL NSANKGEVLV SSKVTVSDLS ADSPSISAPI   60
LVSRARNVMD SEKGIPAQLP IDGENIPSLK VDGNNATTGN FGNPENPDRI RLDPAAVTVQ  120
AAFRGYLARR EFRILKGIIR LQAVIRGHLV RRQAVATLCC TWGIVKLQAL ARGQKVRCSD  180
IAMEIQEKHL RLLQGLKSSN SVGASISSTV KNLSSNVFVQ KLLASSPSVL PLQLQYVPEE  240
PNSSWQLQR WTRSQFWEYP SKPIRSGKTK LSVQKLSFAK AVNGSSHSTL EYEKNKRGLR   300
RISVNSAADS VREHPQNELE RVKRNLRKLS NSSKEVTDKS EFVNEKTKKT LKKYSSSNGP  360
DVLEQESAEK IRDVTATLSE LSILEADLKF SSEHASLGEP IVCPAVDFPP AKNNGKIEHM  420
PLTEELNSKD EQVGDESSNT NQRRASFPAN IDNQANRLNH MPKVPSYMAP TESAKARLRG  480
QGSPRFIPEA VEKNGLNRRY SLPTSTNSNT GSQSPHTQRQ VRVAGKGAII SDKSQSSSKD  540
ANDKVVRAEW RR                                                       552

SEQ ID NO: 30          moltype = AA  length = 570
FEATURE                Location/Qualifiers
source                 1..570
                       mol_type = protein
                       organism = Arabidopsis thaliana
REGION                 1..570
                       note = Public GI ID no.12324824
REGION                 1..570
                       note = Score of 428.7 for HMM of FIGURE 5.
REGION                 1..570
                       note = Functional Homolog Of Ceres CLONE ID no. 1792354 at
                         SEQ ID NO. 2
```

```
REGION                   105..124
                         note = Pfam Name: IQ Pfam Description: IQ
                             calmodulin-binding motif
SEQUENCE: 30
MIVFFFFFC SNYSYNNAQR VVSGKEVLVT SKVEESDVVS DLPSFEVAET NTVDRSGGML    60
ETQNVGPEEI SDDEIELPEG KSTDSQNVAP VQDHSLSDAE RIQREIAATS VQAAFRGYLA  120
RRAFWALKGI IRLQALIRGH LVRRQAVATL FSVMGIVRLQ AFARGREIRK SDIGVQVYRK  180
CRLQLLQGNK LANPTDAYLG IKKLTANAFA QKLLASSPKV LPVHAYDTSN PNSNLIWLEN  240
WSASCFWKPV PQPKKTISRK PQNRLLVEAE SAKPKKSVRK VPASNFESSS VQTSFEFEKP  300
KRSFRKVSSQ SIEPPAVEDP QIELEKVKRS LRKVHNPVVE SSIQPQRSPR KEVEKPKLGV  360
EKTRESSYPL VHETAEEPVN VCDEKKKQEI SEQPEEEVHA LEMEVHTGPG LETNEALDSS  420
LVNQIDSNEK AMVEEKPSME KDTKEEKTPK PNNKENSAGK ENQKSRKKGS ATSKTEREES  480
NGHHETSPSI PSYMQATKSA KAKLRLQGSP KSAEQDGTEK ATVPRRHSLP SPGNGRITSH  540
SPRTTRLANS GDKTGNKKEK PLLSSREGNG                                   570

SEQ ID NO: 31            moltype = AA   length = 570
FEATURE                  Location/Qualifiers
source                   1..570
                         mol_type = protein
                         organism = Arabidopsis thaliana
REGION                   1..570
                         note = Public GI ID no.5882749
REGION                   1..570
                         note = Score of 428.1 for HMM of FIGURE 5.
REGION                   1..570
                         note = Functional Homolog Of Ceres CLONE ID no. 1792354 at
                             SEQ ID NO. 2
REGION                   105..124
                         note = Pfam Name: IQ Pfam Description: IQ
                             calmodulin-binding motif
SEQUENCE: 31
MEMLAYFLSE FQICYNNAQR VVSGKEVLVT SKVEESDVVS DLPSFEVAET NTVDRSGGML    60
ETQNVGPEEI SDDEIELPEG KSTDSQNVAP VQDHSLSDAE RIQREIAATS VQAAFRGYLA  120
RRAFWALKGI IRLQALIRGH LVRRQAVATL FSVMGIVRLQ AFARGREIRK SDIGVQVYRK  180
CRLQLLQGNK LANPTDAYLG IKKLTANAFA QKLLASSPKV LPVHAYDTSN PNSNLIWLEN  240
WSASCFWKPV PQPKKTISRK PQNRLLVEAE SAKPKKSVRK VPASNFESSS VQTSFEFEKP  300
KRSFRKVSSQ SIEPPAVEDP QIELEKVKRS LRKVHNPVVE SSIQPQRSPR KEVEKPKLGV  360
EKTRESSYPL VHETAEEPVN VCDEKKKQEI SEQPEEEVHA LEMEVHTGPG LETNEALDSS  420
LVNQIDSNEK AMVEEKPSME KDTKEEKTPK PNNKENSAGK ENQKSRKKGS ATSKTEREES  480
NGHHETSPSI PSYMQATKSA KAKLRLQGSP KSAEQDGTEK ATVPRRHSLP SPGNGRITSH  540
SPRTTRLANS GDKTGNKKEK PLLSSREGNG                                   570

SEQ ID NO: 32            moltype = DNA   length = 1461
FEATURE                  Location/Qualifiers
source                   1..1461
                         mol_type = other DNA
                         organism = Zea mays
misc_feature             1..1461
                         note = Ceres CLONE ID no.325403
misc_feature             1..1461
                         note = Encodes the peptide sequence at SEQ ID NO 33
SEQUENCE: 32
aaatgcattt gctcgcaagc ttctatcttc atcaattgtg gttgaggctc ttcacttcca    60
gtatgatgag atgaccccta attcagcctt caattggtta gagaggtgga cgataagtca   120
tgtctggaag cccacttccc agccaaggag agttagtgct gatgctaagc cacatacaag   180
gaaggccagc tatgcaatgg aaacagagtc agtgaaatta agcgtaatg cacggaggag   240
ctctgcagtg ccatttgaac cttctcaaac aaacactgcc attgaaattg agaagacaag   300
acggaatcca aggaaattaa gtagcactcc tgctgagtca gttcctgatg ccagttaac   360
agaacttgag aaggttaaac gtagccttag gaaggttact aattctgttg ctgaaacctc   420
gaaggcacct agtccaaaaa ctgagattcc taaccatcaa gaggtccaat gtgagagacc   480
actaagaaga gcaaaacagg ttccaattca tcttgagaat caagagcctg ataatgttaa   540
tctgttggac aatgcaaaga tggatattct ggtacctgat atccagcctg atgtggaagt   600
tgcttcagat ccagtcacca tcactaatga gaaaatgtt gatgaaccac catctgttgt   660
tgctccagtg gccgaaatta tgcccctgca agacatcaac acgatgaaa atgctttggt   720
gaatgatgtg gaagagagat ccaaagaaga acatccttgt actgagagcc tgaaaggcag   780
caagaggagg tcttcattct cagctaagcc tgaatatcca gaaaatggct ccaaaaattc   840
tccagctctg ccaagctaca tggctgctac acaatcagca aaggcgaaac tgcggggaaa   900
tagctcacca aaacttagct ctgattcagc agagaaaaac ggcttcactc gtcgtcactc   960
ccttccatcc tctaacaacg gtaagatggt ttcacattct ccactgtacac aaaggccagc  1020
taatgctggt tgcaaggatg gagcgaaagg tgacaaggct atgctgtcat caagacgatgc  1080
aagcgagaga ccactgaaag ctgagtggag acgttgaggc ggcgaatcaa atccaaatcc  1140
tccatttgat tagcgtgacc gtttgggtgg atggatcgcc cttgcagttt gctcggattt  1200
gttttgtttg tgatgtaaaa aaatgatgtc gtcatcgtcg gcgagatgaa tgaaccggct  1260
ttgttgtga gaatccgctg ggagtcaact tatttattat agggttttcc gtcatgcctt  1320
ttgtgatgta tagctgaagt attttccgg tttgtttgg ttcccagacc cccagacttc  1380
ctcccttctt gttgagagct gctgatgtta gagagaatga gaacatgcat ggattgagtt  1440
gaacaatctt acccatttgg t                                             1461

SEQ ID NO: 33            moltype = AA   length = 371
```

| FEATURE | Location/Qualifiers |
|---|---|
| source | 1..371 |
| | mol_type = protein |
| | organism = Zea mays |
| REGION | 1..371 |
| | note = Ceres CLONE ID no.325403 |
| REGION | 1..371 |
| | note = Score of 576.4 for HMM of FIGURE 5. |
| REGION | 1..371 |
| | note = Functional Homolog Of Ceres CLONE ID no. 1792354 at SEQ ID NO. 2 |

SEQUENCE: 33

```
NAFARKLLSS SIVVEALHFQ YDEMDPNSAF NWLERWTISH VWKPTSQPRR VSADAKPHTR    60
KASYAMETES VKLKRNARRS SAVPFEPSQT NTAIEIEKTR RNPRKLSSTP AESVPDGQLT   120
ELEKVKRSLR KVTNSVAETS KAPSPKTEIP NHQEVQCERP LRRAKQVPIH LENQEPDNVN   180
LLDNAKMDIL VPDIQPDVEV ASDPVTITNE ENVDEPPSVV APVAEIMPLQ DINNDENALV   240
NDVEERSKEE HPCTESLKGS KRRSSFSAKP EYPENGSKNS PALPSYMAAT QSAKAKLRGN   300
SSPKLSSDSA EKNGFTRRHS LPSSNNGKMV SHSPRTQRPA NAGCKDGAKG DKAMLSSRDA   360
SERPLKAEWR R                                                       371
```

| SEQ ID NO: 34 | moltype = DNA   length = 783 |
|---|---|
| FEATURE | Location/Qualifiers |
| source | 1..783 |
| | mol_type = other DNA |
| | organism = Oryza sativa |
| | sub_species = Japonica |
| misc_feature | 1..783 |
| | note = Ceres GI ID no.56784328 |
| misc_feature | 1..783 |
| | note = Encodes the peptide sequence at SEQ ID NO. 35 |

SEQUENCE: 34

```
atgcggggtt tccccgttcc ggtgacgagt tggagctccg ccgcgctcct gggccgctcc    60
atctcctcgg ccaggacgc ggccgaggcc tcctccccca tcaccgccgc ggagatggtc   120
cgggtggcga aggaggtggc caacgccgcc gacgcctgcg gagtctccgg caagaagctg   180
ctggaggctg cggaagcgct gtccaggtcc gacaccgacg cggagccgag gcggcgggcg   240
gccgagcgga ttttcgatgc ggcgtccatg gtggccaagg aggccgacgc gtcaggagcg   300
tcgggtctct cagatgcggc ccaaaatctg acctgcgcga cctacgcgtt ctcggtagcc   360
gcctcggat ggggtcctt gccggagtcc agcacgagcg gagggacgc cggcgacctc   420
ctaaccgagc cccttcttgg gtcatgtcag gacaagaacg agaagatgac cggcgagggc   480
aaggacttca gcgagatgag gaatagtgca gcggactctg atccacttca gcaatcggag   540
attaaggagt cgtccctttt tggaaaatgc aaagaactcc tcaattatgg ttttcttgga   600
ggtcctgccc tcctacccta tctaggctct ggactgagga aaacagtgtc acctgcagc    660
ccgtctgtct tccactacat cttctcgtcg tggtggattt gcattgttgt cggatcacat   720
gaacaaggag acttgaagat attacatatc gatagaatca cttctcatcc aaatgataag   780
tag                                                                783
```

| SEQ ID NO: 35 | moltype = AA  length = 260 |
|---|---|
| FEATURE | Location/Qualifiers |
| source | 1..260 |
| | mol_type = protein |
| | note = subspecies = Japonica |
| | organism = Oryza sativa |
| REGION | 1..260 |
| | note = Ceres GI ID no.56784328 |
| REGION | 1..260 |
| | note = Score of 660.5 for HMM of FIGURE 6. |

SEQUENCE: 35

```
MRGFPVPVTS WSSAALLGRS ISSARDAAEA SSPITAAEMV RVAKEVANAA DACGVSGKKL    60
LEAAEALSRS DTDAEPRRRA AERIFDAASM VAKEADASGA SGLSDAAQNL TCATYAFSVA   120
ASGWGSLPES STSGRDAGDL LTEPLLGSCQ DKNEKMTGEG KDFSEMRNSA ADSDPLQQSE   180
IKESSLFGKC KELLNYGFLG GPALLPYLGS GLRKTVSPCS PSVFHYIFSS WWICIVVGSH   240
EQGDLKILHI DRITSHPNDK                                              260
```

| SEQ ID NO: 36 | moltype = AA  length = 311 |
|---|---|
| FEATURE | Location/Qualifiers |
| source | 1..311 |
| | mol_type = protein |
| | note = subspecies = Japonica |
| | organism = Oryza sativa |
| REGION | 1..311 |
| | note = Public GI ID no.56784330 |
| REGION | 1..311 |
| | note = Score of 826.7 for HMM of FIGURE 6. |
| REGION | 1..311 |
| | note = Functional Homolog Of Ceres GI ID no. 56784328 at SEQ ID NO. 35 |

SEQUENCE: 36

```
MESRLLRSAA LLARAARLAR AAATSTGRAV TAEHLAEVVA SAAGDRGFPS GALRQAALAL    60
ARSSAPEARP RATAEVVRAA AMVFRAAQEA GSPGVAEVAG DLAHAAHDCV RALVESGPAA   120
```

```
ERPRCLLRLW RRKNRHNKNA AGEADLEAPL LHPHERPSSS SSPIGASLSE IIELSESERD   180
FINYGMFGAL AIFPYLTRTG GLKSAYSPLS PSTFHIIFCT WWICVGLDVL CGNRGRAMMK   240
NILAFILAFY ARASARLAIL GVSLLVILYS HLELAPNEIY TLYILLGAAT CMHLLVWAMD   300
YMSRAPGDAA D                                                      311

SEQ ID NO: 37           moltype = AA  length = 311
FEATURE                 Location/Qualifiers
source                  1..311
                        mol_type = protein
                        note = subspecies = Indica
                        organism = Oryza sativa
REGION                  1..311
                        note = Public GI ID no.125528718
REGION                  1..311
                        note = Score of 812.3 for HMM of FIGURE 6.
REGION                  1..311
                        note = Functional Homolog Of Ceres GI ID no. 56784328 at
                         SEQ ID NO. 35
SEQUENCE: 37
MESRLLRSAA LLARAARLAR AAATSTGRAV TAEHLAEVVA SAAGDRGFPS GALRQAALAL    60
ARSSAPEASP RAAAEVVHAA AMVFRAAQEA GSPGVAEVGA DLAHAAHDCV RALVESGPAA   120
ERPRCLLRLW RRKNRHNKNA AGEADLEAPL LHPHERPSSS SSPIGASLSD IIELSQSERD   180
FINYGMFGAL AIFPYLTRTG GLKSAYSPLS PSTFHIIFCT WWICVGLDVL CGNRGRAMMK   240
NILAFILAFY ARASARLAIL GVSLLVILYS HLELAPNEIY TLYILLGAAT CMHLLVWAMD   300
YMSRAPGDAA D                                                      311

SEQ ID NO: 38           moltype = AA  length = 250
FEATURE                 Location/Qualifiers
source                  1..250
                        mol_type = protein
                        note = subspecies = Japonica
                        organism = Oryza sativa
REGION                  1..250
                        note = Public GI ID no.125572975
REGION                  1..250
                        note = Score of 571.2 for HMM of FIGURE 6.
REGION                  1..250
                        note = Functional Homolog Of Ceres GI ID no. 56784328 at
                         SEQ ID NO. 35
SEQUENCE: 38
MRGFPVPVTS WSSAALLGRS ISSARDAAEA SSPITAAEMV RVAKEVANAA DACGVSGKKL    60
LEAAEALSRS DTDAEPRRRA AERIFDAASM VAKEADASGA SGLSDAAQNL TCATYAFSVA   120
ASGWGSLPES STSGRDAGDL LTEPLLGSCQ DKNEKMTGEG KDFSEMRNSA ADSDPLQQSE   180
IKESSLFGKC KELLNYGFLG GPALLPYLGS GLRKTVSPCS PSVFHYIFSS WWICIVVVDE   240
LFVRIIDCSQ                                                         250

SEQ ID NO: 39           moltype = AA  length = 250
FEATURE                 Location/Qualifiers
source                  1..250
                        mol_type = protein
                        note = subspecies =Indica
                        organism = Oryza sativa
REGION                  1..250
                        note = Public GI ID no.125528716
REGION                  1..250
                        note = Score of 567.3 for HMM of FIGURE 6.
REGION                  1..250
                        note = Functional Homolog Of Ceres GI ID no. 56784328 at
                         SEQ ID NO. 35
SEQUENCE: 39
MRGFPVPVTS WSSAALLGRA ISSARDAAEA SSPITAAEMV RVAKEVANAA DACGVSDKKL    60
LEAAEALSRS DTDAEPRRRA AERIFDAASM VAKEADASGA SGLSDAAQNL TCATYAFSVA   120
ASGWGSLPES STSGRDAGDL LTEPLLGSCQ DKNEKMTGEG KDFSEMRNSA ADSDPLQQSE   180
IKESSLFGKC KELLNYGFLG GPALLPYLGS GLRKTVSPCS PSVFHYIFSS WWICIVVVDE   240
LFVRIIDCSQ                                                         250

SEQ ID NO: 40           moltype = DNA  length = 1443
FEATURE                 Location/Qualifiers
source                  1..1443
                        mol_type = other DNA
                        organism = Arabidopsis thaliana
misc_feature            1..1443
                        note = Ceres SEEDLINE ID no.ME06748
misc_feature            1..1443
                        note = Encodes the peptide sequence at SEQ ID NO. 41
SEQUENCE: 40
aattgtctct tcttttcttt ttgtacttgt caaaaacaaa aagaacaaca aaaaaaatct    60
caaccgtaga aaattccgac aagagttcag ttcatacaat gaactaagta tgggtttctt   120
tggaagactt ttcggaagta agaagcaaga aaaggcaaca ccgaacagac gaagatggag   180
```

-continued

```
cttcgctact agatcctcac atcccgagaa tgattcgtct tctcatccaa gcaagagacg    240
tggggatgaa gatgtcttaa acgccgacaa gcatgcgata gccgtcgcgg ctgctacagc    300
tgcagtggct gaagccgcac tcgctgctgc tcgtgcggcg gcggaagtcg tgagactcac    360
caatggtggt agaaactcgt cggtaaaaca aatcagtcgg agtaatcgtc ggtggtctca    420
agagtataaa gcagctatcc gcttttcgtg gctacttgtg gaggagggcg ttgagagcac    480
tgaaggcatt agtgaagctt caagcgttgt tgaagggaca catagtaagg aaacaaacgg    540
ctgatatgct gcgtcgaatg caaacgctgg ttcggctcca agcacgagct agagcttcgc    600
gttcttctca cgtttctgac tcttcccatc cgccaacact aatgattcca tcttccccac    660
aatctttcca tgcacgatgc gtttcagagg ctgagtacga taaagtcatt gccatggatc    720
accaccacaa caaccaccgt tcaccgatgg gttcaagccg gttattagac caatggagga    780
cagaggaaag tctatggagc gcaccaaagt acaatgaaga tgatgacaaa atcctagaag    840
tcgacacttg gaagcctcac ttcagagagt caccaaggaa aagaggatct ctagtggttc    900
ctacaagtgt ggagaacagt ccacaattaa ggtctagaac aggaagcagc agtggtggtt    960
caaggagaaa aactcccttc acgcctgcga gaagcgagta cgagtactac tctgggtatc   1020
accctaacta catggctaac actgagtctt acaaagcaaa agtccgatca caaagcgcac   1080
caagacagag actacaagat ttaccttcag agagtggtta caagaggtct atacagggac   1140
agtattacta ctacacacct gctgcagagc gatcgtttga tcagcgttcg gataacggga   1200
tcgcgggtta cagaggagtt tctgatgggt tagatccaaa ccaaagtgac aaatcgaaga   1260
tgtacacttc gttttcagt tctaatcctc ttttctttca atagtcgaga aggatgaaa    1320
aaagtgagtg gaatgtgtaa aattagattt cgacacacga gtacagagac agccagtgat   1380
caatctgtgt tttgtactat tttctaattg actgtatcca acaagggtcc attcttgtct   1440
gac                                                                 1443
```

```
SEQ ID NO: 41          moltype = AA   length = 252
FEATURE                Location/Qualifiers
source                 1..252
                       mol_type = protein
                       organism = Arabidopsis thaliana
REGION                 1..252
                       note = Ceres SEEDLINE ID no.ME06748
REGION                 1..252
                       note = Score of 176.1 for HMM of FIGURE 2.
SEQUENCE: 41
MLRRMQTLVR LQARARASRS SHVSDSSHPP TLMIPSSPQS FHARCVSEAE YSKVIAMDHH     60
HNNHRSPMGS SRLLDQWRTE ESLWSAPKYN EDDDKILEVD TWKPHFRESP RKRGSLVVPT    120
SVENSPQLRS RTGSSSGGSR RKTPFTPARS EYEYYSGYHP NYMANTESYK AKVRSQSAPR    180
QRLQDLPSES GYKRSIQGQY YYYTPAAERS FDQRSDNGIA GYRGVSDGLD RNQSDKSKMY    240
TSFFSSNPLF FQ                                                       252

SEQ ID NO: 42          moltype = AA   length = 517
FEATURE                Location/Qualifiers
source                 1..517
                       mol_type = protein
                       organism = Arabidopsis thaliana
REGION                 1..517
                       note = Ceres SEEDLINE ID no.ME20711
REGION                 1..517
                       note = Score of 943.4 for HMM of FIGURE 2.
REGION                 1..517
                       note = Functional Homolog Of Ceres SEEDLINE ID no. ME06748
                        at SEQ ID NO.41
REGION                 169..189
                       note = Pfam Name: IQ Pfam Description: IQ
                        calmodulin-binding motif
SEQUENCE: 42
MGKKGSWFSA IKRVFTPHSK EKQLSNNNQE PEIKSENKEK KKKGFGKKLR NGETNSFLPI     60
FRQPSSIEKI LSEAEREHNL VFRPPTPTDR ANSSSTSVAS PLVRPASPKV PSQRYVSSPK    120
PISPRVAYPQ VHYPKPPSPK PPSPRAVSPR IVQRREFVHR PEPSLLVKNA YAIKIQAAFR    180
GYMARRSFRA LKGLVRLQGV VRGHSVKRQT MNAMKYMQLL VRVQTQVQSR RIQMLENRAR    240
NDKDDTKLVS SRMSDDWDDS VLTKEEKDVR LHRKIDAMIK RERSMAYAYS HQLWKNSPKS    300
AQDIRTSGFP LWWNWVDRQK NQNQPFRLTP TRPSLSPQPQ SSNQNHFRLN NSFDTSTPNS    360
SKSTFVTPSR PIHTPQPYSS SVSRYSRGGG RATQDSPFKD DDSLTSCPPF SAPSYMAPTV    420
SAKAKLRANS NPKERMDRTP VSTNEKRRSS FPLGSFKWNK GSLFMSNNSN NKGPGSSSSG    480
AVVLEKHKTL KSVGNLSIDS TVSMPATIGR RAFNRFA                            517

SEQ ID NO: 43          moltype = AA   length = 383
FEATURE                Location/Qualifiers
source                 1..383
                       mol_type = protein
                       organism = Arabidopsis thaliana
REGION                 1..383
                       note = Ceres SEEDLINE ID no.ME18973
REGION                 1..383
                       note = Score of 543.8 for HMM of FIGURE 2.
REGION                 1..383
                       note = Functional Homolog Of Ceres SEEDLINE ID no. ME06748
                        at SEQ ID NO.41
REGION                 115..135
                       note = Pfam Name: IQ Pfam Description: IQ
```

```
                         calmodulin-binding motif
SEQUENCE: 43
MGRATRWFKG LFGIKPSSCS GTDSGTISNR LDRSLCDSYE TIPPNISEKE AAWLRSFYAA    60
GEEEKERRTH AIAVAAATAA AADAAVAAAK AAAAVVRLQG QGKSGPLGGG KSREHRAAMQ   120
IQCAFRGYLA RKALRALRGV VKIQALVRGF LVRNQAAATL RSMEALVRAQ KTVKIQRALR   180
RNGNAAPARK STERFSGSLE NRNNGEETAK IVEVDTGTRP GTYRIRAPVL SGSDFLDNPF   240
RRTLSSPLSG RVPPRLSMPK PEWEECSSKF PTAQSTPRFS GGSPARSVCC SGGGVEAEVD   300
TEADANRFCF LSGEFNSGYM ADTTSFRAKL RSHSAPRQRP ESNASAGGWR RSIGGGGVRM   360
QRQSCSGVRE AVVGNIERRR MRW                                           383

SEQ ID NO: 44           moltype = AA  length = 460
FEATURE                 Location/Qualifiers
source                  1..460
                        mol_type = protein
                        organism = Arabidopsis thaliana
REGION                  1..460
                        note = Ceres SEEDLINE ID no.ME08732
REGION                  1..460
                        note = Score of 822.2 for HMM of FIGURE 2.
REGION                  1..460
                        note = Functional Homolog Of Ceres SEEDLINE ID no. ME06748
                         at SEQ ID NO.41
REGION                  128..148
                        note = Pfam Name: IQ Pfam Description: IQ
                         calmodulin-binding motif
SEQUENCE: 44
MAKKKSWFSL VKRLFIWDTH STQDKKEKRR KWIFGRLKSK RLPSIKAPLP SKGTTLSEAE    60
QEQSKHALTV AIASAAAAEA AVTAAHAAAE VVRLTGQRNE NSEESQPVKT RNGAPQSTYQ   120
CQREIKESAA AIKIQTAFRG YLARKALRAL KGIVKLQAII RGAVRRQAM SSLKCLQSIV    180
SIQSQVCARR LQMVEGRCDY SENEEMQDFK DKIIRMDSNS ERKWDESTVL KEEVDTSCTS   240
KRERTKEYSF NHRRSAESER SKVNGRWRYW LEQWVDTQLS KSKELEDLDS VFSSHSRAGE   300
EYGGRQLKLR SNIQRQNPVE GLDSPILGSR RSFPHRRQCS VGEDHSFLSS PATPAYMAAT   360
ESAKAKARST SSPKIRTGGN VDMNSDSYSP CKKKLSIASS INSEMLSNGR VGKLSVNQQQ   420
RSPSFKGLSV PIKSSRTTIK DLSINSDCSL PNWDRQAFFK                         460

SEQ ID NO: 45           moltype = AA  length = 403
FEATURE                 Location/Qualifiers
source                  1..403
                        mol_type = protein
                        organism = Arabidopsis thaliana
REGION                  1..403
                        note = Ceres SEEDLINE ID no.ME19657
REGION                  1..403
                        note = Score of 695.5 for HMM of FIGURE 2.
REGION                  1..403
                        note = Functional Homolog Of Ceres SEEDLINE ID no. ME06748
                         at SEQ ID NO.41
REGION                  117..137
                        note = Pfam Name: IQ Pfam Description: IQ
                         calmodulin-binding motif
SEQUENCE: 45
MGFFGRLFGS KKKSDKAASS RDKRRWSFTT RSSNSSKRAP AVTSASVVEQ NGLDADKHAI    60
AVAAAATAAVA EAALTAAHAA AEVVRLTSGN GGRNVGGGGN SSVFQIGRSN RRWAQENIAA  120
MKIQSAFRGY LARRALRALK ALVKLQALVR GHIVRKQTAD MLRRMQTLVR LQSQARARAS   180
RSSHSSASFH SSTALLFPSS SSSPRSLHTR CVSNAEVSSL DHRGGSKRLD WQAEESENGD   240
KILEVDTWKP HYHPKPLRSE RNNESPRKRQ QSLLGPRSTE NSPQVGSSGS RRRTPFTPTS   300
RSEYSWGCNN YYYSGYHPNY MANTESYKAK VRSQSAPKQR VEVSNETSGY KRSVQGQYYY   360
YTAVEEESLD VGSAGYYGGG GGDSDRLNRN QSAKSRMHSS FLV                     403

SEQ ID NO: 46           moltype = DNA  length = 1711
FEATURE                 Location/Qualifiers
source                  1..1711
                        mol_type = other DNA
                        organism = Triticum aestivum
misc_feature            1..1711
                        note = Ceres CLONE ID no.835818
misc_feature            1..1711
                        note = Encodes the peptide sequence at SEQ ID NO 47
SEQUENCE: 46
ccaaatccaa tgctctacat ttcttccttc tcgtgccctt tcttgatttg cgcatggaca    60
gtgacttgcg ttgccagcaa agagccatcc tgctaggccc tttgccaaca tctccgtaga   120
tcacattcca gagcagatag acagaagaat ggagaggaag aagaagggt ggttcgagcg    180
catcaagagg ctcttcatct ccgaacccaa gcagaaaccc aaaccagaca agaaggtgaa   240
gagcaagaga tggctggtag ggaagctcaa gacccagcac tcgtttgcc tgccagctcc    300
ggagccggag ccggcgacgg gtcagattca gataaggcag gcggaggagg agcagagcaa   360
gcacgcagtg gcgtgcgcg tcgctccga gcggccgca gaggcagccg tcgcggccgc     420
ccacgcggcc gcggaggtgg tccgcctcac aggaccgccc tcgccggcgc cggcgccggc   480
gcgtgaggac gccgcgtctt ccggccacga actgttcgcc gccgtcgcga tccagtcagc   540
ctaccgcgga tacctcgcgc ggagggcact gcgcgcgctc aagggcctgg tgaggctgca   600
```

-continued

```
ggcggtgatc cgcgggcagg cggtgcggcg gaagacggcg gcgacgctgc ggggcctcga   660
gtcgctggtc aagatccagg cccggcagcg cgccagggcc gacgtcgacc acgagcacga   720
cggcgacggc atggacgccc tgctgaggag aggccgggag ctgtacgccg ccgcgctgca   780
agagcagcag cagagcagcc ggggggtggg acggcagcac cctctccaag gaagagatgg   840
gcgccgtgat gaggagcagg gaggaagccg ccatcaagcg cgtgcgcgcg ctgcagtacg   900
cctccatcca gaacgagaag atcggcatca ggaggcagcc catgtccagg gacgagatgg   960
agacgctcaa ccagcgctgg agctggctgg aggagtgggt cggctcgcag cccttcgaca  1020
aggacgtggc cgtcgacgtg gtcacccacc ccacccgcc gccgcctcgc tccagggact   1080
ccctcgcctg cctcgaggac gacgacgacc atgatgacga cggctatggc aggcggctcg  1140
gctactcgtc caggcggtcc ttcggccgcg ccaggcgcac gccagggagg gggagcgtcg  1200
acgacgggct gcaggcctgc tcgcggcggg tggctttccc ggggtacatg gcgtccacgg  1260
cgtccgccaa ggccaagttc cggtccatga gcacgcccaa ggagcgcttc gccgtgccat  1320
ccgacgcata ctcggagcag tgcttcgccg accgcctcat gtcacccatc ccgtccatgt  1380
cgccgatgcc gtccatcgcc agcgacatgg gtttgcctcg ctccagcagg ccgccggttg  1440
cgcagcggtc gccgcgtgtc aagggggggc cgatgacgcc gtcgaggatc cgctccagga  1500
ggtcccccag ccgccacagc ttcggctctg aagccgcgct gcaccagatg cagatggagc  1560
actacacccc tattcgctag acacaaacaa acttctttgt aatgtgacca atgctgcctt  1620
gtttggcggg cttgctctct ctgggtctga ccatggaaac cttctcaaac tgaccgtgct  1680
gtgcgaatgc aatatggatc tgcaaacttt c                                 1711
```

```
SEQ ID NO: 47           moltype = AA  length = 476
FEATURE                 Location/Qualifiers
source                  1..476
                        mol_type = protein
                        organism = Triticum aestivum
REGION                  1..476
                        note = Ceres CLONE ID no.835818
REGION                  1..476
                        note = Score of 855.1 for HMM of FIGURE 2.
REGION                  1..476
                        note = Functional Homolog Of Ceres SEEDLINE ID no. ME06748
                         at SEQ ID NO.41
REGION                  122..142
                        note = Pfam Name: IQ Pfam Description: IQ
                         calmodulin-binding motif
SEQUENCE: 47
MERKKKGWFE RIKRLFISEP KQKPKPDKKV KSKRWLVGKL KTQHSFALPA PEPEPATGQI    60
QIRQAEEEQS KHAVAVALAS AAAAEAAVAA AHAAAEVVRL TGPPSPAPAP AREDAASSGH   120
ELFAAVAIQS AYRGYLARRA LRALKGLVRL QAVIRGQAVR RKTAATLRGL ESLVKIQARQ   180
RARADVDHEH DGDGMDALLR RGRELYAAAL QEQQQSSRGW DGSTLSKEEM GAVMRSREEA   240
AIKRVRALQY ASIQNEKIGI RRQPMSRDEM ETLNQRWSWL EEWVGSQPFD KDVAVDVVTH   300
PHPPPPRSRD SLACLEDDDD HDDDGYGRRL GYSSRRSFGR ARRTPGRGSV DDGLQACSPA   360
VAFPGYMAST ASAKAKFRSM STPKERFAVP SDAYSEQCFA DRLMSPIPSM SPMPSIASDM   420
GFARSSRPPV AQRSPRVKGG PMTPSRIRSR RSPSRHSFGS EAALHQMQME HYTPIR      476
```

```
SEQ ID NO: 48           moltype = DNA  length = 1651
FEATURE                 Location/Qualifiers
source                  1..1651
                        mol_type = other DNA
                        organism = Panicum virgatum
misc_feature            1..1651
                        note = Ceres CLONE ID no.1796745
misc_feature            1..1651
                        note = Encodes the peptide sequence at SEQ ID NO 49
SEQUENCE: 48
gtagcactag ccactctcac tcccccccggc ggcatggaga aggagaagag gcggaggagc    60
tggttcgagc gcatcaggcg gctcttcacc tcctccgagc caaggagaa acccaaacct   120
gacaagaagg cgaagagcaa gcggtggcta ccggggaagc tgaggacgca gcagtcgttc   180
gctctgccgg cgccggccatc cgcggccgcg gacctgcaga tcaggcaggc ggaggacgag   240
cagagcaagc acgccgtgac cgtcgctctc gccaccgcgg cggccgcggca ggccgcggtc   300
gccgccgcgc acgccgccgc cgaggtcgtc cgcctcaccg ccagcaggc gcggccccg    360
ccggccgggc gggagcggga gctggaggag gaggagcatg ccgccgtctt gatccaatcg   420
gcgtaccgcg ggtacctggc tcggcgggcg ctgcgcgcgc tcaagggtct ggtgcggctg   480
caggcgctga tccggggggca ggcggtgcgg caccagacgg cgccgcctcc   540
gagtcgctga tgaggatcca ggcccagcac cgctcccggg ccgcggcccc cgaccacccg   600
gcggcgctcg acggcaacga cgacgccttc ctgctccggc gcggccggga gctctacgcc   660
gccgcggtcc accagcagca gcaggcgggc agcaaagggt gggacagcag catcctcgcc   720
aaggaggaga tgcgcgccgt gatgcggagc cgggaggagg ccgcccctcaa gcgcgtgcgc   780
gcgctgcagt acgcgtccct gcagagcgag aagatcggcc tcccggcgcc cgccctgccc   840
agggacgagg aggcggacgc gctccaccgc cgctggagct ggctcgagga gtgggtcggc   900
gcgcagccgc ccttcgacaa ggacgtcccc gtggcgcacc agtcgcccta cagcagggac   960
gacgccgccg ccgccagggg ccgccagacg cgggccgggg ccgtcgaccc gctcgccggc  1020
ctcggcggcg gcgacgccga ccggctcggt tgctcggcgc ggcggtcctt cgtcggccgg  1080
aggccgcggc cggccgccgg gggcgactac ttctacgagg ggcgtgctcg tgctcgggga  1140
gcgacgttcc cggggtacat ggcgtccacg gcctccgcca aggccaagtt ccggtccatg  1200
agcacgccca aggagcgctt cgccggagcc gacgccttct ccgagcactg cttcccgttc  1260
gccgaccgca tgctctcgcc gatccgtcc atgtcgccca tccctccat cgccagcgac  1320
atgggcttcc caggtccac caggccgccc gcgcgcagag atcgccgcg ggtggcggcc  1380
aagggccccca tgacgccggc gcggtcgcgc tcacggaggt cgccgagcca ccacagcttc  1440
```

```
ggctccgagg ccgcgctgca ccaactgcag atggagcact acaccccagt ccggtgaaca    1500
agactacaga gagtgccttg cttcgttaca ctcttttgtg aagatacaat tccctgctcc    1560
cattctttttg tttgttcacc tttcttgaca gaagggttca actgttcaag tattcagtaa   1620
tggaatgcaa caacgtaaaa aaaaaaaaaa a                                    1651

SEQ ID NO: 49              moltype = AA   length = 487
FEATURE                    Location/Qualifiers
source                     1..487
                           mol_type = protein
                           organism = Panicum virgatum
REGION                     1..487
                           note = Ceres CLONE ID no.1796745
REGION                     1..487
                           note = Score of 472.4 for HMM of FIGURE 2.
REGION                     1..487
                           note = Functional Homolog Of Ceres SEEDLINE ID no. ME06748
                             at SEQ ID NO.41
REGION                     121..141
                           note = Pfam Name: IQ Pfam Description: IQ
                             calmodulin-binding motif
SEQUENCE: 49
MEKEKRRRSW FERIRRLFTS SEPKEKPKPD KKAKSKRWLP GKLRTQQSFA LPAPASAAAD     60
LQIRQAEDEQ SKHAVTVALA TAAAAEAAVA AAHAAAEVVR LTGQQAAAPP AGRERELEEE    120
EHAAVLIQSA YRGYLARRAL RALKGLVRLQ ALIRGQAVRH QTAATLRGLE SLMRIQAHR    180
SRAGGPDHPA ALDGNDDAFL LRRGRELYAA AVHQQQQAGS KGWDSSILAK EEMRAVMRSR    240
EEAALKRVRA LQYASLQSER LGVRRPPLPR DEEADALHRR WSWLEEWVGA QPPFDKDVPV    300
AHQSPYSRDD AAAARGRQTP GRAVDPLAGL GGGDADRLGC SARRSFVRPR RAPARAGDYF    360
YEDAAPCSPA TFPGYMASTA SAKAKFRSMS TPKERFAGAD AFSEHCFPFA DRMLSPIPSM    420
SPIPSIASDM GFARSTRPPA AQRSPRVAAK GPMTPARSRS RRSPSHHSFG SEAALHQLQM    480
EHYTPVR                                                              487

SEQ ID NO: 50              moltype = AA   length = 501
FEATURE                    Location/Qualifiers
source                     1..501
                           mol_type = protein
                           note = subspecies = Indica
                           organism = Oryza sativa
REGION                     1..501
                           note = Public GI ID no.125543896
REGION                     1..501
                           note = Score of 538.7 for HMM of FIGURE 2.
REGION                     1..501
                           note = Functional Homolog Of Ceres SEEDLINE ID no. ME06748
                             at SEQ ID NO.41
REGION                     122..142
                           note = Pfam Name: IQ Pfam Description: IQ
                             calmodulin-binding motif
SEQUENCE: 50
MERKRRGWLE RIKRLFVSEP KQKPKPDKKV KSKRWMFAGK LKTQHSFALP APAPAVEEEQ     60
IRQAEDEQSK HAMAVALATA AAAEAAVAAA HAAAEVVRLT GKTAALAPAP ATTTTPTPYG    120
HEHAALMIQS VYRGYLARRA LRALKGLVRL QALIRGQAVR RQTAATLRGL ESLMKIQARQ    180
RARASSAAAA GGDHNAANSP APDGMDALLR RGRELYYAAA AAVHEQQLSK GWDSSTLSKE    240
EMSAMSRSRE EAALKRVRAL QYASLHQSEK VRVRRQPMSR EEMETLNQRW SWLEEWVGSQ    300
PPFDKDIPVA HQSPSRDAAG AAMNDDERPP PPPVLRSRSR ADRLACVGGD DDDADRQLGY    360
SARRSFTRAG RRTPARDDDG GGAAAFPGYM ASTASAKAKF RSMSTPKERS GAGAADAYSE    420
QCFPFADRLL SPIPSMSPIP SIASDIVFAR SSRPAAAQRS PRVKGPMTPT RSRSRRSPGR    480
HSFSSEAALH QLQMEQYTPI R                                              501

SEQ ID NO: 51              moltype = DNA   length = 1494
FEATURE                    Location/Qualifiers
source                     1..1494
                           mol_type = other DNA
                           organism = Populus balsamifera
                           sub_species = trichocarpa
misc_feature               1..1494
                           note = Ceres ANNOT ID no.1483984
misc_feature               1..1494
                           note = Encodes the peptide sequence at SEQ ID NO 52
SEQUENCE: 51
atgtcaggtc tatcagagtt gagaaatatg aaagttggaa aaaagatggg aggtcccatg     60
agtcttgaga aggatgttta tatgagttgt ggtgcttcaa tggctaagaa gagaagctgg    120
ttctatcgag tgaagaggtt atttacttct gacacacagt caagcaagaa aaaggaaagg    180
agaagaaaat ggatgttttt tggaaagttt aaggtcaaga atagattggc ctccattgca    240
gctccatcat caccactaag agaagaagca gagaaggagc agacaagca tgctctaagt    300
gttgctcttg ccactgctgc tgctgctgag gcagctgttg tagctgctca ggctgcggcc    360
gaggtggttt tgctcactgg tgttcctcat tctatcaatg aatatgagaa agaaaccgac    420
catttagcct tcgaagttca aggtgatgcc cctcattcca ctcatcaaca tgcgaggggg    480
atcaaagaac tggctgccat caaaattcaa gctacctttta ggggttacct tgcaaggaaa    540
gctttgcggg cgctgaaggg gatagtgaag cttcaagcaa ttatccgagg gcggaacgtg    600
```

```
agacgccaag ccatgactac tctaaaatgc ttgcaatcca ttgtaaatat ccagtcacaa    660
gtctgtgcaa aaaggatcca aatggtggaa ggtgcttgga cctgtagtga aaataaacag    720
ttagaaaatt tgagtgacaa gataataaag atggatatga atagtgaaag aagatgggat    780
agcagccttc tgacaaagga agaggcagtt gcctcgtttc taagcaagaa agaggccgcg    840
attagagag aacggataag agaatactgg ttcaaccgcc ggaattcagc tgaatcggag     900
cgaagcaagc caagtggaag gtggaggtac tggttagatc aatgggtgga tactcaactt    960
gttaagagta aagagcttga agatttggac tcagttttaa cctcaaatcc aaagcctgga   1020
gtggaatata gaggaaagca gattaaactg agaggtttgc agagactgta tcaccttgac   1080
agtgtagatt ctcccatttc agctccaaga aaatccttcc ataagaaagca atgctcgttg   1140
ggagaagaca attccttttc tagatctcct gtggttccaa cttacatggc aacaactgaa   1200
tctgccaagg caaaaacaag atcaatgagc tcaccaaagc taaggccagg gagttttgat   1260
gcttactctg acagctattc tccatgtaag aataagcttt ctctgatatc atctacaact   1320
actgaagtgc cgagcagtgc taggtacgga aggcctagtg cttatcagca aaggtctcca   1380
agcttgaagg gccttccggg tccgataaaa tgtaaccggc caacgtcgaa agttcttagc   1440
tttgattcag attgctcatt aaagacttgg gataaacaaa gttcctttag atga          1494

SEQ ID NO: 52            moltype = AA  length = 464
FEATURE                  Location/Qualifiers
source                   1..464
                         mol_type = protein
                         note = subspecies = trichocarpa
                         organism = Populus balsamifera
REGION                   1..464
                         note = Ceres ANNOT ID no.1483984
REGION                   1..464
                         note = Score of 498.0 for HMM of FIGURE 2.
REGION                   1..464
                         note = Functional Homolog Of Ceres SEEDLINE ID no. ME06748
                          at SEQ ID NO.41
REGION                   130..150
                         note = Pfam Name: IQ Pfam Description: IQ
                          calmodulin-binding motif
SEQUENCE: 52
MAKKRSWFYR VRRLFTSDTQ SRQEKERRRK WMFFGKFKVK NRLASIAAPS SPLREEAEKE     60
QSKHALSVAL ATAAAAEAAV VAAQAAAEVV LLTGVPHSIN EYEKETDHLA FEVQGDAPHS    120
THQHARGIKE LAAIKIQATF RGYLARKALR ALKGIVKLQA IIRGRNVRRQ AMTTLKCLQS    180
IVNIQSQVCA KRIQMVEGAW TCSENKQLEN LSDKIIKMDM NSERRWDSSL LTKEEAVASF    240
LSKKEAAIKR ERIREYWFNR RNSAESERSK PSGRWRYWLD QWVDTQLVKS KELEDLDSVL    300
TSNPKPGVEY RGKQIKLRGL QRLYHLDSVD SPISAPRKSF HRKQCSLGED NSFSRSPVVP    360
TYMATTESAK AKTRSMSSPK LRPGSFDAYS DSYSPCKNKL SLISSTTTEV PSSARYGRPS    420
AYQQRSPSLK GLPGPIKCNR PTSKVLSFDS DCSLKTWDKQ SSFR                      464

SEQ ID NO: 53            moltype = DNA  length = 1579
FEATURE                  Location/Qualifiers
source                   1..1579
                         mol_type = other DNA
                         organism = Gossypium hirsutum
misc_feature             1..1579
                         note = Ceres CLONE ID no.1924654
misc_feature             1..1579
                         note = Encodes the peptide sequence at SEQ ID NO 54
SEQUENCE: 53
aaggaaaaaa aactatagct ttcttcgttt atgtaatgga attcctcgcc aattctctct     60
caatctaagc tatccaagtt ccaaagacta agcttttttt gaagcggtga ttcctgtttg    120
attctcccaa aatatttaag tattcagtgc acctttata cacaatccat atggaattta    180
ccactatact atattatata agatgatgtt aggatgcaga aatgtaaaaa ttcagaaatg    240
tagtacctga agaagtgaga gttctttaat ggcgaagaag aagagctggt tcaatctagt    300
gaagaggttc tttctctttg agacacttat aaatgcacaa aaggataaca gaaggaaatg    360
gatgtttgga aggtttagga ccaaaaggtt agcatccatt aaagctccat caccaccaag    420
agacagcata aaatatgaaa cagaggagga ccagaagaaa catgccttaa cagtggcaat    480
tgccgcagtg gctgctgctg aagcagctgt tgcagctgct caggttgcag ccgaggttgt    540
tcgcctcaca ggcaatgacg cccctaaagc taaagaagaa caaaccaatg atgttaaacc    600
tgactgttct tcatctagtg agcttggcaa caagttccaa caacttgctg ctataaaaat    660
ccaggcttct tttcggggtt accttgcaag gaaagcttta agacgcattga aagggatagt    720
gaagcttcaa gcaattattc gaggccgagt tgtgagacga caagcattga ctgctttaaa    780
atgcttgcaa tcgattgtaa acattcagtc tcaagtttgt gcaaggagat tccaaattgt    840
agaaggcact tggcaacaac atgatgagaa caaagagttg ataactttga agataagat    900
tcttaaggtg gataccaaca gtcaaacaag atgggacaat tgtaatggag gattgaagta    960
ctggttagac caatgggtgg atactaaaag taaagatgtt gaagtcgaag acatagactc   1020
ggttttggact tcgaaccgca agcctacgag gctcaagact ttttcgagac agtatccattg   1080
tgatgcagaa gggtagatt ctccggtacg ggttcaagga cgacgatcat ttcatggaaa    1140
gcagagttct ttaggagaag atagttcttt tattacatct cctgtagttc aacttacat    1200
ggcagcaaca caatctacta aagcaaaggt aaggtcaatg agttccaccaa agctaaggcc   1260
aggaacttgt gatactcaat ccgaaagcta ttcaccatat aagaacaagt cgtgtctcat   1320
atcttcagtt acaagcaagc ctaacgctta tgagcagaga tccccaacac taaagggtgt   1380
aaagtcaaag aaaaccttga aggatcttag ctttaactct taatgttcat tgcctaattg   1440
ggtgcaaaaa agcaccttca aatgactcga ccattgtgat gttttaggtc ccttggaagc   1500
aagtcttgt tattgtgttt gtgtgagatt gctgatgctg ttttgtgctt aaacaattga   1560
atgaatcaag ttttgtgtg                                                1579
```

```
SEQ ID NO: 54           moltype = AA   length = 384
FEATURE                 Location/Qualifiers
source                  1..384
                        mol_type = protein
                        organism = Gossypium hirsutum
REGION                  1..384
                        note = Ceres CLONE ID no.1924654
REGION                  1..384
                        note = Score of 679.6 for HMM of FIGURE 2.
REGION                  1..384
                        note = Functional Homolog Of Ceres SEEDLINE ID no. ME06748
                         at SEQ ID NO.41
REGION                  125..145
                        note = Pfam Name: IQ Pfam Description: IQ
                         calmodulin-binding motif
SEQUENCE: 54
MAKKKSWFNL VKRFFLFETL INAQKDNRRK WMFGRFRTKR LASIKAPSPP RDSIKYETEE    60
DQKKHALTVA IAAVAAAEAA VAAAQVAAEV VRLTGNDAPK AKEEQTNDVK PDCSSSSELG   120
NKFQQLAAIK IQASFRGYLA RKALRALKGI VKLQAIIRGR VVRRQALTAL KCLQSIVNIQ   180
SQVCARRFQI VEGTWQQHDE NKELITLKDK ILKVDTNSQT RWDNCNGGLK YWLDQWVDTK   240
SKDVEVEDID SVWTSNRKPT RLKTFSRQYH CDAEGVDSPV RVQGRRSFHG KQSSLGEDSS   300
FITSPVVPTY MAATQSTKAK VRSMSSPKLR PGTCDTQSES YSPYKNKSCL LSSVTSKPNA   360
YEQRSPTLKG VKSKKTLKDL SFNS                                         384

SEQ ID NO: 55           moltype = DNA  length = 1032
FEATURE                 Location/Qualifiers
source                  1..1032
                        mol_type = other DNA
                        organism = Populus balsamifera
                        sub_species = trichocarpa
misc_feature            1..1032
                        note = Ceres ANNOT ID no.1468861
misc_feature            1..1032
                        note = Encodes the peptide sequence at SEQ ID NO 56
SEQUENCE: 55
atgaaggcaa ggagagcact aagggcacta aaagctttgg tgaagcttca agccttagtg     60
agaggccaca ttgtgagaaa gcaaacagca gacatgctta ggcgtatgca gacattagtg    120
agactgcagg ctcgagcccg tgctagtcgc agttatgtgt cggactcatc gcacactact    180
ggcaagtcct ctcattctcg ttatgctgtc cctgcaagtc cttcaaagga tcacctgttt    240
cgtgtttcta gtaccaaatt tgatgggccc tcgattctca agagatgtgg ttcaaatgca    300
aactttaggg agagcattga ctttgacaaa gtaaatgggg ttcgaactg ctagaccgt     360
tggatggaag aaagtttttt gaatgaccat ggcagcaatc caccgagaag tcgaaatgct    420
gatgatgaga agagtgacaa gattcttgaa gtggacactt ggaagcccca tgtgaaatcc    480
caacaaagta atagaacatt tcagacttca cagcatgctt ggcttcaga tcataacaat    540
cagagcttta tgactttga ctctatgtca aaactatcaa aaaagaacc gaatccaatg     600
ccgagcatct cttcaggaga aattttgcag tctcttaaat tacctctagg aaatgatgaa    660
gcagtttata ggaccgctga gaatagccct cgaatgttct ctgcaacatc tagacctgga    720
agtagtggtc ggagaggagg cccttttaca ccaacaagga gtgagtgctc gtggggcttc    780
tttaatggat actcgggtta cccccaactac atggctaaca ctgaatcatc tcgagccaag    840
gtcaggtcac aaagtgcccc aaggcagagg ctagagtttg agaaatatga ttcaagcaga    900
agatctgttc aggggtattc tgattcagaa actcgttcag aaaggggttt tgctcaaaat    960
actgaacttc aaaacaaagc ttacgtagca tctggctact tgaatagact agggacttcc   1020
gacttgaggt ga                                                      1032

SEQ ID NO: 56           moltype = AA   length = 343
FEATURE                 Location/Qualifiers
source                  1..343
                        mol_type = protein
                        note = subspecies = trichocarpa
                        organism = Populus balsamifera
REGION                  1..343
                        note = Ceres ANNOT ID no.1468861
REGION                  1..343
                        note = Score of 100.0 for HMM of FIGURE 2.
REGION                  1..343
                        note = Functional Homolog Of Ceres SEEDLINE ID no. ME06748
                         at SEQ ID NO.41
REGION                  10..30
                        note = Pfam Name: IQ Pfam Description: IQ
                         calmodulin-binding motif
SEQUENCE: 56
MKARRALRAL KALVKLQALV RGHIVRKQTA DMLRRMQTLV RLQARARASR SYVSDSSHTT    60
GKSSHSRYAV PASPSKDHLF RVSSTKFDGP SILKRCGSNA NFRESIDFDK VKWGSNWLDR   120
WMEESFLNDH GSNPPRSRNA DDEKSDKILE VDTWKPHVKS QQSNRTFQTS QHALASDHNN   180
QSFMTFDSMS KLSKKEPNPM PSISSGEILQ SLKLPLGNDE AVYRTAENSP RMFSATSRPG   240
SSGRRGGPFT PTRSECSWGF FNGYSGYPNY MANTESSRAK VRSQSAPRQR LEFEKYGSSR   300
RSVQGYSDSE TRSERGFAQN TELQNKAYVA SGYLNRLGTS DLR                    343
```

```
SEQ ID NO: 57            moltype = DNA  length = 1646
FEATURE                  Location/Qualifiers
source                   1..1646
                         mol_type = other DNA
                         organism = Glycine max
misc_feature             1..1646
                         note = Ceres CLONE ID no.1641776
misc_feature             1..1646
                         note = Encodes the peptide sequence at SEQ ID NO 58
SEQUENCE: 57
ctctctctca aaacccaaaa ctattccctt gtgagaactg aggagacata ataatgggta    60
aggcgtcgaa gtggtttcgc gggcttcttg gtctcaaaaa aacagagtat gccacctcac   120
ccgccaagcc tcccaaagag aaacgccggt ggagcttcgt taaatcatca tacacagaaa   180
aagacaacac cactgccgcc acgtgtccac cactaagaac aacaacaac cacgcaatgg    240
cagtagcagc agccaccgct gcggtggccc aagcggcggt ggctgccgcc gaagcagccg   300
ccgtcgtggt gagactaact agtaacagcg gcaggtgcgc cgacggcgga cccacccgga   360
ttcgccaaca tttgggctgct gttaagattc aagccgcttt tcgtggctgt ttggcaagga   420
gagcactgcg agcattaaag ggattggtga agttgcaagc attggtgaga ggcacattg    480
agagaaaacg gacggcagag tggctgaaaa gattgcaagc actcttacat gcacagaccc    540
aagtttctgc agggttgacc ctgcatgcct caccttcgag ttcaaagtta tcaagccacc    600
tccaaggtcc agaaacaccc gaaaaatttg aaagccccat tagatctaag agcatgaaac    660
atgagcactc acctatactc aagagaaatg gctccaaact ctgtgccctg atcaatggct    720
atcaagagat atgtgggagt agatcagaga gtcaagggaa tgaacaatta tggaactcag    780
gaagatcaat gaatagagca cacggctcca atgatgaaag aaatggcaag gttcttgaag    840
ttgattctgg aaaaccgcac ttcacactaa agcgtcgaaa cctctcttac tccacaggct    900
ctgatcttta tagtaagagt ttgaacagca caaaggaatc aacatctctt caatctgctc    960
aaagtccatg ttgtgaggtt cagtctcaca gttacagctc gcaaaagtg aacaatgagg    1020
ttgaggagag tccattctgc actgctgaca atagtccaca atacttatct gcctcttcta    1080
aagatgatgg cttcaaaaga agcccttta ctcctactag aagtgatggc tctagaagct    1140
acattcgcgg ttaccctgat tatcctagtt acatggcaga cactgaatct tcaaaggcaa    1200
aggccagatc tctgagtgca ccaaaacaaa ggcctcaaag tgagaggtct ggttcatcgg    1260
atagatactc actcaatgga tttgatatgt caagattggc cactcaaagg gcaatgcaag    1320
caagcttcac caacaaagca tatccaggtt ctggtcgttt ggacaagctt ggtatgcctg    1380
tggggtacag attctgattg agttatgttt atggtaagag ggttatttg tatcttttat     1440
ttttcatagt cttaaagtct taatatctga tcttgctaac caaccggctg tactttgagc    1500
ttccattgcg attttgtgtc agcattagaa atctacaacc aaattaagtg catactgcta    1560
agtctcaact ttcaagtcat tttattactt ggataaactg tgtaaaagaa ttattatctt    1620
tgcctttcaa aaaaaaaaaa aaaaaa                                         1646

SEQ ID NO: 58            moltype = AA  length = 447
FEATURE                  Location/Qualifiers
source                   1..447
                         mol_type = protein
                         organism = Glycine max
REGION                   1..447
                         note = Ceres CLONE ID no.1641776
REGION                   1..447
                         note = Score of 433.6 for HMM of FIGURE 2.
REGION                   1..447
                         note = Functional Homolog Of Ceres SEEDLINE ID no. ME06748
                          at SEQ ID NO.41
REGION                   106..126
                         note = Pfam Name: IQ Pfam Description: IQ
                          calmodulin-binding motif
SEQUENCE: 58
MGKASKWFRG LLGLKKTEYA TSPAKPPKEK RRWSFVKSSY TEKDNTTAAT CPPLRNNNNH     60
AMAVAAATAA VAEAAVAAAE AAAVVVRLTS NSGRCADGGP TRIRQHWAAV KIQAAFRGCL    120
ARRALRALKG LVKLQALVRG HIERKRTAEW LKRLQALLHA QTQVSAGLTL HASPSSSKLS    180
SHLQGPETPE KFESPIRSKS MKHEHSPILK RNGSKSCALI NGYQEICGSR SESQGNEQLW    240
NSGRSMNRAH GSNDERNGKV LEVDSGKPHF TLKRRNLSYS TGSDLYSKSL NSTKESTSLQ    300
SAQSPCCEVQ SHSYSSQKVN NEVEESPFCT ADNSPQYLSA SSKDDGFKRS PFTPTRSDGS    360
RSYIRGYPDY PSYMACTESS KAKARSLSAP KQRPQSERSG SSDRYSLNGF DMSRLATQRA    420
MQASFTNKAY PGSGRLDKLG MPVGYRF                                        447

SEQ ID NO: 59            moltype = DNA  length = 1434
FEATURE                  Location/Qualifiers
source                   1..1434
                         mol_type = other DNA
                         organism = Populus balsamifera
                         sub_species = trichocarpa
misc_feature             1..1434
                         note = Ceres ANNOT ID no.1438750
misc_feature             1..1434
                         note = Encodes the peptide sequence at SEQ ID NO 60
SEQUENCE: 59
atgggcaaag cttccaaatg gttccgtgcc gttctcggat taaaaaaacc cgacccacca     60
ctagaccacc cccaaaccac tcgttctaaa gacaaacgga gatggagttt tgttaagtcc    120
cgccgtgaaa aagaccacga ccaccaacag cgacaacaag atattgaagc cagtaaaact    180
ggtgttctgt acgggcagga gtttgaggag dcccccaaca agcatgcggt cgctgtggct    240
```

```
gctgctaccg ctgcagtcgc ggaggctgct gttgcagcgg ctcaggcagc tgccgaggtt    300
gtgagactta cgagtagtgg gaggtgtgtt aataacagtg tcgcgaacgt tagcgggagt    360
cttggattac gtgaagacct cgctgctgtt aagattcaag ctgctttccg tggctacctg    420
gctaggagag cattacgggc gttaaaggca ttggtgagac ttcaagctct ggtaagaggt    480
cacattggaga ggaagcgaac tgcagagtgg cttcatcgaa tgcaagcttt gctgcgagcg    540
cagtctcgag cacgttctgg acgtgcccaa atttctgaat cttctcattc aagtagcaag    600
tcctctcgct ttcaacaccc tggtccgcca acccctgaaa aattcgagca tgccattcgt    660
gccaggagtg gaaaatatga acaatcatca atacttaaga gaactgggtc aaaatgtaaa    720
ggcagagcaa ttggtgatct agacgttgca cacttatcct taaattggtc agacgtcgg    780
atggatgatc aaacatggga tcaccaagtc cctttggcag gaactggcac tattgatgat    840
gataagagtg acaagatcct tgagattgat actggaaaac cccacattac tcccaagcgt    900
agaaatctct ttcactcttc tcacctttcc ctgtcagatc agtatagcca tagtttcaca    960
actacaaaag actcgacagc ccatcaaact gttccaagtc cctcatcttg tgaagttcaa   1020
tctttaagtc cattgaagtt ttctcatgtt gtcgaaagt cattatgcac tgctgaaaat   1080
agcccacagt tctactctgc atcatcaagg ggtggtagta gtaagagaag tcccttcact   1140
cccagtagga gtgatggctc aagaaacttc ctaatcggtt attatggcta cccaaaattat   1200
atgtgtaaca ctgaatcttc gagggctaag gcgagatctc ttagcgctcc aaaacaaaga   1260
ccccaatatg agagatccag ttcaaccagg agatactcgg ttctcgggtg tggtgagcca   1320
agatcgagta gtgcacagca tgcttctgcc ttgcgtgcaa gttttctcaag caaagcttac   1380
cctggatctg gtcgcttgga caagctggga atgcctattg ggcagggata ctaa          1434

SEQ ID NO: 60           moltype = AA  length = 477
FEATURE                 Location/Qualifiers
source                  1..477
                        mol_type = protein
                        note = subspecies = trichocarpa
                        organism = Populus balsamifera
REGION                  1..477
                        note = Ceres ANNOT ID no.1438750
REGION                  1..477
                        note = Score of 852.9 for HMM of FIGURE 2.
REGION                  1..477
                        note = Functional Homolog Of Ceres SEEDLINE ID no. ME06748
                         at SEQ ID NO.41
REGION                  126..146
                        note = Pfam Name: IQ Pfam Description: IQ
                         calmodulin-binding motif
SEQUENCE: 60
MGKASKWFRA VLGLKKPDPP LDHPQTTRSK DKRRWSFVKS RREKDHDHQQ RQQDIEASKT    60
GVLYGQEFEE DPNKHAVAVA AATAAVAEAA VAAAQAAAEV VRLTSSGRCV NNSVANVSGS   120
LGLREDLAAV KIQAAFRGYL ARRALRALKA LVRLQALVRG HIERKRTAEW LHRMQALLRA   180
QSRARSGRAQ ISESSHSSSK SSRFQHPGPP TPEKFEHAIR ARSGKYEQSS ILKRTGSKCK   240
GRAIGDLDVA HLSLNWSERR MDDQTWDHQV PLAGTGTIDD DKSDKILEID TGKPHITPKR   300
RNLFHSSHLS LSDQYSHSFT TTKDSTAHQT VPSPSSCEVQ SLSPLKFSHV VEEALCTAEN   360
SPQFYSASSR GGSSKRSPFT PSRSDGSRNF LIGYYGYPNY MCNTESSRAK ARSLSAPKQR   420
PQYERSSSTR RYSVLGCGEP RSSSAQHASA LRASFSSKAY PGSGRLDKLG MPIGQGY       477

SEQ ID NO: 61           moltype = DNA  length = 1431
FEATURE                 Location/Qualifiers
source                  1..1431
                        mol_type = other DNA
                        organism = Populus balsamifera
                        sub_species = trichocarpa
misc_feature            1..1431
                        note = Ceres ANNOT ID no.1447395
misc_feature            1..1431
                        note = Encodes the peptide sequence at SEQ ID NO 62
SEQUENCE: 61
atgggtaaag cttccaaatg gttccgtgcc gttctcggcc tcaaaaaacc cgacccacca    60
ccagaccgcc ccgttacaac tcgttctaaa gaaaaaagga gatggagttt tgtcaagtcc   120
caccgtgaaa agaccaaca ccatcaccaa cagcaacaac aagagacgga agccgttaaa   180
gcaggcgttt tgtacgggca ggagtttgag gaggacccaa acaagcatgc gatcgctgtg   240
gctgctgcta ctgctgcagt tgcggaggct gcagttgctg ccgcgcaggc agctgcagag   300
gtggtgcggt taacaagcag tgggaggtgt gttgataaca gtgttgcgta cgttagcggg   360
agtcctggct tacgtgaaga cttcgctgct gttaagatcg aagctgcttt tcgtggctac   420
ctggcaagga gagcgttaag agcattaaaa gcgttggtga ggcttcaggc actggtaaga   480
ggtcaccttg agaggaagcg aacagcagag tggcttcatc gaatgcaagc attgctgaga   540
gcgcaggctc gagcacgtgc aggacgtgcc caaatttctg aatcctccca ctcaagcagc   600
aagtcttctc gctatcacct ccctggtctg caacccatg aaaaatccga gcatgccatt   660
cgtgctacga gtgaaaata tgaacaatca tcaatgctta agaactggg tcaaaaaact   720
aaaggcagag aaattgccga tcaagatgtt gcacacttat ccttcaattg gtcagaacat   780
ggaatggata gtagaacatg ggatcatcaa gccccttcgc caggaactgg ccccattgat   840
gatgacaaga tccttgagat tgattctgga aaacccacata ttactcctaa cgcagaaat   900
ctcttttcacc cttctcacct ttcctttgtct gcggatcagt atagccatcagt tttcacacaa   960
tcaaaaggct ccacagtccg tcaagcagtt ccaagccct catctggcga agttcaatct  1020
ttcagtccat tgaaattctc tcatgaggtt gaggaagcat tttgcaccgc tgataatagc  1080
cgcaattct gctctgcatc atcaaggggt ggcagtggta agagaagtcc cttcactccc  1140
agtaggagtg gtggctctag aagcttcatg agtggatact ctgactaccc aaaattatatg  1200
tgtaacactg aatcttcaag ggctaaggtg agatctctaa gcgctccaaa acaaagaccc  1260
```

```
cagtatgaga gatccagctc aaccaagaga tactcggttc tcggctttgg tgaacaaaga      1320
tcgagtagtg cacagagtgc ttctgccttg cgtgcaagtt ttacaagtaa agcttaccct      1380
ggatctggtc gtttggacag gctgggaatg cctgttgggc agaaatacta a              1431

SEQ ID NO: 62           moltype = AA  length = 476
FEATURE                 Location/Qualifiers
source                  1..476
                        mol_type = protein
                        note = subspecies = trichocarpa
                        organism = Populus balsamifera
REGION                  1..476
                        note = Ceres ANNOT ID no.1447395
REGION                  1..476
                        note = Score of 696.6 for HMM of FIGURE 2.
REGION                  1..476
                        note = Functional Homolog Of Ceres SEEDLINE ID no. ME06748
                         at SEQ ID NO.41
REGION                  149..169
                        note = Pfam Name: IQ Pfam Description: IQ
                         calmodulin-binding motif
SEQUENCE: 62
MGKASKWFRA VLGLKKPDPP PDRPVTTRSK EKRRWSFVKS HREKDQHHHQ QQQQETEAVK      60
AGVLYGQEFE EDPNKHAIAV AAATAAVAEA AVAAAQAAAE VVRLTSSGRC VDNSVAYVSG     120
SPGLREDFAA VKIEAAFRGY LARRALRALK ALVRLQALVR GHLERKRTAE WLHRMQALLR     180
AQARARAGRA QISESSHSSS KSSRYHLPGL PTHEKSEHAI RATSGKYEQS SMLKRTGSKT     240
KGREIADQDV AHLSFNWSEH GMDSRTWDHQ APSPGTGPID DKILEIDSG KPHITPKRRN      300
LFHPSHLSLS ADQYSHSFTT SKGSTVRQAV PSPSSGEVQS FSPLKFSHEV EEAFCTADNS     360
PQFCSASSRG GSGKRSPFTP SRSGGSRSFM SGYSDYPNYM CNTESSRAKV RSLSAPKQRP     420
QYERSSSTKR YSVLGFGEQR SSSAQSASAL RASFTSKAYP GSGRLDRLGM PVGQKY         476

SEQ ID NO: 63           moltype = AA  length = 484
FEATURE                 Location/Qualifiers
source                  1..484
                        mol_type = protein
                        organism = Arabidopsis thaliana
REGION                  1..484
                        note = Public GI ID no.79482785
REGION                  1..484
                        note = Score of 311.2 for HMM of FIGURE 2.
REGION                  1..484
                        note = Functional Homolog Of Ceres SEEDLINE ID no. ME06748
                         at SEQ ID NO.41
REGION                  167..187
                        note = Pfam Name: IQ Pfam Description: IQ
                         calmodulin-binding motif
SEQUENCE: 63
MGKASRWFRS LFGVKKPDPG YPDLSVETPS RSTSSNLKRR WSFVKSKREK ESTPINQVPH      60
TPSLPNSTPP PPSHHQSSPR RRRKQKPMWE DEGSEDSDKH AIAVAAATAA VAEAAVAAAN     120
AAAAVVRLTS TSGRSTRSPV KARFSDGFDD VVAHGSKFYG HGRDSCELAV IKIQSIFRGY     180
LAKRALRALK GLVRLQAIVR GHIERKRMSV HLRRMHALVR AQARVRATRV IVTPESSSSQ     240
SNNTKSSHFQ NPGPPTPEKL EHSISSRSSK LAHSHLFKRN GSKASDNNRL YPAHRETFSA     300
TDEEEKILQI DRKHISSYTR RNRPDMFYSS HLILDNAGLS EPVFATPFSP SSSHEEITSQ     360
FCTAENSPQL YSATSRSKRS AFTASSIAPS DCTKSCCDGD HPSYMACTES SRAKARSASA     420
PKSRPQLFYE RPSSKRFGFV DLPYCGDTKS GPQKGSALHT SFMNKAYPGS GRLDRLGMPI     480
GYRY                                                                  484

SEQ ID NO: 64           moltype = AA  length = 543
FEATURE                 Location/Qualifiers
source                  1..543
                        mol_type = protein
                        organism = Arabidopsis thaliana
REGION                  1..543
                        note = Public GI ID no.3292832
REGION                  1..543
                        note = Score of 277.0 for HMM of FIGURE 2.
REGION                  1..543
                        note = Functional Homolog Of Ceres SEEDLINE ID no. ME06748
                         at SEQ ID NO.41
REGION                  167..187
                        note = Pfam Name: IQ Pfam Description: IQ
                         calmodulin-binding motif
SEQUENCE: 64
MGKASRWFRS LFGVKKPDPG YPDLSVETPS RSTSSNLKRR WSFVKSKREK ESTPINQVPH      60
TPSLPNSTPP PPSHHQSSPR RRRKQKPMWE DEGSEDSDKH AIAVAAATAA VAEAAVAAAN     120
AAAAVVRLTS TSGRSTRSPV KARFSDGFDD VVAHGSKFYG HGRDSCELAV IKIQSIFRGY     180
LAKRALRALK GLVRLQAIVR GHIERKRMSV HLRRMHALVR AQARVRATRV IVTPESSSSQ     240
SNNTKSSHFQ NPVSLVKPFM IVPFNLKHGP PTPEKLEHSI SSRSSKLAHS HLFKVLHFQL     300
LFVSSVFVAC GPISSKFQRL YKLLTLLYVQ NKSNLKWNG SKASDNNRLY PAHRETFSAT      360
DEEEKILQID RKHISSYTRR NRPDMFYSSH LILDNAGLSE PVFATPFSPS SSHEEITSQF     420
```

```
CTAENSPQLY SATSRSKRSA FTASSIAPSD CTKSCCDGDH PSYMACTESS RAKARSASAP    480
KSRPQLFYER PSSKRFGFVD LPYCGDTKSG PQKGSALHTS FMNKAYPGSG RLDRLGMPIG    540
YRY                                                                 543

SEQ ID NO: 65           moltype = DNA   length = 1799
FEATURE                 Location/Qualifiers
source                  1..1799
                        mol_type = other DNA
                        organism = Zea mays
misc_feature            1..1799
                        note = Ceres CLONE ID no.1559074
misc_feature            1..1799
                        note = Encodes the peptide sequence at SEQ ID NO 66
SEQUENCE: 65
aagactctcc cagtcccttc ctctcctgct gcctttctct cttctcggtg aagcgtgtgt     60
tcatttcact gttttggttt catctcccgc tctttcttta ccccgtgctc cggccaagtg    120
ctggaaccaa gaaagcctca tggggcggcc ggccgacggg cggtagagag gcggagatgg    180
gctgggcgcc taggtggctg cgcgggctgc tcggcggcgg caggaaggcc gccgtgacga    240
agccggcgaa ggagaagaag ctctggggat tcgggaagtc cttccgggaa aaggaccccg    300
cgccagcgcc ggaacggcct cggacgcctt cggtgcagcc cacggcgacg cctcgccggg    360
ggtttgcggc ggcgccggat gaggcggacg acgagcagag caagcgtgct atcgctgtgg    420
ccgcggcgac ggcggcggtg gcagaggccg ccgtcgctgc tgcccaggcg gccgccgccg    480
tggtgcggtt gacgagctcc ggccggtgcc caccgccggc cgccgcgaag cgggaggagt    540
gggcggctgt tcggatccag gccgctttcc gtggctacct ggcgaggcgg gcgctgaagg    600
cgttgagggg gctggtgaag ctgcaggcgc tggtccgggg caacattgtg cggcggcagg    660
cggcggagac gctgcgatgc atgcacgcgc tcgtccggcg ccaggcgcgc gcgcgcgcgt    720
gtcgcgcaat tcgctcgcag catgtcgcgg ctcatccgga tccgccaacg ccggagaagt    780
acgatcaggc gggtgcccccc aggcacgccc gttccggctc tctgaaggca aactcttcca    840
agacgccggg cggcgagagg ctgggtaggg agaggtcgga tcttgcgggg aggaactggc    900
tggaccgctg ggtggaggag aggtacacgg acgacgagaa gaacgccaag attctcgaag    960
tggacaacgg caagccaggg cggcacggtt ccaagcggcg cggcggcaac catcaccagt   1020
cgccgtgctc gacgatgacc tccgagcaga cagccggag ctacgcgacc atgccggagt    1080
cgccgtccaa ggactcgacg accgcgcagc agtccgtgcc gagcccgtcg tccgtgggca   1140
tggctgccga ggccctgagc ccgctgcgcg tgccagcgga catcgccgag ctctgcgaca   1200
gccccccagtt cttctcggcg acgtcgcggc ccgggagctc caggaggggg ggcgcgttca   1260
cgccggcggc caagagcgag tgctcgcgca gcctcttcgg cggctactcc gactgcccca   1320
actacatggc gaacacggag tcgttccgcg ccaaggcgcg ttcccagagc gcgcccaagc   1380
agaggccgca gcagcagtac gagaagtcgg gctccctccg cagggcgtcg gcgcacgccc   1440
tcgccggggg gccggcagcg gcacagaggt cggtgcctc gttgcacgcc atgaaggcgt   1500
atccgggctc cggcagattg gaccgacttg gcatgccggt caggtactga tccggatcct   1560
acctagctcg cttcaggata atgtggtgct gcgcctgaac tgattgatac ccagtgtctc   1620
aactcaagcg atgaggatga agtgaattct actagtggtc gttattagat cttgttcctt   1680
cggtggtgcc tattaccgtc aacagttttc tgtttgttgc tttgtgtagc gaagtgtaag   1740
ttgctggtac gtagctggta atactatgcg tgcttaaccg cgaaaaaaaa aaaaaaaaa    1799

SEQ ID NO: 66           moltype = AA   length = 457
FEATURE                 Location/Qualifiers
source                  1..457
                        mol_type = protein
                        organism = Zea mays
REGION                  1..457
                        note = Ceres CLONE ID no.1559074
REGION                  1..457
                        note = Score of 855.0 for HMM of FIGURE 2.
REGION                  1..457
                        note = Functional Homolog Of Ceres SEEDLINE ID no. ME06748
                         at SEQ ID NO.41
REGION                  121..141
                        note = Pfam Name: IQ Pfam Description: IQ
                         calmodulin-binding motif
SEQUENCE: 66
MGWAPRWLRG LLGGGRKAAV TKPAKEKKLW GFGKSFREKD PAPAPERPRT PSVQPTATPR     60
RGFAAAPDEA DDEQSKRAIA VAAATAAVAE AAVAAAQAAA AVVRLTSSGR CPPPAAAKRE    120
EWAAVRIQAA FRGYLARRAL KALRGLVKLQ ALVRGNIVRR QAAETLRCMH ALVRVQARAR    180
ACRAIRSQHV AAHPDDPPTPE KYDQAGAPRH ARSGSLKANS SKTPGGERLG RERSESCGRN   240
WLDRWEERY TDDEKNAKIL EVDNGKPGRH GSKRRGGNHH QSPCSTMTSE QNSRSYATMP    300
ESPSKDSTTA QQSVPSPSSV GMAAEALSPL RVPADIAELC DSPQFFSATS RPGSSRRGGA    360
FTPAAKSECS RSLFGGYSDC PNYMANTESF RAKARSQSAP KQRPQQQYEK SGSLRRASAH    420
ALAAGPAAAQ RSVASLHAMK AYPGSGRLDR LGMPVRY                            457

SEQ ID NO: 67           moltype = DNA   length = 1821
FEATURE                 Location/Qualifiers
source                  1..1821
                        mol_type = other DNA
                        organism = Panicum virgatum
misc_feature            1..1821
                        note = Ceres CLONE ID no.1726548
misc_feature            1..1821
                        note = Encodes the peptide sequence at SEQ ID NO 68
```

```
SEQUENCE: 67
gtctagaccc ttcctttctc tcctgctgtc cctttttgctc ttctcggtgt aagcgtgtgc   60
gcgtttcact gctttggttt catctcccgc tcttttcttc ctccccactg ctcctccggc  120
caagtgctgg aacgaggaag cctcatgcgg ccgccggccg gggagcggta gagcgccgga  180
gatgggctgg gcgcccaggt ggctgcgcgg gctgctcggc ggcggcaaca aggccgccga  240
gacgaagccc gtgaaggaaa agaggcgctg ggggttcggg aagtccttca gggagaaggc  300
gccggcgccg gtggcggcgc ggcctccgac gccgccggtg cagcccacgg cgacgcctcg  360
ccggggctac gcgccggcgc cggacgaggc ggacgacgag cagagcaagc gcgccatcgc  420
ggtggccgcg gccactgcgg cggttgcgga ggccgccgta gccgcggcgc aggcggccgc  480
cgccgtggtg cggctgacga gcagcgggcg gtgcgccgcg gccgccgcca gcgggagga  540
gtgggcgggct gttcggatcc aggccgcttt ccgtggatac ctggcgaggc gggcgctcaa  600
ggcgctgcgg gggctggtga agctgcaggc gctggttcgg ggcaacatcg tgcggcggca  660
ggcggcggag acgctgcgt gcatgcacgc gctcgtccgc gtccaggcgc gcgcccgcgc  720
ctgccgcgca attcgctcgc agcaggtccc ggctcaccca gatccgccga cgcccggagaa  780
gtacgatcag gcgggtgccc ccaggcacgg cgcgttccggc tctctaaagg ggagctcgtc  840
gaagacaccg ggcagcgaga ggctgggcag ggagaggtcg gaatcttgcg ggaggaactg  900
gctggaccgg tgggtggagg agaggtacat ggacgacgag aagaacgcca agatcctgga  960
ggtgacaac ggcaagccag ggcggtatgc ttccaagagg ccggctcgcg gcggcaacca 1020
gcaccagtcg ccgtgctcga cgatgacgtc cgaccagaac agccggagct acgcgaccat 1080
gccggagtcg acgaccgcgc agcggtccgt gccgagcccg ccgtcggtgg catgggcga 1140
ggccctgagc ccgctccgcc tgcccgtgga cattgccgag ctctgcgaca gcccacagtt 1200
cttctcggcg tcgtctcggc cgggagctc ccggcgaggg ccctcaccc cgacaagag 1260
cgagtgctcc cgcagcctct tcgggggcta ctccgactac cccaactaca tggccaacac 1320
ggagtcgttc cgcgccaagg cgcgctccca gagcgcgccc aagcagaggc cgcactacga 1380
caagtccagc tccctccgca aggcgtcggc ggcgcaggcc tacttgacgg ggccgtgcgc 1440
gccgacgcg cagcagaggt cggcggcctc gctgcacgca aagttcacca acaaggcgta 1500
cccgggctct ggcaggctgg atcgactcgg catgcccgtc aagtactgat cctgttatgt 1560
tatcctacca aagttgcttt ctggagtggt gttgcttctt gagcgatcag tgtctcagct 1620
ctcgagcaag gtcgatgaag taaaatctag tagtggtcgt taggcttttg tgtgccttcc 1680
tggtgctgtt accctcgaca gttttctgtt tcttgctttt taatagcgaa gtgtaagttg 1740
gtagtagctg cactgtaata ctatctgtgc tttaacagtt taactgctaa gtgctaactc 1800
caaaaaaaaa aaaaaaaaa a                                            1821

SEQ ID NO: 68       moltype = AA  length = 455
FEATURE             Location/Qualifiers
source              1..455
                    mol_type = protein
                    organism = Panicum virgatum
REGION              1..455
                    note = Ceres CLONE ID no.1726548
REGION              1..455
                    note = Score of 892.2 for HMM of FIGURE 2.
REGION              1..455
                    note = Functional Homolog Of Ceres SEEDLINE ID no. ME06748
                    at SEQ ID NO.41
REGION              120..140
                    note = Pfam Name: IQ Pfam Description: IQ
                    calmodulin-binding motif
SEQUENCE: 68
MGWAPRWLRG LLGGGNKAAE TKPVKEKRRW GFGKSFREKA PAPVAARPPT PPVQPTATPR   60
RGYAPAPDEA DDEQSKRAIA VAAATAAVAE AAVAAAQAAA AVVRLTSSGR CAPAAAKREE  120
WAAVRIQAAF RGYLARRALK ALRGLVKLQA LVRGNIVRRQ AAETLRCMHA LVRVQARARA  180
CRAIRSQQVP AHPDPPTPEK YDQAGAPRHG RSGSLKGSSS KTPGSERLGR ERSESCGRNW  240
LDRWVEERYM DDEKNAKILE VDNGKPGRYA SKRRGGGGNQ HQSPCSTMTS DQNSRSYATM  300
PESTTAQRSV PSPPSVGMGE ALSPLRLPVD IAELCDSPQF FSASSRPGSS RRGPFTPSKS  360
ECSRSLFGGY SDYPNYMANT ESFRAKARSQ SAPKQRPHYD KSSSLRKASA AQAYLTGPCA  420
PTAQQRSAAS LHAKFTNKAY PGSGRLDRLG MPVKY                             455

SEQ ID NO: 69       moltype = AA  length = 464
FEATURE             Location/Qualifiers
source              1..464
                    mol_type = protein
                    note = subspecies = japonica
                    organism = Oryza sativa
REGION              1..464
                    note = Public GI ID no.115459996
REGION              1..464
                    note = Score of 886.1 for HMM of FIGURE 2.
REGION              1..464
                    note = Functional Homolog Of Ceres SEEDLINE ID no. ME06748
                    at SEQ ID NO.41
REGION              124..144
                    note = Pfam Name: IQ Pfam Description: IQ
                    calmodulin-binding motif
SEQUENCE: 69
MGWASRWLRG LLGGGKKPNS GSGDPKPARE KKRWGFGKSF REKSPAHPPP PPPPSAAVQR   60
AVTPRRAYTA SDEGDDEQSK RAIAVAAATA AVAEAAVAAA QAAAAVVRLT SSGRCAPAAA  120
KREEYAAVRI QAAFRGYLAR RALKALRGLV KLQALVRGNI VRRQAAETLR CMHALVRVQR  180
RARACRAIRS QHVSAHPGPP TPEKYDQATH EGVPKHGRSG SLKGSSSKTP GSERLTRERS  240
```

-continued

```
ESCGRNWLDK WVEERYLDDE KNAKILEVDT GKPGRHASRR RSGSHHHHSS CSSMTSEQKS    300
RSYATMPESP SKDSTTAQQS VPSPPSVGMA EALSPLLMAV DIAELCDSPQ FFSATSRPGS    360
SRSRAFTPTK SECSRSLFGG YSDYPNYMAN TESFRAKARS QSAPKQRPQY EKSSSLRKAS    420
AHAFGPGSCA PVAQRTTASL HSKFTNKAYP GSGRLDRLGM PVKY                    464

SEQ ID NO: 70             moltype = DNA   length = 1736
FEATURE                   Location/Qualifiers
source                    1..1736
                          mol_type = other DNA
                          organism = Triticum aestivum
misc_feature              1..1736
                          note = Ceres CLONE ID no.697034
misc_feature              1..1736
                          note = Encodes the peptide sequence at SEQ ID NO 71
SEQUENCE: 70
gcctagactc ttcgtctccg tcctgcacct ttttcttctc tggcaagcct gtgcctgtgc     60
gcgtcgcgcc gttttgggtt tcatctcccg ctctttcttc ctcctccctg ctccggccaa    120
gtgctggaac caagagaagg cgatgggggc ggcggcggag gagcagtagc cggagggagg    180
ggatggggtg ggcttcaagg tggctccgcg ggctgcttgg cggcggcaag aaggccggtc    240
ccgcctccgg cgagcacaag ccggagaggg agaagaagcg ctggggcttc ggcaagtcct    300
tccgggagaa ggacccggtg cgtccaccga cgcctcctgt gcagcgggcg gcgacgcccc    360
gccgcaccta cgccgacgtc gatgacggcg gcgacgagca acaaaaacgc gctatcgcca    420
tggcggcggc gacggcggct gtggccgagg ccgccgttgc cgcggcgcag gcggccgccg    480
ccgtggtgcg gctgacgagc agcgggcggt gcccgccggc cggggcgaag catgaggagt    540
gggcggccgt ccggatccag gccgctttcc gtggctacct ggcgaggcgc gcactgaagg    600
cgctccgcgg gctggtgaag ctgcaggcgc tggtccgcgg caacatcgtc cggcgccgag    660
cggccgagac gctccggtgc atgcaggcgc tcgtcagcgt gcagtccgcc gcgcgcgcca    720
gccgcgcaac ccgatcccgc caggccgcgg cacacccggg cgcgacgacg ccggagaagt    780
acgagcaggc ggcatacgat ggcgcgctca ggcacggccg ttcaggctca ctcaaggag     840
gctcgtcaaa gacaccgggc agcgagagga tgagcaggaa gaggtcagaa tcttgcggag    900
ggaactggct ggatcggtgg gtggaggaga ggtacatgga tgacgagaag aacgccaaga    960
ttctcgaggt ggaccccggc aagcccggcc ggcacgcttc caagaggcga agcagcggcc   1020
gcggccacca ccagtcgtcg tgctcaacca ggacatcaga gcagaacagc cggagctacg   1080
cgacgatgcc ggactcgccg tccagggact cgacgacggc gcagcagtcc gtgcccgacc   1140
cgtcgtcggt gggcatgggc gcgggcgagg ccctcagccc gctgcacatg ccggcagacc   1200
tcgcggcgga gctgtacgag agcccgcagt tcttctcggc gacgtcgcgg ccggggagct   1260
cgaagcgggg cgccttcttc acgccgacca agagcgagtg cgcgcgcagc ctcttcggcg   1320
gctactccga ctaccccaac tacatgtcca acacggagtc gttccgggcc aaggcgcggt   1380
cgcagagcgc gcccaagcag cggccgctgt acgagaagtc cgggtccctc cggaaggcgt   1440
cggcacacgc cttcgcgccg gggcagaggt cgtcggcgtc ggcgtccctg cacgccaggt   1500
tcaccaataa ggcgtaccct ggctccggca ggctggaccg gctgggcatg cctgtcaagt   1560
actgaaccct gccgccatgt gaccagtgtt aggtttgagc ttttgtgatg ctattaccgt   1620
cagaaagtac tttcctgtta ttgactgtga cttgttaagt gtaagttgct actgtactgg   1680
tgttcccgca aaaaaagtg taagttgcta gtaatcaccc aaaaaaaaaa aaaaaa        1736

SEQ ID NO: 71             moltype = AA   length = 460
FEATURE                   Location/Qualifiers
source                    1..460
                          mol_type = protein
                          organism = Triticum aestivum
REGION                    1..460
                          note = Ceres CLONE ID no.697034
REGION                    1..460
                          note = Score of 750.1 for HMM of FIGURE 2.
REGION                    1..460
                          note = Functional Homolog Of Ceres SEEDLINE ID no. ME06748
                           at SEQ ID NO.41
REGION                    119..139
                          note = Pfam Name: IQ Pfam Description: IQ
                           calmodulin-binding motif
SEQUENCE: 71
MGWASRWLRG LLGGGKKAGP ASGEHKPERE KKRWGFGKSF REKDPVRPPT PPVQRAATPR     60
RTYATSDDGG DEQNKRAIAV AAATAAVAEA AVAAAQAAAA VVRLTSSGRC PPAGAKHEEW    120
AAVRIQAAFR GYLARRALKA LRGLVKLQAL VRGNIVRRQA AETLRCMQAL VSVQSRARAS    180
RATRSRQAAA HPGATTPEKY EQAAYDGALR HGRSGSLKGG SSKTPGSERM SRERSESCGR    240
NWLDRWVEER YMDDEKNAKI LEVDPGKPGR HASKRRSSGG GHHQSSCSTR TSEQNSRSYA    300
TMPDSPSRDS TTAQQSVPSP SSVGMGAGEA LSPLHMPADL AAELYESPQF FSATSRPGSS    360
KRGAFFTPTK SECARSLFGG YSDYPNYMSN TESFRAKARS QSAPKQRPLY EKSGSLRKAS    420
AHAFAPGQRS SASASLHARF TNKAYPGSGR LDRLGMPVKY                         460

SEQ ID NO: 72             moltype = DNA   length = 1433
FEATURE                   Location/Qualifiers
source                    1..1433
                          mol_type = other DNA
                          organism = Zea mays
misc_feature              1..1433
                          note = Ceres CLONE ID no.353438
misc_feature              1..1433
                          note = Encodes the peptide sequence at SEQ ID NO 73
```

```
SEQUENCE: 72
atgatgtgta  acctacgagc  tgctctggta  accgcttccc  ctccagcaag  gagaacgcca    60
ccttgtggcg  tcagctctgc  cgtcgtcttt  actgcctgcg  ccttccaggc  ttcttcgttt   120
caggaagcaa  ggcgaggcgg  gcgctgaagg  cgttgcgggg  gctggtgaag  ctgcaggcgc   180
tggtccggcg  caacatcgtg  cggccggcagg cggcggagac  gctgcgatgc  atgcacgcgc   240
tcgtccgcgt  ccaggcgcgc  gcgcgcgcct  gccgcgcaat  tcgctcgcag  catgtcacgg   300
cgcatccgga  cccgccgacg  ccggagaagt  acgagcaggc  gggtgcggcc  aggcacggcc   360
gttccggctc  tctgaaggcg  aactcttcga  ggacaccggg  cggcgagagg  ctgggcaggg   420
agaggtcgga  atcctgcggg  aggaactggc  tggaccgctg  ggtggaggag  aggtacatgg   480
acgacgagaa  gaacgccaag  attctcgagg  tggacaacgg  caagccaggg  cgccggtatg   540
cttccaagag  gcgcggcggc  ggcggcgtcg  gcggaaacca  ccaccaccag  caccaccagt   600
cgccgtgctc  gacgacgatg  ggctccgagc  agaacagccg  gagctacgcg  accatgccgg   660
agtcgccgtc  caaggactcg  acgaccgcgc  agcagtcggt  gccgagcccg  ccgtcggtgg   720
gcatggccga  ggaggaggcc  ctgagcccgc  tgcgcgtgcc  cgtgcccgcg  gacgtggcgg   780
agctctgcga  cagcccccag  ttcttctcgg  ccacgtcgtc  gcggcccggg  agctcgaggc   840
ggggcccgtt  cacgccgacg  gccaagagcg  agtgctcgcg  cagcctcttc  ggcggctact   900
ccgactaccc  gaactacatg  gccaacacgg  agtcgttccg  cgccaaggcg  cggtcgcaga   960
gcgcgccgaa  gcagaggccg  cagtacgagc  ggtccagctc  cctacgcagg  cgctcggcgg  1020
cgcagaggtc  ggcggcggcg  gcggcctcct  ccctgcacgc  caagttcacc  aacaaggcgt  1080
accccgggctc tggcaggctg  gatcggcttg  gcttgccggc  caggtactga  tactgagcct  1140
gcctaattcg  cgtcaggatg  atgtgctgcc  gctgtgtctc  gagcgaggag  gacgacgacg  1200
aagaagtgca  atcgactagt  ggtagttagg  ttccgccgtg  cctggttgt  gctattacca  1260
tcaacagttt  tttctgtttc  ttgctttgtg  tagctagcca  tgtctaaagt  tgctggtagc  1320
tgtaatgatg  ctataatgcg  tgcttaactg  ctgacgaacc  ttttcctct  acatttccgt  1380
ggtatatata  tatgtgccgt  caaatcatgc  atgggaattg  aatgtgttgt  tgc          1433

SEQ ID NO: 73          moltype = AA  length = 299
FEATURE                Location/Qualifiers
source                 1..299
                       mol_type = protein
                       organism = Zea mays
REGION                 1..299
                       note = Ceres CLONE ID no.353438
REGION                 1..299
                       note = Score of 204.3 for HMM of FIGURE 2.
REGION                 1..299
                       note = Functional Homolog Of Ceres SEEDLINE ID no. ME06748
                        at SEQ ID NO.41
SEQUENCE: 73
MHALVRVQAR  ARACRAIRSQ  HVTAHPDPPT  PEKYEQAGAA  RHGRSGSLKA  NSSRTPGGER    60
LGRERSESCG  RNWLDRWVEE  RYMDDEKNAK  ILEVDNGKPG  RRYASKRRGG  GGVGGNHHHQ   120
HHQSPCSTTM  GSEQNSRSYA  TMPESPSKDS  TTAQQSVPSP  PSVGMAEEEA  LSPLRVPVPA   180
DVAELCDSPQ  FFSATSSRPG  SSRRGPFTPT  AKSECSRSLF  GGYSDYPNYM  ANTESFRAKA   240
RSQSAPKQRP  QYERSSSLRR  ASAAQRSAAA  AASSLHAKFT  NKAYPGSGRL  DRLGLPARY    299

SEQ ID NO: 74          moltype = AA  length = 499
FEATURE                Location/Qualifiers
source                 1..499
                       mol_type = protein
                       note = subspecies = japonica
                       organism = Oryza sativa
REGION                 1..499
                       note = Public GI ID no.125593074
REGION                 1..499
                       note = Score of 112.2 for HMM of FIGURE 2.
REGION                 1..499
                       note = Functional Homolog Of Ceres SEEDLINE ID no. ME06748
                        at SEQ ID NO.41
REGION                 134..154
                       note = Pfam Name: IQ Pfam Description: IQ
                        calmodulin-binding motif
SEQUENCE: 74
MGKAARWFRN  MWGGGRKEQK  GEAPASGGKR  WSFGKSSRDS  AEAAAAAAAA  AAEASGGNAA    60
IARAAEAAWL  RSVYADTERE  QSKHAIAVAA  ATAAAADAAV  AAAQAAVAVV  RLTSKGRSAP   120
VLAATVAGDT  RSLAAAAVRI  QTAFRGFLAK  KALRALKALV  KLQALVRGYL  VRRQAAATLQ   180
SMQALVRAQA  TVRAHRSGAG  AAANLPHLHH  APFWPRRSLV  RRWLNLADDI  AMYMFDVDVV   240
CWRWMQQERC  AGDDTRSEHG  VAAYSRRLSA  SIESSSYGYD  RRPQDRGGGH  RGGPSRGRRR   300
RGGRAPPLLL  DARWVRERRR  GLVRQLHVVA  APVLPPRRRA  AAPHRRPDVA  PLPRLRLVRA   360
GEGPAGDGAE  HAAVRARAAD  ADQERVRRRR  RRRHPLVAAQ  LPELHVQHAV  VRGRRCRSQS   420
APKQRPETGG  AGAGGGRKRV  PLSEVVVVES  RASLSGVGMQ  RSCNRVQEAF  NFKTAVVGRL   480
DRSSESGEND  RHAFLQRRW                                                   499

SEQ ID NO: 75          moltype = DNA  length = 1807
FEATURE                Location/Qualifiers
source                 1..1807
                       mol_type = other DNA
                       organism = Gossypium hirsutum
misc_feature           1..1807
                       note = Ceres CLONE ID no.1920115
```

| misc_feature | 1..1807 |
| --- | --- |
| | note = Encodes the peptide sequence at SEQ ID NO 76 |

SEQUENCE: 75

```
ctcctttcct cagtaagctt acgaaacttc ttcttcgctt cttctctgca aatgaatccc    60
gagaaacctc ccaaaccctt atcttattac ccttttcac cttcttctcc atcaccaaac    120
taacgtttcc gtacacaacg aacaaaatca aagcaatggg taaagcttcc aagtggttcc    180
gcagcatcct cggcttcaaa aatccgaccc ccataaccaa ccttctcctt cttcttcaaa    240
accaacttcc cataaagaca aacggcgttg gagtttcgtc aaatcgtacc gtgaaaaaga    300
ctcctccacg aacaatagta atgcgaagtt gccgtcgtct tcgcagcaac agaaagactc    360
tgtttccttc gttgaaagga aaggtgacaa tgaagtaacg gatcctagca agcacggccat    420
cgctgttgct gccgctactg ccgccgttgc cgaagcagcc gttgcggctg ctcaagctgc    480
cgctgcggtg gttaggctca ctagtaacag tggtaggtgc gcgcgtgaat cggcagcggt    540
ttacgtttgc aacaacaata gctatatagc acacgatgag tcatccgcca ttaagataca    600
atctgcattt cgtggatacc tggcaagaag agcattgcga gcactaaaag gattagtgag    660
actccaagca ttggttagag gtcatatcga aggaagaga actgcagaat ggttaagaag    720
gatgcaagca ttattgagag cacaagcacg tgctcgtgct ggccgggccc aaatttccga    780
gtcttcccaa tcaagctgca aatcgtctca cttccatcat ccggatccag caacccctga    840
aaaatttgaa catgttattc gatccaaggg tacaaaatat gaacaatcat caatgttgaa    900
gagaaatgga tcaaagtcaa gtggaaggac tgttgataat caagagaaat tacactcagg    960
ttggtatcgc cgtgttgatg agcaaacatg ggagcattca acaagaattg gtcctaatga    1020
tgatgaaaag aatgacaaaa tccttgaagt tgacactggg aaaccaaatt tcatctctaa    1080
acggagaaac ctctttcatt caacacatct ttctctgaaa tctgatttat atagctgtag    1140
tttcactaat tcgagagact cacaccaaac agctcctagt ccttcatctg gtgaagttca    1200
gtctttaact ccattgatgc tgtctcactc tgaagcaata caggaaagcc ctttctgcgg    1260
tgctgttgat gataatagtc cacaattcta ttctgcatca tcaaaggag ctagttccaa    1320
gagaagcccc ttcactcctg ctaagagtga tggcactaga agctacctaa gtggttactc    1380
agaccatcca aattacatgt cttacactga atcgtcaaaa gctaaggtaa ggtctttcag    1440
tgctccaaaa caaggccctc attatgaaag atctagttca acaaagaggt actccattca    1500
tggttttggt gaattgaaat caactacaca aaggtctgcc atgcatgcaa acttcgccag    1560
caaagcttac cccggttcgg gtaggttgga caggctagga atgccccctg ggtatagata    1620
ctaaataatg gttttaccat ttggctaagg aatgttatgt agtttatgtt tagatgttaa    1680
cgatgatgac tctcacctac cctaatgtat ccatccttta atgttttagt gcatgtgagt    1740
tcccaagtta aaaagaatag tagctgcttt acaagaagtt aaattagaaa aaaaaaaaa    1800
aaaaaaa                                                            1807
```

| SEQ ID NO: 76 | moltype = AA  length = 300 |
| --- | --- |
| FEATURE | Location/Qualifiers |
| source | 1..300 |
| | mol_type = protein |
| | organism = Gossypium hirsutum |
| REGION | 1..300 |
| | note = Ceres CLONE ID no.1920115 |
| REGION | 1..300 |
| | note = Score of 34.2 for HMM of FIGURE 2. |
| REGION | 1..300 |
| | note = Functional Homolog Of Ceres SEEDLINE ID no. ME06748 at SEQ ID NO.41 |

SEQUENCE: 76

```
MQALLRAQAR ARAGRAQISE SSQSSCKSSH FHHPDPATPE KFEHVIRSKG TKYEQSSMLK    60
RNGSKSSGRT VDNQEKLHSG WYRRVDEQTW EHSTRIGPND DEKNDKILEV DTGKPNFISK    120
RRNLFHSTHL SLNSDLYSCS FTNSRDSHQT APSPSSGEVQ SLTPLMLSHS EAIQESPFCG    180
AVDDNSPQFY SASSKGASSK RSPFTPAKSD GTRSYLSGYS DHPNYMSYTE SSKAKVRSFS    240
APKQRPHYER SSSTKRYSIH GFGELKSTTQ RSAMHANFAS KAYPGSGRLD RLGMPLGYRY    300
```

| SEQ ID NO: 77 | moltype = DNA  length = 1614 |
| --- | --- |
| FEATURE | Location/Qualifiers |
| source | 1..1614 |
| | mol_type = other DNA |
| | organism = Arabidopsis thaliana |
| misc_feature | 1..1614 |
| | note = Ceres CLONE ID no.21821 |
| misc_feature | 1..1614 |
| | note = Encodes the peptide sequence at SEQ ID NO 78 |

SEQUENCE: 77

```
ataatttgat gaacagtctt cttctctgat gcagaaaccc tctccctgaa tcttgattct    60
ctcacaatca agatttgaag caaacgtttt gagaaaaatc ttttgacacc atcaaatttg    120
gttggcggat tgtgggagga attccagagc aatatagcag gtgatggttg tacaacaatg    180
gctaagaaga agggcttgtt cactgtattg aaaaggattt ttatttcaga agttaattca    240
gaaaagaaag agaagaaag aaaatggaca ttttggaagc ttaggattaa gaaaagatta    300
ccttccatta cagcacctcc agagcacagg acaagtcatg aatcgcatga ggaacagaag    360
gaggaaattg tgtcagatgt gggtgagatc agccaagtgt cttgtagtcg acagttagat    420
tccatagaag agtcaaaagg ttcaacatca ccagaaactg ctgatctggt agtccagtat    480
caaatgtttc ttaatagaca ggaagaagtt cttgctgcta ctcgcattca gaccgccttt    540
cggggtcatc ttgcaaggaa agctctacgt gccttgaata gatagtgaa ctccaagca    600
tatatcagag gtcgtgctgt gagacgccaa gcaatgacta cactaaaatg cctgcaatct    660
gttgtgaaca ttcagtcaca agtctgtggt aagagaacac agattcccgg aggtgttcac    720
agagattatg aagagagcaa tatattcaat gataacattc tcaaggtgga cacaaacggt    780
caaaagagat gggacgatag tctttttaaca aggaagaaa aggaagcagt ggtaatgagc    840
aagaagaag cttcactaag aagagaaagg ataaggaat atgcagtcac ccaccggaaa    900
```

-continued

```
tctgcggagt cataccagaa acgaagtaac actaaatgga agtactggtt agacgaatgg    960
gtagatacac aactaaccaa gagcaaggag ctcgaagatc tcgacttctc ttcgaaaaca   1020
aaaccgaaag acgaaacttt gaacgagaag cagcttaaaa ctccaaggaa ctcatcacca   1080
agaagattag tgaataatca tagaagacaa gtttcaatag gtgaagatga acaaagccct   1140
gccgcggtca ctatcactac accaacttat atggttgcaa cagagtcagc aaaggcaaag   1200
tcaagatcat taagctcccc aaggataaga ccgagaagtt ttgacacaca gtcagagagt   1260
tactcgccat ataagaacaa gctatgcctg acgacatcaa tgatgagtga agcaccaagc   1320
aaagtaagga ttgccaacaa tggcagtaac actagaccaa gtgcatacca gcaacggtct   1380
ccagggttaa ggggatttaa cataggccct ttgaaatcat gcaataataa taatactcta   1440
ttgaacgatc tcagcattaa ttccagaaaga tctctaccta gctgaacaa gcagagcagc   1500
ttgagatgag tggatattga accctgtata tatacatact acatacgttc aatgtttcct   1560
tttgactttt gagggtcaca ctcacatatg tgtatcatca aatattgttt cgtt         1614
```

```
SEQ ID NO: 78           moltype = AA  length = 443
FEATURE                 Location/Qualifiers
source                  1..443
                        mol_type = protein
                        organism = Arabidopsis thaliana
REGION                  1..443
                        note = Ceres CLONE ID no.21821
REGION                  1..443
                        note = Score of 237.2 for HMM of FIGURE 2.
REGION                  1..443
                        note = Functional Homolog Of Ceres SEEDLINE ID no. ME06748
                         at SEQ ID NO.41
REGION                  111..131
                        note = Pfam Name: IQ Pfam Description: IQ
                         calmodulin-binding motif
SEQUENCE: 78
MAKKKGLFTV LKRIFISEVN SEKKEKRRKW TFWKLRIKKR LPSITAPPEH RTSHESHEEQ    60
KEEIVSDVGE ISQVSCSRQL DSIEESKGST SPETADLVVQ YQMFLNRQEE VLAATRIQTA   120
FRGHLARKAL RALKGIVKLQ AYIRGRAVRR QAMTTLKCLQ SVVNIQSQVC GKRTQIPGGV   180
HRDYEESNIF NDNILKVDTN GQKRWDDSLL TKEEKEAVVM SKKEASLRRE RIKEYAVTHR   240
KSAESYQKRS NTKWKYWLDE WVDTQLTKSK ELEDLDFSSK TKPKDETLNE KQLKTPRNSS   300
PRRLVNNHRR QVSIGEDEQS PAAVTITTPT YMVATESAKA KSRSLSSPRI RPRSFDTQSE   360
SYSPYKNKLC LTTSMMSEAP SKVRIANNGS NTRPSAYQQR SPGLRGFNIG PLKSCNNNNT   420
LLNDLSINSE RSLPSWNKQS SLR                                           443
```

```
SEQ ID NO: 79           moltype = DNA  length = 1689
FEATURE                 Location/Qualifiers
source                  1..1689
                        mol_type = other DNA
                        organism = Glycine max
misc_feature            1..1689
                        note = Ceres CLONE ID no.560066
misc_feature            1..1689
                        note = Encodes the peptide sequence at SEQ ID NO 80
SEQUENCE: 79
tttttttatgg gatttgaaaa aatggatcac agacattgaa gttgacctat gtgttgatat    60
tcttaaaatgg ccaaaaagaa gagctggttt agtctggtga agaggctctt tatatgggac   120
acacattcca cacaagataa gaaggagaaa agaaggaaat ggatatttgg aaggctaaaa   180
agcaagagat tgccttcaat taaagctcca ctaccctcaa aaggaacaac actaagtgag   240
gcagagcaag aacagagcaa gcatgctttta acagtggcca ttgcctcagc agcagctgct   300
gaagctgctg ttactgctgc tcatgctgct gctgaggttg ttcgcctcac tgggcaacgc   360
aacgaaaact cagaagaatc tcaacctgtt aaaactgaga atggtgctcc acaatcccaa   420
taccagtgcc agagggagat taaagaatct gctgcagcca tcaaaattca aactgcattt   480
cggggttacc tggcaaggaa ggctttgagg gcgttgaagg gaatagtgaa gcttcaagct   540
atcattcgtg gcagagccgt aagacgccaa gctatgagta gtcttaagtg cttacagtcc   600
attgtgagca tccagtcaca ggtctgtgca aggaggctcc aaatggttga agggagatgt   660
gattactctg aaaatgaaga gatgcaagat tttaaagaca aataattag gatggactca   720
aacagtgaaa gaaagtggga tgaaagcact gtattgaagg aagaggtaga cacctcttgc   780
acaagcaaga gagaaagaac aaaagaatac tcatttaacc acagaaggtc agcagagtca   840
gaaagaagta agtaaatgg aagatggagg tactggctag agcagtgggt agatacacaa   900
ctttcaaaga gtaaagagct tgaagattta gactcagtt ttagctcaca ttctagagct   960
ggggaggaat atggaggaag gcaacttaag ctgagaagta atattcagag acaaaatcca  1020
gttgaaggat tggattctcc aatacttggt tcaagaagat cttttcctca taggaggcag  1080
tgttcagtgg gagaggacca ctcatttttta agctctcctg caactccagc atacatggct  1140
gcaacagaat cagcaaaagc aaaagcaaga tcaacaagct ccccaaaaat aaggactggg  1200
gggaatgtgg acatgaactc tgatagctat tcaccatgca gaaaaagct atccattgca  1260
tcttctatta acagtgaaat gcttagtaat ggtagggtgg gcaagctcag tgttaaccag  1320
cagcaaagat caccaagctt taagggactt tcagtgccta aaaatcaag ccgaacaact  1380
atcaaggatc tcagtattaa ttcagattgc tcactcccta ttgggatcg acaggctttc  1440
ttcaaatgaa tctatgaatg ctgatgttac tcttttcttgc attaacacaa ttccttgtat  1500
catgtgaagg cttgaaaca ataactgttt ataaatatgt atgatatact atatgctatt  1560
ggatgttatt ttggttggga attgaacatt aatgtgacag aaaatagtta ttctggagat  1620
ataagatgaa ttgtatgatt aagaaagaag agatataaga tggattgtat gattaagaaa  1680
gaaggaaag                                                          1689
```

```
SEQ ID NO: 80           moltype = AA  length = 460
```

```
FEATURE                 Location/Qualifiers
source                  1..460
                        mol_type = protein
                        organism = Glycine max
REGION                  1..460
                        note = Ceres CLONE ID no.560066
REGION                  1..460
                        note = Score of 822.2 for HMM of FIGURE 2.
REGION                  1..460
                        note = Functional Homolog Of Ceres SEEDLINE ID no. ME06748
                         at SEQ ID NO.41
REGION                  128..148
                        note = Pfam Name: IQ Pfam Description: IQ
                         calmodulin-binding motif
SEQUENCE: 80
MAKKKSWFSL VKRLFIWDTH STQDKKEKRR KWIFGRLKSK RLPSIKAPLP SKGTTLSEAE   60
QEQSKHALTV AIASAAAAEA AVTAAHAAAE VVRLTGQRNE NSEESQPVKT RNGAPQSTYQ  120
CQREIKESAA AIKIQTAFRG YLARKALRAL KGIVKLQAII RGRAVRRQAM SSLKCLQSIV  180
SIQSQVCARR LQMVEGRCDY SENEEMQDFK DKIIRMDSNS ERKWDESTVL KEEVDTSCTS  240
KRERTKEYSF NHRRSAESER SKVNGRWRYW LEQWVDTQLS KSKELEDLDS VFSSHSRAGE  300
EYGGRQLKLR SNIQRQNPVE GLDSPILGSR RSFPHRRQCS VGEDHSFLSS PATPAYMAAT  360
ESAKAKARST SSPKIRTGGN VDMNSDSYSP CKKKLSIASS INSEMLSNGR VGKLSVNQQQ  420
RSPSFKGLSV PIKSSRTTIK DLSINSDCSL PNWDRQAFFK                       460

SEQ ID NO: 81           moltype = AA  length = 501
FEATURE                 Location/Qualifiers
source                  1..501
                        mol_type = protein
                        note = subspecies = japonica
                        organism = Oryza sativa
REGION                  1..501
                        note = Public GI ID no.115453071
REGION                  1..501
                        note = Score of 546.0 for HMM of FIGURE 2.
REGION                  1..501
                        note = Functional Homolog Of Ceres SEEDLINE ID no. ME06748
                         at SEQ ID NO.41
REGION                  122..142
                        note = Pfam Name: IQ Pfam Description: IQ
                         calmodulin-binding motif
SEQUENCE: 81
MERKRRGWLE RIKRLFVSEP KQKPKPDKKV KSKRWMFAGK LKTQHSFALP APAPAVEEEQ   60
IRQAEDEQSK HAMAVALATA AAAEAAVAAA HAAAEVVRLT GKTAALAPAP ATTTTPTPYG  120
HEHAALMIQS VYRGYLARRA LRALKGLVRL QALIRGQAVR RQTAATLRGL ESLMKIQARQ  180
RARASSAAAA GGDHNAANSP APDGMDALLR RGRELYYAAA AAVHEQQLSK GWDSSTLSKE  240
EMSAMSRSRE EAALKRVRAL QYASLHQSEK VGVRRQPMSR EEMETLNQRW SWLEEWVGSQ  300
PPFDKDIPVA HQSPSRDAAG AAMNDDERPP PPPVLRSRSR ADRLACVGGD DDDADRQLGY  360
SARRSFTRAG RRTPARDDDG GGAAAFPGYM ASTASAKAKF RSMSTPKERS GAGAADAYSE  420
QCFPFADRLL SPIPSMSPIP SIASDIVFAR SSRPAAAQRS PRVKGPMTPT RSRSRRSPGR  480
HSFGSEAALH QLQMEQYTPI R                                           501

SEQ ID NO: 82           moltype = DNA  length = 1814
FEATURE                 Location/Qualifiers
source                  1..1814
                        mol_type = other DNA
                        organism = Gossypium hirsutum
misc_feature            1..1814
                        note = Ceres CLONE ID no.1968211
misc_feature            1..1814
                        note = Encodes the peptide sequence at SEQ ID NO 83
SEQUENCE: 82
aatttccccc ttcctctctc cctcctttcc tcagtaagct tacgaaactt cttcttcgct   60
tcttctctgc aaatgaatcc cgagaaacct cccaaaccct tatctttta cccttttca  120
ccttcttctc catcaccaaa ctaacgtttc cgtacacaga gaacaaaatc aaagcaattg  180
gtaaagcttc caagtggttc cgcagcatcc tcggcttcaa aaaatccgac ccccataacc  240
aaccttctcc ttcttcttca aaaccaactt cccataaaga caaacggcgt tggagtttcg  300
tcaaatcgta ccgtgaaaaa gactcctcca cgaacaatag taatgcgaag ttgccgtcgt  360
cttcgcagca acagaaagac tctgtttcct tcgttgaaga gaaggtgaat aatgaagtaa  420
cggatcctag caagcacgcc atcgtcgttg ctgccgctac tgccgccgtt gccgaagcag  480
ccgttgcggc tgctcaagct gccgctgcgg tggttaggcg cactagtaac agtggtaggt  540
gcgcgcgtga atcggcagcg gtttacgttt gcaacaacaa tagctatata gcacacgatg  600
agtcatccgc cattaagata caatctgcat ttcgtggata cctggcaaga agagcattgc  660
gagcactaaa aggattagtg agactccaag cattggttag aggtcatata gaaaggaaga  720
gaactgcaga atgttaaga aggatgcaag cattattgag acgacaagca cgtgctcgtg  780
ctggccgggc ccaaatttcc gagtcttccc aatcaagctg caaatcgtct cacttccatc  840
atccggatcc agcaacccct gaaaaatttg aacatgttat tcgatccaag ggtacaaaat  900
atgaacaatc atcaatgttg aagagaaatg gatcaaagtc aagtgaagg actgttgata  960
atcaagagaa attacactca ggttggtatc gccgtgttga tgagcaaaca tgggagcatt 1020
caacaagaat tggtcctaat gatgatgaaa agaatgacaa aatcccttgaa gttgacactg 1080
```

```
ggaaaccaaa tttcatctct aaacggagaa acctctttca ttcaacacat ctttctctga   1140
attctgattt atatagctgt agtttcacta attcgagaga ctcacaccaa acagctccta   1200
gtccttcatc tggtgaagtt cagtctttaa ctccattgat gctgtctcac tctgaagcaa   1260
tacaggaaag cccttctgc ggtgctgttg atgataatag tccacaattc tattctgcat    1320
catcaaaagg agctagttcc aagagaagcc ccttcactcc tgctaagagt gatggcacta   1380
gaagctacct aagtggttac tcagaccatc caaattacat gtcttacact gaatcgtcaa   1440
aagctaaggt aaggtctttc agtgctccaa aacaaaggcc tcattatgaa agatctagtt   1500
caacaaagag gtactccatt catggttttg gtgaattgaa atcaactaca caaaggtctg   1560
ccatgcatgc aaacttcgcc agcaaagctt accccggttc gggtaggttg gacaggctag   1620
gaatgcccct tgggtataga tactaaataa tggttttacc atttggctaa ggaatgttat   1680
gtagtttatg tttagatgtt aacgatgatg actctcacct accctaatgt atccatcctg   1740
taatgtttta gtgcatgtga gttcccaagt taaaagaat agtagctgct ttacaaaaaa    1800
aaaaaaaaaa aaaa                                                     1814

SEQ ID NO: 83           moltype = AA  length = 489
FEATURE                 Location/Qualifiers
source                  1..489
                        mol_type = protein
                        organism = Gossypium hirsutum
REGION                  1..489
                        note = Ceres CLONE ID no.1968211
REGION                  1..489
                        note = Score of 555.8 for HMM of FIGURE 2.
REGION                  1..489
                        note = Functional Homolog Of Ceres SEEDLINE ID no. ME06748
                         at SEQ ID NO.41
REGION                  142..162
                        note = Pfam Name: IQ Pfam Description: IQ
                         calmodulin-binding motif
SEQUENCE: 83
MGKASKWFRS ILGFKKSDPH NQPSPSSSKP TSHKDKRRWS FVKSYREKDS STNNSNAKLP   60
SSSQQQKDSV SFVERKGDNE VTDPSKHAIA VAAATAAVAE AAVAAAQAAA AVVRLTSNSG   120
RCARESAAVY VCNNNSYIAH DESSAIKIQS AFRGYLARRA LRALKGLVRL QALVRGHIER   180
KRTAEWLRRM QALLRAQARA RAGRAQISES SQSSCKSSHF HHPDPATPEK FEHVIRSKGT   240
KYEQSSMLKR NGSKSSGRTV DNQEKLHSGW YRRVDEQTWE HSTRIGPNDD EKNDKILEVD   300
TGKPNFISKR RNLFHSTHLS LNSDLYSCSF TNSRDSHQTA PSPSSGEVQS LTPLMLSHSE   360
AIQESPFCGA VDDNSPQFYS ASSKGASSKR SPFTPAKSDG TRSYLSGYSD HPNYMSYTES   420
SKAKVRSFSA PKQRPHYERS SSTKRYSIHG FGELKSTTQR SAMHANFASK AYPGSGRLDR   480
LGMPLGYRY                                                           489

SEQ ID NO: 84           moltype = AA  length = 464
FEATURE                 Location/Qualifiers
source                  1..464
                        mol_type = protein
                        note = subspecies = indica
                        organism = Oryza sativa
REGION                  1..464
                        note = Public GI ID no.116310011
REGION                  1..464
                        note = Score of 886.7 for HMM of FIGURE 2.
REGION                  1..464
                        note = Functional Homolog Of Ceres SEEDLINE ID no. ME06748
                         at SEQ ID NO.41
REGION                  124..144
                        note = Pfam Name: IQ Pfam Description: IQ
                         calmodulin-binding motif
SEQUENCE: 84
MGWASRWLRG LLGGGKKPNS GSGDPKPARE KKRWGFGKSF REKSPAHPPP PPPPSAAVQR   60
AVTPRRAYTA SDEGDDEQSK RAIAVAAATA AVAEAAVAAA QAAAAVVRLT SSGRCAPAAA   120
KREEYAAVRI QAAFRGYLAR RALKALRGLV KLQALVRGNI VRRQAAETLR CMHALVRVQR   180
RARACRAIRS QHVSAHPGPP TPEKYDQATH EGVPKHGRSG SLKGSSSKTP GSERLTRERS   240
ESCGRNWLDK WVEERYLDDE KNAKILEVDT GKPGRHASRR RSGSHHHHSS CSSMTSEQKS   300
RSYATMPESP SKDSTTAQQS VPSPPSVGMA EALSPLRMAV DIAELCDSPQ FFSATSRPGS   360
SRSRAFTPTK SECSRSLFGG YSDYPNYMAN TESFRAKARS QSAPKQRPQY EKSSSLRKAS   420
AHAFGPGSCA PVAQRTTASL HSKFTNKAYP GSGRLDRLGM PVKY                    464

SEQ ID NO: 85           moltype = DNA  length = 1019
FEATURE                 Location/Qualifiers
source                  1..1019
                        mol_type = other DNA
                        organism = Arabidopsis thaliana
misc_feature            1..1019
                        note = Ceres SEEDLINE ID no.ME08768
misc_feature            1..1019
                        note = Encodes the peptide sequence at SEQ ID NO. 86
SEQUENCE: 85
gttactaatc tcacgcacat tctttctctc tctaaattct gcaccacaat ccgcaaaatg   60
accaaatact tcttgctgtg aatgtcgaaa atgcctgcag gcacaacatg tgaagtgatg   120
caaaacggca acacttgttt caccagatcc tttcgtcatt gatggggaag aaaggaggca   180
```

```
gctggttctc atctgtgaag aaagttttca agtcatcttc taaagattcg ccccagcctg    240
agaagaagaa ggacaacaca cagaaattac agcatgaagt ggcagaggtg gtgtcctttg    300
agcattttcc tgcagagagt tctccagata atgtgagcaa tgcagagatg agtacgacat    360
caacgccagt gaccaacgaa gatagaagcc atgcgattgc cgttcagca  gcaactgccg    420
cagctgcaga agctgctgtg gtggctgctc aagcagctgc aagagttgta agattggcag    480
gaagttacgg gcggcagtcc aaggaagaaa gagcagcaac actcattcaa tcatactata    540
gaggctacct ggctcgacgt gcactacgag cattgaaggg attagtgagg ctgcaagcac    600
tggtgagggc acacaatgtg cggaagcaag cgcagatgac gatgcggtgc atgcaagcac    660
tggtgagggt gcaggcacga gtacgggctc gccgattcca attgagtcac gcggatcagg    720
aaagagagaa gaaagaagag cccaagccca tacccgtgcc cgtgcccatg agccccctga    780
gaagaataga cgacattaat gactgggaca ataggcgtca aagtagctac aaaattaagg    840
aaaacgattt gcggaaacat gaagctgtaa tgaagagaga gagagctctt gcatacgctt    900
tcaactatca acaggttagt taatttgtca tgattaaatg ggaatatagt ggataaaata    960
gcttagtcta atattctttc aaaacggtac gtgcaattta atttatctat atcttcttt    1019

SEQ ID NO: 86              moltype = AA   length = 253
FEATURE                    Location/Qualifiers
source                     1..253
                           mol_type = protein
                           organism = Arabidopsis thaliana
REGION                     1..253
                           note = Ceres SEEDLINE ID no.ME08768
REGION                     1..253
                           note = Score of 467.7 for HMM of FIGURE 1.
REGION                     116..136
                           note = Pfam Name: IQ Pfam Description: IQ
                             calmodulin-binding motif
SEQUENCE: 86
MGKKGGSWFS SVKKVFKSSS KDSPQPEKKK DNTQKLQHEV AEVVSFEHFP AESSPDNVSN     60
AEMSTTSTPV TNEDRSHAIA VAAATAAAAE AAVVAAQAAA RVVRLAGSYG RQSKEERAAT    120
LIQSYYRGYL ARRALRALKG LVRLQALVRG HNVRKQAQMT MRCMQALVRV QARVRARRFQ    180
LSHADQEREK KEEPKPIPVP VPMSPLRRID DINDWDNRRQ SSYKIKENDL RKHEAVMKRE    240
RALAYAFNYQ QVS                                                      253

SEQ ID NO: 87              moltype = DNA   length = 1906
FEATURE                    Location/Qualifiers
source                     1..1906
                           mol_type = other DNA
                           organism = Gossypium hirsutum
misc_feature               1..1906
                           note = Ceres CLONE ID no.1943807
misc_feature               1..1906
                           note = Encodes the peptide sequence at SEQ ID NO 88
SEQUENCE: 87
atctttttta tcttcacagt gttggtgtct tggctccttc ttcaaagctt cttttagctg     60
taaatgtagc ttggtttaac cctatccttt tgaatgggga tgaaaggagg gacttcatgg    120
ttgactgctg tgaaaagggc tttagatct  cctactaaag ataccatga  agatgaaaag    180
gtaagtgttt caatctattt taatggctgt ttatgaatct aaaaagaaaa cccttttgatt   240
ttttttttata tagaagagag ataaacggag gtggatctttt aggaaacaaa atacaagtcc  300
tgtgaagagt gtaggtaata atggtggtgg tggtgcaagt acggcagcag cggagcaaag    360
acatgctatt gctgtggcgg tggctaaagc agctgaagct gaagctgcgg tggcgacggc    420
acaagcagct ttacaagctg ctcggttgac taaacctagt tatggcagga acatcactt    480
tgctgctatt gttattcaga cagcttttag aggctacctg gccaggagag ctctacgtgc    540
gttaaaaggg ctagtgaagt tacaagcttt agtgagaggt cacaacgtga aaagcaagc    600
caagatgacg cttcgttgca tgcaagcact ggttaaagtt cagtctcgtg ttttagacca    660
aagaatgagg ctctcgcacg atggttgcag ccggaaatca gcatttagcg acaccaacag    720
tgtatgggaa tcacggtatc ttcaagatat atcggataga agatcattat cgagagaagg    780
aagtagcata gcagatgatt gggacgaaag gccacacaca gttgaagaag tgaaagctat    840
gttacaacat aggaaaaag ctgctttgaa acgtgaaaag agcttgtcac aagcactgtc    900
acaacagatg aggagagctc gaaggagtcc atcaatgggg ggacaagatg agtggcttga    960
tcgttggatg cctgctaaac catgggataa cagaggaaga gcttcaatgg atcaaagaga   1020
taatgtcaaa actgttgaaa tggacacttc acagccttat tcatatttag caccaaatta   1080
tagaagaaca aattcaaacc attatcacca aaggcctagt tcacctctcc ataggggtca   1140
acacaatgca caacctttcc acccttctcc aattacaccc tctccatcga aaacacgtcc   1200
ggttcaagta cggtccgcga gccctcgttg cgttagggaa gaccgaacat cgttttcatc   1260
atcacaaaca ccaagtttaa ggtccaatta ttattacaca ggaagggtta gtactcaagc   1320
tagtactagc ataaacaatg ctactacatt gcctaattac atggcagcaa cagagtctgc   1380
aaaggctagg attaggtctc aaagtgcacc aagacagagg ccatcgacac cagagaggga   1440
ccgaatcggt tcagcaagga aaaggctatc gtttcccgtc ccggaaccat atggtgatcgg   1500
gatgggggtac ggaggttatg gtcatagctt gaggagcccg agttttaaaa gtgtaagcgg   1560
gtcgcaattc ggattggaac gacagtctaa ctattcatct tgttgtactg agagccttgg   1620
tggtgaaatg tcaccatctt caactagtga tctaagaagg tggttgaggt gatcccatca   1680
atgtagctgt tggttttac  tagttttata gtgtgttttcc attgttgatt ttaccaattc   1740
ttggttgaaa ttcaagcttt ataagtgagg caactgcgat gaacccttcc ttactgggat   1800
ctttcatgag attcataacc aaattgagtg tgtaatacta taaagtaact ctgtaattct   1860
gttttgtcat aactttttaa tatattaaag cttatcatct tttccg                  1906

SEQ ID NO: 88              moltype = AA   length = 355
FEATURE                    Location/Qualifiers
```

```
source                  1..355
                        mol_type = protein
                        organism = Gossypium hirsutum
REGION                  1..355
                        note = Ceres CLONE ID no.1943807
REGION                  1..355
                        note = Score of 667.2 for HMM of FIGURE 1.
REGION                  1..355
                        note = Functional Homolog Of Ceres SEEDLINE ID no. ME08768
                         at SEQ ID NO.86
SEQUENCE: 88
MTLRCMQALV KVQSRVLDQR MRLSHDGCSR KSAFSDTNSV WESRYLQDIS DRRSLSREGS   60
SIADDWDERP HTVEEVKAML QHRKEAALKR EKSLSQALSQ QMRRARRSPS MGGQDEWLDR  120
WMPAKPWDNR GRASMDQRDN VKTVEMDTSQ PYSYLAPNYR RTNSNHYHQR PSSPLHRAQH  180
NAQPFHPSPI TPSPSKTRPV QVRSASPRCV REDRTSFSSS QTPSLRSNYY YTGRVSTQAS  240
TSINNATTLP NYMAATESAK ARIRSQSAPR QRPSTPERDR IGSARKRLSF PVPEPYGIGM  300
GYGGYGHSLR SPSFKSVSGS QFGLERQSNY SSCCTESLGG EMSPSSTSDL RRWLR       355

SEQ ID NO: 89           moltype = DNA  length = 1677
FEATURE                 Location/Qualifiers
source                  1..1677
                        mol_type = other DNA
                        organism = Populus balsamifera
                        sub_species = trichocarpa
misc_feature            1..1677
                        note = Ceres ANNOT ID no.1471392
misc_feature            1..1677
                        note = Encodes the peptide sequence at SEQ ID NO 90
SEQUENCE: 89
atggggaaga agggaggtag ctcatggttg accgttgtga aaagggcttt tagatctcct    60
aataaagaaa atgacaagag aactgctggg actacaggcc atgaccaaga agaagatgaa   120
gaaaagaaga gagagaagag gaggtggctg tttaggaaac ctacgaatca agaaacagtg   180
acacaacaga tcctatcaaa ggcaggaaat gtcaaggcct ccacgggtgg tggtggaggt   240
gcaccgacag accatgtgtc ggcagctgca gcagctgagc aaaggcatgc aattgctgta   300
gctgttgcca ctgcagctgc agctgaaact gcattagcca ctgcccaggc ggccgtggga   360
gtggctaggc tcactaggcc ttcttatcac cctagagaac gttccgctgc cattgtcatt   420
caaaccgctt ttagaggata cctggcaagg cgggctcttc gcgcgcttaa agggctagtg   480
aagttgcaag ctttagtgag gggacacaat gtgagaaagc aggccaagat gaccctgaga   540
tgcatgcaag ctctggttcg agtgcaggct cgagtacttg accaacgcat gaggctttca   600
catgaaggca gcagggaatc tgcattcagt gacaccaata gcgtgtttga atcgcgatat   660
cttcaagaaa tttcagaaag aaagtcgatg tcaagacgt gcagcagcat tgcagatgat   720
tgggatgatc ggccacgcac aattgaggaa gtcaaggcca tgttgcaacg caggaaagaa   780
gttgcattca agcgtgagaa ggcctatct caaggttttct ctcaacagat atggagaaac   840
cgtaggagcc catcaatggg caatgaaggt gagctccaag aaagatcaca atggcttgat   900
cattggatgc ctgcaaagcc gtgggacaat agcagcagag cacgagcctc aactgatcaa   960
agaaacccca tcaaaactgt agaaattgaa acctcccaac cttgctcata tttagctcct  1020
aattttggaa gaacgaacca aaaccaatat caccaacacc agagtccaa ttcaataaac  1080
aatggtgtta catgctcggc tcctcctcca ctccatagag ctcatcaaaa tgcttctctc  1140
cgcaactctc ctattacacc ctccccgtca agaactaggc ctcttcaggt tcgttcagcg  1200
agtccccgat gtgctagaga agatagaagc tgtaattcct ctcgaacacc gagtttaagg  1260
tccaattacc tctataatgg caatctgaaa caacatggaa tcaggggtgg tgctgctagt  1320
gttagtggaa atgctaatgc tacattgcca aattacatgg ctacaactga gtccgccaag  1380
gctagattga gatcacagag tgcgccaagg caaagaccat caacaccaga gcgagacagg  1440
gttgggtctg caagaaaacg gcttttgtat cctgtcccg accettacgg tgtcgggatg  1500
ggttatggtg gtgttggtta cgggcatggt ttcaggagtc ccagctttaa aagtgtaagt  1560
ggttcacatt ttggtggatt agaacaacaa tctaactatt cttcttgctg cactgatacc  1620
tcggtgctg agatttcccc ttcttcaacg agcgaccaga aaggtggtt gagataa      1677

SEQ ID NO: 90           moltype = AA  length = 382
FEATURE                 Location/Qualifiers
source                  1..382
                        mol_type = protein
                        note = subspecies = trichocarpa
                        organism = Populus balsamifera
REGION                  1..382
                        note = Ceres ANNOT ID no.1471392
REGION                  1..382
                        note = Score of 422.0 for HMM of FIGURE 1.
REGION                  1..382
                        note = Functional Homolog Of Ceres SEEDLINE ID no. ME08768
                         at SEQ ID NO.86
SEQUENCE: 90
MTLRCMQALV RVQARVLDQR MRLSHEGSRE SAFSDTNSVF ESRYLQEISE RKSMSRDGSS   60
IADDWDDRPR TIEEVKAMLQ RRKEVAFKRE KALSQGFSQQ IWRNRRSPSM GNEGELQERS  120
QWLDHWMPAK PWDNSRARA STDQRNPIKT VEIETSQPCS YLAPNFGRTN QNQYHQHQRS  180
NSINNGVTCS APPPLHRAHQ NASLRNSPIT PSPSRTRPLQ VRSASPRCAR EDRSCNSSRT  240
PSLRSNYLYN GNLKQHGIRG GAASVSGNAN ATLPNYMATT ESAKARLRSQ SAPRQRPSTP  300
ERDRVGSARK RLLYPVPDPY GVGMGYGGVG YGHGFRSPSF KSVSGSHFGG LEQQSNYSSC  360
CTDTFGAEIS PSSTSDQRRW LR                                          382
```

```
SEQ ID NO: 91            moltype = AA  length = 527
FEATURE                  Location/Qualifiers
source                   1..527
                         mol_type = protein
                         organism = Arabidopsis thaliana
REGION                   1..527
                         note = Public GI ID no.6715635
REGION                   1..527
                         note = Score of 916.5 for HMM of FIGURE 1.
REGION                   1..527
                         note = Functional Homolog Of Ceres SEEDLINE ID no. ME08768
                           at SEQ ID NO.86
REGION                   121..141
                         note = Pfam Name: IQ Pfam Description: IQ
                           calmodulin-binding motif
SEQUENCE: 91
MGKKNGSSSW LTAVKRAFRS PTKKDHSNDV EEDEEKKREK RRWFRKPATQ ESPVKSSGIS   60
PPAPQEDSLN VNSKPSPETA PSYATTTPPS NAGKPPSAVV PIATSASKTL APRRIYYARE  120
NYAAVVIQTS FRGYLARRAL RALKGLVKLQ ALVRGHNVRK QAKMTLRCMQ ALVRVQSRVL  180
DQRKRLSHDG SRKSAFSDSH AVFESRYLQD LSDRQSMSRE GSSAAEDWDD RPHTIDAVKV  240
MLQRRRDTAL RHDKTNLSQA FSQKMWRTVG NQSTEGHHEV ELEEERPKWL DRWMATRPWD  300
KRASSRASVD QRVSVKTVEI DTSQPYSRTG AGSPSRGQRP SSPSRTSHHY QSRNNFSATP  360
SPAKSRPILI RSASPRCQRD PREDRDRAAY SYTSNTPSLR SNYSFTARSG CSISTTMVNN  420
ASLLPNYMAS TESEAKARIRS HSAPRQRPST PERDRAGLVK KRLSYPVPPP AEYEDNNSLR  480
SPSFKSVAGS HFGGMLEQQS NYSSCCTESN GVEISPASTS DFRNWLR              527

SEQ ID NO: 92            moltype = DNA  length = 1946
FEATURE                  Location/Qualifiers
source                   1..1946
                         mol_type = other DNA
                         organism = Triticum aestivum
misc_feature             1..1946
                         note = Ceres CLONE ID no.910109
misc_feature             1..1946
                         note = Encodes the peptide sequence at SEQ ID NO 93
SEQUENCE: 92
atcaaacccc ccactgcccg cgccagccag ccgcggcaat aataataact ccgccgcctc    60
ctgccatgcc gcacgctagt agtagcacgc taggatcgag tagctcgtag cgtagccgtg   120
cgagggaggg aggtgggtcg atgcccgcgc ccgtgcaacc acagcaaccg cgagccggtg   180
gtgttggcca tggggaataa gaagggcggg tcgtcgtggc tcaccgccgt caagcgggcc   240
ttccgctcgc cgtccaagga ggacagcccc aagaagtctg cacgcctccg cgaggaccct   300
gacgccgacg aggacaagac caaggcggag aggaggagat ggcttcttag gagatcctca   360
tccccgtctc cgtctccggc gtctgccccc gcgccgccgg agcagcagca gtcggcgtcg   420
aggtcggcac ctgcacccgc tgtgacggac gagcagcgtc acgccatcgc gctggccgtg   480
gcgaccgcgg cgacggccga ggctgccgtg gccacgcgc aggcggcggc cgaggtcgtc   540
cgcctgaccc gcccctcctc cagcttcgtg cgggagcact cgccgccat cgtcgtacag   600
accgccttcc gaggctacct ggcgaggcgt gctctgcgcg cgctcaaggg gctggtgaag   660
ctgcaagcgc tagtcgcgcg gcacaacgtg cggaagcagg ccaacatgac gctgcggtgc   720
atgcaggcgc tggtgcgcgt ccaggcgcgg gtgcgcgacc agcggctgcg actctcccag   780
gagtccttgt ccgccgccgg tgcggctgcg tgcggcagca gcaaatcctc gtacagcgtt   840
gacacctccg cttctctggga ctccaagtac acccaagaat acgccgaacg ccgctctgtg   900
gagcggtcgc gagacggcag cagcttcgcc gccgaagact gggacgaccg gccgcggacg   960
atagaggaga ttcaggcgat gctgcagacg aggaaagacg ctgctctcaa gcgtgagaga  1020
gcgctctcat acgccttttc tcaccaaatt tggaggaacg ccgctccgtc agtcgaggag  1080
gagatgaacg tcgacgggca gccgcgctgg gcggagaagt ggatggcgtc cgcgcgcgtc  1140
tttgatacaa acaggagcag cgccccgaact gccgcggcgg cggctgctgc ggcaccaggg  1200
cgcgcgtcca cggaccaccg cgaccaggtc aagacgttgg agatcgacac cgcacggcca  1260
ttctcctact ccacgcctcg ccggcatgcc ccaccgctcg agcacgggaa cggctcgccg  1320
atgcaccgtg cgcaccacca ggcttcggtc acgccgtcac cggggaaggc gaggccaccg  1380
attcaggtgc gctccgcgag cccgcgagtg gagcgcggca caagtggtgg aggaggaagc  1440
tacacaccga gcttgcactc ccagcgccac gcgtcctccg gctcggcggt gccgaactac  1500
atggcggcca cggaatctgc aaaggcacgt atccgctccc agagcgcgcc acggcaacgc  1560
cctgcaaccc cggagcgcga ccggccacag accgcctata ccgcctata agggagcgtc  1620
aagaagcggc tgtcgttccc cgtcccgcag gacccgtacg gcgttgggta cgcgcagagc  1680
ctgcggagcc cgagcttcaa gagcgcgacg gggcggttca cctccgagca gcgttcgacc  1740
gtctcgtctc tgtcgtgcgc agagagcgtc ggcggggaac cagtctcccc gtcgtccacc  1800
actgacctcc gccgctggct ccgttgagtt gagccccgg cgaggtgttc gttgtaatac  1860
ctgcgttgct aattttctcg taatctcctc ggagaaaaat gaccttctcg taatctatt  1920
ttttgctgct aaaaaaaaaa aaaaaa                                      1946

SEQ ID NO: 93            moltype = AA  length = 543
FEATURE                  Location/Qualifiers
source                   1..543
                         mol_type = protein
                         organism = Triticum aestivum
REGION                   1..543
                         note = Ceres CLONE ID no.910109
REGION                   1..543
```

```
                        note = Score of 1259.0 for HMM of FIGURE 1.
REGION                  1..543
                        note = Functional Homolog Of Ceres SEEDLINE ID no. ME08768
                          at SEQ ID NO.86
REGION                  130..150
                        note = Pfam Name: IQ Pfam Description: IQ
                          calmodulin-binding motif
SEQUENCE: 93
MGKKAGTTSS WLTAVKRAFR SPSKDDSPNK AARLRDDTDD DKGKRERRRW LFRKSSSPSP    60
APPTPPPPQQ QQQQSRAAAV TEEQRHAIAL AVATAATAEA AVATAQAAAE VVRLTRPSSS   120
FVREHYAAIV VQTAFRGYLA RRALRALKGL VKLQALVRGH NVRKQANMTL RCMQALVRVQ   180
ARVRDQRMRL SQDSISLSAA AASAAPCGSS KSSYSVDTST FWDSKYTHDF AAADRRSIER   240
SRDGSSFAAG DDWDDRPRTI EEIQAMLQTR KDAALKRERA LSYAFSHQIW RNPAPSVEEM   300
DVDGQPRWAE RWMASRASFD TSRSTVRASA AAAPGRASTD HRDQVKTLEI DTARPFSYST   360
PRRHGNASYH ASSSPMHRAH HHSPVTPSPS KARPPIQVRS ASPRVERGGG GGGSYTPSLH   420
SHRHHASSGG AAAVPNYMAA TESAKARVRS QSAPRQRPAT PERDRMSFGG GGGGGGAKKR   480
LSFPVPIDPY GAYAQSLRSP SFKSAAGRFS SEQRSNVSSS CAESLGGDVV SPSSTTDLRR   540
WLR                                                                 543

SEQ ID NO: 94           moltype = AA  length = 543
FEATURE                 Location/Qualifiers
source                  1..543
                        mol_type = protein
                        note = subspecies = japonica
                        organism = Oryza sativa
REGION                  1..543
                        note = Public GI ID no.115474509
REGION                  1..543
                        note = Score of 1167.6 for HMM of FIGURE 1.
REGION                  1..543
                        note = Functional Homolog Of Ceres SEEDLINE ID no. ME08768
                          at SEQ ID NO.86
REGION                  125..145
                        note = Pfam Name: IQ Pfam Description: IQ
                          calmodulin-binding motif
SEQUENCE: 94
MGKKAGTTSS WLTAVKRAFR SPSKDDSPNK AARLRDDTDD DKGKRERRRW LFRKSSSPSP    60
APPTPPPPQQ QQQQSRAAAV TEEQRHAIAL AVATAATAEA AVATAQAAAE VVRLTRPSSS   120
FVREHYAAIV VQTAFRGYLA RRALRALKGL VKLQALVRGH NVRKQANMTL RCMQALVRVQ   180
ARVRDQRMRL SQDSISLSAA AASAAPCGSS KSSYSVDTST FWDSKYTHDF AAADRRSIER   240
SRDGSSFAAG DDWDDRPRTI EEIQAMLQTR KDAALKRERA LSYAFSHQIW RNPAPSVEEM   300
DVDGQPRWAE RWMASRASFD TSRSTVRASA AAAPGRASTD HRDQVKTLEI DTARPFSYST   360
PRRHGNASYH ASSSPMHRAH HHSPVTPSPS KARPPIQVRS ASPRVERGGG GGGSYTPSLH   420
SHRHHASSGG AAAVPNYMAA TESAKARVRS QSAPRQRPAT PERDRMSFGG GGGGGGAKKR   480
LSFPVPIDPY GAYAQSLRSP SFKSAAGRFS SEQRSNVSSS CAESLGGDVV SPSSTTDLRR   540
WLR                                                                 543

SEQ ID NO: 95           moltype = DNA  length = 1812
FEATURE                 Location/Qualifiers
source                  1..1812
                        mol_type = other DNA
                        organism = Panicum virgatum
misc_feature            1..1812
                        note = Ceres CLONE ID no.1780908
misc_feature            1..1812
                        note = Encodes the peptide sequence at SEQ ID NO 96
SEQUENCE: 95
gtgaccagcc agccatggag cgcggccaac gccccccgcg ccagcaataa tacaaccccc    60
ccaccacccg ggccgcgcct gcccgtcgcc ggacatgggc aagaagggcg gcgccacgtc   120
ctgactcacc gccgtcaagc gggcgcttcc ctcgccctcc aaggacgagc cgcctcgcg   180
cgcaaggaag gcctcgcgcc tccgcgaccg cgacgacgcc cccgccgacg ccgaccaaga   240
caagcagggg aagcgggagc agcgccggcg atggctgttc cggaggtcct cctcccccgtc   300
cccgtcccct gccccgccg cgccggagca cccggccgtc acgagggagc agcgccacgc   360
catcgccgctg gcgctggcga ccgccgccac ggccgaggcc gccgtggcca cggccgggcg   420
ggcggcggag gtggtccgcc tcaccctccc cggcggcctc gccgcccgcg agcactacgc   480
cgccgtcctc atccagaccg cctttcgggg ctacctggcg cgccgcgcgc tgcgggcgct   540
cagggggcctc gtcaagctgc aaacgctcgt gcgcggccac aacgtccgca agcaggccaa   600
catgacgctc cgctgcatgc aggcgctggt gcgcgtccag gcgcgcgtcc gggaccagcg   660
gatgcgcctc tcccaggact ccatgtccct gtccatgccg cgtccgccg tcgggcgcgc   720
cgcggcgccg tgcggcagca gcaagtcgtc gtacagcgtc gacacatcca cgttctggga   780
ctccaagtac acccacgact acgccgaccg ccgtccgtc gagcggtcgc gcgacggcag   840
cagcttcgcc gccgacgact gggacgaccg gccgcggacg atagaggaga tccaggccat   900
gctgcagacg aggaaggacg cggcgctcaa gcgtgagagg gcgctgtcct acgccttctc   960
gcatcaactt tggaggaacc cggcgccggc ggcggatgga atggacgtgg acggcgagcc  1020
gcagcagccc cggtgatga cgtcgcgcgc gtccttcgac acgaaccgga gcagcagcat  1080
ccgcggcgcg gcggtgcccg ggcgcgcgtc catggaccac cgcgagcccg tgaagacgct  1140
ggggatggac acgcgcggc ccttctcgta ctcgacgccg cggcagcagg cgccgtcgtc  1200
ctcgccgatg caccaccgcg ggcactgccc ggtgacgccc tcgccgggga aggcgcggcc  1260
cccgatccag gtccggtcgg cgagcccgcg cgtggaccgc ggcgcgggcg gcgggagcta  1320
```

```
cacgccgagc ctgctgcact cccagcggca ccaccaccac caggcggggg cggcggtgcc  1380
caactacatg gcggcgacgg agtcggccaa ggcccgggtg cggtcccaga gcgcgccgcg  1440
gcagcggccc gcgacgcccg agcgcgaccg gctctccggc ggcggcggga gcgcgaagaa  1500
gcggctgtcg ttcccggcgg cggcagaggc gtacgcgcag tccctgcgga gcccgagctt  1560
caagcgcgcg gcgggcgcgt tctcgtcgga gcagcggtcg acggtgtcgt cgtcgtgcgc  1620
ggagagcctc ggcggagagc cggcgtcgcc gtcgtccacc accgacctcc gccgctggct  1680
ccgctgaggg ccggccggcc gtccgttctc cgttgtagca gtaacgccgc ttttggctc   1740
ggcagacacg accacgtgcc cctgtagcat catcttctct ctcggtgtaa ttcatggcag  1800
cttttttcga gc                                                     1812

SEQ ID NO: 96           moltype = AA   length = 361
FEATURE                 Location/Qualifiers
source                  1..361
                        mol_type = protein
                        organism = Panicum virgatum
REGION                  1..361
                        note = Ceres CLONE ID no.1780908
REGION                  1..361
                        note = Score of 598.0 for HMM of FIGURE 1.
REGION                  1..361
                        note = Functional Homolog Of Ceres SEEDLINE ID no. ME08768
                         at SEQ ID NO.86
SEQUENCE: 96
MTLRCMQALV RVQARVRDQR MRLSQDSMSL SMPLSAAGAA AAPCGSSKSS YSVDTSTFWD   60
SKYTHDYADR RSVERSRDGS SFAADDWDDR PRTIEEIQAM LQTRKDAALK RERALSYAFS  120
HQLWRNPAPA ADEMDVDGGG QQPRWMTSRA SFDTNRSSSI RGAAVPGRAS MDHREPVKTL  180
GMDTARPFSY STPRQQAPSS SPMHHRGHSP VTPSPGKARP PIQVRSASPR VDRGAGGGSY  240
TPSLLHSQRH HHHQAGAAVP NYMAATESAK ARVRSQSAPR QRPATPERDR LSGGGGSAKK  300
RLSFPAAAEA YAQSLRSPSF KSAAGRFSSE QRSTVSSSCA ESLGGEPASP SSTTDLRRWL  360
R                                                                 361

SEQ ID NO: 97           moltype = DNA  length = 1398
FEATURE                 Location/Qualifiers
source                  1..1398
                        mol_type = other DNA
                        organism = Populus balsamifera
                        sub_species = trichocarpa
misc_feature            1..1398
                        note = Ceres ANNOT ID no.1520883
misc_feature            1..1398
                        note = Encodes the peptide sequence at SEQ ID NO 98
SEQUENCE: 97
atgggggaaga aaggaaaagg atggtttaca tctgtgaaga gagtgttcaa atcatcatct   60
cctaaggaat taccagtagg gaaaaagaaa gacaacgcag agaaatggca acatgaggct  120
ccagaagttg tgtcattaga gcattttcct actggaagtt ctcctgatgt tacaaatgat  180
gagagcaatg tatcaactcc agtaactgaa gatagaaatc atgccattgc tgtggcagta  240
gcgactgctg ccgcagcaga agctgcggtt gcagctgcct caagcggcgc taaagttgtt  300
cgcttagctg gttatggacg acaatcaaag gaagaaagag ctgccatcct catacaatca  360
ttctataggg gctaccttgc tcggcgtgcc ttacgcgcat tgaagggatt ggtgaggctc  420
caagcattag tgagaggcca caatgtaaga agcaagcac aaatgacaat gagaagcatg   480
caagctcttg ttcgtgtgca agcaagagta agagcaagaa gacttgaatt agctcacgag  540
aagcttcaaa ggaagacaga ggaagaagat gaacgaagac taccagtgga cgaagacttt  600
atgaatccaa agaatccatt gaagagttat aaatgggata ggaggaatca aagttcagat  660
aatttcaaag aaaatgcttc aaagaagcat gatgctgtca tgaaaagaga gagaccctt   720
gcttatgctt atgccttcca gcagcagcag cagcaacaat tactctcaca aaatagtcct  780
aatggtaaag aaacaggaca ttttgtgaac gaacacgaga agatgcaatg gggatggaat  840
tggcttgaga gatggatgtc agcacaatca tataacgtgc gtcaatcggg tccaaatgaa  900
gggtcttacg tgacagtaaa cacaactaca accacgacca ccacagagga catgtccgag  960
aagacagtag agatggacat ggtgacccca acaggccatc gcaatcccaa catgggcatg 1020
ctagacacca atccatattc gaatcgaccc caatggcaat caagttcaag caatgtacgt 1080
agctacatgg ctccgaccca gtccgcaaag gcgaaagtgc gttctcaaag tttgatcaag 1140
caacgtgccc cagcgacacc tctgtggaat ccatccacca agaaagattc aagcattgtt 1200
ggtccaggtt gtgattcttc cagttcaggt ggtggaacaa caacttatca cgctccaaga 1260
agtcctagcc ccaaacataa cgggatgcgc ctgcattcga agacatgc tggtggatat   1320
agccctgatt tcaatggcgg tgatgattgg aggttgcctc ctcttgatgg tcatggatgg 1380
aggaatgatt ttggttga                                               1398

SEQ ID NO: 98           moltype = AA   length = 309
FEATURE                 Location/Qualifiers
source                  1..309
                        mol_type = protein
                        note = subspecies = trichocarpa
                        organism = Populus balsamifera
REGION                  1..309
                        note = Ceres ANNOT ID no.1520883
REGION                  1..309
                        note = Score of 495.7 for HMM of FIGURE 1.
REGION                  1..309
                        note = Functional Homolog Of Ceres SEEDLINE ID no. ME08768
```

```
                        at SEQ ID NO.86
SEQUENCE: 98
MRSMQALVRV QARVRARRLE LAHEKLQRKT EEEDERRLPV DEDFMNPKNP LKSYKWDRRN      60
QSSDNFKENA SKKHDAVMKR ERALAYAYAF QQQQQQQLLS QNSPNGKETG HFVNEHEKMQ     120
WGWNWLERWM SAQSYNVRQS GPNEGSYVTV NTTTTTTTTE DMSEKTVEMD MVTPTGTSNP     180
NMGMLDTNPY SNRPQWQSSS SNVRSYMAPT QSAKAKVRSQ SLIKQRAPAT PLWNPSTKKD     240
SSIVGPGCDS SSSGGGTTTY HAPRSPSPKH NGMRLHSRRH AGGYSPDFNG GDDWRLPPLD     300
GHGWRNDFG                                                             309

SEQ ID NO: 99           moltype = DNA  length = 1445
FEATURE                 Location/Qualifiers
source                  1..1445
                        mol_type = other DNA
                        organism = Arabidopsis thaliana
misc_feature            1..1445
                        note = Ceres CLONE ID no.148018
misc_feature            1..1445
                        note = Encodes the peptide sequence at SEQ ID NO 100
SEQUENCE: 99
attgggattt catttagata atttttttt gggtcttgat ctaagttttg ttctttctaa      60
tttggtaagg caagaagagc attaagagca ttaaaagggt tagtgaagct acaagcattg    120
gtgagggggac ataatgtgag aaagcaagct aaaatgcat taaggtgtat gcaagctctg    180
gttcgagtcc agtctcgtgt gcttgaccaa cgcaaacgct tgtctcatga cggtagtcgc    240
aaatccgcgt tcagtgactc tcacgctgtt tttgaatctc gctatcttca agatttgtca    300
gatcgacaat ccatgtcaag agaaggaagc agcgccgcgg aagattggga tgaccgacca    360
cacacgatag acgcagtgaa agtgatgcta aacggacgg gagacacagt attgagacat     420
gacaagacta atttgtcaca agcttttctct caaaagatgt ggaggacggt tggtaaccaa   480
tccacggaag acaccacga ggtagaactt gaagaggaaa ggccaaaatg gcttgaccgg    540
tggatggcta ctagaccgtg ggataaacga gctagtagta gagcttcggt tgaccaaagg    600
gtttcagtta aaaccgttga aatcgacact tctcagcctt actcaagaac aggagcagga    660
agcccgagtc gtggccaaag acctagtcc ccatcaagaa ctagccacca ttaccaatcc     720
cgcaataatt tctcagccac tccatctccg gctaagtcta gaccaatact tattcggtca    780
gctagtccac ggtgccagag agacccgagg gaagaccgtg accgagcagc ttatagttat    840
acatcaaaca caccaagctt gagatccaat tatagtttca cagctaggag tggatgtaca    900
ttagtaccac aatggttaat aatgcatcat tgttgcctaa ttacatggcg agtacagagt    960
cagctaaagc gaggatccgg tctcatagtc caccgaggca acggccctca actcccgaga   1020
gggaccgtgc ggstttrgct acaagaaacg rytctsgtat ccggtaccac cgccagcgga   1080
gtatgaggac aataatagct taaggagtcc aagctttaag agtgtggctg gttcacattt   1140
tggtgaaatg ttagagcagc aatcgaatta tccttcatgt tgcactgagt ctaacggtgt   1200
tgagatctct ccagcttcta ctagtgactt taggaattgg cttagatgat tggtggtgat   1260
gccaaatcaa ctgtcaagat cttttcatcat cctccaggaa aagaacgttt taaaatttta   1320
tattccagaa gaaaacaaac acttttatat tgtgtcgttg aggttgattt gtgtttggaa    1380
gataagttta ttgacctatt gatctgtaac ttcataagat tttgaaacgt tagaagattc   1440
aaaag                                                               1445

SEQ ID NO: 100          moltype = AA  length = 310
FEATURE                 Location/Qualifiers
source                  1..310
                        mol_type = protein
                        organism = Arabidopsis thaliana
REGION                  1..310
                        note = Ceres CLONE ID no.148018
REGION                  1..310
                        note = Score of 458.7 for HMM of FIGURE 1.
REGION                  1..310
                        note = Functional Homolog Of Ceres SEEDLINE ID no. ME08768
                        at SEQ ID NO.86
SITE                    294
                        note = Xaa is any aa, unknown, or other
SITE                    295
                        note = Xaa is any aa, unknown, or other
SITE                    300
                        note = Xaa is any aa, unknown, or other
SITE                    301
                        note = Xaa is any aa, unknown, or other
SEQUENCE: 100
MTLRCMQALV RVQSRVLDQR KRLSHDGSRK SAFSDSHAVF ESRYLQDLSD RQSMSREGSS      60
AAEDWDDRPH TIDAVKVMLQ RRRDTALRHD KTNLSQAFSQ KMWRTVGNQS TEGHHEVELE    120
EERPKWLDRW MATRPWDKRA SSRASVDQRV SVKTVEIDTS QPYSRTGAGS PSRGQRPSSP    180
SRTSHHYQSR NNFSATPSPA KSRPILIRSA SPRCQRDPRE DRDRAAYSYT SNTPSLRSNY    240
SFTARSGCTL VPQWLIMHHC CLITWRVQSQ LKRGSGLIVH RGNGPQLPRG TVRXXLQETX    300
XVSGTTASGV                                                           310

SEQ ID NO: 101          moltype = AA  length = 364
FEATURE                 Location/Qualifiers
source                  1..364
                        mol_type = protein
                        organism = Arabidopsis thaliana
REGION                  1..364
```

```
                        note = Public GI ID no.18378797
REGION                  1..364
                        note = Score of 546.8 for HMM of FIGURE 1.
REGION                  1..364
                        note = Functional Homolog Of Ceres SEEDLINE ID no. ME08768
                         at SEQ ID NO.86
SEQUENCE: 101
MTLRCMQALV RVQSRVLDQR KRLSHDGSRK SAFSDSHAVF ESRYLQDLSD RQSMSREGSS   60
AAEDWDDRPH TIDAVKVMLQ RRRDTALRHD KTNLSQAFSQ KMWRTVGNQS TEGHHEVELE  120
EERPKWLDRW MATRPWDKRA SSRASVDQRV SVKTVEIDTS QPYSRTGAGS PSRGQRPSSP  180
SRTSHHYQSR NNFSATPSPA KSRPILIRSA SPRCQRDPRE DRDRAAYSYT SNTPSLRSNY  240
SFTARSGCSI STTMVNNASL LPNYMASTES AKARIRSHSA PRQRPSTPER DRAGLVKKRL  300
SYPVPPPAEY EDNNSLRSPS FKSVAGSHFG GMLEQQSNYS SCCTESNGVE ISPASTSDFR  360
NWLR                                                               364

SEQ ID NO: 102          moltype = AA  length = 364
FEATURE                 Location/Qualifiers
source                  1..364
                        mol_type = protein
                        organism = Arabidopsis thaliana
REGION                  1..364
                        note = Public GI ID no.21553500
REGION                  1..364
                        note = Score of 524.9 for HMM of FIGURE 1.
REGION                  1..364
                        note = Functional Homolog Of Ceres SEEDLINE ID no. ME08768
                         at SEQ ID NO.86
SITE                    288
                        note = Xaa is any aa, unknown, or other
SITE                    294
                        note = Xaa is any aa, unknown, or other
SITE                    296
                        note = Xaa is any aa, unknown, or other
SITE                    300
                        note = Xaa is any aa, unknown, or other
SITE                    301
                        note = Xaa is any aa, unknown, or other
SEQUENCE: 102
MTLRCMQALV RVQSRVLDQR KRLSHDGSRK SAFSDSHAVF ESRYLQDLSD RQSMSREGSS   60
AAEDWDDRPH TIDAVKVMLQ RRRDTALRHD KTNLSQAFSQ KMWRTVGNQS TEGHHEVELE  120
EERPKWLDRW MATRPWDKRA SSRASVDQRV SVKTVEIDTS QPYSRTGAGS PSRGQRPSSP  180
SRTSHHYQSR NNFSATPSPA KSRPILIRSA SPRCQRDPRE DRDRAAYSYT SNTPSLRSNY  240
SFTARSGCSI STTMVNNASL LPNYMASTES AKARIRSHSA PRQRPSTXER DRAXLXKKRX  300
XYPVPPPAEY EDNNSLRSPS FKSVAGSHFG GMLEQQSNYS SCCTESNGVE ISPASTSDFR  360
NWLR                                                               364

SEQ ID NO: 103          moltype = DNA  length = 1713
FEATURE                 Location/Qualifiers
source                  1..1713
                        mol_type = other DNA
                        organism = Populus balsamifera
                        sub_species = trichocarpa
misc_feature            1..1713
                        note = Ceres ANNOT ID no.1444522
misc_feature            1..1713
                        note = Encodes the peptide sequence at SEQ ID NO 104
SEQUENCE: 103
atggggaaga agggaggtag ctcatggttg actgctgtga aagggcgtt tagatctcca    60
actaaagaaa gtgacaagag ggctactggg gttggccatg accaagaaga agatgaagaa   120
aagaagagag ggaagagaag atggttattg aggaaaccta caaatcaaga aacggcgaca   180
caacagaacc tgtcaaaggc aggaaatgtt aaggcatccc caggtggtgg tggaggtgct   240
ccagcagacc atgtgtcggc agctgcagca gctgagcaaa gcatgcaat tgcagtagca    300
gttgctactg cagctgcagc tgaagctgct gtagccactg cccaggcggc ggcggaggtt   360
gctcggctca ctaggccttc atatcatcct agagaacatt atgctgccat tgtcattcaa   420
acagctttta gaggatactt ggcaaggcgg gctcttcgtg cacttaaagg gctagtgaag   480
ttgcaagctt tagtaagggg acacaatgtg agaaaacagg ccaagatgac cctgcgatgc   540
atgcaagctc tggctcgagt gcaggctcga gtgcttgatc aacgcgtgag actttcacat   600
gaaggcagca ggaaatctgc atttagtgac accaatagcg tgcttgaatc gcgatatctt   660
caagacattt cagatagaaa atccatgtca agagaaagca gtagcattgc agatgattga   720
gatgatcggc cacactccat tgaggaagtc aaggccatgt tgcaacgcag gaaagaagct   780
gcgttcaagc gtgaaaagac cttatctcaa gcttctctc agcagctcat ggctaattgg    840
ttcaattttt tcaaacccat gtccaagata tggagaaatg gcagaagccc atcaaatggc   900
aatgaagatg agctccaaga aagaccacaa tggcttgatc aatggatgcc tgcaaagcca   960
tgggacaata gcagcagagc aagagcttca actgatcaag gacccaccct caaactgta   1020
gaaattgaca cctcccaacc ttattcatat ttagttccta attttagaag aacaaaccaa  1080
aaccaacatc accaacacaa gagatccaat tcatcaaaca atggtgtggc acactctgct  1140
ccttctccac tccatagagc tcatcaaact gctccactcc accactctcc tatcacaccc  1200
tccccatcaa aaactaggcc tcttcaggtt cgttcagcta gtccacgatg tgcaagagaa  1260
gatagaagtt gtaattcctc tcaaacacca agtttaaggt ccaattattt ttacaatgga  1320
```

```
agtttgaatc aacatggaat caggggtggt gctagtgtta gtagtaatgg taatgctaca  1380
ttgccaaatt acatggctgc aaccgagtct gccaaggcta gattgagatc acagagtgca  1440
ccaaggcaaa gaccatcaac accagaacga gaccggattg ggtctgcaag aaaacggctt  1500
tcgtatccag cccccgaccc ttgtgatgtc ggtatagttt atggcggtgc tggttacggc  1560
catggtttaa ggagtccaag ctttaagagc gtgagcggtc cacgtttggg tggactagaa  1620
caacagtcta actattcttc ttgctgtacg gatagctttg gtggtgagct ttccccttct  1680
tcaactaacg atcttaggag gtggttgaga tga                                1713

SEQ ID NO: 104            moltype = AA  length = 395
FEATURE                   Location/Qualifiers
source                    1..395
                          mol_type = protein
                          note = subspecies = trichocarpa
                          organism = Populus balsamifera
REGION                    1..395
                          note = Ceres ANNOT ID no.1444522
REGION                    1..395
                          note = Score of 439.2 for HMM of FIGURE 1.
REGION                    1..395
                          note = Functional Homolog Of Ceres SEEDLINE ID no. ME08768
                          at SEQ ID NO.86
SEQUENCE: 104
MTLRCMQALA RVQARVLDQR VRLSHEGSRK SAFSDTNSVL ESRYLQDISD RKSMSRESSS   60
IADDWDDRPH SIEEVKAMLQ RRKEAAFKRE KTLSQAFSQQ LMANWFNFFK PMSKIWRNGR  120
SPSNGNEDEL QERPQWLDQW MPAKPWDNSS RARASTDQRD PIKTVEIDTS QPYSYLVPNF  180
RRTNQNQHHQ HQRSNSSNNG VAHSAPSPLH RAHQTAPLHH SPITPSPSKT RPLQVRSASP  240
RCAREDRSCN SSQTPSLRSN YFYNGSLNQH GIRGGASVSS NGNATLPNYM AATESAKARL  300
RSQSAPRQRP STPERDRIGS ARKRLSYPAP DPCDVGIVYG GAGYGHGLRS PSFKSVSGSR  360
LGGLEQQSNY SSCCTDSFGG ELSPSSTNDL RRWLR                             395

SEQ ID NO: 105            moltype = DNA  length = 1443
FEATURE                   Location/Qualifiers
source                    1..1443
                          mol_type = other DNA
                          organism = Populus balsamifera
                          sub_species = trichocarpa
misc_feature              1..1443
                          note = Ceres ANNOT ID no.1467519
misc_feature              1..1443
                          note = Encodes the peptide sequence at SEQ ID NO 106
SEQUENCE: 105
atggggaaga aaggaaaagg atggtttaca tctgtgaaga gagtgttcaa atcatcatct   60
cctaaggaat taccagtagg gaaaaagaaa gacaacgcag agaaatggca acatgaggct  120
ccagaagttg tgtcattaga gcattttcct actggaagtt ctcctgatgt acaaatgat   180
gagagcaatg tatcaactcc agtaactgaa gatagaaatc atgccattgc tgtggcagta  240
gcgactgctg ccgcagcaga agctgcggtt gcagctgctc aagcggcggc taaagttgtt  300
cgcttagctg gttatggacg acaatcaaag gaagaaagag tgccatcct catacaatca  360
ttctataggg gctaccttgt aatccctttc ttcatttcac tttatttga tcaatataat  420
ctggctcggc gtgccttacg cgcattgaag ggattggtga ggctccaagc attagtgaga  480
ggccacaatg taagaaagca agcacaaatg acaatgaga gcatgcaagc tcttgttcgt  540
gtgcaagcaa gagtaagagc aagaagactt gaattagctc acgagaagct tcaaaggaag  600
acagaggaag aagatgaacg aagactacca gtggacgaag actttatgaa tccaaagaat  660
ccattgaaga gttataaatg ggataggagg aatcaaagtt cagataattt caaagaaaat  720
gcttcaaaga agcatgatgc tgtcatgaaa agagagagag cccttgctta tgcttatgcc  780
ttccagcagc agcagcagca acaattactc tcacaaaata gtcctaatgg taaagaaaca  840
ggacattttg tgaacgaaca cgagaagatg caatggggat ggaattggct tgagagatgg  900
atgtcagcac aatcatataa cgtgcgtcaa tcgggtccaa atgaagggtc ttacgtgaca  960
gtaaacacaa ctacaaccac gaccaccaca gaggacatgt ccgagaagac agtagagatg 1020
gacatggtga ccccaacagg cactagcaat cccaacatgg gcatgctaga caccaatcca 1080
tattcgaatc gaccccaatg gcaatcaagt tcaagcaatg tacgtagcta catggctccg 1140
acccagtccg caaaggcgaa agtgcgttct caaagtttga tcaagcaacg tgccccagcg 1200
acacctctgt ggaatccatc caccaagaaa gattcaagca ttgttggtcc aggttgtgat 1260
tcttccagtt caggtggtgg aacaacaact tatcacgctc caagaagtcc tagccccaaa 1320
cataacggga tgcgcctgca ttcgagaaga catgctggtg gatatagccc tgatttcaat 1380
ggcggtgatg attggaggtt gcctcctctt gatggtcatg gatggaggaa tgattttggt 1440
tga                                                                1443

SEQ ID NO: 106            moltype = AA  length = 309
FEATURE                   Location/Qualifiers
source                    1..309
                          mol_type = protein
                          note = subspecies = trichocarpa
                          organism = Populus balsamifera
REGION                    1..309
                          note = Ceres ANNOT ID no.1467519
REGION                    1..309
                          note = Score of 495.7 for HMM of FIGURE 1.
REGION                    1..309
                          note = Functional Homolog Of Ceres SEEDLINE ID no. ME08768
```

```
                              at SEQ ID NO.86
SEQUENCE: 106
MRSMQALVRV QARVRARRLE LAHEKLQRKT EEEDERRLPV DEDFMNPKNP LKSYKWDRRN     60
QSSDNFKENA SKKHDAVMKR ERALAYAYAF QQQQQQQLLS QNSPNGKETG HFVNEHEKMQ    120
WGWNWLERWM SAQSYNVRQS GPNEGSYVTV NTTTTTTTTE DMSEKTVEMD MVTPTGTSNP    180
NMGMLDTNPY SNRPQWQSSS SNVRSYMAPT QSAKAKVRSQ SLIKQRAPAT PLWNPSTKKD    240
SSIVGPGCDS SSSGGGTTTY HAPRSPSPKH NGMRLHSRRH AGGYSPDFNG GDDWRLPPLD    300
GHGWRNDFG                                                             309

SEQ ID NO: 107           moltype = AA   length = 291
FEATURE                  Location/Qualifiers
source                   1..291
                         mol_type = protein
                         note = subspecies = indica
                         organism = Oryza sativa
REGION                   1..291
                         note = Public GI ID no.125559938
REGION                   1..291
                         note = Score of 403.9 for HMM of FIGURE 1.
REGION                   1..291
                         note = Functional Homolog Of Ceres SEEDLINE ID no. ME08768
                              at SEQ ID NO.86
SEQUENCE: 107
MQRLQERSRD GSSFAAGDDW DDRPRTIEEI QAMLQTRKDA ALKRERALSY AFSHQIWRNP     60
APSVEEMDVD GQPRWAERWM ASRASFDTSR STVRASAAAA PGRASTDHRD QVKTLEIDTA    120
RPFSYSTPRR HGNASYHASS SPMHRAHHHS PVTPSPSKAR PPIQVRSASP RVERGGGGGG    180
SYTPSLHSHR HHASSGGAAA VPNYMAATES AKARDVIRGA ARRGAKKRLS FPVPIDPYGA    240
YAQSLRSPSF KSAAGRFSSE QRSNVSSSCA ESLGGDVVSP SSTTDLRRWL R             291

SEQ ID NO: 108           moltype = DNA  length = 1509
FEATURE                  Location/Qualifiers
source                   1..1509
                         mol_type = other DNA
                         organism = Arabidopsis thaliana
misc_feature             1..1509
                         note = Ceres SEEDLINE ID no.ME19173
misc_feature             1..1509
                         note = Encodes the peptide sequence at SEQ ID NO. 109
SEQUENCE: 108
acattctccg atattctctc tctctctatc aatctctcac tctcaaactt tctacatacc     60
tgaagaaaaa aataatctac gaattcgagc caaaaagatc gaaactttttt aatctatggg   120
tgcttcaggg aaatgggtca agtccattat cggtctcaag aagctagaga aggatgaaat    180
cgaaaagggt aatgggaaaa acaagaaatg gaagctactt cagtagattc                240
atggaagggt tttcgaggaa acatcggttc tgattcagac ggtgttgatt cttctactgt    300
ttactctgct gctgttgcta ctgttcttag agctcctcct aaagatttca aagctgttag    360
agaagaatgg gctgctatta gaatccaaac cgcttttcgt ggattcttgg cgagaagagc    420
gttgagggca ttgaaaggga tagtgaggtt acaagcttta gtgagaggaa gacaagttag    480
gaaacaagca gctgttacat tgagatgcat gcaagctttg gtgagagtac aagctcgtgt    540
tagagctcgt cgtgtgagga tgactgttga aggacaagct gttcaaaagc ttttagatga    600
acatagaacc aaatctgatc tcttgaaaga agtcgaggaa gggtggtgtg ataggaaagg    660
tactgtggat gatattaagt caaagttgca gcagagacaa gaaggtgctt ttaagaggga    720
acgtgctttg gcttatgctc ttgctcaaaa gcaatggagg tcaactacta gctcaaacct    780
taagacgaat agttcgattt cgtatcttaa aagtcaagag tttgataaga atagttgggg    840
atggagttgg ttggagcgtt ggatggctgc taggccatgg gagactagac ttatggacac    900
tgttgatacc gctgccacgc ctcctcctct gcctcataaa catttgaaat caccggaaac    960
tgcggatgtt gttcaagtta gagaaacaa tgtgaccact agagtatctg caaaacctcc   1020
tcctcatatg ctgtcttcaa gtcctggtta tgagtttaac gagagctcag gttcatcctc   1080
gatttgtact tcaactacgc ctgtttctgg aaaaactgga cttgtttcag ataactctag   1140
cagtcaagca aaaaagcaca agccaagtta catgagcttg actgaatcga caaaggctaa   1200
gcgaagaact aaccgcggtc tcaggcaatc tatgatgag tttcagttta tgaagaactc    1260
tggaatgttt acaggggaat tgaagactag tccttcctca gatcctttttg ttagtttctc   1320
caaaccactc ggtgttccta ctcgattcga gaagccgaga ggttaaatgt gaccttgtta   1380
gattggagtt tcaacagctt gttgttgtct tgtgtgttgt gagatatctg tgtatgttgt   1440
taattgttct ttttccttttg gaactacatt ggagtttga atttaaatat aaatttcagt   1500
cttgctttt                                                            1509

SEQ ID NO: 109           moltype = AA   length = 416
FEATURE                  Location/Qualifiers
source                   1..416
                         mol_type = protein
                         organism = Arabidopsis thaliana
REGION                   1..416
                         note = Ceres SEEDLINE ID no.ME19173
REGION                   1..416
                         note = Score of 954.4 for HMM of FIGURE 3.
REGION                   84..104
                         note = Pfam Name: IQ Pfam Description: IQ
                              calmodulin-binding motif
SEQUENCE: 109
```

```
MGASGKWVKS IIGLKKLEKD EIEKGNGKNK KWKLWRTTSV DSWKGFRGKH RSDSDGVDSS    60
TVYSAAVATV LRAPPKDFKA VREEWAAIRI QTAFRGFLAR RALRALKGIV RLQALVRGRQ   120
VRKQAAVTLR CMQALVRVQA RVRARRVRMT VEGQAVQKLL DEHRTKSDLL KEVEEGWCDR   180
KGTVDDIKSK LQQRQEGAFK RERALAYALA QKQWRSTTSS NLKTNSSISY LKSQEFDKNS   240
WGWSWLERWM AARPWETRLM DTVDTAATPP PLPHKHLKSP ETADVVQVRR NNVTTRVSAK   300
PPPHMLSSSP GYEFNESSGS SSICTSTTPV SGKTGLVSDN SSSQAKKHKP SYMSLTESTK   360
AKRRTNRGLR QSMDEFQFMK NSGMFTGELK TSPSSDPFVS FSKPLGVPTR FEKPRG      416

SEQ ID NO: 110           moltype = AA   length = 442
FEATURE                  Location/Qualifiers
source                   1..442
                         mol_type = protein
                         note = subspecies = japonica
                         organism = Oryza sativa
REGION                   1..442
                         note = Public GI ID no.115435054
REGION                   1..442
                         note = Score of 949.2 for HMM of FIGURE 3.
REGION                   1..442
                         note = Functional Homolog Of Ceres SEEDLINE ID no. ME19173
                           at SEQ ID NO.109
REGION                   109..129
                         note = Pfam Name: IQ Pfam Description: IQ
                           calmodulin-binding motif
SEQUENCE: 110
MGGSGKWVKS LIGLKKPDRE DCKEKLQVPS VNGRGGGKGR KWKLWRSSSG DHGSLWRGSR    60
GGGGGGGHHR SASSDASDDA SSAAADPFTA AVATVARAPA KDFMAVRQEW AAIRVQTAFR   120
GPFLARRALRA LKGLVRLQAI VRGRQVRKQA AVTLRCMQAL VRVQARIRAR RVRMSTEGQA   180
VQKLLEARRT KLDILREAEE GWCDSQGTLE DVRVKLQKRQ EGAIKRERAI AYAYSQQIEG   240
ATKCNQQPKP TSYGRLNQSG MLLKHQHFDK SNGNWSWLER WMAARPWENR LMEEHNQTNS   300
SSPDLLSSKN CEDSFGILGD FSEPNSVKVR KNNVSKRVCA KPPVVSHHQR IKAQSISSLS   360
TELHNDESSA SSSSCFASTP ISFSTFVTTE KTEDSIRARP NYMNMTESIK AKRKACNAQR   420
TTAGKLMEDR KASGVELKVA QV                                           442

SEQ ID NO: 111           moltype = DNA   length = 1661
FEATURE                  Location/Qualifiers
source                   1..1661
                         mol_type = other DNA
                         organism = Gossypium hirsutum
misc_feature             1..1661
                         note = Ceres CLONE ID no.1847857
misc_feature             1..1661
                         note = Encodes the peptide sequence at SEQ ID NO 112
SEQUENCE: 111
atttttttc tctttgagtc ttgttgaaga cttgaggttc tctcccccc cccacccttt     60
ttttggtgca aaaagatttc cttttgtca ctcatactct gttatcaatt gtttccatcg   120
tagcccattt cctttttctt ttcttaaata acagttgttt gtatctctga gaaaaatata   180
tactttgaaa ctaccatggg tgcttcagcg aaatgggtga atctcttat tggtctcaag    240
aaaactgtaa aagatgacca agaaaagatg ggtggcaaga gcaagaaatg gaagctatgg   300
aggagttctt caggggatgg aataggttcc tcatggaagg gttttaaagg aaagtttaaa    360
gcagattacg aaggatctga ttcttcacca aggtctgaca cttctctgc tgccatggct    420
gctgtggttc gagctcctcc taaagatttc agggttgtaa ggcaagaatg ggctgctatc   480
cgcattcaaa ctgctttccg aggcttcttg gcaagaaggg ctttaagggc tttaaaggga   540
gtcgttagga tccaagcctt tgttcgcggt cgacaggtga ggaaacaggc tgctgtgaca    600
ctccggtgca tgcaagctct cgttcgtgtc aagctcgtg ttagagctcg tcgtgtccga   660
atgtccatcg agggccaggc agttcaaaag atactcgatg aacaccgcag caaggccgaa    720
ctcttgaaac aagccgagga gggctggtgt gatagtaaag gaacattgga tgatgttaca   780
ataaagctac aactgagaca agaaggtgct ttcaagagag aacgagcact tgcttattct    840
cttgcacaaa agcaatggag attgaacatg gattcaaata ctcgaacaaa tagttcggtt   900
tcagttccat atctcaaaaa ccaagtgttt gataagaata gttggggatg gagttggctt    960
gaacgttgga tggcagcccg gccgtgggaa actcgattga tggagcaatc acaggcagac  1020
ccttccgaac caactccacc atcgaaaact tgttcagagt ctagaaagat tactagaccg  1080
accgaaccat gttcagtgaa ggtacgaaag aacaatgtca caactaggat ttcagcaaag  1140
cctccccata ttggtcaagg tactagatca tcatccgatca caagttccga attccggttc  1200
gaagagagct ccgcatcatc atcgatatgc acatctacaa cacgggtctc gtggaataca  1260
atgccgactt cagagagaac ggagaagacg gggaatagta ggccaaacta tgaacttg    1320
acagagtcta ccaaggccaa acaaagagct gcaaatcatg ccttacgaag aatccaaatg  1380
cagtccatgg atgagttcca gttaaagaaa acagctggtt tgtatgatgg ggattcaaag  1440
agtagtgtgg ggtcggatcc tacggtccat atgtctcggc cactgtatcc accaacaaga  1500
ttaggttaaa agtggttgtg tctgtgatta agtagatcgt cagtttttatt atgttttcca  1560
acatcttgtt tagttttagt gtgatgtagc aaacaagttg ttgagtgttt ttgtatctaa  1620
ttcgacggca attcattctg caaaaaaaaa aaaaaaaaa a                       1661

SEQ ID NO: 112           moltype = AA   length = 437
FEATURE                  Location/Qualifiers
source                   1..437
                         mol_type = protein
                         organism = Gossypium hirsutum
REGION                   1..437
```

```
                        note = Ceres CLONE ID no.1847857
REGION                  1..437
                        note = Score of 1019.5 for HMM of FIGURE 3.
REGION                  1..437
                        note = Functional Homolog Of Ceres SEEDLINE ID no. ME19173
                          at SEQ ID NO.109
REGION                  91..111
                        note = Pfam Name: IQ Pfam Description: IQ
                          calmodulin-binding motif
SEQUENCE: 112
MGASAKWVKS LIGLKKTVKD DQEKMGGKSK KWKLWRSSSG DGIGSSWKGF KGKFKADYEG    60
SDSSPRSEAF SAAMAAVVRA PPKDFRVVRQ EWAAIRIQTA FRGFLARRAL RALKGVVRIQ   120
APVRGRQVRK QAAVTLRCMQ ALVRVQARVR ARRVRMSIEG QAVQKILDEH RSKAELLKQA   180
EEGWCDSKGT LDDVTIKLQL RQEGAFKRER ALAYSLAQKQ WRLNMDSNTR TNSSVSVPYL   240
KNQVFDKNSW GWSWLERWMA ARPWETRLME QSQADPSEPT PPSKTCSESR KITRPTEPCS   300
VKVRKNNVTT RISAKPPHIG QGTRSSSSPS SEFRFEESSA SSSICTSTTR VSWNTMPTSE   360
RTEKTGNSRP NYMNLTESTK AKQRAANHAL RRIQMQSMDE FQLKKTAGLY DGDSKSSVGS   420
DPTVHMSRPL YPPTRLG                                                 437

SEQ ID NO: 113           moltype = DNA  length = 1353
FEATURE                  Location/Qualifiers
source                   1..1353
                         mol_type = other DNA
                         organism = Populus balsamifera
                         sub_species = trichocarpa
misc_feature             1..1353
                         note = Ceres ANNOT ID no.1455219
misc_feature             1..1353
                         note = Encodes the peptide sequence at SEQ ID NO 114
SEQUENCE: 113
atgggtgcat caggaaaatg ggtgaaatcc attataggtc taaaaaagtc tgataaagat    60
caagaccaat atgagaaggt gagtggaaag agcaagaaat ggaagctatg gaggagttca   120
tcaggagatt tgggtcttc atggaagggt ttcaagggga accacagagc agcatcagag    180
gcatcgggtt cttcaccact ggctgatcca tttactgctg caatggctac tgtggttaga   240
gctcctccta aggatttcag ggttgtcagg caagaatggg ctgctatcag gattcaaact   300
gcttttcgtg gattcttggc aagaagggct ctgagggcct tgaaggagt ggtgagactc    360
caagctctag ttcgaggtcg acaagtgagg aagcaggctg cagtgacact taagtgcatg   420
caagctcttg ttcgtgttca agctcatgtt agggctcgtc gtgtgcgaat gtccttagaa   480
gggcaggcag tgcagaatat gctgaatgag cgacgtagca aggctgacct cttgaaacat   540
gctgaggaag ggtggtgtga taaaaggggg acattagaag acgtgaagtc aaaactgcaa   600
atgaggcaag aaggagcctt caagagagaa agagctattg cttactccct tgctcaaaaa   660
caatggagat caaaccccag ctcaaacact cgacccaata actcggtata ttcttttcaag  720
aatgaggagt ttgataagaa tagctgggga tggagttggc ttgaacgttg gatggcagcc   780
aagccatggg agactagatt gatggaacaa acccatactg atccctcagt gactccacca   840
cccaagtcct gtgtagatgc aagcacacat tcgaaatcct ttgaacaaag ttcagtgaaa   900
gtgagaaaga acaatgtaac cactagaatt tcagcgagac ctccaatcgg gcatgttact   960
cgctcatctt caagtccaag ttctgaagtc cgctttgatg agagctcaag ttcttcatca  1020
atttgtactt ctacaacacc aatatcagga aacactggct tggcctcaga taaaacagag  1080
gagagtggta acagcaggcc aaactacatg aacctgaccg agtcaaccaa ggcaaagcaa  1140
aacacatcca gtcatttatt tcataggatt caaaggcagt ccatggatga gtttcagttt  1200
ttcaaaaagt cagcggcgtt ctcaaatgga gattcaaaaa gcagtgctgg ttctgatcct  1260
tcagttaatt tatccaagcc actttgcttg ccgacaagat ttgataagaa ctcgatgaaa  1320
caaataagag gaacggatca tttgtatgcc tag                               1353

SEQ ID NO: 114           moltype = AA  length = 450
FEATURE                  Location/Qualifiers
source                   1..450
                         mol_type = protein
                         note = subspecies = trichocarpa
                         organism = Populus balsamifera
REGION                   1..450
                         note = Ceres ANNOT ID no.1455219
REGION                   1..450
                         note = Score of 1091.4 for HMM of FIGURE 3.
REGION                   1..450
                         note = Functional Homolog Of Ceres SEEDLINE ID no. ME19173
                           at SEQ ID NO.109
REGION                   92..112
                         note = Pfam Name: IQ Pfam Description: IQ
                           calmodulin-binding motif
SEQUENCE: 114
MGASGKWVKS IIGLKKSDKD QDQYEKVSGK SKKWKLWRSS SGDLGSSWKG FKGNHRAASE    60
ASGSSPLADP FTAAMATVVR APPKDFRVVR QEWAAIRIQT AFRGFLARRA LRALKGVVRL   120
QALVRGRQVR KQAAVTLRCM QALVRVQAHV RARRVRMSLE GQAVQNMLNE RRSKADLLKH   180
AEEGWCDRKG TLEDVKSKLQ MRQEGAFKRE RAIAYSLAQK QWRSNPSSNT RPNNSVYSFK   240
NEEFDKNSWG WSWLERWMAA KPWETRLMEQ THTDPSVTPP PKSCVDASTH SKSFEQSSVK   300
VRKNNVTTRI SARPPIGHVT RSSSSPSSEV RFDESSASSS ICTSTTPISG NTGLASDKTE   360
ESGNSRPNYM NLTESTKAKQ NTSSHLFHRI QRQSMDEFQF FKKSAAFSNG DSKSSAGSDP   420
SVNLSKPLCL PTRFDKNSMK QIRGTDHLYA                                   450
```

-continued

```
SEQ ID NO: 115          moltype = DNA  length = 1433
FEATURE                 Location/Qualifiers
source                  1..1433
                        mol_type = other DNA
                        organism = Zea mays
misc_feature            1..1433
                        note = Ceres CLONE ID no.352452
misc_feature            1..1433
                        note = Encodes the peptide sequence at SEQ ID NO 116
SEQUENCE: 115
cccacacggc agcaggcagg gcgccatctc ctagcagctc ctcccatggc gtcctctgcc    60
cttcttctcc tccatggccg ccgaagcccc tcccatggcc gacgctctct gctccagccc   120
ctccagcagc tatgcgtcc cccctcctcc ccttcttctt cctcaagcca gcaggcacct   180
ccctctactc cctgcgcgca gcagcagcca tggcgctgcc tctcttctcc atggcgagta   240
gcagctcatt cacctctctc tcccatggcg tgctgctcca gtcggcctcc cttctccccc   300
tcggctcctt cctccaggcc gggccgtgca gaagctgctc gaggcgcgcc gcacccagat   360
ggatatcctc agggaagccg aggaaggatg gtgtgacagc cagggaacac ttgaacaagt   420
gagggtcaag ctgcagaagc ggcaggaggg cgcaatcaag cgtgagcggg ctatcgccta   480
tgcatattcg cagcaggccg acggtgctgc caaatgcaat ccaccgaagc ttacttccaa   540
tggactggtg aaccactccg gcatgctgct caagcaccag aacttagaca agggcaacgg   600
caactggagc tggctggaga ggtggatggc agcgcggcca ggctgatgga   660
ggagcacaac tccagctccc cggacttccg gtcctccaag aactgcgagg actcctttgg   720
tgtgctcggc gacttctctg aaccgaactc agtgaaggtg cgcaagaaca atgtcagcaa   780
gcgggtctgc gcaaaacctc cagggccaac acacgcccac ggacatcatc agcgcctcaa   840
ggcccagtcg atctcgtctc tgagcactga gctgcacaac gacgagagct ccgcgtcctc   900
ctcgtcttgc tttgcgtcta cccctatatc attcacactt gtggcttcgg agaagaccga   960
ggacagcgtc aggacgagac ccaactacat gagcatgacg gagtcgatca aggctaagca  1020
gaaggcatgc agcgcccaga ggacggtggc gctgaagcaa tgtgatgata ggaaagccat  1080
gagcgccgag ttgaaggtcg ctcaggtgtg actgtttcgt ggaactccat gcagagatgg  1140
agccgacttc gacatcctct ctatgcccta ggatgtgttg cttggtgtct tgccacattc  1200
ttgagtggct cggtgctgca ttcctgagtt gtcctcctgt tgctgggtgt ctgattattc  1260
aacttcttgt tgtcagattg catctttgtt cagtcattgt ggctgcatct ttgttcagcc  1320
gttgtggctt tgtcagtggt agagtctctg taagatagtt ctttgagtag acagcattgt  1380
ggatttcttt cctgggtgtt gatttcaggt caaaaaagac aggataattt act          1433

SEQ ID NO: 116          moltype = AA  length = 250
FEATURE                 Location/Qualifiers
source                  1..250
                        mol_type = protein
                        organism = Zea mays
REGION                  1..250
                        note = Ceres CLONE ID no.352452
REGION                  1..250
                        note = Score of 121.9 for HMM of FIGURE 3.
REGION                  1..250
                        note = Functional Homolog Of Ceres SEEDLINE ID no. ME19173
                          at SEQ ID NO.109
SEQUENCE: 116
MDILREAEEG WCDSQGTLEQ VRVKLQKRQE GAIKRERAIA YAYSQQADGA AKCNPPKLTS    60
NGLVNHSGML LKHQNLDKGN GNWSWLERWM AARPWENRLM EEHNSSSPDF RSSKNCEDSF   120
GVLGDFSEPN SVKVRKNNVS KRVCAKPPGP THAHGHHQRL KAQSISSLST ELHNDESSAS   180
SSSCFASTPI SFTLVASEKT EDSVRTRPNY MSMTESIKAK QKACSAQRTV ALKQCDDRKA   240
MSAELKVAQV                                                          250

SEQ ID NO: 117          moltype = DNA  length = 1949
FEATURE                 Location/Qualifiers
source                  1..1949
                        mol_type = other DNA
                        organism = Triticum aestivum
misc_feature            1..1949
                        note = Ceres CLONE ID no.787908
misc_feature            1..1949
                        note = Encodes the peptide sequence at SEQ ID NO 118
SEQUENCE: 117
acacaggcag gcagccgagc cgagcgagca ataattcgca ccggcacaca ggagcggcag    60
taatggccgc gtggtgccgg tgccagtagc aggcaggcag gcaggggagt agcgccactg   120
cactgggcac tgctgacgct tcgagcccac gctcttccct ccaccttgc cctccctcc    180
cgaaactccc tccctccctt ggcctcctca ggcctcccaa tctcgcagag cggcggccgt   240
cattggccgg cggcggtgcg cggccccggt tgtttcctcc ggcgtcaggt gcccgtgatc   300
tggttgttgc agaggcggcg aggtgaggtg acgcggcggc gcgatgaggt ggctcaagtc   360
gttggttggg ctgaggaagg tggagaggca gcagcagcgc gcaaggagg atggcgacgc   420
cggcccaaca aaaacagatg ccgtcgatca gttccacttc caggatcagc actcccagga   480
tcacgctagc cttgtcggac cagaagagtt ccctgatgaa aatggtccgt cagaagatga   540
gtgcgataca ccttcatgct caggacctgg tttcagtatg cttagtgtgc cactgcctca   600
aacagaagag gagctcaaag agatctgggc tgccacaatt attcgactg catatagagc   660
cctactggct aggagagccc gccgagcttt aaaaggactg ttaggcttc aagcccttgt   720
aagggggtca t atagtgagaa agcaagctgc tataacactc ggtgtatgc aagctttggt   780
cagggtacaa gcccgtgtta gagcaaggcg ggttcgtgtg gccttggaaa atcagatgga   840
```

```
tgagcaacaa aataatgtag aagagcaaac ggacgaggca catgttcgag aagttgagga   900
tgggtggtgc gatagtatag ggtctgtgga agacatccaa gcaaaattgt tgaagaggca   960
ggaagcagca gccaagcgtg agagagccat ggcctatgcc ctttctcacc agtggcaagc  1020
aggttcaagg caacaggcag ccattacagc ttctgaacta gacaggaaca gctggagctg  1080
gaattggctg gagagatgga tggccgtccg cccgtgggaa agtcggttcc ttggcatgta  1140
cgcagcagat ggaattgcca ttgataccgg agcgcacaat gctgagggaa atgcaaccaa  1200
ggctccatac aggaaacctg tgaaaaagca ggtttcagct cttcattcaa gtgtgttgat  1260
ccagaaggcc cgccctcga  actcggaggg tggtggctcc ttgtcgaacc cgtctgccgg  1320
ttcggcgtca gctaaaccga aacggaagct gccaccaaag gaaggttctg atgaagtctc  1380
gtctcgtctt tcgggacttg gtgcccggag cagtagtaat cctaaggagg ggcctgggca  1440
gttacaacct cgggccaaca agaggttctc cttgcctggc actggcacag aagttggcaa  1500
acggcaagtg aataaacctg cggtgaaccg atccccaag  gctaccgaag actcccagc   1560
gctggaaggg aagcatcgcc gtgccggttc cgttggtctg ctgctcaaga gagttgagct  1620
gcaggcttga caagccatct gaagcccat  ctaccgtcgt caaggttcga agtcagcatg  1680
ctgcgctctg atacatgggc ggccttagat tctggaaggt ccattggagc aatgtgcatt  1740
tatttcttag ccatattata ggtatgcagt caaaatgctc atctcaggag atgagatcta  1800
gctagtgctt ggatatgtat gtgctggtca gctggtgcct ctagtcctgg aggttaccat  1860
agcttgtact gttgtatttg tagctaagag caagtatggg ctcacatttt ctggaactat  1920
tttttgtaca atgaaaaaaa aaaaaaaaa                                    1949

SEQ ID NO: 118              moltype = AA  length = 428
FEATURE                     Location/Qualifiers
source                      1..428
                            mol_type = protein
                            organism = Triticum aestivum
REGION                      1..428
                            note = Ceres CLONE ID no.787908
REGION                      1..428
                            note = Score of 891.9 for HMM of FIGURE 3.
REGION                      1..428
                            note = Functional Homolog Of Ceres SEEDLINE ID no. ME19173
                             at SEQ ID NO.109
REGION                      94..112
                            note = Pfam Name: IQ Pfam Description: IQ
                             calmodulin-binding motif
SEQUENCE: 118
MRWLKSLVGL RKVERQQQRR KEDGDAGPTK TDAVDQFHFQ DQHSQDHASL VGPEEFPDEN   60
GPSEDECDTP SCSGPGFSML SVPLPQTEEE LKEIWAATII QTAYRALLAR RARRALKGLV  120
RLQALVRGHI VRKQAAITLR CMQALVRVQA RVRARRVRVA LENQMDEQQN NVEEQTDEAH  180
VREVEDGWCD SIGSVEDIQA KLLKRQEAAA KRERAMAYAL SHQWQAGSRQ QAAITASELD  240
RNSWSWNWLE RWMAVRPWES RFLGMYAADG IAIDTGAHNA EGNATKAPYR KPVKKQVSAL  300
HSSVLIQKAR PSNSEGGGSL SNPSAGSASA KPKRKLPPKE GSDEVSSRLS GLGARSSSNP  360
KERPGQLQPR ANKRFSLPGT GTEVGKRQVN KPAVNRSPKA TEDSPALEGK HRRAGSVGLL  420
LKRVELQA                                                          428

SEQ ID NO: 119              moltype = AA  length = 442
FEATURE                     Location/Qualifiers
source                      1..442
                            mol_type = protein
                            organism = unidentified
REGION                      1..442
                            note = Plant derived amino acid sequence
REGION                      1..442
                            note = Ceres LOCUS ID no. Os01m00929_AP002743
REGION                      1..442
                            note = Score of 949.2 for HMM of FIGURE 3.
REGION                      1..442
                            note = Functional Homolog Of Ceres SEEDLINE ID no. ME19173
                             at SEQ ID NO.109
REGION                      109..129
                            note = Pfam Name: IQ Pfam Description: IQ
                             calmodulin-binding motif
SEQUENCE: 119
MGGSGKWVKS LIGLKKPDRE DCKEKLQVPS VNGRGGGKGR KWKLWRSSSG DHGSLWRGSR   60
GGGGGGGHHR SASSDASDDA SSAAADPFTA AVATVARAPA KDFMAVRQEW AAIRVQTAFR  120
GFLARRALRA LKGLVRLQAI VRGRQVRKQA AVTLRCMQAL VRVQARIRAR RVRMSTEGQA  180
VQKLLEARRT KLDILREAEE GWCDSQGTLE DVRVKLQKRQ EGAIKRERAI AYAYSQQIEG  240
ATKCNQQPKP TSYGRLNQSG MLLKHQHFDK SNGNWSWLER WMAARPWENR LMEEHNQTNS  300
SSPDLLSSKN CEDSFGILGD FSEPNSVKVR KNNVSKRVCA KPPVVSHHQR IKAQSISSLS  360
TELHNDESSA SSSSCFASTP ISFSTFVTTE KTEDSIRARP NYMNMTESIK AKRKACNAQR  420
TTAGKLMEDR KASGVELKVA QV                                          442

SEQ ID NO: 120              moltype = DNA  length = 1801
FEATURE                     Location/Qualifiers
source                      1..1801
                            mol_type = other DNA
                            organism = Zea mays
misc_feature                1..1801
                            note = Ceres CLONE ID no.246398
```

```
misc_feature            1..1801
                        note = Encodes the peptide sequence at SEQ ID NO 121
SEQUENCE: 120
gtctcgtctc tacgcccgct ctccactctt cctcccaaag cctgccgccg cgtgggggt    60
tgcttgctgg ctgcccgctc ctctccctgc tcctcctgtg tctgccgccc accgcttccg   120
ggaacaagtc cggttgccgc cgccgccgtc gctgctctgt ccgagaggag ggaggaacag   180
agcgggatgg gagggtccgg gaagtgggtc aagtcgctga tagggctcaa gaagcagccc   240
gagaaggaag actgcaagga caagctgcag ctcccatcag tccacggcgg aggattgcga   300
ggcaagggcc gcaggtggaa gctgtggcgg acctcctccg gcgaccaggg ctccatgtgg   360
cgcggctcca gaggcgggca ccagcgctcg gcggcgtcgg aggcctcgga cgacgcgtcc   420
tcggtggccg ccgtccccgc cgacccgttc acggccgccg tcgccaccgt cgcccgcgcc   480
ccggccaggg acttcatggc cgtccgccag gagtgggccg ccatccgcgt ccagaccgcg   540
ttccgcgggt tcttggctcg gcgggcgctc cgggcgctca aggggctggt gcggctccag   600
gcgatcgtgc gcgggcggca ggtgcggaag caggcgcgcg tgacgctgcg gtgcatgcag   660
gcgctggtgc gggtgcaggc gcgcatccgg gcgcgccgcg tgcgcatgtc caccgagggc   720
caggccgtgc agaagctgct cgaggcgcgc cgcacccaga tggatatcct cagggaagcc   780
gaggaaggat ggtgtgacag ccaggaaaca cttgaacaag tgagggtcaa gctgcagaag   840
cggcaggagg gcgcaatcaa gcgtgagcgg ggctatcgcc tatgcatatt cgcagcaggc   900
cgacggtgct gccaaatgca atccaccgaa gcttacttcc aatggactgg tgaaccactc   960
cggcatgctg ctcaagcacc agaacttaga caagggcaac ggcaactgga gctggctgga  1020
gaggtggatg gcagcgcggc catggagaa caggctgatg gaggagcaca actccagctc  1080
cccggacttc cggtccttcca agaactgcga ggactccttt ggtgtgctcg gcgacttctc  1140
tgaaccgaac tcagtgaaga tgcgcaagaa caatgtcagc aagcgggtct gcgcaaaacc  1200
tccagggcca acacacgccc acggacatca tcagcgcctc aaggcccagt cgatctcgtc  1260
tctgagcact gagctgcaca acgacgagag ctccgcgtcc tcctcgtctt gctttgcgtc  1320
taccctata tcattcacac ttgtggcttc ggagaagacc tcaggacgag  1380
acccaactac atgagcatga cggagtcgat caaggctaag cagaaggcat cgcagcgccca  1440
gaggacggtg cgcgctgagc aatgtcgatga taggaaagcc atgagcgccg agttgaaggt  1500
cgctcaggtg tgactgtttc gtggaactcc atgcagagat ggagccgact tcgacatcct  1560
ctctatgccc taggatgtgt tgcttggtgt cttgccacat tcttgagtgg ccggtgctg   1620
cattcctgag ttgtcctcct gttgctgggt gtctgattat tcaacttctt gttgtcagat  1680
tgcatctttg ttcagtcatt gtggctgcat ctttgttcag ccgttgtggc tttgtcagtg  1740
gtagagtctc tgtaagatag ttctttgagt akryagtwtt gkggatktct ktcctrkgtk  1800
t                                                                  1801

SEQ ID NO: 121          moltype = AA  length = 318
FEATURE                 Location/Qualifiers
source                  1..318
                        mol_type = protein
                        organism = Zea mays
REGION                  1..318
                        note = Ceres CLONE ID no.246398
REGION                  1..318
                        note = Score of 291.2 for HMM of FIGURE 3.
REGION                  1..318
                        note = Functional Homolog Of Ceres SEEDLINE ID no. ME19173
                         at SEQ ID NO.109
REGION                  109..129
                        note = Pfam Name: IQ Pfam Description: IQ
                         calmodulin-binding motif
SEQUENCE: 121
MGGSGKWVKS LIGLKKQPEK EDCKDKLQLP SVHGGGLRGK GRRWKLWRTS SGDQGSMWRG    60
SRGGSQRSAA SEASDDASSV AAVPADPFTA AVATVARAPA RDFMAVRQEW AAIRVQTAFR   120
GFLARRALRA LKGLVRLQAI VRGRQVRKQA AVTLRCMQAL VRVQARIRAR RVRMSTEGQA   180
VQKLLEARRT QMDILREAEE GWCDSQGTLE QVRVKLQKRQ EGAIKRERGY RLCIFAAGRR   240
CCQMQSTEAY FQWTGEPLRH AAQAPELRQG QRQLELAGEV DGSAAMGEQA DGGAQLQLPG   300
LPVLQELRGL LWCARRLL                                                318

SEQ ID NO: 122          moltype = AA  length = 440
FEATURE                 Location/Qualifiers
source                  1..440
                        mol_type = protein
                        note = subspecies = indica
                        organism = Oryza sativa
REGION                  1..440
                        note = Public GI ID no.125527441
REGION                  1..440
                        note = Score of 619.5 for HMM of FIGURE 3.
REGION                  1..440
                        note = Functional Homolog Of Ceres SEEDLINE ID no. ME19173
                         at SEQ ID NO.109
REGION                  87..107
                        note = Pfam Name: IQ Pfam Description: IQ
                         calmodulin-binding motif
SEQUENCE: 122
MGASGKWIRT LVGLRPAAER EKERGGGGGK GRKWSRLWRS SSSQRGGGNA SASEVYSETS    60
SSADALSSVV AAVVRAPPRD FRLIRQEWAA VRIQTAFRAF LARRALRALR GIVRLQALVR   120
GRRVRKQLAV TLKCMQALVR VQARARDRRA RISADGLDSQ DMLDERGGRV DPVKEAEAGW   180
CDSQGTADDV RSKIHMRHEG AIKRERALTY AQSHQRCSNH GGRPSSPAVS LKHHGNGATR   240
```

```
SNHSWSYLEG WMATKPWESR LMEQTHTENS TNSRCSESVE EVSVGGPKLS DASSVKIRRN    300
NVTKRVAAKP PSMISATSSD FVCDESSPST SSVTPLSANN SLATERRSDC GQVGGPSYMS    360
LTKSAKARLS GYGSHKPPLQ RQRSGDLLHH NRMAFSSIDV QSTAGSEVSV TSKRLNSLAL    420
KGRATRSLDK ENERRPSSLL                                                440

SEQ ID NO: 123            moltype = AA  length = 420
FEATURE                   Location/Qualifiers
source                    1..420
                          mol_type = protein
                          note = subspecies = japonica
                          organism = Oryza sativa
REGION                    1..420
                          note = Public GI ID no.125595056
REGION                    1..420
                          note = Score of 536.3 for HMM of FIGURE 3.
REGION                    1..420
                          note = Functional Homolog Of Ceres SEEDLINE ID no. ME19173
                            at SEQ ID NO.109
REGION                    79..99
                          note = Pfam Name: IQ Pfam Description: IQ
                            calmodulin-binding motif
SEQUENCE: 123
MGASGKWIKS LVSLKAAPEG TTKGRRWTRL WRSSSSASAS ASTAGDASES ASSEADAFSS     60
VVAAVVRAPP RDFRVIRQEW AAVRVQAAFR AFLARRALKA LRGIVRLQAL VRGRLVRRQL    120
AVTLKCMNAL LRVQERARER RARCSADGRD SQDAVGERDG RADPIKQAEA LILQLLPPFH    180
NEQWCDSQGS VSEVRSKIHM RHDAVAKRER AIAYALSHEQ RSSKQSARPS SPARSLRNHE    240
SNRCNHDWSY IEGWMATKPW ESRLMEQSHA ELKCSKNSGE LNLAGAQLSN ASSVKMRGNR    300
VAAKPPSVLS ASSSDFPCDV SSASTSSATP ARSDGGHGEG PSYMSLTKSA KARQSCNSPF    360
QIQRQRSGGM SSYKRVALSP LDVQSNACSE FSVTSRKLNS LSLKGRSMTR SLDKENDNLF    420

SEQ ID NO: 124            moltype = DNA  length = 1682
FEATURE                   Location/Qualifiers
source                    1..1682
                          mol_type = other DNA
                          organism = Zea mays
misc_feature              1..1682
                          note = Ceres CLONE ID no.236071
misc_feature              1..1682
                          note = Encodes the peptide sequence at SEQ ID NO 125
SEQUENCE: 124
acatcccagt gccgagtgtc cccacacaac caagcggaag cttcggtcga acagagggag     60
taagcagttg cgtttcgcat tgcgcggcgc cgatgggggc gtcggggaag tggatcaagt    120
cgctggtggc cctgaaggcg cccgagaagg cggcgggagc caaggcggt cgcaaatggc    180
gtctctggcg gagctcgtcg gccacgtcca gggccagcgc cggcgagggc agtgcgctgg    240
cgtccgagtc ttcttcggcg tcggccgact cgttcaactc ggtcctcgcc gccgtggtcc    300
gcgcgccgcc cagggatttc ctgctcatca ggcaggaatg gccgccgtc cgcatccata    360
ccgccttccg cggattcttg gcgagacggg cgttgaaggc gctgagggc atcgtccggc    420
tgcaggcgct ggtgcgcggc cggcgcgtgc gcaagcaact ggccgtcacg ctcaagtgca    480
tgcacgcact gctgcgggtg caggaacgcg cccgggagcg ccgggcgcgc tcctccgctg    540
atggccacgc tcacagggc caggacgcgc tcaacgctgc tgccagttct accaaagacg    600
ctatggaaca atggtgtgac cgccacggat ctgttgctga agtaagatca aatttacaca    660
tgaagcatga aggtgcagca aagagagaaa gggcaattgc ctatgctgtg tctcaccagc    720
ctcggggttc aagacagaag gggagaccaa gctctcctgc taactgcgtt agaagccatg    780
atcctaatgg tgtcgatcag gacttcagtt acttagacgg atggatgca acgaagccat    840
gggagaccag atctacggag cgaaaccata gcgactcgca gtcgcgaag cacgaggagc    900
tgaacttgcc cgcctccaag cttttccgatg ccagctcagt taagatcaga agaaacaatg    960
tcacaactag ggtatctgca gcaaagcgtc tcctccatc ttcagtgctg tcagctgctt   1020
cttccgactc cgcgtgcggc ggcgagagct ctcggtcgag accatcggtg accctgacgt   1080
ctgctaccac caacactgtc ttagcgtcag aagcaagatc agacagtggc gacaccggag   1140
gcccgaacta catgagcttg accaagtctg ccaaggcgag gctgagtgga tgcagcggca   1200
gcagccatca caggtcgttc cagcgaccac ggtccgggga catgtcgagg gtgacactgt   1260
cttcgatcga cacccagagc aacgcgggct cggagatttc agtcacctcg aagagactga   1320
acagcatgtc cctgaacctg aaaggccgga gcttggacaa ggagaacgag gaggattgat   1380
ccatccacca acggacaaag cagctgtcgt aggtctggtg cagtactacc acgcgttcaa   1440
agcagcatct ctgtatttac ggaatttacg gaggaagacg cggttatct ctttcataaa   1500
ctccacacat gtcacatgtg agagagctct ggcactaggt caccgcttct atcatcatta   1560
tcatccttag tttagtttag tgcgtaagtt ttgtacacat ccaatcgatg tccagttcct   1620
aatttccttg tctctagttt gtacccataa attagtaata taagtactta tatcagcacg   1680
cg                                                                   1682

SEQ ID NO: 125            moltype = AA  length = 428
FEATURE                   Location/Qualifiers
source                    1..428
                          mol_type = protein
                          organism = Zea mays
REGION                    1..428
                          note = Ceres CLONE ID no.236071
REGION                    1..428
                          note = Score of 873.4 for HMM of FIGURE 3.
```

```
REGION                  1..428
                        note = Functional Homolog Of Ceres SEEDLINE ID no. ME19173
                         at SEQ ID NO.109
REGION                  82..102
                        note = Pfam Name: IQ Pfam Description: IQ
                         calmodulin-binding motif
SEQUENCE: 125
MGASGKWIKS LVALKAPEKA AGHKGGRKWR LWRSSSATSR ASAGEGSALA SESSSASADS    60
FNSVLAAVVR APPRDFLLIR QEWAAVRIHT AFRGFLARRA LKALRGIVRL QALVRGRRVR   120
KQLAVTLKCM HALLRVQERA RERRARSSAD GHGSQGQDAL NGCASSTKDA MEQWCDRHGS   180
VAEVRSNLHM KHEGAAKRER AIAYAVSHQP RGSRQKGRPS SPANCVRSHD PNGCDQDFSY   240
LDGWMATKPW ETRSTERNHS DSQLAKHEEL NLPASKLSDA SSVKIRRNNV TTRVSAAKRP   300
PPSSVLSAAS SDSACGGESS RSRPSVTLTS ATTNTVLASE ARSDSGDTGG PNYMSLTKSA   360
KARLSGCSGS SHHRSFQRPR SGDMSRVTLS SIDTQSNAGS EISVTSKRLN SMSLNLKGRS   420
LDKENEED                                                            428

SEQ ID NO: 126          moltype = AA  length = 455
FEATURE                 Location/Qualifiers
source                  1..455
                        mol_type = protein
                        note = subspecies = indica
                        organism = Oryza sativa
REGION                  1..455
                        note = Public GI ID no.125524760
REGION                  1..455
                        note = Score of 926.5 for HMM of FIGURE 3.
REGION                  1..455
                        note = Functional Homolog Of Ceres SEEDLINE ID no. ME19173
                         at SEQ ID NO.109
REGION                  109..129
                        note = Pfam Name: IQ Pfam Description: IQ
                         calmodulin-binding motif
SEQUENCE: 126
MGGSGKWVKS LIGLKKPDRE DCKEKLQVPS VNGGGGKGR KWKLWRSSSG DHGSLWRGSR     60
GGGGGGHHR SASSDASDDA SSAAGDPFTA AVATVARAPA KDFMAVRQEW AAIRVQTAFR    120
GFLARRALRA LKGLVRLQAI VRGRQVRKQA AVTLRCMQAL VRVQARIRAR RVRMSTEGQA   180
VQKLLEARRT KLDILREAEE GWCDSQGTLE DVRVKLQKRQ EGAIKRERAI AYAYSQQIEG   240
ATKCNFWTKC VIFLVFAQQQ PKPTSYGRLN QSGMLLKHQH FDKSNGNWSW LERWMAARPW   300
ENRLMEEHNQ TNSSSPDLLS SKNCEDSFGI LGDFSEPNSV KVRKNNVSKR VCAKPPVVSH   360
HQRIKAQSIS SLSTELHNDE SSASSSSCFA STPISFSTFV TTEKTEDSIR ARPNYMNMTE   420
SIKAKRKACN AQRTTAGKLM EDRKASGVEL KVAQV                               455

SEQ ID NO: 127          moltype = AA  length = 455
FEATURE                 Location/Qualifiers
source                  1..455
                        mol_type = protein
                        note = subspecies = japonica
                        organism = Oryza sativa
REGION                  1..455
                        note = Public GI ID no.125569365
REGION                  1..455
                        note = Score of 926.7 for HMM of FIGURE 3.
REGION                  1..455
                        note = Functional Homolog Of Ceres SEEDLINE ID no. ME19173
                         at SEQ ID NO.109
REGION                  109..129
                        note = Pfam Name: IQ Pfam Description: IQ
                         calmodulin-binding motif
SEQUENCE: 127
MGGSGKWVKS LIGLKKPDRE DCKEKLQVPS VNGRGGGKGR KWKLWRSSSG DHGSLWRGSR    60
GGGCCGGHHR SASSDASDDA SSAAADPFTA AVATVARAPA KDFMAVRQEW AAIRVQTAFR   120
GFLARRALRA LKGLVRLQAI VRGRQVRKQA AVTLRCMQAL VRVQARIRAR RVRMSTEGQA   180
VQKLLEARRT KLDILREAEE GWCDSQGTLE DVRVKLQKRQ EGAIKRERAI AYAYSQQIEG   240
ATKCNFWTEC VIFLVFAQQQ PKPTSYGRLN QSGMLLKHQH FDKSNGNWSW LERWMAARPW   300
ENRLMEEHNQ TNSSSPDLLS SKNCEDSFGI LGDFSEPNSV KVRKNNVSKR VCAKPPVVSH   360
HQRIKAQSIS SLSTELHNDE SSASSSSCFA STPISFSTFV TTEKTEDSIR ARPNYMNMTE   420
SIKAKRKACN AQRTTAGKLM EDRKASGVEL KVAQV                               455

SEQ ID NO: 128          moltype = AA  length = 441
FEATURE                 Location/Qualifiers
source                  1..441
                        mol_type = protein
                        note = subspecies = japonica
                        organism = Oryza sativa
REGION                  1..441
                        note = Public GI ID no.115439499
REGION                  1..441
                        note = Score of 617.2 for HMM of FIGURE 3.
REGION                  1..441
```

```
                        note = Functional Homolog Of Ceres SEEDLINE ID no. ME19173
                          at SEQ ID NO.109
REGION                  87..107
                        note = Pfam Name: IQ Pfam Description: IQ
                          calmodulin-binding motif
SEQUENCE: 128
MGASGKWIRT LVGLRPAAER EKERGGGGGK GRKWSRLWRS SSSQRGGGNA SASEVYSETS    60
SSADALSSVV AAVVRAPPRD FRLIRQEWAA VRIQTAFRAF LARRALRALR GIVRLQALVR   120
GRRVRKQLAV TLKCMQALVR VQARARDRRA RISADGLDSQ DMLDERGGRV DHVKEAEAGW   180
CDSQGTADDV RSKIHMRHEG AIKRERARTY AQSHQRCSNH GGRPSSPAVS LKHHGNGATR   240
SNHSWSYLEG WMATKPWESR LMEQTHTENS TNSRCSESVE EVSVGGPKLS DASSVKIRRN   300
NVTTRVAAKP PSMISATSSD FVCDESSPST SSVTPLSANN SLATERRSDC GQVGGPSYMS   360
LTKSAKARLS GYGSHKPPLQ RQRSGDLLHH NNRMAFSSID VQSTAGSEVS VTSKRLNSLA   420
LKGRATRSLD KENERRPSSL L                                             441

SEQ ID NO: 129          moltype = AA  length = 416
FEATURE                 Location/Qualifiers
source                  1..416
                        mol_type = protein
                        organism = Arabidopsis thaliana
REGION                  1..416
                        note = Public GI ID no.15225258
REGION                  1..416
                        note = Score of 954.4 for HMM of FIGURE 3.
REGION                  1..416
                        note = Functional Homolog Of Ceres SEEDLINE ID no. ME19173
                          at SEQ ID NO.109
REGION                  84..104
                        note = Pfam Name: IQ Pfam Description: IQ
                          calmodulin-binding motif
SEQUENCE: 129
MGASGKWVKS IIGLKKLEKD EIEKGNGKNK KWKLWRTTSV DSWKGFRGKH RSDSDGVDSS    60
TVYSAAVATV LRAPPKDFKA VREEWAAIRI QTAFRGFLAR RALRALKGIV RLQALVRGRQ   120
VRKQAAVTLR CMQALVRVQA RVRARRVRMT VEGQAVQKLL DEHRTKSDLL KEVEEGWCDR   180
KGTVDDIKSK LQQRQEGAPK RERALAYALA QKQWRSTTSS NLKTNSSISY LKSQEFDKNS   240
WGWSWLERWM AARPWETRLM DTVDTAATPP PLPHKHLKSP ETADVVQVRR NNVTTRVSAK   300
PPPHMLSSSP GYEFNESSGS SSICTSTTPV SGKTGLVSDN SSSQAKKHKP SYMSLTESTK   360
AKRRTNRGLR QSMDEFQFMK NSGMFTGELK TSPSSDPFVS FSKPLGVPTR FEKPRG       416

SEQ ID NO: 130          moltype = AA  length = 408
FEATURE                 Location/Qualifiers
source                  1..408
                        mol_type = protein
                        organism = Oryza sativa
REGION                  79..99
                        note = Pfam Name: IQ Pfam Description: IQ
                          calmodulin-binding motif
REGION                  1..408
                        note = Functional Homolog Of Ceres SEEDLINE ID no. ME19173
                          at SEQ ID NO.109
REGION                  1..408
                        note = Score of 554.2 for HMM of FIGURE 3.
REGION                  1..408
                        note = Public GI ID no.115465173
SEQUENCE: 130
MGASGKWIKS LVSLKAAPEG TTKGRRWTRL WRSSSSASAS ASTAGDASES ASSEADAFSS    60
VVAAVVRAPP RDFRVIRQEW AAVRVQAAFR AFLARRALKA LRGIVRLQAL VRGRLVRRQL   120
AVTLKCMNAL LRVQERARER RARCSADGRD SQDAVGERDG RADPIKQAEE QWCDSQGSVS   180
EVRSKIHMRH DAVAKRERAI AYALSHQPRS SKQSARPSSP SKQSARPSSP RCNHDWSYIE   240
GWMATKPWES RLMEQSHAEL KCSKNSGELN LAGAQLSNAS SVKMRGNRVA AKPPSVLSAS   300
SSDFPCDVSS ASTSSATPAR SDGGHGEGPS YMSLTKSAKA RQSCNSPFQI QRQRSGGMSS   360
YKRVALSPLD VQSNACSEFS VTSRKLNSLS LKGRSMTRSL DKENDNLF                408

SEQ ID NO: 131          moltype = DNA  length = 1164
FEATURE                 Location/Qualifiers
source                  1..1164
                        mol_type = other DNA
                        organism = Populus balsamifera
                        sub_species = trichocarpa
misc_feature            1..1164
                        note = Ceres ANNOT ID no.1477059
misc_feature            1..1164
                        note = Encodes the peptide sequence at SEQ ID NO 132
SEQUENCE: 131
atgggtgcat caggaaaatg ggtgaaatcc cttataggtt ttaaaaagtc tgataaagat    60
caagaccatg taaatggcaa gagcaagaaa tggaagctat ggaggagctc atctggtgac   120
ttgggggtctt catggaagga tttttaaggg aaacatagaa cagcgtcaga ggcatcgggt   180
tcttcaccat taactgatcc atttactacc gcaatggcta ctgtggttag agctcctcct   240
aagggtttta gggttgtcag gcaagagtgg gctgctatca ggattcaaac tgcttttcgt   300
```

```
ggattcttgg caagaagggc tctgagggct ttgaaagcag tggtgagact ccaagctata  360
gttcgaggtc gacaagtgag aaagcaggct gctgtgatgc tttggtgtat gcaggctctt  420
gttcgagttc aagctcgagt cagggctcat cctgtgcgaa tgtccataga agggcaggca  480
gtgcagaata tgctaaatga gcgacatagc aaggctgatc tcttgaaaca tgctgaggaa  540
gggtggtgcg atggcaaggg gacattggaa gatgtgaagt caaaactgca aatgaggcaa  600
gaaggagcct tcaagagaga aagagcaatt gcatactccc ttgctcagaa acaatggaga  660
tcaaaccccca gctcaaatac tcgaaccaat agctcagtat actcattcaa gaatcaggag  720
tttgataaga atagctgggg atggactagg cctccaattg gcatattac tcgctcatct  780
tccagtccaa gttctgaatt ccgctttgat gagagttcag cttcttcatc aatttgtaca  840
tctacaacac caatatcagg aaacactggc ttggcctctg ataaaacaga ggagagtggt  900
aacagtaggc caaattacat gaacctgacc gagtcaacca aggcaaagca aaaaacatcc  960
ggtcattttat ctcataggat ccaaaggcag tctatggatg agtttcagtt ctcaaaaag  1020
tcaggagcat tctcaaatgg agattcgaaa acagtactg gttctgatcc gtcagttaat  1080
ttatctaagc cactttgctt gccaacaaga tttgataaga actcgacgaa acaactaaga  1140
ggaatggatc atttgtatga ttag                                       1164

SEQ ID NO: 132         moltype = AA   length = 387
FEATURE                Location/Qualifiers
source                 1..387
                       mol_type = protein
                       note = subspecies = trichocarpa
                       organism = Populus balsamifera
REGION                 1..387
                       note = Ceres ANNOT ID no.1477059
REGION                 1..387
                       note = Score of 765.3 for HMM of FIGURE 3.
REGION                 1..387
                       note = Functional Homolog Of Ceres SEEDLINE ID no. ME19173
                        at SEQ ID NO.109
REGION                 89..109
                       note = Pfam Name: IQ Pfam Description: IQ
                        calmodulin-binding motif
SEQUENCE: 132
MGASGKWVKS LIGFKKSDKD QDHVNGKSKK WKLWRSSSGD LGSSWKDFKG KHRTASEASG   60
SSPLTDPFTT AMATVVRAPP KGFRVVRQEW AAIRIQTAFR GFLARRALRA LKAVVRLQAI  120
VRGRQVRKQA AVMLWCMQAL VRVQARVRAH PVRMSIEGQA VQNMLNERHS KADLLKHAEE  180
GWCDGKGTLE DVKSKLQMRQ EGAFKRERAI AYSLAQKQWR SNPSSNTRTN SSVYSFKNQE  240
FDKNSWGWTR PPIGHITRSS SSPSSEFRFD ESSASSSICT STTPISGNTG LASDKTEESG  300
NSRPNYMNLT ESTKAKQKTS GHLSHRIQRQ SMDEFQFLKK SGAFSNGDSK NSTGSDPSVN  360
LSKPLCLPTR FDKNSTKQLR GMDHLYD                                     387

SEQ ID NO: 133         moltype = DNA   length = 1059
FEATURE                Location/Qualifiers
source                 1..1059
                       mol_type = other DNA
                       organism = Populus balsamifera
                       sub_species = trichocarpa
misc_feature           1..1059
                       note = Ceres ANNOT ID no.1530547
misc_feature           1..1059
                       note = Encodes the peptide sequence at SEQ ID NO 134
SEQUENCE: 133
atgggtgcat caggaaaatg ggtgaaatcc cttataggtt ttaaaaagtc tgataaagat   60
caagaccatg taaatggcaa gagcaagaaa tggaagctat ggaggagctc atctggtgac  120
ttggggtctt catggaagga tttaaaggg aaacataagaa cagcgtcaga ggcatcgggt  180
tcttcaccat taactgatcc atttactacc gcaatggcta ctgtggttag agctcctcct  240
aagggttttta gggttgtcag gcaagagtgg gctgctatca ggattcaaac tgcttttcgt  300
ggattcttgg ctcttgttcg agttcaagct cgagtcaggg ctcatcctgt gcgaatgtcc  360
atagaagggc aggcagtgca gaatatgcta aatgagcgac atagcaaggc tgatctcttg  420
aaacatgctg aggaagggtg gtgcgatggc aaggggacat tggaagatgt gaagtcaaaa  480
ctgcaaatga ggcaagaagg agccttcaag agagaaagag caattgcata ctcccttgct  540
cagaaacaat ggagatcaaa ccccagctca aatactcgaa ccaatagctc agtatactca  600
ttcaagaatc aggagtttga taagaatagc tggggatgga ctaggcctcc aattgggcat  660
attactcgct catcttccag tccaagttct gaattccgct ttgatgagag ttcagcttct  720
tcatcaattt gtacatctac aacaccaata tcaggaaaca ctggcttggc ctctgataaa  780
acagaggaga gtggtaacag taggccaaat tacatgaacc tgaccgagtc aaccaaggca  840
aagcaaaaaa catccggtca tttatctcat aggatccaaa ggcagtctat ggatgagttt  900
cagtttctca aaaagtcagg agcattctca aatggagatt cgaaaacag tactggttct  960
gatccgtcag ttaatttatc taagccactt tgcttgccaa caagatttga taagaactcg 1020
acgaaacaac taagaggaat ggatcatttg tatgattag                        1059

SEQ ID NO: 134         moltype = AA   length = 352
FEATURE                Location/Qualifiers
source                 1..352
                       mol_type = protein
                       note = subspecies = trichocarpa
                       organism = Populus balsamifera
REGION                 1..352
                       note = Ceres ANNOT ID no.1530547
```

| | | |
|---|---|---|
| REGION | 1..352 | |
| | note = Score of 607.6 for HMM of FIGURE 3. | |
| REGION | 1..352 | |
| | note = Functional Homolog Of Ceres SEEDLINE ID no. ME19173 at SEQ ID NO.109 | |
| REGION | 89..109 | |
| | note = Pfam Name: IQ Pfam Description: IQ calmodulin-binding motif | |

SEQUENCE: 134

```
MGASGKWVKS LIGFKKSDKD QDHVNGKSKK WKLWRSSSGD LGSSWKDFKG KHRTASEASG   60
SSPLTDPFTT AMATVVRAPP KGFRVVRQEW AAIRIQTAFR GFLALVRVQA RVRAHPVRMS  120
IEGQAVQNML NERHSKADLL KHAEEGWCDG KGTLEDVKSK LQMRQEGAFK RERAIAYSLA  180
QKQWRSNPSS NTRTNSSVYS FKNQEFDKNS WGWTRPPIGH ITRSSSSPSS EFRFDESSAS  240
SSICTSTTPI SGNTGLASDK TEESGNSRPN YMNLTESTKA KQKTSGHLSH RIQRQSMDEF  300
QFLKKSGAFS NGDSKNSTGS DPSVNLSKPL CLPTRFDKNS TKQLRGMDHL YD          352
```

| | | |
|---|---|---|
| SEQ ID NO: 135 | moltype = DNA length = 1923 | |
| FEATURE | Location/Qualifiers | |
| source | 1..1923 | |
| | mol_type = other DNA | |
| | organism = Arabidopsis thaliana | |
| misc_feature | 1..1923 | |
| | note = Ceres SEEDLINE ID no.ME24091 | |
| misc_feature | 1..1923 | |
| | note = Encodes the peptide sequence at SEQ ID NO. 136 | |

SEQUENCE: 135

```
acaaatactc ttcttcacac agctttgaat ccatctgtct tctcctctct ctctcttctc   60
catttgcaat tacgataatg tgaaagcaat aagaagagga aaagttatct tcgcacctca  120
gcaaagatcc aatcgattcg attcttaagc ttttcgtct tctccgataa ggtcactact  180
tagaagccgc gttgtggttt agttgactcc tccaggtttt atcttcaagc tttttcgtct  240
atcagatctg gtgtcactgt cttctcatag gattacatag agatggggaa aaaagctaaa  300
tggttttcaa gtgttaagaa agcattcagc ccagattcaa agaagtcgaa gcaaaaattg  360
gctgagggac aaaatggtgt tatctctaat cctcctgttg tggataatgt tagacaatct  420
tcttcttctc ctcctcctgc tcttgctcct cgtgaagtga gagtagctga agtgattgtt  480
gaacggaaca gggatctttc acctccttct acagcagatg ctgtgaatgt tacagctact  540
gatgtycctg tagttccatc ttcatctgct cctggtgttg ttcgtcgcgc tacacctact  600
cgatttgctg gaaagtcaaa cgaagaagcc gctgctatct tgatccagac tatatttaga  660
ggttatttgg caaggagagc gttgcgggca atgaggggtt tggtcagact taagttattg  720
atggaaggat ctgttgttaa gcggcaagct gcaaatactc taaaatgtat gcagactctc  780
tctcgtgtac agtcgcagat ccgagctagg agaatcaggr tgtcagaaga gaatcaggct  840
cgccagaaac aactccttca gaaacatgct aaagagctag ctggcttgaa gaacggggat  900
aactggaatg atagcattca atcaaaggag aaagttgaag cgaatttgct aagcaagtac  960
gaggcaacaa tgagaaggga aagggcattg gcttattcat actctcatca scaaaactgg 1020
aagaacaact ctaaatctgg aaacccgatg ttcatggatc caagcaaccc gacatggggt 1080
tggagctggt tggagagatg gatggctggt aggccactag agagttccga gaaagaacaa 1140
agcaacagca acaatgacaa tgctgcctcg gtcaagggct ctattaaccg caacgaagct 1200
gcaaaatctc taaccccgcaa tggctcaact caaccaaaca caccatcatc gcaagagggg 1260
accccaagaa acaaaaacag ttcttctca cctccaactc cctcaaggct aaaccaatcc 1320
tcgaggaaat ccaatgacga cgactccaaa agcacaatct cggtcctgtc cgagaggaac 1380
cgcagacaca scattgctgg ttcatcagtc asagacgatg agagcctcgc tggctcacca 1440
gctctcccga gctacatggt tccaactaaa tcagctcgaa ccaggctcaa gccccaaagc 1500
ccattaggtg gtaccacaca ggaaaacgaa gggttcacag acaaggcatc agctaagaaa 1560
cggctctcgt atccaacttc gcctgcattg cctaaaccac ggcggttctc agctccccct 1620
aaggtggaga gtggcggcgt taccgtgacc aacggagcag gcagctgagg tatttattt 1680
aatataatta ttttcccact tatgaatgtg tccgagattg ttgtctctta tgtgttccct 1740
tcatttcgta attcatttgt gcagtgtaag cgccagtcat ttatttttt actataataa 1800
attttataac ctttaaaat tcatgttctt ttgtttcttt gaatatttaa gttattttta 1860
ttaatgttgg atgaattgga atatgatgat gttatttgta ttgtaatgca gatccttaa 1920
agc                                                                1923
```

| | | |
|---|---|---|
| SEQ ID NO: 136 | moltype = AA length = 461 | |
| FEATURE | Location/Qualifiers | |
| source | 1..461 | |
| | mol_type = protein | |
| | organism = Arabidopsis thaliana | |
| REGION | 1..461 | |
| | note = Ceres SEEDLINE ID no.ME24091 | |
| REGION | 1..461 | |
| | note = Score of 1104.8 for HMM of FIGURE 4. | |
| SITE | 88 | |
| | note = Xaa is any aa, unknown, or other | |
| REGION | 115..135 | |
| | note = Pfam Name: IQ Pfam Description: IQ calmodulin-binding motif | |
| SITE | 180 | |
| | note = Xaa is any aa, unknown, or other | |
| SITE | 243 | |
| | note = Xaa is any aa, unknown, or other | |
| SITE | 370 | |

```
                        note = Xaa is any aa, unknown, or other
SITE                    377
                        note = Xaa is any aa, unknown, or other
SEQUENCE: 136
MGKKAKWFSS VKKAFSPDSK KSKQKLAEGQ NGVISNPPVV DNVRQSSSSP PPALAPREVR    60
VAEVIVERNR DLSPPSTADA VNVTATDXPV VPSSSAPGVV RRATPTRFAG KSNEEAAAIL   120
IQTIFRGYLA RRALRAMRGL VRLKLLMEGS VVKRQAANTL KCMQTLSRVQ SQIRARRIRX   180
SEENQARQKQ LLQKHAKELA GLKNGDNWND SIQSKEKVEA NLLSKYEATM RRERALAYSY   240
SHXQNWKNNS KSGNPMFMDP SNPTWGWSWL ERWMAGRPLE SSEKEQSNSN NDNAASVKGS   300
INRNEAAKSL TRNGSTQPNT PSSARGTPRN KNSFFSPPTP SRLNQSSRKS NDDDSKSTIS   360
VLSERNRRHX IAGSSVXDDE SLAGSPALPS YMVPTKSARA RLKPQSPLGG TTQENEGFTD   420
KASAKKRLSY PTSPALPKPR RFSAPPKVES GGVTVTNGAG S                      461

SEQ ID NO: 137          moltype = DNA  length = 1930
FEATURE                 Location/Qualifiers
source                  1..1930
                        mol_type = other DNA
                        organism = Zea mays
misc_feature            1..1930
                        note = Ceres CLONE ID no.375578
exon                    223..1716
                        note = Encodes the peptide sequence at SEQ ID NO 138
SEQUENCE: 137
aattcgagtg agcttattgg agactgacat cctaatcgaa aacccggttt atttttttctt    60
cgtcctggat gcgtcggtcg cgtgtttgat ctgactaagc cgcggaggag ggtgctagat   120
gtccgtgcgg tgggcggtgg ctcccgaggg cgaccggagt taggtccttg ccgccttcag   180
tgcggtgggg aagcgagaca ttgaaggcgc agaacccaaa gaatgggtaa gagaggaaag   240
tggtttagtg cggtgaagaa agtcttcagc tcctccgatc cagatggaaa ggaagccaag   300
gcccagaagg cagacaaatc gaaatccaag gatggaaagg aagccaaggc ccagaaggca   360
gacaaatcga aatccaagac ggtgccaggc actgctccag cagtagctcc gttgccatca   420
ccaccagcaa ctcagcccca ctctctggag atcaaagatg tcaatccagt tgaaacagac   480
agtgagcaga acaagcatgc ctactccgtt gcgcttgcgt ctgctgtcgc tgctgaagct   540
gcagcagttg ctgcccaggc tgctgcggaa gttgtccgcc tcacagcagt taccacggct   600
gcaccaaaga tgcctgttag ttcgagggaa gaacttgccg ccaccaagat tcagactgcc   660
ttcaggggtt atctggcaag gagagcattg cgtgcactaa gagggctagtt gaggttatct   720
ctggcaagga gagcattgcg tgcactaaga gggctagtta gaggttatct ggcaaggaga   780
gcattgcgtg cactaagagg gctagttaga tctagaaggg tgaagttgga ggaggagaaa   840
caggctcttc aaaagacaact ccaattgaaa catcaaaggg aacttgagaa aatgaagatt   900
gatgaagatt gggatcacag ccatcaatcc aaagagcaaa ttgaggccaa cctaatgatg   960
aaacaggaag ctgcactgag gcgagagaga gcacttgcat atgcattttc tcaccagtgg  1020
aggaattctg gtcgaactat aacccctact tttacggaac ctgggaaccc caactggggc  1080
tggagctgga tggagcgctg gatgacagca agaccatggg agagtcggtt ggcggcggca  1140
tcggacaagg acccctaaaga acgtgctgtg acaaagaatg cagccaccag tgctgttcga  1200
gtacctgtat cccgtgccat ctcgattcag agaccagcac accaaacaa gtcgagccgc  1260
ccaccaagcc ggcagtcact ttcaaccccg ccatcgaaga ccccgtcagc ctcaggaaag  1320
gccaggccga caagtccaag gaacagttgg ctgtacaagg aggatgacct gaggagcatc  1380
acgagcatcc gctccgagcg cccaaggagg cagagccagg gtggaggctc ggtccgggac  1440
gataccagcc tgaccagcac accacctctc cccagctaca tgcagtcgac cgagtctcga  1500
cgggccaagt ctcggtaccg cagtctctacta ctgactgaga agcttgaggt tcctgagaga  1560
gcgcctctgg cccactccgt tgtcaagaag cgcctgtcgt tccccgtcgt cgagaagcca  1620
agcgttgtgc cgacagagaa gcccagggaa agagtgaggc gccattccga ccctccgaag  1680
gtcgatcctg cgacgctcaa ggatgcccct gctgcctgac cagtgaccag gccttatgtg  1740
attgttaggt ttcgtgctct tttaacaccg tgatgtatta tctgagttag ttgctttgt  1800
tcgtgtcatc gtatgatctg tccgggttga ttttgagaca gttctaactg tgtttacaga  1860
caatgcgtga tgctaaatgt atgtgtggtt ggttggcttt aaatgtactg atatgatagt  1920
atttgatttc                                                        1930

SEQ ID NO: 138          moltype = AA  length = 498
FEATURE                 Location/Qualifiers
source                  1..498
                        mol_type = protein
                        organism = Zea mays
REGION                  1..498
                        note = Ceres CLONE ID no.375578
REGION                  1..498
                        note = Score of 1275.4 for HMM of FIGURE 4.
REGION                  1..498
                        note = Functional Homolog Of Ceres SEEDLINE ID no. ME24091
                         at SEQ ID NO.136
REGION                  137..157
                        note = Pfam Name: IQ Pfam Description: IQ
                         calmodulin-binding motif
SEQUENCE: 138
MGKRGKWFSA VKKVFSSSDP DGKEAKAQKA DKSKSKRRWP FGKSKHSEPS ISTVPGTAPA    60
VAPLPSPPAT QPHSLEIKDV NPVETDSEQN KHAYSVALAS AVAAEAAAVA AQAAAEVVRL   120
TAVTTAAPKM PVSSREELAA TKIQTAFRGY LARRALRALR GLVRLKSLVD GNAVKRQTAH   180
TLQCTQAMTR VQTQIYSRRV KLEEEQALQ RQLQLKHQRE LEKMKIDEDW DHSHQSKEQI   240
EANLMMKQEA ALRRERALAY AFSHQWRNSG RTITPTFTEP GNPNWGWSWM ERWMTARPWE   300
SRLAAASDKD PKERAVTKNA STSAVRVPVS RAISIQRPAT PNKSSRPPSR QSLSTPPSKT   360
```

```
PSASGKARPA SPRNSWLYKE DDLRSITSIR SERPRRQSTG GGSVRDDTSL TSTPPLPSYM   420
QSTESARAKS RYRSLLLTEK LEVPERAPLA HSVVKKRLSF PVVEKPSVVP TEKPRERVRR   480
HSDPPKVDPA TLKDAPAA                                                 498

SEQ ID NO: 139           moltype = DNA  length = 1930
FEATURE                  Location/Qualifiers
source                   1..1930
                         mol_type = other DNA
                         organism = Zea mays
misc_feature             1..1930
                         note = Ceres CLONE ID no.375578
SEQUENCE: 139
aattcgagtg agcttattgg agactgacat cctaatcgaa aacccggttt attttttctt    60
cgtcctggat gcgtcggtcg cgtgtttgat ctgactaagc cgcggggag ggtgctagat   120
gtccgtgcgg tgggcggtgg ctcccgaggg cgaccggagt taggtccttg ccgccttcag   180
tgcggtgggg aagcgagaca ttgaaggcgc agaacccaaa gaatgggtaa gagaggaaag   240
tggtttagtg cggtgaagaa agtcttcagc tcctccgatc cagatggaaa ggaagccaag   300
gcccagaagg cagacaaatc gaaatccaag aggagatgcc catttggaaa gtccaagcac   360
tcggagcctt ccatatcgac ggtgccaggc actgctccag cagtagcctc cgttgccatca   420
ccaccagcaa ctcagcccca ctctctggag atcaaagatg tcaatccagt tgaaacagac   480
agtgagcaga acaagcatgc ctactccgtt gcgcttgcgt ctgctgtcgc tgctgaagct   540
gcagcagttg ctgcccaggc tgctgcggaa gtttgtccgc tcacagcagt taccacggct   600
gcaccaaaga tgcctgttag ttcgagggaa taacttgccg ccaccaagat tcagactgcc   660
ttcagggggtt atctggcaag agagcattg cgtgcactaa gagggctagt tagattgaag   720
tcgcttgttg atgaaatgc tgtcaaacgc caaaccgctc acaccttgca atgcacacaa   780
gcaatgacaa gagttcaaac tcaaatctac tctagaaggg tgaagttgga gggagaaa    840
caggctcttc aaagacaact ccaattgaaa catcaaaggg aacttgagaa atgaagatt    900
gatgaagatt gggatcacag ccatcaatcc aaagagcaaa ttgaggccaa cctaatgatg   960
aaacaggaag ctgcactgag gcgagagaga gcacttgcat atgcattttc tcaccagtgg  1020
aggaattctg gtcgaactat aacccctact tttacggaac ctggaaccc caactgggggc  1080
tggagctgga tggagcgctg gatgacagca agaccatgag agagtcggtt ggcggcggca  1140
tcggacaagg accctaaaga acgtgctgtg acaaagaatg cgagcaccag tgctgttcga  1200
gtacctgtat cccgtgccat ctcgattcag agaccagcaa caccaaacaa gtcgagccgc  1260
ccaccaagcc ggcagtcact ttcaaccccg ccatcgaaga tccgtcagc ctcaggaaag   1320
gccaggccgg caagtccaag gaacagttgg ctgtacaagg aggatgacct gaggagcatc   1380
acgagcatcc gctccgagcg cccaaggagg cagagcacgg tggaggctc ggtccgggac    1440
gataccagcc tgaccagcac accacctctc cccagctaca tgcagtcgac cgagtctgca  1500
cgggccaagt ctcggtaccg cagtctacta ctgactgaga agcttgaggt tcctgagaga  1560
gcgcctctgg cccactccgt tgtcaagaag cgcctgtcgt tccccgtcgt cgagaagcca  1620
agcgttgtgc cgacagagaa gcccagggaa agagtgaggc gccattccga ccctccgaag  1680
gtcgatcctg cgacgctcaa ggatgcccct gctgctgac cagtgaccag gccttatgtg   1740
attgttaggt ttcgtgctct tttaacaccg tgatgtatta tctgagttag gttgctttgt   1800
tcgtgtcatc gtatgatctg tccggggttga tttttgagaca gttctaactg tgtttacaga  1860
caatgcgtga tgctaaatgt atgtgtggtt ggttggcttt aaatgtactg atatgatagt   1920
atttgatttc                                                         1930

SEQ ID NO: 140           moltype = AA  length = 311
FEATURE                  Location/Qualifiers
source                   1..311
                         mol_type = protein
                         organism = Zea mays
REGION                   1..311
                         note = Ceres CLONE ID no.375578
REGION                   1..311
                         note = Score of 653.4 for HMM of FIGURE 4.
REGION                   1..311
                         note = Functional Homolog Of Ceres SEEDLINE ID no. ME24091
                           at SEQ ID NO.136
SEQUENCE: 140
MTRVQTQIYS RRVKLEEEKQ ALQRQLQLKH QRELEKMKID EDWDHSHQSK EQIEANLMMK    60
QEEAALRRERA LAYAFSHQWR NSGRTITPTF TEPGNPNWGW SWMERWMTAR PWESRLAAAS  120
DKDPKERAVT KNASTSAVRV PVSRAISIQR PATPNKSSRP PSRQSLSTPP SKTPSASGKA  180
RPASPRNSWL YKEDDLRSIT SIRSERPRRQ STGGSVRDD TSLTSTPPLP SYMQSTESAR   240
AKSRYRSLLL TEKLEVPERA PLAHSVVKKR LSFPVVEKPS VVPTEKPRER VRRHSDPPKV  300
DPATLKDAPA A                                                       311

SEQ ID NO: 141           moltype = AA  length = 217
FEATURE                  Location/Qualifiers
source                   1..217
                         mol_type = protein
                         organism = Arabidopsis thaliana
REGION                   1..217
                         note = Ceres SEEDLINE ID no.ME10681
REGION                   1..217
                         note = Score of 322.9 for HMM of FIGURE 4.
REGION                   1..217
                         note = Functional Homolog Of Ceres SEEDLINE ID no. ME24091
                           at SEQ ID NO.136
SEQUENCE: 141
```

```
MGKKGKWFGA VKKVFSPESK EKKEESNIDR GSVKSMSLNL GEGEITKAFN RRDSKLEKPS  60
PPTPRPARPT SRHSPLTPSA RVAPIPARRK SVTPKNGLSQ VDDDARSVLS VQSERPRRHS  120
IATSTVRDDE SLTSSPSLPS YMVPTESARA KSRLQGSAMA NGAETPEKGG STGPAKKRLS  180
FQGGTAAASP MRRHSGPPKV EIAPPQPEAL VVNGGSK                          217

SEQ ID NO: 142          moltype = AA   length = 311
FEATURE                 Location/Qualifiers
source                  1..311
                        mol_type = protein
                        organism = Arabidopsis thaliana
REGION                  1..311
                        note = Ceres SEEDLINE ID no.ME03140
REGION                  1..311
                        note = Score of 653.4 for HMM of FIGURE 4.
REGION                  1..311
                        note = Functional Homolog Of Ceres SEEDLINE ID no. ME24091
                           at SEQ ID NO.136
SEQUENCE: 142
MTRVQTQIYS RRVKLEEEKQ ALQRQLQLKH QRELEKMKID EDWDHSHQSK EQIEANLMMK  60
QEAALRRERA LAYAFSHQWR NSGRTITPTF TEPGNPNWGW SWMERWMTAR PWESRLAAAS  120
DKDPKERAVT KNASTSAVRV PVSRAISIQR PATPNKSSRP PSRQSLSTPP SKTPSASGKA  180
RPASPRNSWL YKEDDLRSIT SIRSERPRRQ STGGGSVRDD TSLTSTPPLP SYMQSTESAR  240
AKSRYRSLLL TEKLEVPERA PLAHSVVKKR LSFPVVEKPS VVPTEKPRER VRRHSDPPKV  300
DPATLKDAPA A                                                      311

SEQ ID NO: 143          moltype = AA   length = 421
FEATURE                 Location/Qualifiers
source                  1..421
                        mol_type = protein
                        organism = Arabidopsis thaliana
REGION                  1..421
                        note = Ceres SEEDLINE ID no.ME24076
REGION                  1..421
                        note = Score of 908.3 for HMM of FIGURE 4.
REGION                  1..421
                        note = Functional Homolog Of Ceres SEEDLINE ID no. ME24091
                           at SEQ ID NO.136
REGION                  60..80
                        note = Pfam Name: IQ Pfam Description: IQ
                           calmodulin-binding motif
SEQUENCE: 143
LEVNLSVPPP PAPPPVLHQA EEVGVPEAEQ EQSKHVAVEE APAAAPAQAS VLPPAVPTQE  60
LAAVKIQTAF RGYLARRALR ALRGLVRLKS LVEGNSVKRQ SASTLRCMQT LSRVQSQISS  120
RRAKMSEENQ ALQRQLLLKQ ELENFRMGEN WDDSTQSKEQ IEASLISRQE AAIRRERALA  180
YAFSHQWKST SRSVNPMFVD PNNLQWGWSW LERWMAAKPW EGRNGADKES NIDRGSVKSM  240
SLNLGEGEIT KAFNRRDSKL EKPSPPTPRP ARPTSRHSPL TPSARVAPIP ARRKSVTPKN  300
GLSQVDDDAR SVLSVQSERP RRHSIATSTV RDDESLTSSP SLPSYMVPTE SARAKSRLQG  360
SAMANGAETP EKGGSTGPAK KRLSFQGGTA AASPMRRHSG PPKVEIAPPQ PEALVVNGGS  420
K                                                                 421

SEQ ID NO: 144          moltype = AA   length = 311
FEATURE                 Location/Qualifiers
source                  1..311
                        mol_type = protein
                        note = subspecies = japonica
                        organism = Oryza sativa
REGION                  1..311
                        note = Ceres SEEDLINE ID no.ME24217
REGION                  1..311
                        note = Score of 653.4 for HMM of FIGURE 4.
REGION                  1..311
                        note = Functional Homolog Of Ceres SEEDLINE ID no. ME24091
                           at SEQ ID NO.136
SEQUENCE: 144
MTRVQTQIYS RRVKLEEEKQ ALQRQLQLKH QRELEKMKID EDWDHSHQSK EQIEANLMMK  60
QEAALRRERA LAYAFSHQWR NSGRTITPTF TEPGNPNWGW SWMERWMTAR PWESRLAAAS  120
DKDPKERAVT KNASTSAVRV PVSRAISIQR PATPNKSSRP PSRQSLSTPP SKTPSASGKA  180
RPASPRNSWL YKEDDLRSIT SIRSERPRRQ STGGGSVRDD TSLTSTPPLP SYMQSTESAR  240
AKSRYRSLLL TEKLEVPERA PLAHSVVKKR LSFPVVEKPS VVPTEKPRER VRRHSDPPKV  300
DPATLKDAPA A                                                      311

SEQ ID NO: 145          moltype = AA   length = 500
FEATURE                 Location/Qualifiers
source                  1..500
                        mol_type = protein
                        note = subspecies = japonica
                        organism = Oryza sativa
REGION                  1..500
                        note = Public GI ID no.115440873
```

```
REGION                      1..500
                            note = Score of 1281.0 for HMM of FIGURE 4.
REGION                      1..500
                            note = Functional Homolog Of Ceres SEEDLINE ID no. ME24091
                              at SEQ ID NO.136
REGION                      142..162
                            note = Pfam Name: IQ Pfam Description: IQ
                              calmodulin-binding motif
SEQUENCE: 145
MGKKGNWFSA VKKVFSSSDP DGREAKIEKA DKSRSRRKWP FGKSKKSDPW TSTVAVPTST     60
APPPQPPPPP PTHPIQPQPE EIKDVKAVET DSEQNKHAYS VALASAVAAE AAAVAAQAAA    120
EVVRLTTATT AVPKSPVSSK DELAAIKIQT AFRGYLARRA LRALRGLVRL KSLVDGNAVK    180
RQTAHTLHCT QTMTRVQTQI YSRRVKMEEE KQALQRQLQL KHQRELEKMK IDEDWDHSHQ    240
SKEQVETSLM MKQEAALRRE RALAYAFSHQ WKNSGRTITP TFTDQGNPNW GWSWMERWMT    300
SRPWESRVIS DKDPKDHYST KNPSTSASRT YVPRAISIQR PATPNKSSRP PSRQSPSTPP    360
SRVPSVTGKI RPASPRDSWL YKEDDLRSIT SIRSERPRRQ STGGASVRDD ASLTSTPALP    420
SYMQSTESAR AKSRYRSLLT DRFEVPERVP LVHSSIKKRL SFPVADKPNG EHADKLMERG    480
RRHSDPPKVD PASLKDVPVS                                                500

SEQ ID NO: 146              moltype = DNA  length = 1695
FEATURE                     Location/Qualifiers
source                      1..1695
                            mol_type = other DNA
                            organism = Triticum aestivum
misc_feature                1..1695
                            note = Ceres CLONE ID no.826796
misc_feature                1..1695
                            note = Encodes the peptide sequence at SEQ ID NO 147
SEQUENCE: 146
ataggacttc acagacagac tgactcaatc ctaacccaat ccctcccatg cttccatcta     60
ctctagcaga aattgcagag gaggttggcc gccgccggct ccagcgcagg cgcagcctac    120
ccgcgggatc tgacgccctc cgcctcctac ctcgaggcac gcgcctcagg ctcagctccc    180
ccgcccgccc tccccgcta ccccgacgac ttccaagagg aggagcatga aattgagcat    240
gtcgccgccg cgccagcgcc agcgccagcc acggatgcgc cgctcctgc ccctcctgcc    300
gccgcaccac cacaggttca ggctgccatt gcgccgcgtt cttcctcttg tgtcatgtcc    360
agggagctcg ccgccaccaa gatccagacc gccttccgag gtcacctggc aagaagggcg    420
ctgcgggcat tgaaaggcct ggtcagactc aagtcgctgg tccaaggcca ctccgtcaag    480
cgccaggcca ccagcacgct tcgctgcatg cagactctgt cccgggtcca gtccaagata    540
cggacgagga ggatcaagat ggccgacgag aaccaggccc ttcagcgcca gctcttgttg    600
aaccaggaac tagagactct caggatggga gatcagtgga ataccagcct gcagtccaag    660
gagcaaatcg aggcgagcct cgtgagcagg caagaggccg cggctagaag agaacgggct    720
ctcgcatacg cattctccca ccagtggaag agcacctcaa ggtctgccaa cccgatgttc    780
gtggacccga gtaacccgca ctgggggctgg agctggctgg agtggatgga ggcgtcgagg    840
ccgttcgacg gccgcaacgg ggcgtccgag aaggagggca gcagcgtcga ccgcacgtcg    900
gtgcacagca ccagcctgag catgaacctc ggagaaggtg agacggtcac aaaggcggac    960
aaccaggtgg tggactcttt gaagccgaat gatgataagc cgccgccgct ttcgactccg    1020
aagccgtccg gccctgcccc caggcagtcc ccgtcgaccg cctcgccgg gctggcgagg    1080
aagaagagcg cgacgcccaa gagtggagac tgcgacggcg acgacgcgag gagcgtggtc    1140
agcactgtcc ggtccgagcg gccccggagg cacagcatcg gcgcgtccag cgtgcgtgac    1200
gacgcgggct cttcccgtc ggtgccgagc tacatggcgg ccaccaagtc ggcgtcggcc    1260
agggccaagt cgcgtgtgca gagcccgacg ctgaccgagg tgctgctca agctgagacg    1320
ctggagaaag gatggtcttc tgtgggttca gcgaagaagc ggctgtcctt tccggctggg    1380
acgccaccgc cggtgccggc ggcggcggcg aggcggcact ccgggcctcc caaggtgcgg    1440
caggcgggcg tggaaggtgg tacggaggaa cgggactcgt cccttgcgtg acatcatggg    1500
aagcagatta tggtgtggag cagagcagag cggaatttgt tgcatttgtt gagtgaaagg    1560
aacgcagaat gtgtgttgtg tggatccatt ggatttgatt tgatttgtat gatggcagta    1620
ttcctatttg attattcatt gaataatata agtatctgta atgaagataa aaggagggga    1680
cacgaacatt atttc                                                    1695

SEQ ID NO: 147              moltype = AA  length = 378
FEATURE                     Location/Qualifiers
source                      1..378
                            mol_type = protein
                            organism = Triticum aestivum
REGION                      1..378
                            note = Ceres CLONE ID no.826796
REGION                      1..378
                            note = Score of 903.8 for HMM of FIGURE 4.
REGION                      1..378
                            note = Functional Homolog Of Ceres SEEDLINE ID no. ME24091
                              at SEQ ID NO.136
REGION                      4..24
                            note = Pfam Name: IQ Pfam Description: IQ
                              calmodulin-binding motif
SEQUENCE: 147
MSRELAATKI QTAFRGHLAR RALRALKGLV RLKSLVQGHS VKRQATSTLR CMQTLSRVQS     60
KIRTRRIKMA EENQALQRQL LLNQELETLR MGDQWNTSLQ SKEQIEASLV SRQEAAARRE    120
RALAYAFSHQ WKSTSRSANP MFVDPSNPHW GWSWLERWMA SRPFDGRNGA SEKEGSSVDR    180
TSVHSTSLSM NLGEGETVTK ADNQVVDSLK PNDDKPPPLS TPKPSGPAPR QSPSTPSPAL    240
```

```
ARKKSATPKS GDCDGDDARS VVSTVRSERP RRHSIGASSV RDDAGSSPSV PSYMAATKSA    300
SARAKSRVQS PTLTEGAAQA ETLEKGWSSV GSAKKRLSFP AGTPPPVPAA AARRHSGPPK    360
VRQAGVEGGT EERDSSLA                                                  378

SEQ ID NO: 148          moltype = DNA  length = 1470
FEATURE                 Location/Qualifiers
source                  1..1470
                        mol_type = other DNA
                        organism = Populus balsamifera
                        sub_species = trichocarpa
misc_feature            1..1470
                        note = Ceres ANNOT ID no.1465047
misc_feature            1..1470
                        note = Encodes the peptide sequence at SEQ ID NO 149
SEQUENCE: 148
atggggaaaa gagggagttg gttctctgct ttgaagaaag ccctcggttc ctctaagaaa    60
tccaaatcaa agaagaaatg gtcagaaaaa gagaagaacc gggatctagg tgtttcttca    120
catgaagaaa ccgttgcacc ctctctttct cctcctcgta caccacctcc tcctacagca    180
gaagatgtga aattaactga agctgagaac gagcagagca agcatgctta ttccgtggcg    240
cttgccactg ctgtggcagc tgaggcagct gttgcagccg cccaggctgc cgctgaggtt    300
gttcggctta ctacagtggc acattactct ggaaaatcga aggaggaaat agctgcaatc    360
aggattcaaa cagcatttag aggatacctg gcgagggagg cattacgtgc tttgagaggg    420
ctggtgagat tgaagtcatt gatacaaggg caatctgtca aacggcaagc aactgccaca    480
ttacgagcca tgcagactct tgctcgtgtg cagtctcaga ttcgtgcaag aaggatcaga    540
atgtccgagg aaaatgaggc cctccaacgg cagctccagc agaaacatga caagaaactt    600
gagaagttga gaacttctat tggagaacaa tgggatgaaa gcccacaatc aaaggaagaa    660
gttgaagcca gcctactaca aaagcaagaa gctgccatga aagagaaaag gcactggctt    720
tatgcatact cgcatcagca aatgtggaag caatcttcaa aatcagcaaa tgctacattc    780
atggatccaa acaatcctcg ttggggatgg agttggttag agaggtggat ggcagcccga    840
ccttgggaga gccgaagcac aatagataac aatgatcggg cctctgttaa gagtacaaca    900
agccgtacca tgtctcttgg agaaatcagc agagcttatt ctcgtcgtga tcttaaccat    960
gacaataaag cttctcctgg tgcgcaaaaa tcaagtcggc ctcccagtcg gcaatccctt    1020
tctactcccc cctctaaggc accatctaca tcttcagtaa cagggaaagc aaagccacca    1080
agccctagag ggagtgcttg gggaggagac gaggactcca ggagcacatt cagtgtccag    1140
tctgagcgct atcggagaca tagcatagca gggtcatcaa taagagatga tgagagtctt    1200
gcaagttcgc cttcagttcc aagttacatg gcacccacac ggtcacagtc agcaaaggca    1260
aaatcccgct tgtcaagccc gttaggcata gataataatg gacaccagaa taaggcatca    1320
gtgggttatg taaagaagcg gctttccttc tctgcttcac cagctggagc aaggagacac    1380
tctggtcctc ctagggtgga tgccagtgct gttaaagaca ttcaaatgca cagagaagag    1440
aaaatgagca atggagcaag cagcaagtag                                     1470

SEQ ID NO: 149          moltype = AA  length = 326
FEATURE                 Location/Qualifiers
source                  1..326
                        mol_type = protein
                        note = subspecies = trichocarpa
                        organism = Populus balsamifera
REGION                  1..326
                        note = Ceres ANNOT ID no.1465047
REGION                  1..326
                        note = Score of 746.5 for HMM of FIGURE 4.
REGION                  1..326
                        note = Functional Homolog Of Ceres SEEDLINE ID no. ME24091
                          at SEQ ID NO.136
SEQUENCE: 149
MQTLARVQSQ IRARRIRMSE ENEALQRQLQ QKHDKELEKL RTSIGEQWDD SPQSKEEVEA    60
SLLQKQEAAM RRERALAYAY SHQQMWKQSS KSANATFMDP NNPRWGWSWL ERWMAARPWE    120
SRSTIDNNDR ASVKSTTSRT MSLGEISRAY SRRDLNHDNK ASPGAQKSSR PPSRQSPSTP    180
PSKAPSTSSV TGKAKPPSPR GSAWGGDEDS RSTFSVQSER YRRHSIAGSS IRDDESLASS    240
PSVPSYMAPT RSQSAKAKSR LSSPLGIDNN GTPDKASVGY VKKRLSFSAS PAGARRHSGP    300
PRVDASAVKD IQMHREEKMS NGASSK                                          326

SEQ ID NO: 150          moltype = DNA  length = 1901
FEATURE                 Location/Qualifiers
source                  1..1901
                        mol_type = other DNA
                        organism = Gossypium hirsutum
misc_feature            1..1901
                        note = Ceres CLONE ID no.1919901
misc_feature            1..1901
                        note = Encodes the peptide sequence at SEQ ID NO 151
SEQUENCE: 150
aacttttctt agttatcctc tgcaaatgcc aacctgttct tttattatta ttttccgcca    60
tttttgctct cttttcaagca tttttttttt gcctagatcc acttctctct ctttgatttt    120
taattactgc atttttgttt taatacacaa taagaacaac taagagatag aatgtgactt    180
atcaatcttt taactgagat ctgtgagaat ttttctatgt accaaggaat tatttacaga    240
tgggaaaaaa aggtggctgg cttttctatt gtgaagaaagc tttgagccct gaatccaaga    300
aatccagcca ccaaactcca aagcaaagaa aaaatggtt cggaaaaagc aaaaatttga    360
gccctgtgtc tgtgcctgaa gaaactgaag tgataactga agatgcaaag ctaaaagaag    420
```

```
ctgaaaacga acaaagcaaa catgcctact ctgtggctct tgccaccgct gtggcggccg    480
aggcagcggt ggcagctgct caggcggctg ctgaagttgt ccgtctcact tctcagccgc    540
gccatctggg gaagtcaaag gaggaaatag ctgctatcag gattcaaaca gcatttcgtg    600
gatatttggc taggagggca ctgcgagctt tgagagggtt ggtaaggttg aaatcgttga    660
tcagagggca atccgtcaaa cgccaagcaa ctacaacgtt aagatgcatg cagactctag    720
ctcgtctgca gtctgagatt tctgcaagga ggattagaat gtcagaagag aaccaggctc    780
ttcagcgcca gcttcaacag aaatgccaga aagagctcga gaagttgaga gctcccatga    840
gagaagactg gaacgatagt acacagtcga aggagcagat cgaagcaaga caacaaaata    900
agcaaggagc tactatgaaa agggaaagag cattggctta tgcatactgt caccagcaga    960
cgtggaagaa ctgttctaga tcagtgaatc aaacatttat ggatccgagt aattcacact   1020
ggggttggag ttggttagag cgatggatgg cagcccgacc atgggaagtc aaagcacaa    1080
ctgataacaa tgaccgtggc tcagtcaaga gtatgggtgc ttgttcgata tctataagtg   1140
aaatcagcag agcttattct cgaagagatc ttaacaatga taacaaacca tctccaacac   1200
ctcagaagtc aagtcgagtt cctagccgcc agtctccatc gactccacct tcaaaggcac   1260
cttcgatttc atcggtttct ggtaaaacaa gactgccaag tccgagagga agtcaatggg   1320
gagggtatga agactcaagg agcatactca gtacccggtc tgatcgttat aggagacata   1380
gcattgcagg gtcctcaatg agagacgatg agagccttac aagctcacct gcagttccaa   1440
gttatatggc accaacacag tccacaaagg ccaggtccca cataccaagc ccccttaggaa   1500
gtggcacacc agataggaga gtggcagggt ctgcaaagaa acggcttttg ttcccagcat   1560
ccccagccag tagtaggaga cattcagagc ctcctaaagt ggacataagt gaggctagaa   1620
agaatcagca tgcaccaagc aatggaaggc aagtggcttg tgaagagtg caacaaaagt    1680
tagattgaat aaacatggaa gggttatttc aacttgaagt tcttgtagtg tggttgtgat   1740
tatcttttc ttcctaggtt ttatgattat taattataaa agggttactt ttttctgggt    1800
gagatttagt ttattgtttg tggttgacaa acattcttaa aaatcttcaa gtttagtttc   1860
aattcatgaa atttgtaatt aaaaaaaaaaa aaaaaaaaa a                        1901

SEQ ID NO: 151           moltype = AA  length = 474
FEATURE                  Location/Qualifiers
source                   1..474
                         mol_type = protein
                         organism = Gossypium hirsutum
REGION                   1..474
                         note = Ceres CLONE ID no.1919901
REGION                   1..474
                         note = Score of 1214.2 for HMM of FIGURE 4.
REGION                   1..474
                         note = Functional Homolog Of Ceres SEEDLINE ID no. ME24091
                           at SEQ ID NO.136
REGION                   109..129
                         note = Pfam Name: IQ Pfam Description: IQ
                           calmodulin-binding motif
SEQUENCE: 151
MGKKGGWLSI VKKALSPESK KSQHQTPKPK KWFGKSKNL SPVSVPEETE VITEDAKLKE     60
AENEQSKHAY SVALATAVAA EAAVAAAQAA AEVVRLTSQP RHLGKSKEEI AAIRIQTAFR   120
GYLARRALRA LRGLVRLKSL IRGQSVKRQA TTTLRCMQTL ARLQSEISAR RIRMSEENQA   180
LQRQLQQKCQ KELEKLRAPM REDWNDSTQS KEQIEARQQN KQGATMKRER ALAYAYCHQR   240
SWKNCSRSVN QTFMDPSNSH WGWSWLERWM AARPWEVQST TDNNDRGSVK SMGACSISIS   300
EISRAYSRRD LNNDNKPSPT PQKSSRVPSR QSPSTPPSKA PSISSVSGKT RLPSPRGSQW   360
GGYEDSRSIL STRSDRYRRH SIAGSSMRDD ESLTSSPAVP SYMAPTQSTK ARSHIPSPLG   420
SGTPDRRVAG SAKKRLLFPA SPASSRRHSE PPKVDISEAR KNQHAPSNGR QVAW          474

SEQ ID NO: 152           moltype = DNA  length = 1362
FEATURE                  Location/Qualifiers
source                   1..1362
                         mol_type = other DNA
                         organism = Glycine max
misc_feature             1..1362
                         note = Ceres CLONE ID no.520008
misc_feature             1..1362
                         note = Encodes the peptide sequence at SEQ ID NO 153
SEQUENCE: 152
atgcattcac tcatcaggtt tttttaaaaa aaaaaaattc tcatcaattt acacatgcga     60
gaaaatgggt gaaaaattta atacgaactg aaaaatcttt caaaaatatc gcatattata   120
aacactaaaa tgagaaatca agcatccttc ttatactata tggatatact cttcactgtt   180
tctttatctc ttgaatctgt tatactttcc aactgagact taggcctgat tcctgataag   240
tgcacgagtc ctttcctatc ttgtcactat cttcagagcc atatcctctg cactctcctt   300
tctcactgcc acgatgatct tttgcataat ccaatgatat gctaatgctt tgttaagtaa   360
gttgcagcgt aaattcttcc tcaatttttgt caatggaagt attttgttac tgaaataaag   420
tggcatgcta tattatgtaa catattttga atgaatagca ttctgcctat gatatgattt   480
tcaatcataa gtgtaagttc cttgatgctg tcaacaaatt cagtgtttga tatttggggg   540
caaaaaatat ttggcagcaa aactggaaga actcgtctag atctgtaaat ccaatgttta   600
tggatccaac taatccgagc tggggttgga gctggttgga acgatggatg gcagcccgac   660
cttgggagag ccgtagccat atggataaag agttgaatga ccactcctcc ataagaagct   720
caagccgcag cattaccggt ggagaaatca gcaagtcatt tgctcgtttc cagctcaatt   780
cggaaaagca ctctccaaca gccagccaga atcctggctc ccctagcttt cagtccactc   840
cttccaagcc agcttcatca tctgctaaga aaccaaagaa ggtaagtcca agcccaaggg   900
gcagctgggt tatggacgag gactccaaaa gcttggtcag tgtacactct gaccggttcc   960
ggaggcactc cattgccggt tcatcggtga gagatgacga gagccttgct agctctccag   1020
cagttccaag ctacatggtg ccaactcaat ctgcaaaagc caagtccagg acacaaagtc  1080
```

```
cattagcctc agaaaatgca aaagcagaga aaggttcctt tgggagtgca aagaagcggc   1140
tttctttccc agcttcacct gccaggccaa ggcgccattc aggtccacca aaggttgaaa   1200
gcagcagctt aaatgcagag ttagctgtgg acaagggtgt ggacagttga tcatacaagt   1260
aaaaggatgg aaaagcatta aagtaggatt gaaaatatat cactgaagaa ataaaacaaa   1320
aagagtttat ttaaaaaaaa aaaaaaaaaa aaaaaaaaaa aa                      1362

SEQ ID NO: 153          moltype = AA   length = 218
FEATURE                 Location/Qualifiers
source                  1..218
                        mol_type = protein
                        organism = Glycine max
REGION                  1..218
                        note = Ceres CLONE ID no.520008
REGION                  1..218
                        note = Score of 156.2 for HMM of FIGURE 4.
REGION                  1..218
                        note = Functional Homolog Of Ceres SEEDLINE ID no. ME24091
                          at SEQ ID NO.136
SEQUENCE: 153
MFMDPTNPSW GWSWLERWMA ARPWESRSHM DKELNDHSSI RSSSRSITGG EISKSFARFQ    60
LNSEKHSPTA SQNPGSPSFQ STPSKPASSS AKKPKKVSPS PRGSWVMDED SKSLVSVHSD   120
RPFRHSIAGS SVRDDESLAS SPAVPSYMVP TQSAKAKSRT QSPLASENAK AEKGSFGSAK   180
KRLSFPASPA RPRRHSGPPK VESSSLNAEL AVDKGVDS                           218

SEQ ID NO: 154          moltype = AA   length = 445
FEATURE                 Location/Qualifiers
source                  1..445
                        mol_type = protein
                        organism = Arabidopsis thaliana
REGION                  1..445
                        note = Public GI ID no.7413581
REGION                  1..445
                        note = Score of 1020.8 for HMM of FIGURE 4.
REGION                  1..445
                        note = Functional Homolog Of Ceres SEEDLINE ID no. ME24091
                          at SEQ ID NO.136
REGION                  114..134
                        note = Pfam Name: IQ Pfam Description: IQ
                          calmodulin-binding motif
SEQUENCE: 154
MGKKAKWFSS VKKAFSPDSK SKQKLAEGQN GVISNPPVVD NVRQSSSSPP PALAPREVRV    60
AEVIVERNRD LSPPSTADAV NVTATDVPVV PSSSAPGVVR RATPTRFAGK SNEEAAAILI   120
QTIFRGYLAR RALRAMRGLV RLKLLMEGSV VKRQAANTLK CMQTLSRVQS QIRARRIRMS   180
EENQARQKQL LQKHAKELAG LKNGDNWNDS IQSKEKVEAN LLSKYEATMR RERALAYSYS   240
HQQNWKNNSK SGNPMFMDPS NPTWVPRKNK SNSNNDNAAS VKGSINRNEA AKSLTRNGST   300
QPNTPSSARG TPRNKNSFFS PPTPSRLNQS SRKSNDDDSK STISVLSERN RRHSIAGSSV   360
RDDESLAGSP ALPSYMVPTK SARARLKPQS PLGGTTQENE GFTDKASAKK RLSYPTSPAL   420
PKPRRFSAPP KVESGGVTVT NGAGS                                         445

SEQ ID NO: 155          moltype = DNA   length = 1806
FEATURE                 Location/Qualifiers
source                  1..1806
                        mol_type = other DNA
                        organism = Zea mays
misc_feature            1..1806
                        note = Ceres CLONE ID no.228069
misc_feature            1..1806
                        note = Encodes the peptide sequence at SEQ ID NO 156
SEQUENCE: 155
gagccgcgga ggagcagcgg cgcatcgcaa cactaaccaa agtcctcctc tccaggtgcc    60
gagccagggt gactgttccg aggagcgtgg cgtggaccca tggggaagaa gggcaagtgg   120
ttcggtgccg tcaagaaggt cttcagcccc gaatccaagg agaagaaaga ggagaggcta   180
aggaggaaat cagcagctag caacccagca ccggtagatc tgaccccatc tacctccctg   240
gaagtcaatg tttcggtgcc acccctccg gctcctcctc ccagcctccg                300
gaggtcaggg tccccgaagc cgagcaggag cagagcaagc atgtcaccct ggaggaggcc   360
cctgctgctg ctgctgcccc agcacaggcg tcggtgctgc cacctggtgc gccaaccgaa   420
gagctcgccc caatcaagat ccagaccgcc ttccgaggtt acctggcaag agggcactaa   480
agagcactac gaggccttgt acgattgaag tcattggttg aggtaattc agttaagcgt    540
caatctgcaa gcactctgcg ctgtatgcaa actctatcg gggtgcagtc acaaatacga   600
tctaggagag caaagatgtc cgaggagaac caggccctcc aacgccagct cctacttaaa   660
caggaactgg agaatttcag aatgggtgag aactgggacg cagcactca atccaaggag   720
caaatcgagg caagcctaat aagcaggcaa gaggcagcga taagaagaga aagagctctt   780
gcatatgcat tttcacatca gtggaagagc acatcaagat ctgcgaaccc aatgtttgta   840
gacccaaata acttgcaggt gggctggagc tggttggacg gtgatggc agcaaaacct   900
tgggaggac gcaatgggac cgacaaggag agcaacattg atcgcggctc cgtcaagaat   960
atgagcttga accttggagt tggagagggt gagatcacaa aagctttcaa ccgcgggac   1020
tcaaagccag agaagccatc accaccgact ccaaaaccgg cccgtccagc ttccaggcaa  1080
tccccttcga cgccctctgc tagagtggcc ccaatacctg cgaggaggaa atccagcacg  1140
ccaaagaatg ggctttcaca ggtggacgat gacgtgagga gcgtgctcag tgtgcagtct  1200
```

```
gagcgaccaa ggaggcacag catagccacg acgtcgacca tgcgggacga tgagagcctc 1260
gcgagctccc cgtcgctccc gagctacatg gttcccacag aatctgcgag ggccaaatct 1320
cgcacagcaa cggccaatgg cgcagagacg cctgagaaag gaggctctgc tggaccagtc 1380
aagaagaggt tgtctttcca aggtggagct gcggctgcct caccgatgcg acggcattct 1440
ggccctccca aggtggagag cgctgtgaag gacattgctg cgccaccaca gcctgaggcc 1500
ttggtagcca atggtggtgg aagcaagtga cttgtattga caagttccag gatgggggag 1560
cgggttatgg tcttatggag ggacatgttt catccgtgaa cagaagttaa gagtggtgcc 1620
ggatctacga atggtttgaa ttgttttccc gttacaacca cattgtttgc tgtataagat 1680
tcactgtacc tgccagttgg ttccattgt tgttttctgt aaaacaaaca tcaatttgtc 1740
actagaatct gtgatgcttg tatgtaaaca ggtcctctat ttatgtgagc catatatttc 1800
attttc                                                         1806

SEQ ID NO: 156          moltype = AA  length = 476
FEATURE                 Location/Qualifiers
source                  1..476
                        mol_type = protein
                        organism = Zea mays
REGION                  1..476
                        note = Ceres CLONE ID no.228069
REGION                  1..476
                        note = Score of 953.8 for HMM of FIGURE 4.
REGION                  1..476
                        note = Functional Homolog Of Ceres SEEDLINE ID no. ME24091
                          at SEQ ID NO.136
REGION                  108..128
                        note = Pfam Name: IQ Pfam Description: IQ
                          calmodulin-binding motif
SEQUENCE: 156
MGKKGKWFGA VKKVFSPESK EKKEERLRRK SAASNPAPVD LTPSTSLEVN VSVPPPPAPP  60
PVPRQTDEVR VPEAEQEQSK HVTLEEAPAA AAAPAQASVL PPGAPTEELA AIKIQTAFRG 120
YLARRALRAL RGLVRLKSLV EGNSVKRQSA STLRCMQTLS RVQSQIRSRR AKMSEENQAL 180
QRQLLLKQEL ENFRMGENWD DSTQSKEQIE ASLISRQEAA IRRERALAYA FSHQWKSTSR 240
SANPMFVDPN NLQWGWSWLE RWMAAKPWEG RNGTDKESNI DRGSVKNMSL NLGVGEGEIT 300
KAFNRRDSKP EKPSPPTPKP ARPASRQSPS TPSARVAPIP ARRKSSTPKN GLSQVDDDVR 360
SVLSVQSERP RRHSIATTST MRDDESLASS PSLPSYMVPT ESARAKSRTA TANGAETPEK 420
GGSAGPVKKR LSFQGGAAAA SPMRRHSGPP KVESAVKDIA APPQPEALVA NGGGSK     476

SEQ ID NO: 157          moltype = DNA  length = 1703
FEATURE                 Location/Qualifiers
source                  1..1703
                        mol_type = other DNA
                        organism = Glycine max
misc_feature            1..1703
                        note = Ceres CLONE ID no.467508
misc_feature            1..1703
                        note = Encodes the peptide sequence at SEQ ID NO 158
SEQUENCE: 157
aaaccatcct ctcttagcat ttggcaagat ctgatttccc tcttcacaag gagagaaata   60
gaaaggcata tgatcttctt caagttgcaa tctttttaga gagagagggt tagaagaaca  120
acatacttga gatctgtcac tttgtttgag ttcagatctt caaagtttcc ttccttgttc  180
ttttggtgca aaggatcaaa ttaaggaatg ccaaatggtg aggaagggga attggttttc  240
cagtgtgatg aaagctctca gtcctgactc aaaggagaag aaagaacaga atcaagtaa   300
atctaagaag aaatggtttg ggaagcaaaa attggagact tcagtctcat actcagaagc  360
tcataaagca ccaccaccac cgcgacctat tcctccacca gaagcgatta aattaactga  420
tattgaaaat gaaatcagtc atgatcacga ctatgttgtt gaagttgcaa ctgccatgga  480
tgccgaggaa cctgttcctt ctgttcagat agaacctgtt agggttgaag ctgccccaat  540
tgctcattat gctggtaaac caaggatga agtggcagct atcaaaattc aaacagcttt  600
tcgtggatac ttggcaagaa gagcattgcg ggctttaagg gggctggtca ggttgaaatt  660
attgatggaa gggccagttg ttaaacgcca agccacaagt accctccact ctatgcagac  720
attatctcgc ttgcagtctc agattcgttc aaggaggatc agaatgttag aggagaatca  780
ggctctgcag agacagctct tacagaagca tgcaagagag cttgagagct tgcggatggg  840
agaggaatgg gatgacagcc tacaatcaaa agaacaaatc gaagcaagt tacttagcaa  900
gtatgaagct actacgagaa gagaaagagc gctggcttat gcattcactc atcagcaaaa  960
ttggaagaac tcatctagat ctgtaaatcc aatgttcatg tgccaacca atccaagctg 1020
gggttggagc tggttggaac gatggatggc agcccgacct tgggagagcc gtagccatat 1080
ggataaagag ttgaatgacc actcatccgt aagaagctca agccgcagta ttaccggtgg 1140
agaaatcagc aagtcatttg ctcgtttcca gctcaatttg gaaagcact ctccaacagc 1200
ctgccagaat cctggcctcac ctagctttca gtccactcct tccaagccag cttcaatatc 1260
tgctaagaaa ccaaagaagg taagtccaag cccaagggc agctgggta cagacgagga 1320
ctccaaaagc ttggtcagtg tacagtcaga ccggttccgg aggcactcca ttgccggttc 1380
attggtgaga gatgatgaga gccttgctag ctctccagca gttccaagct acatggtgcc 1440
aactcaatct gcaaaagcca agtccaggac acaaagtcca ttagcccag aaaatggaaa 1500
agcagagaaa ggttcctttg ggagtgcgaa gaagcggctt tctttcccag cttcacctgc 1560
caggccaagg cgccattcag gtccaccaaa ggtagaaagc agcagcttaa atgcagagtt 1620
agctgcttggac aagggtgtgg acagttgatc atacaagtaa aaggatggaa aacattaaa 1680
gtaggattga aaatatatca ctg                                         1703

SEQ ID NO: 158          moltype = AA  length = 477
FEATURE                 Location/Qualifiers
```

```
source                  1..477
                        mol_type = protein
                        organism = Glycine max
REGION                  1..477
                        note = Ceres CLONE ID no.467508
REGION                  1..477
                        note = Score of 852.8 for HMM of FIGURE 4.
REGION                  1..477
                        note = Functional Homolog Of Ceres SEEDLINE ID no. ME24091
                          at SEQ ID NO.136
REGION                  119..139
                        note = Pfam Name: IQ Pfam Description: IQ
                          calmodulin-binding motif
SEQUENCE: 158
MGRKGNWFSS VMKALSPDSK EKKEQKSSKS KKKWFGKQKL ETSVSYSEAH KAPPPPRPIP    60
PPEAIKLTDI ENEISHDHDY VVEVATAMDA EEPVPSVQIE PVRVEAAPIA HYAGKPKDEV   120
AAIKIQTAFR GYLARRALRA LRGLVRLKLL MEGPVVKRQA TSTLHSMQTL SRLQSQIRSR   180
RIRMLEENQA LQRQLLQKHA RELESLRMGE EWDDSLQSKE QIEAKLLSKY EATTRRERAL   240
AYAFTHQQNW KNSSRSVNPM FMDPTNPSWG WSWLERWMAA RPWESRSHMD KELNDHSSVR   300
SSSRSITGGE ISKSFARFQL NLEKHSPTAC QNPGSPSFQS TPSKPASISA KKPKKVSPSP   360
RGSWVTDEDS KSLVSVQSDR FRRHSIAGSL VRDDESLASS PAVPSYMVPT QSAKAKSRTQ   420
SPLAPENGKA EKGSFGSAKK RLSFPASPAR PRRHSGPPKV ESSSLNAELA VDKGVDS      477

SEQ ID NO: 159          moltype = DNA  length = 1495
FEATURE                 Location/Qualifiers
source                  1..1495
                        mol_type = other DNA
                        organism = Gossypium hirsutum
misc_feature            1..1495
                        note = Ceres CLONE ID no.1829581
misc_feature            1..1495
                        note = Encodes the peptide sequence at SEQ ID NO 160
SEQUENCE: 159
attattttca atgcaattta agagttttat ttattttatg ttataaattt tttaacctct    60
aaatatgatt tgaaatgtta attccattgg ttgttttttgg ttttgaagga gaatttattg   120
aggaatgggc aaaaaaggaa gctggtttac tgctgtgaag aaagttctaa gccttgaacc   180
caacaaagaa gagaagattc aaaaatccaa gaaaatgggg gttaaattac ctgagaagat   240
caaaggaagc aaacgtgaca actggttcgc tccggccacc accatggtga ccggcgcgtt   300
ggttcgcctt actttgtcgc cacactactt gggaaaatca atggaggaaa tagctactgt   360
taagattcaa actgtgtttc gaggataccT ggcgaggaag gcattgcgag atttgagagg   420
gttagagagg ttgaaatcat tgatacaagg gcaatccatg aaacgacaag ccactattac   480
gttacgatgc atgcggacac ttgctcgagt gcagtcccaa actcgaacaa ggcaactcag   540
agtgtctgaa caaaaccgag cacttcaaaa gcatcttcaa actaaatacg aaaaaacagtt   600
gcaaaattcc aaatcttaca tgggagaaga ttggaatgta agtactaagt ctaaagcaga   660
aatgcaagca aacaacaat atagacaagt agcagccatg cgaagggaga gagctttagc   720
ttactcattt actcatcagc gatcctggaa ggtcacttgt agatcgatga atcacacatc   780
tatggatcca tttaatccta aatggagctg gagttggtta gagcgatgga tgtcaactcg   840
accatgggag attcaaaatg caccggataa caatgatcat ggcccaagta agagtgttga   900
tgctgagata accaaagcta agtctcaaag tgatgttaac aatgatcaca ataaacaatc   960
ttcaacaccg gcaaaaccga ttcgacctcc gaaccgtagg tcctcttcga ctccaccgtc  1020
taaaacgcat tctatttcta gcaagaaggg atttggaaatgg ccccagtccga cacgaattca  1080
gttgcctgat tgttacaaga ggcatagcat cggaggctta tcattggaga gagacgatga  1140
ggtctttgca aactcaccac ctaataataa aatccggca cgttcgtcat caaaggaccg  1200
gtctcgacca ccgagcatta tagaaatcc agttaatact aggagacatt ctggtcctcc  1260
gaaagttgat atttttttcca actaaggaag aaatgccaaa caatgacaaa ggcaggtagt  1320
ttatgaagca tagacacttt agtcgcgagt gccggccaca tgtttaatat tgaaatggct  1380
ccgacacaat caaatgtgtg ttggttatat gacgatatat tttttcaaaa aatcaaatac  1440
tatcagaaaa aaatataaag aaagattaat tggataaaaa aaaaaaaaaa aaaaa        1495

SEQ ID NO: 160          moltype = AA  length = 386
FEATURE                 Location/Qualifiers
source                  1..386
                        mol_type = protein
                        organism = Gossypium hirsutum
REGION                  1..386
                        note = Ceres CLONE ID no.1829581
REGION                  1..386
                        note = Score of 365.8 for HMM of FIGURE 4.
REGION                  1..386
                        note = Functional Homolog Of Ceres SEEDLINE ID no. ME24091
                          at SEQ ID NO.136
REGION                  75..95
                        note = Pfam Name: IQ Pfam Description: IQ
                          calmodulin-binding motif
SEQUENCE: 160
MGKKGSWFTA VKKVLSLEPN KEEKIQKSKK NGVKLPEKIK GSKRDNWFAP ATTMVTGALV    60
RLTLSPHYLG KSMEEIATVK IQTVFRGYLA RKALRDLRGL ERLKSLIQGQ SMKRQATITL   120
RCMRTLARVQ SQTRTRQLRV SEQNRALQKH LQTKYEKQLQ NSKSYMGEDW NVSTKSKEQM   180
QAKQQYRQVA AMRRERALAY SFTHQRSWKV TCRSMNHTSM DPFNPKWSWS WLERWMSTRP   240
```

```
WEIQNAPDNN DHGPSKSVGA EITKAKSQSD VNNDHNKQSS TPAKPIRPPN RRSSSTPPSK    300
THSISSKKGL ESPSPTRIQL PDCYKRHSIG GLSLERDDEV FANSPPNNKI PARSSSKDRS    360
RPPSINRNPV NTRRHSGPPK VDIFSN                                        386

SEQ ID NO: 161          moltype = DNA  length = 1543
FEATURE                 Location/Qualifiers
source                  1..1543
                        mol_type = other DNA
                        organism = Zea mays
misc_feature            1..1543
                        note = Ceres CLONE ID no.229668
misc_feature            1..1543
                        note = Encodes the peptide sequence at SEQ ID NO 162
SEQUENCE: 161
cttggaagtc aatctttcgg tgccaccgcc tccagctcct cccccagttc ttcaccaggc    60
cgaggaggtt ggggtccctg aagccgagca ggagcagagc aagcatgtcg ccgtggagga   120
ggcccctgct gccgcccag cgcaggcgtc ggtgctgcca cctgctgtgc aacccaaga    180
gctcgccgca gtcaagatcc agaccgcctt ccgaggttac ctggcaagga gggcactacg   240
agcactgcga ggccttgttc gattgaagtc attggttgag ggtaattcag taaagcgtca   300
atctgcaagc actctgcgct gcatgcaaac tctatcacgg gtgcagtcac agatatcttc   360
caggagagca aagatgtccg aggagaacca ggctctccaa cgccagctcc tacttaaaca   420
ggaactggag aatttcagaa tgggtgagaa ctgggatgac agcacccaat ccaaggagca   480
aatcgaggca agcctgataa gcaggcaaga ggcggcgata agaagagaaa gagcgcttgc   540
atatgcattt tcacaccagt ggaagagtac atcgagatct gtcaacccaa tgtttgtaga   600
cccaaacaac ctgcagtggg gctggagctg gctggagcgc tggatggcag caaaaccatg   660
ggaaggccgc aatggggctg acaaggagag caacattgac cgggatccg ttaagagcat    720
gagcttgaac cttggagagg gtgagatcac aaaagctttc aaccgccggg actcaaagct   780
agaaaagcca tcgccgccaa ctccaagacc ggcccgtcca acttccaggc attccccttt   840
gacgccctct gctagagtgg caccgatacc tgcgaggaga aaatctgtca cgcccaagaa   900
cgggctttca caggtggacg atgacggag gagcgtgctc agtgtgcagt ctgagcggc    960
aaggaggcac agtatagcca cctcgactgt gcgggacgac gagagcctca cgagctcccc   1020
gtcgctccca agctacatgg ttcccacaga atctgcaagg ccaaatctc gcctccaggg   1080
ttcagcaatg gccaatggcg cagagacacc tgagaaagga ggctcaactg gaccagccaa   1140
gaagaggtta tccttccagg gtggaactgc ggctgcctcg ccaatgcgac gacattctgg   1200
tcctcccaag gtggagatcg cgccaccaca accagaggcc ttggtagtca atggtgggag   1260
caagtgacac atatgtgatg agtaccagga tgagaaacgg attatgaaga tattagtttc   1320
attttcatcc atgaatagaa gttaaaagtg gtatcatatc tatgaatggt ttcaattgtt   1380
tttctgttac aaccacatta tttgctatat acgattcaca gtacctgcca gttgattcca   1440
tggtttgttt ctgtaaaaca aatatcaatt tgtcactaga atctctgatg tttgtatgta   1500
aacagatcct ctatttatgt gagacatata tttcttttct ttc                    1543

SEQ ID NO: 162          moltype = AA  length = 421
FEATURE                 Location/Qualifiers
source                  1..421
                        mol_type = protein
                        organism = Zea mays
REGION                  1..421
                        note = Ceres CLONE ID no.229668
REGION                  1..421
                        note = Score of 908.3 for HMM of FIGURE 4.
REGION                  1..421
                        note = Functional Homolog Of Ceres SEEDLINE ID no. ME24091
                         at SEQ ID NO.136
REGION                  60..80
                        note = Pfam Name: IQ Pfam Description: IQ
                         calmodulin-binding motif
SEQUENCE: 162
LEVNLSVPPP PAPPPVLHQA EEVGVPEAEQ EQSKHVAVEE APAAAPAQAS VLPPAVPTQE    60
LAAVKIQTAF RGYLARRALR ALRGLVRLKS LVEGNSVKRQ SASTLRCMQT LSRVQSQISS   120
RRAKMSEENQ ALQRQLLLKQ ELENFRMGEN WDDSTQSKEQ IEASLISRQE AAIRRERALA   180
YAFSHQWKST SRSVNPMFVD PNNLQWGWSW LERWMAAKPW EGRNGADKES NIDRGSVKSM   240
SLNLGEGEIT KAFNRRDSKL EKPSPPTPRP ARPTSRHSPL TPSARVAPIP ARRKSVTPKN   300
GLSQVDDDAR SVLSVQSERP RRHSIATSTV RDDESLTSSP SLPSYMVPTE SARAKSRLQG   360
SAMANGAETP EKGGSTGPAK KRLSFQGGTA AASPMRRHSG PPKVEIAPPQ PEALVVNGGS   420
K                                                                  421

SEQ ID NO: 163          moltype = AA  length = 500
FEATURE                 Location/Qualifiers
source                  1..500
                        mol_type = protein
                        note = subspecies = indica
                        organism = Oryza sativa
REGION                  1..500
                        note = Public GI ID no.125550655
REGION                  1..500
                        note = Score of 911.0 for HMM of FIGURE 4.
REGION                  1..500
                        note = Functional Homolog Of Ceres SEEDLINE ID no. ME24091
                         at SEQ ID NO.136
```

```
REGION                  107..121
                        note = Pfam Name: IQ Pfam Description: IQ
                        calmodulin-binding motif
SEQUENCE: 163
MGKKGKWFGA  VKKVFSPESK  EKKEERLRRK  LAASNPNPPD  LTPSASLEVN  VSVPPPPPPP   60
PVQQIEEVKV  PEVEQEQSKH  VTVEAVPEAV  PVPAQTSSLP  PGVSREEQAA  IKIQTAFRGY  120
LLSENSSWLF  ISSAAFIYHC  VGANITKARR  ALRALRGLVR  LKSLVEGNSV  KRQAASTLRC  180
MQTLARVQSQ  IRSRRLKMSE  ENQALQRQLL  LKQELESLRM  GEQWDDSTQS  KEQIEASLIS  240
RQEAAVRRER  ALAYAFSHQW  KSTSRSVNPM  FVDPNNPQWG  WSWLERWMAA  KPWEGRAGTD  300
KESNLDRASA  KSASLNLGEG  EITKAFNRRG  SKPDKSSPTT  PKLTRPASRQ  SPSTPSAKVS  360
PIFAKKKSAT  PKNGLSQVDD  DAKSVFSVQS  ERPRRHSIAT  STVRDDESLA  SSPSVPSYMA  420
PTKSARAKLR  LQGSAVTDGA  ETPPEKVASV  GSVKKKLSFQ  AGMVPPSPMR  RHSGPPKVEV  480
VKDIAEPPQP  EALVINGGSK                                                 500

SEQ ID NO: 164          moltype = DNA  length = 1923
FEATURE                 Location/Qualifiers
source                  1..1923
                        mol_type = other DNA
                        organism = Arabidopsis thaliana
misc_feature            1..1923
                        note = Ceres CLONE ID no.106263
misc_feature            1..1923
                        note = Encodes the peptide sequence at SEQ ID NO 165
SEQUENCE: 164
acaaatactc ttcttcacac agctttgaat ccatctgtct tctcctctct ctctcttctc   60
catttgcaat tacgataatg tgaaagcaat aagaagagga aaagttatct tcgcaccctca  120
gcaaagatcc aatcgattcg attcttaagc ttttttcgtct tctccgataa ggtcactact  180
tagaagccgc gttgtggttt agttgactcc tccaggtttt atcttcaagc ttttttcgtct  240
atcagatctg tgtcactgt cttctcatag gattacatag agatgggaa aaaagctaaa  300
tggtttttcaa gtgttaagaa agcattcagc ccagattcag agaagtcgaa gcaaaaattg  360
gctgagggac aaaatggtgt tatctctaat cctcctgttg tggataatgt tagacaatct  420
tcttcttctc ctcctcctgc tcttgctcct cgtgaagtga gagtagctga agtgattgtt  480
gaacggaaca gggatctttc acctccttct acagcagatg ctgtgaatgt tacagctact  540
gatgtyccctg tagttccatc ttcatctgct cctggtgttg ttcgtcgcgc tacacctact  600
cgatttgctg gaaagtcaaa cgaagaagcc gctgctatct tgatccagac tatatttaga  660
ggttatttgg caaggagagc gttgcgggca atgaggggtt tggtcagact taagttattg  720
atggaaggat ctgttgttaa gcggcaagct gcaaatactc taaatgtat gcagactctc  780
tctcgtgtac agtcgcagat ccgagctagg agaatcaggr tgtcagaaga gaatcaggct  840
cgccagaaac aactccttca gaaacatgct gaagagctag ctggcttgaa gaacgggat  900
aactggaatg atagcattca atcaaaggag aaagttgaag cgaatttgct aagcaagtac  960
gaggcaacaa tgagaaggga aagggcattg gcttattcat actctcatca scaaaactgg 1020
aagaacaact ctaaatctgg aaacccgatg ttcatggatc caagcaaccc gacatggggt 1080
tggagctggt tggagagatg gatggctggt aggccactag agagttccga gaaagaacaa 1140
agcaacagca acaatgacaa tgctgcctcg gtcaagggct ctattaaccg caacgaagct 1200
gcaaaatctc taacccgcaa tggctcaact caaccaaaca caccatcatc cgcaagaggg 1260
accccaagaa acaaaaacag tttcttctca cctccaactc cctcaaggct aaaccaatcc 1320
tcgagggaaat ccaatgacga cgactccaaa agcacaatct cggtcctgtc cgagagggaac 1380
cgcagacaca scattgctgg ttcatcagtc asagacgatg agagcctcgc tggctcacca 1440
gctctcccga gctacatggt tccaactaaa tcagctcgag ccaggctcaa gccccaaagc 1500
ccattaggtg gtaccacaca ggaaaacgaa gggttcacag acaaggcatc agctaagaaa 1560
cggctctcgt atccaacttc gcctgcattg cctaaaccac ggcggttctc agctcccat 1620
aaggtggaga gtggcggcgt taccgtgacc aacggagcag gcagctgagg tatttttattt 1680
aatataatta ttttcccact tatgaatgtg tccgagattg ttgtctctta tgtgttccct 1740
tcatttcgta attcatttgt gcagtgtaag cgccagtcat ttattttttt actataataa 1800
attttataac cttttaaaat tcatgttctt ttgtttcttt gaatatttaa gttattttta 1860
ttaatgttgg atgaattgga atatgatgat gttatttgta ttgtaatgca gatcctttaa 1920
agc                                                                1923

SEQ ID NO: 165          moltype = AA   length = 461
FEATURE                 Location/Qualifiers
source                  1..461
                        mol_type = protein
                        organism = Arabidopsis thaliana
REGION                  1..461
                        note = Ceres CLONE ID no.106263
REGION                  1..461
                        note = Score of 1104.8 for HMM of FIGURE 4.
REGION                  1..461
                        note = Functional Homolog Of Ceres SEEDLINE ID no. ME24091
                        at SEQ ID NO.136
SITE                    88
                        note = Xaa is any aa, unknown, or other
REGION                  115..135
                        note = Pfam Name: IQ Pfam Description: IQ
                        calmodulin-binding motif
SITE                    180
                        note = Xaa is any aa, unknown, or other
SITE                    243
                        note = Xaa is any aa, unknown, or other
```

```
SITE                        370
                            note = Xaa is any aa, unknown, or other
SITE                        377
                            note = Xaa is any aa, unknown, or other
SEQUENCE: 165
MGKKAKWFSS VKKAFSPDSK KSKQKLAEGQ NGVISNPPVV DNVRQSSSSP PPALAPREVR    60
VAEVIVERNR DLSPPSTADA VNVTATDXPV VPSSSAPGVV RRATPTRFAG KSNEEAAAIL   120
IQTIFRGYLA RRALRAMRGL VRLKLLMEGS VVKRQAANTL KCMQTLSRVQ SQIRARRIRX   180
SEENQARQKQ LLQKHAKELA GLKNGDNWND SIQSKEKVEA NLLSKYEATM RRERALAYSY   240
SHXQNWKNNS KSGNPMFMDP SNPTWGWSWL ERWMAGRPLE SSEKEQSNSN NDNAASVKGS   300
INRNEAAKSL TRNGSTQPNT PSSARGTPRN KNSFFSPPTP SRLNQSSRKS NDDDSKSTIS   360
VLSERNRRHX IAGSSVXDDE SLAGSPALPS YMVPTKSARA RLKPQSPLGG TTQENEGFTD   420
KASAKKRLSY PTSPALPKPR RFSAPPKVES GGVTVTNGAG S                       461

SEQ ID NO: 166              moltype = AA   length = 430
FEATURE                     Location/Qualifiers
source                      1..430
                            mol_type = protein
                            organism = Arabidopsis thaliana
REGION                      1..430
                            note = Public GI ID no.15231175
REGION                      1..430
                            note = Score of 592.8 for HMM of FIGURE 4.
REGION                      1..430
                            note = Functional Homolog Of Ceres SEEDLINE ID no. ME24091
                             at SEQ ID NO.136
REGION                      108..128
                            note = Pfam Name: IQ Pfam Description: IQ
                             calmodulin-binding motif
SEQUENCE: 166
MGKSWFSAVK KALSPEPKQK KEQKPHKSKK WFGKSKKLDV TNSGAAYSPR TVKDAKLKEI    60
EEQQSRHAYS VAIATAAAAE AAVAAAQAAA EVVRLSALSR FPGKSMEEIA AIKIQTAFRG   120
YMARRALRAL RGLVRLKSLV QGKCVRRQAT STLQSMQTLA RVQYQIRERR LRLSEDKQAL   180
TRQLQQKHNK DFDKTGENWN DSTLSREKVE ANMLNKQVAT MRREKALAYA FSHQNTWKNS   240
TKMGSQTFMD PNNPHWGWSW LERWMAARPN ENHSLTPDNA EKDSSARSVA SRAMSEMIPR   300
GKNLSPRGKT PNSRRGSSPR VRQVPSEDSN SIVSFQSEQP CNRRHSTCGS IPSTRDDESF   360
TSSFSQSVPG YMAPTQAAKA RARFSNLSPL SSEKTAKKRL SFSGSPKTVR RFSGPPKLES   420
NVTKKDTNLA                                                          430

SEQ ID NO: 167              moltype = AA   length = 461
FEATURE                     Location/Qualifiers
source                      1..461
                            mol_type = protein
                            organism = Arabidopsis thaliana
REGION                      1..461
                            note = Public GI ID no.145357576
REGION                      1..461
                            note = Score of 1118.9 for HMM of FIGURE 4.
REGION                      1..461
                            note = Functional Homolog Of Ceres SEEDLINE ID no. ME24091
                             at SEQ ID NO.136
REGION                      115..135
                            note = Pfam Name: IQ Pfam Description: IQ
                             calmodulin-binding motif
SEQUENCE: 167
MGKKAKWFSS VKKAFSPDSK KSKQKLAEGQ NGVISNPPVV DNVRQSSSSP PPALAPREVR    60
VAEVIVERNR DLSPPSTADA VNVTATDVPV VPSSSAPGVV RRATPTRFAG KSNEEAAAIL   120
IQTIFRGYLA RRALRAMRGL VRLKLLMEGS VVKRQAANTL KCMQTLSRVQ SQIRARRIRM   180
SEENQARQKQ LLQKHAKELA GLKNGDNWND SIQSKEKVEA NLLSKYEATM RRERALAYSY   240
SHQQNWKNNS KSGNPMFMDP SNPTWGWSWL ERWMAGRPLE SSEKEQSNSN NDNAASVKGS   300
INRNEAAKSL TRNGSTQPNT PSSARGTPRN KNSFFSPPTP SRLNQSSRKS NDDDSKSTIS   360
VLSERNRRHS IAGSSVRDDE SLAGSPALPS YMVPTKSARA RLKPQSPLGG TTQENEGFTD   420
KASAKKRLSY PTSPALPKPR RFSAPPKVES GGVTVTNGAG S                       461

SEQ ID NO: 168              moltype = AA   length = 474
FEATURE                     Location/Qualifiers
REGION                      1..474
                            note = Public GI ID no.125528277
REGION                      1..474
                            note = Score of 1169.9 for HMM of FIGURE 4.
REGION                      1..474
                            note = Functional Homolog Of Ceres SEEDLINE ID no. ME24091
                             at SEQ ID NO.136
REGION                      142..162
                            note = Pfam Name: IQ Pfam Description: IQ
                             calmodulin-binding motif
source                      1..474
                            mol_type = protein
                            note = subspecies = indica
```

-continued

```
                   organism = Oryza sativa
SEQUENCE: 168
MGKKGNWFSA VKKVFSSSDP DGREAKIEKA DKSRSRRKWP FGKSKKSDPW TSTVAVPTST  60
APPPQPPPPP PTHPIQPQPE EIKDVKAVET DSEQNKHAYS VALASAVAAE AAAVAAQAAA  120
EVVRLTTATT AVPKSPVSSK DELAAIKIQT AFRGYLARRA LRALRGLVRL KSLVDGNAVK  180
RQTAHTLHCT QTMTRVQTQI YSRRVKMEEE KQALQRQLQL KHQRELEKMK IDEDWDHSHQ  240
SKEQWKNSGR TITPTFTDQG NPNWGWSWME RWMTSRPWES RVISDKDPKD HYSTKNPSTS  300
ASRTYVPRAI SIQRPATPNK SSRPPSRQSP STPPSRVPSV TGKIRPASPR DSWLYKEDDL  360
RSITSIRSER PRRQSTGGAS VRDDASLTST PALPSYMQST ESARAKSRYR SLLTDRFEVP  420
ERVPLVHSSI KKRLSFPVAD KPNGEHADKL MERGRRHSDP PKVDPASLKD VPVS        474
```